US012575768B2

(12) United States Patent
Mccanless et al.

(10) Patent No.: US 12,575,768 B2

(45) Date of Patent: Mar. 17, 2026

(54) ANALYTE SENSOR ANTIMICROBIAL CONFIGURATIONS AND ADHESIVES

(71) Applicant: Abbott Diabetes Care, Inc., Alameda, CA (US)

(72) Inventors: Jonathan D. Mccanless, Oakland, CA (US); Udo Hoss, Castro Valley, CA (US); Benjamin J. Feldman, Berkeley, CA (US); Frank David Fujimoto, Fremont, CA (US); Steven T. Mitchell, Pleasant Hill, CA (US)

(73) Assignee: Abbott Diabetes Care, Inc., Alameda, CA (US)

( * ) Notice: Subject to any disclaimer, the term of this patent is extended or adjusted under 35 U.S.C. 154(b) by 0 days.

(21) Appl. No.: 17/820,213

(22) Filed: Aug. 16, 2022

(65) Prior Publication Data

US 2022/0386911 A1 Dec. 8, 2022

Related U.S. Application Data

(63) Continuation of application No. 17/052,705, filed as application No. PCT/US2019/032848 on May 17, 2019.

(Continued)

(51) Int. Cl.

*A61B 5/1486* (2006.01)
*A61B 5/00* (2006.01)
*A61B 5/145* (2006.01)

(52) U.S. Cl.

CPC ...... *A61B 5/14865* (2013.01); *A61B 5/14503* (2013.01); *A61B 5/14532* (2013.01);

(Continued)

(58) Field of Classification Search

CPC ........... A61M 5/14248; A61B 5/14503; A61B 5/1451; A61B 5/14532; A61B 5/14735;

(Continued)

(56) References Cited

U.S. PATENT DOCUMENTS

| | | | |
|---|---|---|---|
| 5,008,110 | A | 4/1991 | Benecke et al. |
| 6,134,461 | A | 10/2000 | Say et al. |

(Continued)

FOREIGN PATENT DOCUMENTS

| | | | | |
|---|---|---|---|---|
| WO | WO-0143969 A1 * | 6/2001 | ........... | A61F 13/514 |
| WO | WO-2007092350 A1 * | 8/2007 | ........... | A61F 13/023 |

(Continued)

OTHER PUBLICATIONS

International Search Report and Written Opinion of related PCT/US2019/032848 dated Apr. 9, 2019.

(Continued)

*Primary Examiner* — Tse W Chen
*Assistant Examiner* — Alice Ling Zou
(74) *Attorney, Agent, or Firm* — Sterne, Kessler, Goldstein & Fox P.L.L.C.

(57) ABSTRACT

An analyte sensor and methods and systems related thereto, where at least one or more of a lower portion of a sensor tail substrate, at least one electrode, a sensing element, a membrane, and an optional non-electrochemical functional layer comprise an antimicrobial quality. Asymmetric, double-sided adhesive binders suitable for adhering the analyte sensor to a skin surface comprising a non-woven scrim, a first pressure-sensitive adhesive layer, a second pressure-sensitive adhesive layer. Overbandages comprising a vapor-permeable backing, an aperture to circumferentially surround a sensor housing, a contact adhesive layer, first and (Continued)

second peelable release liners, and a third peelable release liner disposed upon an anchoring adhesive strip of the contact adhesive layer.

30 Claims, 33 Drawing Sheets

Related U.S. Application Data

(60) Provisional application No. 62/788,364, filed on Jan. 4, 2019, provisional application No. 62/672,773, filed on May 17, 2018, provisional application No. 62/672,756, filed on May 17, 2018.

(52) U.S. Cl.
CPC .... *A61B 5/6833* (2013.01); *A61B 2560/0468* (2013.01); *A61B 2562/0295* (2013.01); *A61B 2562/14* (2013.01); *A61B 2562/18* (2013.01)

(58) Field of Classification Search
CPC .... A61B 5/14865; A61B 5/6832–6833; A61B 5/6833–68335; A61B 5/14–1495; A61F 2013/00412; A61F 2013/00421; A61F 2013/00604; A61F 2013/00655; A61F 2013/00727; A61F 2013/00761; A61F 2013/00855; A61F 2013/00863; A61F 2013/0087; A61F 15/004
See application file for complete search history.

(56) References Cited

U.S. PATENT DOCUMENTS

| | | | | |
|---|---|---|---|---|
| 6,565,509 | B1 | 5/2003 | Say et al. | |
| 6,605,200 | B1 | 8/2003 | Mao et al. | |
| 6,605,201 | B1 | 8/2003 | Mao et al. | |
| 6,736,957 | B1 | 5/2004 | Forrow et al. | |
| 7,153,265 | B2 | 12/2006 | Vachon | |
| 7,501,053 | B2 | 3/2009 | Karinka et al. | |
| 7,736,310 | B2 | 6/2010 | Taub | |
| 7,754,093 | B2 | 7/2010 | Forrow et al. | |
| 7,883,464 | B2 | 2/2011 | Stafford | |
| 8,268,143 | B2 | 9/2012 | Liu et al. | |
| 8,443,647 | B1 | 5/2013 | Kolmakov et al. | |
| 8,444,834 | B2 | 5/2013 | Liu et al. | |
| 8,983,568 | B2 | 3/2015 | Bommakanti et al. | |
| 9,572,534 | B2 | 2/2017 | Stafford | |
| 9,668,686 | B2 | 6/2017 | Feldman et al. | |
| 10,052,055 | B2 | 8/2018 | Li et al. | |
| 10,531,831 | B2 | 1/2020 | Pace | |
| 2003/0042137 | A1 | 3/2003 | Mao et al. | |
| 2004/0242770 | A1 | 12/2004 | Feldstein et al. | |
| 2006/0057191 | A1 | 3/2006 | Wellinghoff | |
| 2007/0135699 | A1 | 6/2007 | Ward et al. | |
| 2008/0242961 | A1 | 10/2008 | Brister et al. | |
| 2008/0249383 | A1 * | 10/2008 | Sass | A61B 5/6849 600/345 |
| 2009/0088614 | A1 * | 4/2009 | Taub | A61B 5/14865 600/316 |
| 2009/0247856 | A1 | 10/2009 | Boock et al. | |
| 2009/0260418 | A1 | 10/2009 | Flaherty et al. | |
| 2009/0294306 | A1 | 12/2009 | Feldman et al. | |
| 2011/0076504 | A1 | 3/2011 | Van De Weerdt et al. | |
| 2011/0213225 | A1 | 9/2011 | Bernstein et al. | |
| 2012/0150005 | A1 | 6/2012 | Hoss et al. | |
| 2012/0190941 | A1 | 7/2012 | Donnay et al. | |
| 2014/0255952 | A1 | 9/2014 | Kumta et al. | |
| 2015/0359946 | A1 | 12/2015 | Dehnad et al. | |
| 2016/0058380 | A1 * | 3/2016 | Lee | A61B 5/6832 600/365 |
| 2016/0135747 | A1 * | 5/2016 | Frey | A61F 13/0269 600/365 |
| 2016/0213322 | A1 * | 7/2016 | Goldberg | A61M 25/02 |
| 2016/0235365 | A1 | 8/2016 | Liu et al. | |
| 2016/0331232 | A1 | 11/2016 | Love et al. | |
| 2016/0331283 | A1 | 11/2016 | Rao et al. | |
| 2017/0020456 | A1 * | 1/2017 | Pace | A61B 5/002 |
| 2017/0112533 | A1 * | 4/2017 | Schoonmaker | A61B 5/14532 |
| 2017/0191955 | A1 | 7/2017 | Zou et al. | |
| 2017/0196487 | A1 | 7/2017 | Feldman et al. | |
| 2018/0168873 | A1 * | 6/2018 | Lebron | A61F 13/15203 |
| 2019/0004005 | A1 | 1/2019 | Oja et al. | |
| 2019/0060511 | A1 | 2/2019 | Larson et al. | |
| 2019/0167167 | A1 | 6/2019 | Mitchell et al. | |
| 2019/0386711 | A1 | 12/2019 | He et al. | |

FOREIGN PATENT DOCUMENTS

| | | | | |
|---|---|---|---|---|
| WO | WO-2012158202 | A2 | 11/2012 | |
| WO | WO-2018119193 | A1 * | 6/2018 | A61F 13/00051 |
| WO | WO-2019222615 | A1 | 11/2019 | |

OTHER PUBLICATIONS

Product No. 9917 3M Double Coated Polyester Nonwoven Medical Tape, 3M Medical Materials & Technology, Double Sided Adhesive Datasheet (2022), Effective: Nov. 2020, 2 pages.

* cited by examiner

ANALYTE SENSOR ANTIMICROBIAL CONFIGURATIONS AND ADHESIVES

CROSS-REFERENCE TO RELATED APPLICATIONS

This application claims priority to U.S. provisional application 62/672,773 entitled "Asymmetric, Double-Sided Adhesive Binders for On-Body Analyte Sensors," filed on May 17, 2018; U.S. provisional application 62/672,756 entitled "Adhesive Overbandages for On-Body Analyte Sensors" filed on May 17, 2018; and U.S. provisional application 62/788,364 entitled "Antimicrobial Analyte Sensors and Methods and Systems Thereof" filed on Jan. 4, 2019.

STATEMENT REGARDING FEDERALLY SPONSORED RESEARCH OR DEVELOPMENT

Not applicable.

BACKGROUND

The detection of various analytes within an individual can sometimes be vital for monitoring the condition of their health and well-being. Deviation from normal analyte levels can often be indicative of an underlying physiological condition, such as a metabolic condition or illness, or exposure to particular environmental factors or stimuli. Glucose levels, for example, can be particularly important to detect and monitor in diabetic individuals.

Analyte monitoring in an individual may take place periodically or continuously over a period of time. Periodic analyte monitoring may take place by withdrawing a sample of bodily fluid, such as blood, at set time intervals and analyzing ex vivo. Continuous analyte monitoring may be conducted using one or more sensors that remain implanted within a tissue of an individual, such as dermally, subcutaneously, or intravenously, through which analyses may take place in vivo. Implanted sensors may collect analyte data continuously, at planned intervals, or sporadically, depending on an individual's particular health needs and/or previously determined analyte levels.

Although the entirety of a sensor or sensing system may be implanted within an individual (e.g., surgically), it is more common for primarily the bioactive and communication path (e.g., flex circuit) portions of the sensor to be implanted internally (e.g., through a skin penetration), with one or more additional sensor components remaining external to the individual's body. In many instances, sensors suitable for measuring analyte levels in vivo may extend from a sensor housing that is designed to be worn "on-body" for extended periods of time, such as upon the skin. Such on-body analyte sensors may be especially desirable, since they often may be applied directly by a wearer, rather than relying on a medical professional to perform an invasive sensor implantation procedure.

Despite the desirability of on-body analyte sensors, their use may not be without complications. When positioning an on-body analyte sensor onto the skin of a wearer, a needle or other introducer is used to puncture the skin and allow implantation of at least a portion of a sensor through the dermal region. Accordingly, a transdermal skin wound is created in order for the sensor to undergo positioning for analyte monitoring (i.e., the "insertion site," including the actual wound and areas adjacent thereto), and at least an active portion of the sensor remains within the skin for the wear duration of the on-body analyte sensor. Both during localization and during wear, microorganism incursion into the wound at the sensor insertion site and along any length of the sensor, including the active area, may occur, such as by exposure to skin microorganisms and/or the external environment. The possibility of existing microorganisms near the insertion site and/or migration of microorganisms from adjacent areas, including the external environment, may create a rich environment for microorganism growth. Such growth may be harmful to the wearer and/or may lead to altered functioning of the analyte sensor itself, such as causing a shortened life of the sensor and/or providing erroneous or altered data or perceived sensitivity and/or response times.

Further, to prevent sensor pullout or displacement, on-body analyte sensors are usually adhesively bonded to a skin surface, using either a liquid adhesive or a pressure-sensitive adhesive. While both types of adhesives can be suitable for preventing sensor pullout or displacement, they can be problematic in other respects. One particular issue associated with many types of adhesives is that they are not sufficiently breathable to avoid skin issues such as maceration, infection, and/or irritation. For on-body analyte sensors having expected sensor lifetimes measured in weeks, these issues can become significant and possibly compromise the viability of in vivo analyte measurements for management of chronic physiological conditions. Other issues associated with adhesive coupling of on-body analyte sensors to a skin surface can include, for example, premature adhesive failure, achieving mutual compatibility of a given adhesive to both a skin surface and a sensor housing, and potential allergic reactions of some individuals to certain types of adhesives. Any of the foregoing issues may necessitate premature removal of an on-body analyte sensor from the skin surface of a wearer, which can be undesirable in terms of the cost of wasted sensor lifetime and/or detrimental impacts on an individual's health while the on-body analyte sensor is removed and not collecting analyte data.

Additionally, one issue associated with on-body analyte sensors is that an adhesive holding the analyte sensor on the surface of the skin may fail before the sensor has reached the end of its usable lifetime. For example, perspiration, bathing, dirt accumulation, oil secretion, and the like may lead to adhesive failure and sensor decoupling or movement. As such, an overbandage may be employed in combination with an on-body analyte sensor to aid in securing the on-body analyte sensor in place, even after a primary adhesive securing the analyte sensor to a skin surface has failed or become less effective. Moreover, if the adhesive in the overbandage itself fails, a fresh overbandage may be applied, provided that the sensor still remains within its usable lifetime. Each of these solutions is considerably more cost-effective than is prematurely replacing the sensor itself. Unfortunately, overbandages themselves are not without challenges. In some instances, an on-body analyte sensor may be worn in a position that can make it difficult for a wearer to access the sensor housing for applying an overbandage thereto. For example, some continuous glucose monitoring sensors may be worn on the underside of the triceps, which may be problematic for some wearers to access when applying an overbandage. If an overbandage is misapplied and needs to be removed, overbandage removal itself may lead to sensor displacement or removal (i.e., sensor pullout or movement). Alternately, an improperly seated overbandage may tug on the sensor housing as the overbandage stretches and contracts with wearer movement, again leading to potential sensor displacement. It may be desirable to avoid even marginal displacement of an implanted analyte sensor, since even small variations in the sensor's internal position can skew measured analyte readings. The foregoing issues can be especially problematic when a wearer has difficulty accessing the site of sensor attachment.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure generally describes analyte sensors, and systems and methods related thereto, that promote skin health and sensor functionality by incorporation of an antimicrobial quality. The present disclosure generally describes moisture management systems and methods associated with on-body analyte sensors and, more specifically, adhesive binders and associated constructs for promoting attachment of on-body analyte sensors to a skin surface, as well as promoting skin health. The present disclosure generally describes adhesive overbandages for on-body analyte sensors and, more specifically, guidable overbandages for on-body analyte sensors and methods for attachment thereof, as well as for promoting skin health. Each of the embodiments described herein may be combined in any combination.

Before describing the various embodiments of the present disclosure in more detail, a brief overview of suitable in vivo analyte sensor configurations will first be provided so that the embodiments of the present disclosure may be better understood.

Figure 1:
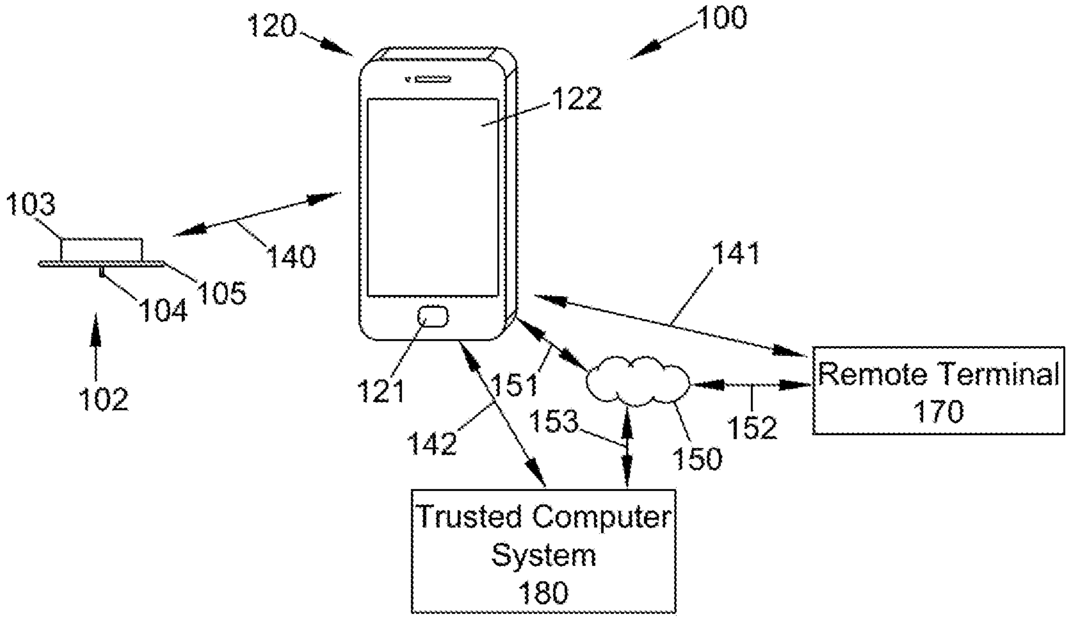
FIG. 1 shows a diagram of an illustrative sensing system that may incorporate an analyte sensor of the present disclosure.

FIG. 1 shows a diagram of an illustrative sensing system that may incorporate an analyte sensor of the present disclosure. As shown, sensing system 100 includes sensor control device 102 and receiver 120 (e.g., a reader device) that are configured to communicate with one another over a local or remote communication path or link, which may be wired or wireless, uni- or bi-directional, and encrypted or non-encrypted. Such communication may be referred to as "electrical communication" and may be intermittent or constant (e.g., may automatically receive transmitted signals from the sensor control device 102 or may only receive transmitted signals periodically or upon a prompt from a user of the receiver 120). Receiver 120 may constitute an output medium for viewing analyte concentrations, such as a glucose concentration, and alerts or notifications determined by a sensing element(s) of sensor tail 104 or a processor associated therewith, as well as allowing for one or more user inputs, according to some embodiments. Receiver 120 may be a multi-purpose smartphone or a dedicated electronic reader instrument. While only one receiver 120 is shown, more than one receiver 120 may be present in certain instances. Multiple receivers 120 may be in communication with one another (e.g., to share and synchronize data). Receiver 120 may also be in electrical communication with remote terminal 170 and/or trusted computer system 180 via communication path(s)/link(s) 141 and/or 142, respectively, which also may be wired or wireless, uni- or bi-directional, and encrypted or non-encrypted. Receiver 120 may also or alternately be in communication with network 150 (e.g., a mobile telephone network, the internet, a cloud server, or the link) via communication path/link 151. Network 150 may be further communicatively coupled to remote terminal 170 via communication path/link 152 and/or trusted computer system 180 via communication path/link 153. Remote terminal 170 and/or trusted computer system 180, in turn, may communicate with network 150, in some embodiments. Alternately, sensor 102 may communicate directly with remote terminal 170 and/or trusted computer system 180 without an intervening receiver 120 being present. For example, sensor 102 may communicate with remote terminal 170 and/or trusted computer system 180 through a direct communication link to network 150, according to some embodiments, as described in U.S. Patent Application Publication 2011/0213225 and incorporated herein by reference in its entirety. Any suitable electronic communication protocol may be used for each of the communication paths or links, such as near field communication (NFC), radio frequency identification (RFID), BLUETOOTH® or BLUETOOTH® Low Energy protocols, WiFi, or the like. Remote terminal 170 and/or trusted computer system 180 may be accessible, according to some embodiments, by individuals other than a primary user who have an interest in the user's analyte levels. Receiver 120 may comprise display 122 and optional input component 121. Receiver 120 may be a device specific to the sensing system (e.g., an analyte reader and/or analyte meter, and the like) or alternatively a mobile phone (e.g., iPhone or Android) or other personal mobile device or evaluation module (e.g., RFID transponder evaluation module (EVM)), for example.

Display 122 may comprise a touch-screen interface or other tactile interface, according to some embodiments.

Sensor control device 102 includes sensor housing 103, which may house circuitry and a power source for operating sensor tail 104. Optionally, the power source and/or active circuitry may be omitted. A processor (not shown) may be communicatively coupled to sensor tail 104, with the processor being physically located within sensor housing 103 or receiver 120. Sensor tail 104 protrudes from the underside of sensor housing 103 and extends through adhesive layer 105, which is adapted for adhering sensor housing 103 to a tissue surface, such as skin, according to some embodiments. That is, the sensor tail 104 extends from the base of the components of the analyte sensor that are external to a tissue of a wearer.

Sensor tail 104 is adapted to be at least partially inserted into a tissue of interest, such as within the dermal or subcutaneous layer of the skin. Sensor tail 104 may be of sufficient length for insertion to a desired depth in a given tissue. The sensor tail may comprise a working electrode and one or more sensing elements (sensing regions/spots or sensing layers) located upon the working electrode and that are active for sensing an analyte of interest, such as glucose or other analyte (e.g., lactate, oxygen, pH, A1c, ketones, drug levels, toxins, and the like). Both single analytes and any combination of the foregoing analytes may be assayed. According to one or more embodiments of the present disclosure, each sensing element may comprise an analyte-responsive enzyme (e.g., glucose oxidase or glucose dehydrogenase). The sensing elements may include a polymeric material to which the enzyme is covalently bonded, according to some embodiments. In various embodiments of the present disclosure, the analyte of interest may be monitored in any biological fluid of interest such as dermal fluid, interstitial fluid, plasma, blood, lymph, synovial fluid, cerebrospinal fluid, saliva, bronchoalveolar lavage, amniotic fluid, or the like. In particular embodiments, the analyte sensors of the present disclosure may be adapted for assaying interstitial fluid in the dermis or subcutaneous regions.

In some embodiments, sensor tail 104 may be configured to automatically forward data to receiver 120. For example, analyte concentration data may be communicated automatically and periodically, such as at a certain frequency as data is obtained or after a certain time period has passed, with the data being stored in a memory until transmittal (e.g., every minute, five minutes, or other predetermined time period). In other embodiments, sensor tail 104 may communicate with receiver 120 in a non-automatic manner and not according to a set schedule. For example, data may be communicated from sensor tail 104 using RFID technology when the sensor electronics are brought into communication range of receiver 120. Until communicated to receiver 120, data may remain stored in a memory of sensor tail 104. Thus, a patient does not have to maintain close proximity to receiver 120 at all times and can instead upload data at a convenient time. In yet other embodiments, a combination of automatic and non-automatic data transfer may be implemented. For example, data transfer may continue on an automatic basis until receiver 120 is no longer in communication range of sensor tail 104.

An introducer may be present transiently to promote introduction and localization of sensor tail 104 into a tissue. In illustrative embodiments, the introducer may comprise a needle or similar sharp. It is to be recognized that other types of introducers, such as sheaths or blades, may be present in alternative embodiments. More specifically, the needle or other introducer may transiently reside in proximity to sensor tail 104 prior to tissue insertion and then be withdrawn afterward. While present, the needle or other introducer may facilitate insertion of sensor tail 104 into a tissue by opening an access pathway for sensor tail 104 to follow. For example, the needle may facilitate penetration of the epidermis as an access pathway to the dermis to allow implantation of sensor tail 104 to take place, according to one or more embodiments. After opening the access pathway, the needle or other introducer may be withdrawn so that it does not represent a sharps hazard. In illustrative embodiments, suitable needles may be solid or hollow, beveled or non-beveled, channeled or non-channeled, and/or circular or non-circular in cross-section. Cross-sections need not be consistent throughout the entire length of the introducer. In more particular embodiments, suitable needles may be comparable in cross-sectional diameter and/or tip design to an acupuncture needle, which may have a cross-sectional diameter of about 450 microns or less. It is to be recognized, however, that suitable needles may have a larger or smaller cross-sectional diameter if needed for particular applications, without departing from the scope of the present disclosure.

In some embodiments, a tip of the needle (while present) may be angled over the terminus (i.e., tip or distal most portion) of sensor tail 104, such that the needle penetrates a tissue first and opens an access pathway for sensor tail 104. In other illustrative embodiments, sensor tail 104 may reside within a lumen or groove of the needle, with the needle similarly opening an access pathway for sensor tail 104. In either case, the needle is subsequently withdrawn after facilitating sensor insertion.

It is to be appreciated that in other embodiments, the sensor tail 104 itself may be sufficiently rigid to allow implantation into a tissue without the use of an introducer.

Antimicrobial Analyte Sensors, Methods, and Systems

In some instances, on-body analyte sensors may provide a number of advantages when assaying physiological levels of various analytes, such as glucose. Continuous analyte monitoring using an implanted sensor can be advantageous, but there may be certain challenges associated with these types of measurements. Intravenous analyte sensors are invasive and can sometimes be painful for an individual to wear, particularly over an extended period. Subcutaneous, interstitial, or dermal analyte sensors can often be less painful for an individual to wear and can provide sufficient measurement accuracy in many cases.

Non-intravenous in vivo glucose-responsive analyte sensors have been developed over the past two decades by several manufacturers, and some have recently gained regulatory approval for monitoring glucose levels in diabetic individuals. Such glucose-responsive analyte sensors employ glucose oxidase that is covalently bound to a polymer to facilitate glucose detection and a transition metal complex (electron transfer agent or electron transfer mediator) to aid in conveyance of electrons released during the oxidation of glucose. In such sensors, the glucose-responsive analyte sensors respond rapidly to a change in glucose levels and provide a stable sensor response over a wear period of up to 10-14 days or longer. In vivo glucose-responsive analyte sensors available from other manufacturers also employ glucose oxidase and other glucose-related enzymes (e.g., flavin adenine dinucleotide-dependent glucose dehydrogenase (FAD-GDH)) as the basis for sensing but vary the sensing chemistry/protocol in various ways.

In vivo analyte sensors for assaying glucose and other analytes may include a membrane disposed over at least a portion of the implanted portion of the analyte sensor. In one aspect, the membrane may improve biocompatibility of the analyte sensor. In another aspect, the membrane may be permeable or semi-permeable to an analyte of interest and limit the overall analyte flux to the active area of the analyte sensor (i.e., sensing element(s)), such that the membrane functions as a mass transport limiting membrane. Limiting analyte access to the sensing element(s) of the analyte sensor with a mass transport limiting membrane can aid in avoiding sensor overload (saturation), thereby improving detection performance and accuracy. Such membranes may be highly specific toward limiting mass transport of a particular analyte, with other substances permeating through the membrane at significantly different rates, reducing background and interference signals from non-specific redox reactions with analyte molecules other than those of interests.

The wear duration of an on-body analyte sensor over an extended period of time (e.g., greater than two weeks, or even longer) may be limited in some instances. For example, analyte sensor chemistry can support long wear times, but there is also a desire to minimize the risk of infection or biofilm formation at or near the insertion site and the active area of the analyte sensor. Microorganism incursion into or near the operational components of an analyte sensor, such as the membrane or any other active area thereof (i.e., the sensing element(s)), may result in decreased accuracy and/or other loss of functionality, particularly during extended wear over multiple days or even longer over multiple weeks if microorganism incursion has occurred. In vivo on-body analyte sensors comprise a sensor tail component that may be implanted into a tissue of a user (e.g., transdermally, dermally, subcutaneously, or intravenously) and in some instances, as previously herein, the sensor tail includes one or more sensing elements at at least the distal tip thereof. As used herein, the term "sensor tail," and grammatical variants thereof, refers to the portion of the analyte sensor extending from the base of an external component thereof and of which at least a lower portion is inserted into the tissue of a wearer; the sensor tail of the present disclosure typically comprises one or more sensing elements at at least a lower portion thereof (e.g., at or near the distal tip), as described in greater detail herein below. In other embodiments, however, the distal tip of the sensor tail may not comprise the sensing elements, which may be located at a different (e.g., less distal) portion along the sensor tail. Regardless of the implantation qualities of the sensor as a whole (e.g., whether it be wholly or partially implanted into a tissue of a user), at least a portion of the sensor tail and active area thereof is in contact with bodily fluid once introduced to a tissue of a wearer.

Performance of on-body analyte sensors may be highly dependent upon biologic events local to or near the sensor tail. Typically, for accurate analyte measurement, an analyte sensor permits an undisturbed (i.e., consistent or predictable) pathway to communicate with the sensing element(s); likewise, the sensing element(s) (and potentially other elements, such as reference materials) must maintain communication with the intended body fluid of interest in an undisturbed or predictable manner. Moreover, for electrochemical sensors, stable connectivity (e.g., electrode connectivity and other electronics) is necessary to ensure proper analyte sensor functionality. Accordingly, maintaining such pathways and connectivity during the life of an on-body analyte sensor may be critical, including preventing microorganism incursion thereto.

Microorganisms may disturb the functionality of an on-body analyte sensor in one or more ways. For example, the disturbance may be a chemical disturbance and/or a physical disturbance. Accordingly, the antimicrobial (including microstatic) agents described herein for use in preventing or reducing microorganism interference with the functionality of an analyte sensor may be designed to combat any one or all types of potential microorganism disturbances.

For chemical disturbances, microorganisms may populate the insertion site and influence analyte concentration located adjacent to the sensing element(s), thereby resulting in false analyte measurement readings. For example, such microorganisms may artificially increase or decrease the analyte level being measured by the sensing element(s). In certain instances, a microorganism layer (e.g., a dense microorganism layer or biofilm) may consume a portion of the one or more analytes being measured, such as glucose, before it contacts the sensing element(s) thereof, resulting in an artificially low analyte measurement. In other instances, an on-body analyte sensor may measure a host cell analyte and such analyte may be erroneously measured due to microorganism infection at or near the insertion site, in which the microorganism generates the same analyte as metabolite or other secreted substance (e.g., cytokines, enzymes, etc.). In such instances, the measurement may be artificially high due to an additive effect between the host metabolite level and that of the microorganism. In yet another scenario, microorganisms can interfere with analyte sensor measurement by causing an immune response at or near the insertion site. For example, the measured analyte may be a host cell metabolite and an accumulation of such host cells in response to the infection may result in an artificially high analyte measurement. Because microorganisms and eukaryotic cells produce acidic metabolites, in another scenario, an analyte sensor that is pH-sensitive may produce artificially low or high analyte measurements due to microorganism infection or resultant user immune response. That is, the presence of the microorganism or immune response to such may result in increased cell densities and heightened metabolic activity by producing acid, which may reduce pH and lead to false analyte measurements.

For physical disturbances, microorganism incursion, such as infection at the insertion site or along the sensor tail, may result in formation of a biofilm. Biofilms are typically dense networks of microorganism cells (e.g., bacteria cells) embedded in DNA, proteins, polysaccharides, or other compounds and may result in erroneous analyte measurements by an analyte sensor. For example, the biofilm may interfere with diffusion of one or more analytes of interest to the sensing element(s) of the analyte sensor. In other scenarios, biofouling from protein or other molecule adsorption onto a surface of an analyte sensor, particularly the sensing element (s) thereof, may also interfere with diffusion of one or more analytes of interest, thereby resulting in artificially low analyte measurements. In certain situations, the membrane of a sensor may become desiccated or otherwise dried due to wound healing (e.g., healing at the insertion site of an on-body analyte sensor), effectively walling off the sensing element(s) and influencing the functionality of the analyte sensor. Moreover, such membrane desiccation may block the pathway to the sensing element(s) of the analyte sensor. In some instances, the various electrodes (e.g., working, reference, and/or counter electrodes) may lose connectivity due directly to the microorganism incursion (e.g., due to the desiccation of the membrane or biofilm formation) or indirectly from native immune cell recruitment in response to microorganism incursion.

The embodiments of the present disclosure accordingly impart an antimicrobial quality of one or more portions of an on-body analyte sensor in order to reduce or prevent malfunction due to microorganism incursion by incorporating antimicrobial compounds therewith. As used herein, the terms "antimicrobial" or "antimicrobial agent" or "antimicrobial compound," and grammatical variants thereof, refer to a substance or material that is detrimental (i.e., microbicidal) or microstatic (i.e., preventing or reducing colonization, expansion, and/or proliferation without necessarily being detrimental) to a microorganism, including bacteria, fungi, viruses, protozoans, and the like. The term "antimicrobial quality," used interchangeably herein with term "antimicrobial characteristic," and grammatical variants thereof, refers to any one or more components of the analyte sensors described herein having the ability to be detrimental or microstatic to a microorganism, and includes any mechanism, structure, system, or other technique for imparting said ability to a tangible material, including one or more components of the analyte sensors described herein.

In particular, the embodiments of the present disclosure utilize the membrane, printed region, sensor substrate, sensing element(s), reference material, and/or non-electrochemical functional layer as a delivery system or substrate (e.g., carrier) for delivering an antimicrobial compound and, therefore, reducing or preventing erroneous analyte measurements of an on-body analyte sensor due to one or more of the microorganism disturbances described above.

Suitable configurations for the analyte sensors of the present disclosure may employ two-electrode or three-electrode detection motifs, which are described further hereinafter with reference to FIGS. 2A-2C.

Three-electrode detection motifs may comprise a working electrode, a counter electrode, and a reference electrode. Related two-electrode detection motifs may comprise a working electrode and a second electrode, in which the second electrode functions as both a counter electrode and a reference electrode (i.e., a counter/reference electrode). In both two-electrode and three-electrode detection motifs, one or more sensing elements (i.e., biologically active area(s) that can be used to detect and quantify an analyte of interest) of the analyte sensor may be in contact with the working electrode and located at or near the distal tip of the sensor tail, as described in greater detail hereinbelow. The sensing element(s) may comprise at least an analyte-responsive enzyme (e.g., a glucose-responsive enzyme) and, optionally, a stabilizer, mediator, and/or crosslinker, according to some embodiments of the present disclosure. In some embodiments, the various electrodes may be at least partially stacked (layered) upon one another, as described in further detail hereinafter. In some or other embodiments, the various electrodes may be laterally spaced apart from one another upon the sensor tail. In either case, the various electrodes may be electrically isolated from one another by a dielectric material or similar insulator.

Antimicrobial Analyte Sensors and Methods and Systems Thereof

Figure 2A:
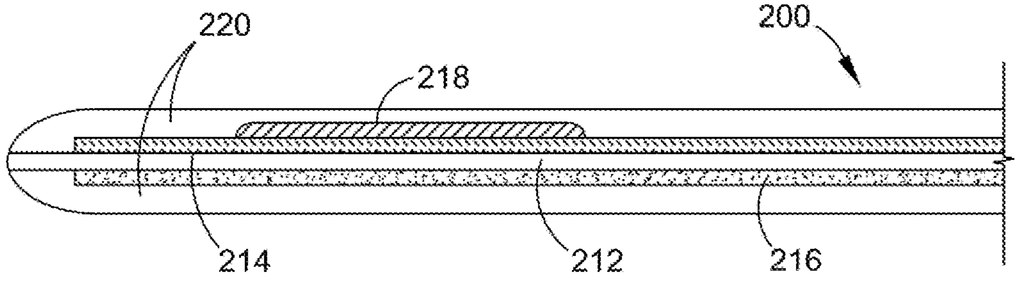
FIG. 2A shows a diagram of an illustrative two-electrode analyte sensor configuration, which is compatible for use in some embodiments of the disclosure herein.

FIG. 2A shows a diagram of an illustrative two-electrode analyte sensor configuration, which is compatible for use in some embodiments of the disclosure herein. As shown, analyte sensor tail 200 (showing the tip or lower portion thereof) comprises substrate 212 disposed between working electrode 214 and counter/reference electrode 216. Alternately, working electrode 214 and counter/reference electrode 216 may be located upon the same side of substrate 212 with a dielectric material interposed in between (configuration not shown). Sensing element 218 is disposed as at least one layer upon at least a portion of working electrode 214. In various embodiments of the present disclosure, sensing element 218 may comprise multiple spots or a single spot configured for detection of an analyte of interest, and such spots need not be identical.

Referring still to FIG. 2A, membrane 220 overcoats at least active area 218 and may optionally overcoat some or all of working electrode 214 and/or counter/reference electrode 216, according to some embodiments. One or both faces of analyte sensor tail 200 may be overcoated with membrane 220. Membrane 220 may comprise one or more polymeric membrane materials having capabilities of limiting analyte flux to sensing element 218 (e.g., membrane 220 may be a mass transport limiting membrane). The composition of membrane 220 may vary to promote a desired flux of analyte to sensing element 218, thereby providing a desired signal intensity and stability, for example. Analyte sensor tail 200 may be operable for assaying for the analyte of interest, such as glucose, by any of coulometric, amperometric, voltammetric, or potentiometric electrochemical detection techniques.

Figure 2B:
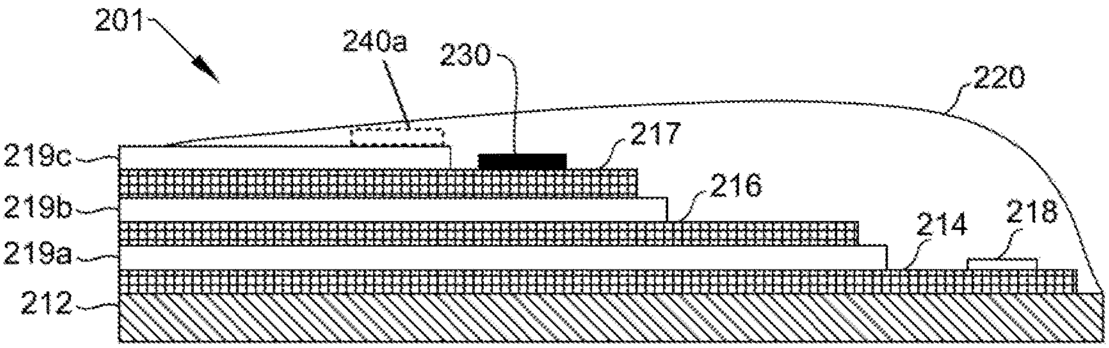
FIGS. 2B and 2C show diagrams of illustrative three-electrode analyte sensor configurations, which are compatible for use in some embodiments of the disclosure herein.
Figure 2C:
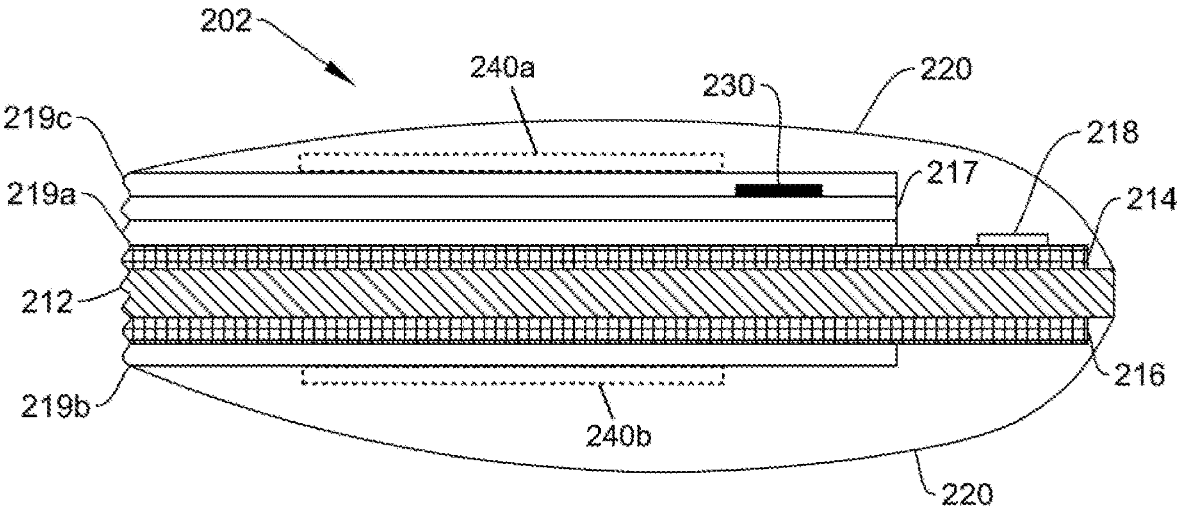

FIGS. 2B and 2C show diagrams of illustrative three-electrode analyte sensor configurations, which are also compatible for use in some embodiments of the disclosure herein. Three-electrode analyte sensor configurations may be similar to that shown for analyte sensor tail 200 in FIG. 2A, except for the inclusion of additional electrode 217 in analyte sensors tails 201 and 202 (FIGS. 2B and 2C, and showing the tip or lower portion thereof). With additional electrode 217, counter/reference electrode 216 may then function as either a counter electrode or a reference electrode, and additional electrode 217 fulfills the other electrode function not otherwise accounted for. Working electrode 214 continues to fulfill its original function. Additional electrode 217 may be disposed upon either working electrode 214 or electrode 216, with a separating layer of dielectric material in between. For example, as depicted in FIG. 2B, dielectric layers 219*a*, 219*b* and 219*C* separate electrodes 214, 216, and 217 from one another and provide electrical isolation. Alternately, at least one of electrodes 214, 216, and 217 may be located upon opposite faces of substrate 212, as shown in FIG. 2C. Thus, in some embodiments, electrode 214 (working electrode) and electrode 216 (counter electrode) may be located upon opposite faces of substrate 212, with electrode 217 (reference electrode) being located upon one of electrodes 214 or 216 and spaced apart therefrom with a dielectric material. Reference material layer 230 (e.g., Ag/AgCl) may be present upon electrode 217, with the location of reference material layer 230 not being limited to that depicted in FIGS. 2B and 2C. As with sensor tail 200 shown in FIG. 2A, sensing element 218 in analyte sensor tails 201 and 202 may comprise multiple spots or a single spot configured for detection of an analyte of interest, such as glucose. Additionally, analyte sensor tails 201 and 202 may be operable for assaying the analyte of interest by any of coulometric, amperometric, voltammetric, or potentiometric electrochemical detection techniques.

Like in analyte sensor tail 200, membrane 220 may also overcoat sensing element 218, as well as other sensor components, in analyte sensor tails 201 and 202, thereby serving as a mass transport limiting membrane. Additional electrode 217 may be overcoated with membrane 220 in some embodiments. Although FIGS. 2B and 2C have depicted all of electrodes 214, 216 and 217 as being overcoated with membrane 220, it is to be recognized that only working electrode 214 may be overcoated in some embodiments. Moreover, the thickness of membrane 220 at each of electrodes 214, 216 and 217 may be the same or different. As in two-electrode analyte sensor configurations (FIG. 2A), one or both faces of analyte sensor tails 201 and 202 may be overcoated with membrane 220 in the sensor configurations of FIGS. 2B and 2C. Accordingly, the three-electrode sensor configurations shown in FIGS. 2B and 2C should be understood as being non-limiting of the embodiments disclosed herein, with alternative electrode and/or layer configurations remaining within the scope of the present disclosure.

A non-electrochemical functional layer may be disposed at one or more locations of an analyte sensor, such as the sensor tail of FIGS. 2B and 2C. As shown, the non-electrochemical functional layer(s) 240*a*, 240*b* may be disposed on dielectric layers 219*b* and/or 219*C*. Alternatively, the non-electrochemical functional layer(s) may be disposed on any of dielectric layers 219*a*, 219*b*, and 219*C* and/or electrodes 214, 216, and 217. In some embodiments, the non-electrochemical functional layer(s) may be formed from an otherwise electrochemically active substance (e.g., salt or metal), in which case the non-electrochemical functional layer(s) would be disposed on one or more dielectric layers. Alternatively, the non-electrochemical functional layer may be formed from a substance that is not electrochemically active, or active at potentials that are outside of the range of potentials of the electrodes 214, 215, and 217 (or other configuration of electrodes in the analyte sensor). In such cases, the non-electrochemical functional layer may be directly disposed (e.g., printed) onto one or more of electrodes 214, 215, ad 217. Notably, the particular size of layers 240*a*, 240*b* are non-limiting and they may span the expanse of the layer upon which they are disposed or only a portion thereof, without departing from the scope of the present disclosure. Moreover, more than one discrete non-electrochemical functional layer may be provided along a layer, in some instances.

In some embodiments, the sensor tail of the analyte sensors described herein may have a length extending from the base of the external component of the analyte sensor within a range of less than about 20 millimeters (mm), such as in the range of about 1 mm to about 15 mm, or about 1 mm to about 7 mm, encompassing any value and subset therebetween. Longer sensor tails are also possible and may be inserted into a tissue at an angle in some embodiments.

The substrate forming a portion of the analyte sensor tails described hereinabove may be flexible or rigid. Suitable materials for a flexible substrate include, but are not limited to, non-conducting plastic or polymeric materials and other non-conducting, flexible, deformable materials. Examples of useful plastic or polymeric materials include thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate). Examples of rigid materials that may be used as the substrate include, but are not limited to, poorly conducting ceramics, such as aluminum oxide and silicon dioxide.

According to various embodiments of the present disclosure, an electron transfer agent may be present in the sensing element(s) of any of the analyte sensors or analyte sensor configurations disclosed herein. Suitable electron transfer agents (also referred to as redox mediators) may facilitate conveyance of electrons to or from the working electrode when an analyte (enzyme substrate), such as glucose, undergoes an oxidation-reduction reaction. Particular embodiments of the analyte sensors disclosed herein may feature one or more sensing elements (e.g., active area layers, spots, and the like) comprising glucose oxidase or glucose dehydrogenase and an electron transfer agent in combination with a mass transport limiting membrane compatible with glucose, as described further hereinbelow.

Suitable electron transfer agents may include electroreducible and electrooxidizable ions, complexes, or molecules (e.g., quinones) having oxidation-reduction potentials that are a few hundred millivolts above or below the oxidation-reduction potential of the standard calomel electrode (SCE). According to some embodiments, suitable electron transfer agents may include low-potential osmium complexes, such as those described in U.S. Pat. Nos. 6,134,461 and 6,605,200, which are incorporated herein by reference in their entirety. Additional examples include those described in U.S. Pat. Nos. 6,736,957, 7,501,053 and 7,754,093, the disclosures of each of which are incorporated herein by reference in their entirety. Other suitable electron transfer agents may comprise metal compounds or complexes of ruthenium, osmium, iron (e.g., polyvinylferrocene or hexacyanoferrate), or cobalt, including metallocene compounds thereof, for example. Suitable examples of electron transfer agents and polymer-bound electron transfer agents may include those described in U.S. Pat. Nos. 8,444,834, 8,268,143 and 6,605,201, the disclosures of which are incorporated herein by reference in their entirety. Suitable ligands for the metal complexes may also include, for example, bidentate or higher denticity ligands such as, for example, bipyridine, biimidazole, phenanthroline, or pyridyl(imidazole). Other suitable bidentate ligands may include, for example, amino acids, oxalic acid, acetylacetone, diaminoalkanes, or o-diaminoarenes. Any combination of monodentate, bidentate, tridentate, tetradentate, or higher denticity ligands may be present in a metal complex to achieve a full coordination sphere. Any combination of the aforementioned electron transfer agents may additionally be used, without departing from the scope of the present disclosure.

According to various embodiments of the present disclosure, a polymer may be present in each sensing element of the analyte sensors or analyte sensor configurations disclosed herein. Suitable polymers for inclusion in the sensing element(s) may include, but are not limited to, polyvinylpyridines (e.g., poly(4-vinylpyridine)), polyvinylimidazoles (e.g., poly(1-vinylimidazole)), any mixture thereof, or any copolymer thereof. Illustrative copolymers that may be suitable for inclusion in the sensing element(s) include those containing monomer units such as styrene, acrylamide, methacrylamide, or acrylonitrile, for example. In illustrative embodiments, the polymer within the active area of the analyte sensors disclosed herein may be a poly(4-vinylpyridine), in which a portion of the monomer units are functionalized with an alkylcarboxylate side chain, a portion of the monomer units are appended to the electron transfer agent with an amido spacer group (see Formula 1 below, for example), and a portion of the monomer units are unfunctionalized. Any combination of the aforementioned polymers may also be used, without departing from the scope of the present disclosure.

Formula 1

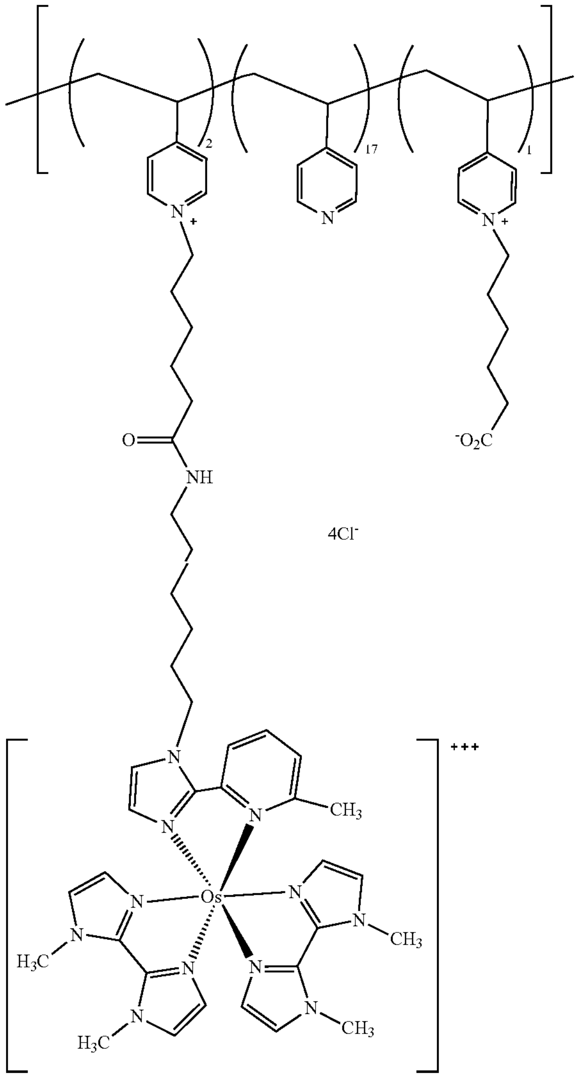

According to various embodiments of the present disclosure, the electron transfer agent may be covalently bonded to the polymer in the sensing element(s). The manner of covalent bonding is not considered to be particularly limited. Covalent bonding of the electron transfer agent to the polymer may take place by polymerizing a monomer unit bearing a covalently bound electron transfer agent, or the electron transfer agent may be reacted with the polymer separately after the polymer has already been synthesized. According to some embodiments, a bifunctional spacer may covalently bond the electron transfer agent to the polymer within the sensing element(s) (or active area), with a first functional group being reactive with the polymer (e.g., a functional group capable of quaternizing a pyridine nitrogen atom or an imidazole nitrogen atom) and a second functional group being reactive with the electron transfer agent (e.g., a functional group that is reactive with a ligand coordinating a metal ion).

Similarly, according to some or other various embodiments of the present disclosure, the enzyme within the sensing element(s) may be covalently bonded to the polymer. According to more specific embodiments, covalent bonding of the enzyme to the polymer may take place via crosslinking using a suitable crosslinking agent. Suitable crosslinking agents for reaction with free amino groups in the enzyme may include crosslinking agents such as, for example, polyethylene glycol diglycidylether (PEGDGE), glycerol triglycidyl ether (Gly3), or other polyepoxides, cyanuric chloride, N-hydroxysuccinimide, imidoesters, epichlorohydrin, or derivatized variants thereof. Suitable crosslinking agents for reaction with free carboxylic acid groups in the enzyme may include, for example, carbodiimides. The crosslinking is generally intermolecular, but can be intramolecular in some embodiments.

The electron transfer agent and/or the enzyme may be associated with the polymer in the sensing element(s) through means other than covalent bonding as well. In some embodiments, the electron transfer agent and/or the enzyme may be ionically or coordinatively associated with the polymer. For example, a charged polymer may be ionically associated with an oppositely charged electron transfer agent or enzyme. In still other embodiments, the electron transfer agent and/or the enzyme may be physically entrained within the polymer without being bonded thereto.

In some embodiments, a stabilizer may be incorporated into the sensing element(s) of the analyte sensors described herein to improve the functionality of the sensors and achieve desired sensitivity and stability. Such stabilizers may include an antioxidant and/or companion protein to stabilize the enzyme, for instance. Examples of suitable stabilizers may include, but are not limited to serum albumin (e.g., humane or bovine serum albumin or other compatible albumin), catalase, other enzyme antioxidants, and the like, and any combination thereof. The stabilizers may be conjugated or non-conjugated.

In certain embodiments, the mass transport limiting membrane discussed above is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like.

In some embodiments, a membrane may be formed by crosslinking in situ a polymer, including those discussed above, modified with a zwitterionic moiety, a non-pyridine copolymer component, and optionally another moiety that is either hydrophilic or hydrophobic, and/or has other desirable properties, in an buffer solution (e.g., an alcohol-buffer solution). The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly(ethylene glycol), hydroxyl or polyhydroxyl modifiers, and the like, and any combinations thereof, may be used to enhance the biocompatibility of the polymer or the resulting membrane.

In some embodiments, the membrane may comprise a compound including, but not limited to, poly(styrene-co-maleic anhydride), dodecylamine and poly(propylene glycol)-block-poly(ethylene glycol)-block-poly(propylene glycol) (2-aminopropyl ether) crosslinked with poly(propylene glycol)-block-poly(ethylene glycol)-block-poly(propylene glycol) bis(2-aminopropyl ether); poly(N-isopropyl acrylamide); a copolymer of poly(ethylene oxide) and poly (propylene oxide); polyvinylpyridine; a derivative of polyvinylpyridine; polyvinylimidazole; a derivative of polyvinylimidazole; and the like; and any combination thereof. In some embodiments, the membrane may be comprised of a polyvinylpyridine-co-styrene polymer, in which a portion of the pyridine nitrogen atoms are functionalized with a non-crosslinked poly(ethylene glycol) tail and a portion of the pyridine nitrogen atoms are functionalized with an alkylsulfonic acid group ("Formula 1").

Other membrane compounds, alone or in combination with any aforementioned membrane compounds, may comprise a suitable copolymer of 4-vinylpyridine and styrene and an amine-free polyether arm having the structure defined by Formula 2.

Formula 2

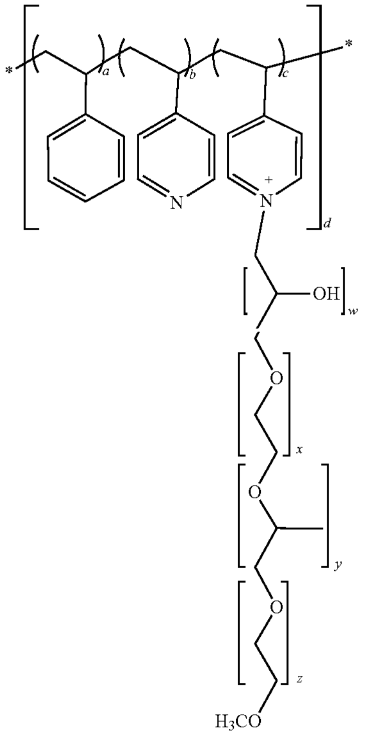

Each of a, b, and c are all zero or positive integers. Variables a and b may be about 0 and about 1000. Variable c may be 0 or 1, provided that at least one functionalized pyridine having an amine-free polyether arm is present in the polymer; variable d may be about 10 to about 100,000; variable w may be equal to 0 or 1; variable x may be in the range of about 4 to about 24; variable y may be in the range of about 8 to about 60; and variable z may be in the range of about 6 to about 36. As noted above, at least one functionalized pyridine having an amine-free polyether arm is present in the polymer of Formula 2, preferably at least 5% at loading of the total monomer.

The polymer of Formula 2 may feature a polymer chain that is a random copolymer. Alternately, the polymer chain may be non-random, such as a block copolymer having a regular repeat cycle of at least a portion of the monomers. Hence, any particular monomer ordering shown in the structural formulas of the present disclosure is intended to be illustrative and non-limiting. Moreover, the structural formulas herein have depicted a head-to-tail bonding between adjacent monomers, but it is to be appreciated that head-to-head bonding also falls within the scope of the present disclosure.

The membrane compounds described herein may further be crosslinked with one or more crosslinking agents, including those listed above with reference to the enzyme described herein. For example, suitable crosslinking agents may include, but are not limited to, polyethylene glycol diglycidylether (PEGDGE), glycerol triglycidyl ether (Gly3), polydimethylsiloxane diglycidylether (PDMS-DGE), or other polyepoxides, cyanuric chloride, N-hydroxysuccinimide, imidoesters, epichlorohydrin, or derivatized variants thereof, and any combination thereof. Branched versions with similar terminal chemistry are also suitable for the present disclosure. For example, in some embodiments, Formula 1 may be crosslinking with triglycidyl glycerol ether and/or PEDGE and/or polydimethylsiloxane diglycidylether (PDMS-DGE).

A membrane may be formed in situ by applying an alcohol-buffer solution of a crosslinker and a modified polymer over the sensing element(s) and any additional compounds included in the sensing element(s) area (e.g., electron transfer agent) and allowing the solution to cure for about one to two days or other appropriate time period. The crosslinker-polymer solution may be applied over the sensing element(s) by placing a droplet or droplets of the membrane solution on at least the sensor element(s) of the sensor tail, by dipping the sensor tail into the membrane solution, by spraying the membrane solution on the sensor, by heat pressing or melting the membrane in any sized layer (such as discrete or all encompassing) and either before or after singulation, vapor deposition of the membrane, powder coating of the membrane, and the like, and any combination thereof. In order to coat the distal and side edges of the sensor, the membrane material may be applied subsequent to application (e.g., singulation) of the sensor electronic precursors (e.g., electrodes). In some embodiments, the analyte sensor is dip-coated following electronic precursor application to apply one or more membranes. Alternatively, the analyte sensor could be slot-die coated wherein each side of the analyte sensor is coated separately. A membrane applied in the above manner may have any of various functions including, but not limited to, mass transport limitation (i.e., reduction or elimination of the flux of one or more analytes and/or compounds that reach the sensing elements), biocompatibility enhancement, interferent reduction, and the like, and any combination thereof.

Generally, the thickness of the membrane is controlled by the concentration of the membrane solution, by the number of droplets of the membrane solution applied, by the number of times the sensor is dipped in the membrane solution, by the volume of membrane solution sprayed on the sensor, and the like, and by any combination of these factors. In some embodiments, the membrane described herein may have a thickness ranging from about 0.1 micrometers (μm) to about 1000 μm, encompassing any value and subset therebetween, such as from about 1 μm to and about 500 μm, or about 10 μm to about 100 μm. As stated above, the membrane may overlay one or more sensing elements, and in some embodiments, the sensing elements may have a thickness of from about 0.1 μm to about 10 μm, encompassing any value and subset therebetween. In some embodiments, a series of droplets may be applied atop one another to achieve the desired thickness of the sensing element and/or membrane, without substantially increasing the diameter of the applied droplets (i.e., maintaining the desired diameter or range thereof). Each single droplet for example may be applied and then allowed to cool or dry, followed by one or more additional droplets. Sensing elements and membrane may, but need not be, the same thickness throughout or composition throughout.

In some embodiments, the membrane composition for use as a mass transport limiting layer of the present disclosure may comprise polydimethylsiloxane (PDMS), polydimethylsiloxane diglycidylether (PDMS-DGE), aminopropyl terminated polydimethylsiloxane, and the like, and any combination thereof for use as a leveling agent (e.g., for reducing the contact angel of the membrane composition or sensing element(s) composition). Branched versions with similar terminal chemistry are also suitable for the present disclosure. Certain leveling agents may additionally be included, such as those found, for example, in U.S. Pat. No. 8,983,568, the disclosure of which is incorporated by reference herein in its entirety.

In some instances, the membrane may form one or more bonds with the sensing element(s). As used herein, the term "bonds," and grammatical variants thereof, refers to any type of an interaction between atoms or molecules that allows chemical compounds to form associations with each other, such as, but not limited to, covalent bonds, ionic bonds, dipole-dipole interactions, hydrogen bonds, London dispersion forces, and the like, and any combination thereof. For example, in situ polymerization of the membrane can form crosslinks between the polymers of the membrane and the polymers in the sensing element(s). In some embodiments, crosslinking of the membrane to the sensing element (s) facilitates a reduction in the occurrence of delamination of the membrane from the sensor.

As previously described, microorganism incursion into an analyte sensor insertion site, including migration at or near the sensing element(s) disposed on a lower portion of a sensor tail, may result in harm to the wearer and/or may lead to altered functioning of the analyte sensor itself, including false positive or false negative analyte measurements, shortening the life of the sensor or sensing element(s), and the like.

Various microorganisms (e.g., bacteria, fungi, viruses, and the like) are present naturally on the skin (i.e., skin flora) and in the surrounding environment (e.g., air, clothing, bedding, water, social engagement, and the like), which may contact the insertion site (e.g., wound area) or adjacent skin while the analyte sensor is in use and migrate to the sensing element(s) thereof. Microorganisms on the sensor tail or on skin may be introduced during insertion as well. Moisture contact (e.g., during daily showering, bathing, or submersion (e.g., such as when swimming, for example in a public pool or natural body of water), inability to access and wash skin having the sensor applied thereto, failure to adequately clean the skin prior to insertion of the sensor tail and application of the sensor, nosocomial (i.e., hospital) exposure to microorganisms (e.g., a nurse or other medical professional may apply an analyte sensor in a hospital setting), and the like, may further exacerbate the possibility of microorganism growth. As used herein, the term "skin flora," and grammatical variants thereof, refers to microorganisms that innately reside on human skin and/or within a human body that may contact human skin. While various embodiments of the present disclosure may be discussed with reference to protecting against such skin flora, it is to be understood that other microorganisms (e.g., bacteria, fungi, viruses, and the like) may also be controlled or otherwise treated to protect at least the sensing element(s) of an on-body analyte sensor, such as for better sensor functionality and protection of the wearer.

The various microorganisms that may be desirably controlled or otherwise treated as part of the use of an analyte sensor described herein are not believed to be particularly limited and include any such microorganisms generally encountered by a person during various life activities, including symbiotic microorganisms and parasitic microorganisms.

Microorganisms in skin flora may include, but are not limited to, actinobacteria (e.g., *Corynebacterium, Propionibacterium*, and the like), firmicutes (e.g., *Staphylococcus, Clostridia, Lactobacillus*, and the like), proteobacteria (e.g., alphaproteobacteria, betaproteobacteria, gammaproteobacteria, and the like), bacteriodetes (e.g., flavobacteriales, and the like), cyanobacteria, and the like, and any combination thereof. Examples of specific such skin flora may include, but are not limited to, *Staphylococcus epidermidis, Staphylococcus aureus, Staphylococcus warneri, Streptococcus pyogenes, Streptococcus mitis, Staphylococcus hominis, Propionibacterium acnes, Corynebacterium* spp., *Acinetobacter johnsonii, Pseudomonas aeruginosa, Demodex folliculorum, Bacillus oleronius, Bacteroides fragilis, Bacteroides melaninogenicus, Bacteroides oralis, Enterococcus faecalis, Escherichia coli, Enterobacter* spp., *Klebsiella* spp., *Bifidobacterium bifidum, Lactobacillus* spp., *Clostridium perfringens, Clostridium tetani, Clostridium septicum, Proteus mirabilis, Pseudomonas aeruginosa, Salmonella enterica, Faecalibacterium prausnitzii, Peptostreptococcus* spp., *Peptococcus* spp., and the like, and any combination thereof.

Environmental microorganisms may be any microorganisms that overlap with the skin flora described above, and further include microorganisms that are present in the environment, including internal and external environments and encountered during various life activities. For example, such microorganisms may include those that are encountered during sleeping, bathing and/or showering, working, exercising, eating, attending recreational excursions or events, handling pets, and the like. Such microorganisms may include, but are not limited to, those listed above, as well as *Escherichia* (e.g., *E. coli*, and the like), firmicutes, *Mycobacterium* (e.g., *Mycobacterium avium* subspecies paratuberculosis, and the like), enterobacteriaceae (e.g., *Salmonella*, and the like), yeast, bacteriophages, and the like, and any combination thereof.

Accordingly, the embodiments of the present disclosure provide for inclusion of an antimicrobial quality (i.e., by incorporating an antimicrobial compound) to a sensor tail, and in certain embodiments at a lower portion of a sensor tail comprising the sensing element(s), to prevent or reduce microorganism incursion.

In some embodiments, the present disclosure provides for an analyte sensor comprising a sensor tail substrate, as described above. The sensor tail substrate includes a lower portion and an upper portion and is configured for insertion into a tissue. The tissue may be, for example, a dermal layer, an interstitial layer, or a subcutaneous layer below the surface of the skin. In some embodiments, the tissue is a subcutaneous layer. The analyte sensor may further comprise at least one electrode disposed on the lower portion of the sensor tail substrate, a sensing element(s) disposed upon a surface of the electrode, a membrane disposed over at least the sensing element(s) (and thus, over at least part of the lower portion of the sensor tail substrate), and optionally a non-electrochemical functional layer located at least at the lower portion of the sensor tail substrate; that is, the non-electrochemical functional layer is provided in the lower portion of the sensor tail substrate at any location and disposed on any other layer, where applicable (e.g., disposed on the lower portion of the sensor tail substrate).

At least one or more of the lower portion of the sensor tail substrate (e.g., substrate 212 of FIGS. 2A, 2B), the at least one electrode (e.g., electrodes 214, 216, 218 of FIGS. 2A, 2B), the sensing element(s) (e.g., sensing element 218 of FIGS. 2A, 2B), the membrane (e.g., membrane 220 of FIGS. 2A, 2B), and the optional non-electrochemical functional layer (e.g., layers 240*a*, 240*b* of FIGS. 2B and 2C) comprises an antimicrobial quality. These may be referred to herein collectively as "sensor tail components."

The sensor tail substrate may have an antimicrobial quality, such as by any methods described herein for imparting said antimicrobial quality. In some embodiments, the sensor tail substrate may be doped with or otherwise coated, for example, with one or more antimicrobial compounds, which may leach to the surrounding tissue and/or to other sensor tail components.

The at least one electrode which may have an antimicrobial quality may comprise any part or all of one or more working electrode(s), counter electrode(s), reference electrode(s), counter/reference electrode(s), and any combination thereof disposed on the lower portion of the sensor tail substrate. In specific embodiments, the at least one electrode is a working electrode upon which the sensing element(s) is disposed. Further, one or more electrodes may be disposed on the lower portion of the sensor tail substrate, including duplicates in type, without departing from the scope of the present disclosure.

In other embodiments, the electrodes may themselves have an antimicrobial quality that can be "activated" through use of the analyte sensor itself. For example, the counter or reference electrode (or combination thereof) may comprise a material that may be reduced or oxidized to provide compounds, elements, or ions that are themselves antimicrobial. As one example, the counter or reference electrode (or combination thereof) may comprise silver/silver iodide (Ag/AgI) the Ag/AgI is reduced to form silver metal (Ag) and iodide ions ($I^-$). As another example, the counter or reference electrode (or combination thereof) may comprise silver/silver chloride (Ag/AgCl) the Ag/AgCl is reduced to form silver metal (Ag) and chloride ions ($Cl^-$). The silver metal and iodide ions provide an antimicrobial quality and, accordingly, the mere generation of the analyte sensor provides antimicrobial protection (alone or in combination with any other antimicrobial quality, such as those described herein). Further, Ag may be released from silver metal to provide additional antimicrobial protection. Accordingly, the electrode may be comprised of any biocompatible antimicrobial compound that also functions as a reference or counter electrode.

Alternatively or additionally, a non-electrochemical functional layer may be overlaid or otherwise disposed onto the counter and/or reference electrode (or combination thereof) which is separately or additionally "activated" by the functioning of the electrode (and does not interfere with its measuring). In such cases, the electrode and the non-electrochemical functional layer may be composed of the same composition (e.g., AgI or Ag/AgCl, and the like) or alternatively of a different composition provided that the two compositions do not interfere with the functioning and measurement of the analyte sensor.

The sensing element(s) which may have an antimicrobial quality may for use in forming the analyte sensors of the present disclosure may be in the form of a continuous layer, a single layer, or alternatively, may be an array of sensing areas or "spots," without being bound by shape or size or composition, such as those described in U.S. Patent Publication 2012/0150005, the entirety of which is incorporated herein by reference. For example, two or more sensing elements, such as about two to about 100 sensing elements may be used in the analyte sensors described herein. Moreover, the sensing elements may be the same or different in size, shape, and analyte sensitivity (i.e., the sensing elements may be targeting to detecting the same or different analytes within a tissue), without departing from the scope of the present disclosure.

The membrane which may have an antimicrobial quality may for use in the embodiments of the present disclosure may similarly be a single layer or multiple areas or "spots," without being bound by shape or size or composition. The membrane is at least disposed over the sensing element(s) included in the analyte sensor (located at the lower portion of the sensor tail), but may additionally be disposed over any portion of the sensor tail (upper or lower portion), without departing from the scope of the present disclosure. For example, the membrane may be disposed over areas of the sensor tail excluding the sensing element(s), such as to ensure proper mass transport limiting qualities to the sensing element(s), for ease of manufacturing (e.g., ease of coating the membrane onto the sensor tail in a single step), and the like, and any combination thereof.

It is to be appreciated that typical analyte sensor tails do not include a non-electrochemical functional layer (separate and apart from the one or more electrodes of the analyte sensor), as described herein. The non-electrochemical functional layer(s) of the present disclosure are designed specifically to impart an antimicrobial quality to analyte sensors described in accordance with the embodiments described herein. The optional non-electrochemical functional layer may be one or more of a polymer, ceramic, metal, and/or metal salt material that is not in electrical communication with the sensor electronics. Accordingly, in some embodiments, the non-electrochemical functional layer is separate from the one or more electrodes and does not interfere with the electrical communication characteristics of the analyte sensor. In some embodiments, the non-chemical functional layer is disposed upon a portion of the sensor tail substrate below the sensing element(s) and/or below the membrane.

The optional non-electrochemical functional layer may alternatively, or in addition to being disposed on at least the lower portion of the sensor tail substrate, be included in the analyte sensor as an independent layer and be located between any other layer or component. In such cases, the component(s) of the non-electrochemical functional layer may leach out to the exterior portions of the analyte sensor (e.g., sides thereof), such as during singulation. In other embodiments, alone or in combination with other locations, the non-electrochemical functional layer may be disposed on any layer of the analyte sensor (e.g., the substrate and/or membrane), such that the non-electrochemical functional layer is located at at least a portion of an outer face of the analyte sensor. Such an outer non-electrochemical functional layer may be discontiguous or contiguous and may expand the entirety of one or more outer faces or only a portion. The non-electrochemical functional layer accordingly may be at any location (or layer or face) of the analyte sensor described herein, provided that it is electrically isolated from the working electrode(s) if it is composed of an otherwise electrochemically active composition within the functioning electrochemical range of the sensor. That is, the non-electrochemical functional layer is not intended to interfere with analyte measurement performed by the analyte sensor and should otherwise be isolated from the electrode(s) of the analyte sensor if it could interfere or otherwise be detrimental to any antimicrobial qualities imparted to the sensor, such as those described herein.

Such non-electrochemical functional layer may itself serve as the antimicrobial quality (e.g., composed of one or more antimicrobial compounds), and/or may be intermixed, chemically bound to, or otherwise serve as a carrier for an antimicrobial quality, as described hereinbelow and thereafter coated, for example, onto the sensor tail substrate (e.g., by spray coating, screen printing, 3D printing, dipping, and the like). In some embodiments, the non-electrical functional layer may be comprised of silver, silver chloride, copper, silver iodide, silver salts and oxides, copper oxalate, copper salts and oxides, cobalt, cobalt salts and oxides, nickel, nickel salts and oxides, zinc, zinc salts and oxides, zirconium, zirconium salts and oxides, molybdenum, molybdenum salts and oxides, lead, and lead salts and oxides, and the like, and any combination thereof.

While the non-electrochemical functional layer is preferably at least located at the lower portion of the sensor tail substrate, it may further be located anywhere along the length of the sensor tail (i.e., the upper and/or lower portion), without departing from the scope of the present disclosure. As such, its antimicrobial quality and/or the antimicrobial quality imparted thereto in accordance with the embodiments of the present disclosure may provide antimicrobial protection to the entirety of the sensor tail and surrounding tissue, including the insertion site. Moreover, the non-electrochemical functional layer may be in the form of a single layer, or alternatively, may be an array of sensing areas or "spots," without being bound by shape or size or composition. Further, the non-electrochemical functional layer may be preferably coated onto the sensor tail substrate, such as by screen print coating, 3D print coating, spray coating, dipping, and the like. It is to be understood, however, that the non-electrochemical functional layer may be applied by other means, without departing from the scope of the present disclosure.

In one or more embodiments, the analyte sensor comprises a dielectric material (e.g., dielectric layers 219*a*, 219*b* and 219*C* of FIG. 2B) may provide an antimicrobial quality, such as by being formed by one or more antimicrobial compounds or otherwise being able to itself impart antimicrobial qualities. The dielectric material may comprise one or more of the various antimicrobial compounds described herein (e.g., which may leach therefrom or provide the antimicrobial protection by virtue of remaining part of the dielectric), provided that the dielectric material provides the requisite electrical isolation required for the functionality of the analyte sensors of the present disclosure. In some embodiments, the dielectric comprises one or more of the antimicrobial polymers described hereinbelow.

In some embodiments, the present disclosure further provides for a method comprising diffusing an antimicrobial quality into a tissue from an analyte sensor. As described above, the analyte sensor includes a sensor tail having a lower portion and an upper portion and configured for insertion into the tissue; at least one electrode disposed on the lower portion of the sensor tail substrate; a sensing element disposed upon a surface of the electrode; a membrane disposed over at least the sensing element; and an optional non-electrochemical functional layer disposed at least on the lower portion of the sensor tail substrate. At least one or more of the lower portion of the sensor tail substrate, the at least one electrode, the sensing element, the membrane, and the optional non-electrochemical functional layer comprise an antimicrobial quality. The diffusing may be bolus diffusing, sustained delivery diffusing, or dynamic diffusing, as described in greater detail hereinbelow. As a result of such diffusion, microorganism infection of the tissue may be reduced or prevented, thereby maintaining the functionality of the analyte sensor measurements and lifetime (e.g., improving sensor longevity), as well as the health of the tissue. In some embodiments, the analyte sensor, as described above, detects one or more analytes, such as glucose in the bodily fluid from the tissue (e.g., interstitial fluid) with the sensing element located upon the sensor tail.

Additionally, the present disclosure provides for a system comprising a receiver (e.g., receiver 120 of FIG. 1) and an analyte sensor in electrical communication with the analyte sensor. As described above, the analyte sensor includes a sensor tail having a lower portion and an upper portion and configured for insertion into the tissue; at least one electrode disposed on the lower portion of the sensor tail substrate; a sensing element disposed upon a surface of the electrode; a membrane disposed over at least the sensing element; and an optional non-electrochemical functional layer disposed at least on the lower portion of the sensor tail substrate. At least one or more of the lower portion of the sensor tail substrate, the at least one electrode, the sensing element, the membrane, and the optional non-electrochemical functional layer comprise an antimicrobial quality.

As used herein, the terms "upper portion of the sensor tail substrate" or "upper portion of the sensor tail," and grammatical variants thereof, refers to a portion of the sensor tail that does not extend beyond the dermis and, generally, includes the top 25% by length of the sensor tail beginning from the proximal-most part of the sensor tail extending from the base of an analyte sensor, encompassing any value and subset therebetween. The "upper portion" of the sensor tail is more proximal to the skin surface than the sensing element(s) of the sensor tail comprising electrode(s) and analyte sensing element(s). Accordingly, the terms "lower portion of the sensor tail substrate" or "lower portion of the sensor tail," and grammatical variants thereof, refers to a portion of the sensor tail that extends beyond the upper portion and, generally, includes the bottom 75% by length of the sensor tail beginning from the end of the upper portion to the tip (most distal part) of the sensor tail (or alternatively from the tip of the sensor tail to the upper portion). The "lower portion" of the sensor tail includes at least the sensing element(s) located at least at or near the tip of the sensor tail and is more distal from the base of the analyte sensor compared to the upper portion thereof. That is, the lower portion is defined as at most 75% by length of the sensor tail beginning at the tip thereof (i.e., beginning at the distal-most part of the sensor tail from the base of the analyte sensor).

Accordingly, in some embodiments, the lower portion of the sensor tail substrate and other components associated therewith, comprising an antimicrobial quality, includes at least all of the lower 75% of the sensor tail substrate extending distally from the tip of the sensor tail (and to the upper portion), encompassing any value and subset therebetween. In some embodiments, the lower portion of the sensor tail and other components associated therewith, comprising an antimicrobial quality, includes at least the lower 50% or at least the lower 25% of the sensor tail substrate extending proximally from the tip of the sensor tail (and toward the upper portion), encompassing any value and subset therebetween. In each instance, the lower portion does not comprise the upper portion of the sensor tail (upper 25%), as described herein.

Generally, the sensing element(s) of an analyte sensor according to one or more embodiments of the present disclosure may be within the lower portion of the sensor tail, including less than about 50% of the length of the sensor tail beginning at the tip (or distal-most portion), encompassing any value and subset therebetween. That is, if the sensor tail extending from the base of an external component of an analyte sensor is determined, the sensing element(s) may be located at a position that is within about 50% of the length of the sensor tail beginning from the deepest point within the skin of a wearer. In other embodiments, the sensing region is included in less than about 45%, 40%, 35%, 30%, 35%, 20%, 15%, or 10% of the length of the sensor tail beginning at the tip or distal-most portion, encompassing any value and subset therebetween. The location of the sensing region may depend on the length of the sensor tail, the length or area of the sensing element(s), and the like, and any combination thereof.

The embodiments described herein accordingly incorporate an antimicrobial quality to one or more of the lower portion of the sensor tail substrate, at least one electrode, a sensing element, a membrane, and an optional non-electrochemical functional layer comprise an antimicrobial quality. In some instances, the electrode is one or more counter or reference electrode. In other embodiments, one or more dielectric layers are included in the composition of the analyte sensor and such layers comprise an antimicrobial quality. The antimicrobial quality preferably prevents or reduces environmental effects at and adjacent to the sensing element(s) produced by microorganisms that may result in erroneous measurements.

The antimicrobial quality may be incorporated into the sensor tail components by any means suitable including, but not limited to, intermixing with an antimicrobial compound (i.e., mixing any one or more antimicrobial compounds with the sensor tail components without chemical binding), coating an antimicrobial compound onto a surface of one or more of the sensor tail components (e.g., spray coating, dip coating, screen print coating, 3D print coating, thin layer coating, powder coating, press-forming, and the like), or chemical binding with an antimicrobial compound (e.g., covalent bonding, ionic bonding, metallic bonding, hydrogen bonding, polar bonding, van der Waals bonding, functionalized, and the like) to the one or more sensor tail components, including the sensor tail substrate, one or more electrodes (e.g., reference and/or counter electrode), the sensing element(s), the membrane, and any optional non-electrochemical functional layer and/or dielectric layer of the analyte sensor. As discussed in greater detail below, the antimicrobial compounds may themselves further be encapsulated or impregnated, without departing from the scope of the present disclosure.

In certain embodiments, for example, the antimicrobial compounds may be intermixed within the membrane (e.g., homogeneously or spatially intermixed (e.g., heterogeneously, such as in a gradient, or in pockets, or only on a surface layer or dip layer, or on a specific side, or only within a specified depth range, and the like, and any combination thereof), added to the sensor tail substrate below the membrane (e.g., sensor tail substrate or a printed region (typically carbon), including any of the substrate, sensing element(s), dielectric layer(s), electrode(s), or any other component of the analyte sensor), coated directly on the membrane surface, printed directly onto the membrane, and/or chemically bound (e.g., covalently bound) to the surface of the substrate or membrane. Spatially intermixed antimicrobial compounds are accordingly tuned and purposely localized such that a desired release profile, localized release profile, or localized contact with tissue or an element of the analyte sensor is achieved. In certain embodiments, surface coatings (e.g., thin film or thin layer coatings) of the antimicrobial compound to impart an antimicrobial quality to the one or more components of the sensor tails described herein may be applied to produce a chemistry layer that is unfavorable to microorganism colonization and/or proliferation (e.g., biofilm formation, colony formation, increased colony-forming units (CFUs)) and/or microorganism attachment (e.g., particular surface energy, hydrophobicity, hydrophilicity, micro-topography, and/or nano-topography, and the like, and any combination thereof).

The antimicrobial compound(s) may diffuse from the one or more components of the sensor tail to the surrounding tissue in which it is inserted to provide protection against microorganism incursion at or near the sensor tail and sensing element(s) thereof. Further, the present disclosure provides a multi-tiered technique (e.g., antimicrobial compounds diffusing from different sensor tail locals, combinations of antimicrobial compounds diffusing, different concentrations of antimicrobial compounds diffusing, and the like) for combating microorganism incursion. Thus, increasing tissue health, reducing immune cell infiltration (e.g., by reducing or eliminating host wearer infection immune response which leads to high immune cell density and tissue encapsulation), and the like. Accordingly, in some instances, the analyte sensors of the present disclosure are themselves designed to be self-preserving (and have increase operative longevity). Moreover, they may be designed to permit the use of the disclosed analyte sensors in already infected or wounded tissue, if necessary, without compromising the functionality of the analyte sensor due to the antimicrobial quality. Diffusion of the antimicrobial quality may occur by any mechanism, examples of which are described hereinbelow.

In some embodiments, the antimicrobial quality for use in the present disclosure is designed to slowly release an antimicrobial compound. The mechanism by which the antimicrobial compound may be slowly released is not considered to be particularly limited. In some embodiments, the antimicrobial compound is released slowly by contact with water (e.g., bodily fluids), exposure to elevated temperature, encapsulation, impregnation, carrier degradation, bond degradation/cleavage, and the like, and any combination thereof. As used herein, the term "encapsulation," and grammatical variants thereof, refers to envelopment in whole or in part (i.e., less than 100%) of an antimicrobial compound, such as by a biocompatible wax, degradable biopolymer, degradable polymer, or other suitably biocompatible and degradable material. The term "impregnation," and grammatical variants thereof, as used herein, refers to filling, permeating, doping, chemically binding (e.g., covalently binding), or saturating of an antimicrobial compound into a carrier, such as an biocompatible alcohol, a biocompatible nanoparticle, and the like. Encapsulated antimicrobial compounds may generally be released as the encapsulation material degrades or at least are released in greater amounts as such degradation occurs (e.g., if the encapsulation is not in whole). Impregnated antimicrobial compounds may generally be released as the antimicrobial leaches out of voids in various carrier materials or as the carrier materials degrade.

Prolonged exposure to an antimicrobial quality may be particularly advantageous for the embodiments of the present disclosure because the analyte sensor may be worn over an extended period of time, and thus may experience potential contact with microorganisms, such as skin or environmental flora, over that period of time. Accordingly, the action of the antimicrobial can occur throughout the duration in which the sensor is in use, not merely at a beginning portion, thereby ensuring protection to the wearer and proper functioning of the analyte sensor.

In some embodiments, the antimicrobial quality may be designed such that any one or more antimicrobial compounds are homogeneously or spatially intermixed with one or more components of the sensor tail, such as the membrane (or the electrode ink (e.g., reference electrode material or ink), dielectric ink, non-electrochemical functional layer, or sensing element(s), and the like, and any combination thereof) to achieve prolonged, localized, and/or sequential diffusion of the antimicrobial compound(s). For example, homogenous intermixing of an antimicrobial compound(s) may cause sustained delivery diffusion such that the antimicrobial compound slowly leaches from the sensor tail component over time. In other embodiments, the antimicrobial compound(s) may be spatially intermixed such that the tissue surrounding certain portions of the sensor tail or certain portions of the sensing element(s) receive a greater dosage of the antimicrobial compound. For example, the entirety of the lower portion of a sensor tail may have a membrane coating, where only some of the membrane coats the sensing element(s) and the remaining membrane does not coat the sensing element(s) (e.g., only coats the sensor substrate or one or more electrodes). In such instances, the antimicrobial quality may be designed to be spatially intermixed such that a greater amount of antimicrobial compound is associated with the membrane portion coating the sensing element(s) and a lesser amount of antimicrobial compound is associated with the membrane portion that is not coating the sensing element(s).

In some instances, therefore, the antimicrobial quality may be provided such that diffusion into the surrounding tissue is in the form of a bolus or, alternatively, a sustained (e.g., prolonged) diffusion. The bolus may be a single dose of antimicrobial compound(s) that diffuses in total or a large diffusion followed by residual diffusion, either of which may be achieved, for example, by the spatial intermixing discussed above. In some embodiments, the proximal layers of the one or more sensor tail components relative to the tissue of a wearer (i.e., farther from the sensor tail substrate) may include the antimicrobial quality in greater amount compared to the more distal layers to the tissue, such that greater concentration of the antimicrobial quality is diffused into the surrounding tissue during the initial or earlier duration of the life of the analyte sensor compared to later. Alternatively, the proximal layers of the one or more sensor tail components relative to the tissue of a wearer may include the antimicrobial quality in lesser amount compared to the more distal layers to the tissue, such that as the antimicrobial is exhausted in the proximal layers, it is replenished by the more distal layers.

Alternatively, localized placement of one or more antimicrobial compounds may be provided such that delivery of a particular antimicrobial compound occurs prior to delivery of a second (or third, etc.) antimicrobial compound. For example, it may be known that a particular microorganism is likely to be most problematic during the initial implantation of an analyte sensor, followed by a different microorganism over time; the controlled release of two or more antimicrobial compounds in accordance with the embodiments described herein may be provided to address such a situation. In yet other alternatives, the combination of multiple antimicrobial compounds may be used simultaneously to combat against a larger spectrum of microorganisms as compared to any one alone (e.g., the use of rifampin and minocycline together). In still other alternatives, the localized placement of various antimicrobial(s) maybe used to create a wave-like effect where higher doses of antimicrobial compound are followed by lower or no antimicrobial compound dosage. In these ways, the amount and type of antimicrobial compound diffusing to the tissue adjacent to the implanted sensor tail may be controlled to achieve desired tolerance levels (e.g., lower drug load to the wearer). Accordingly, the present disclosure provides for multiple release profiles of the antimicrobial quality described herein.

In some embodiments, the sensor tail components themselves act as the media through which the antimicrobial compound(s) diffuses to the surface of the particular component, potentially through other components when appropriate (e.g., depending on the relationship between the components), and to the surrounding tissue at the insertion site of a wearer. For example, in some embodiments and as described above, the membrane of the analyte sensors themselves are used as a means of diffusing one or more antimicrobial compounds to both the surface of the membrane (and, typically, also the surface of the sensor tail comprising the sensing element(s)) and to surrounding tissue. The membrane already functions as a mass transport limiting membrane and, accordingly, the selected antimicrobial compounds may be based on the composition of the membrane to customize diffusion of the antimicrobial compound, thereby maximizing qualities already part of the analyte sensor.

In some embodiments, the antimicrobial quality is imparted to the sensor tail components described herein, where the sensor tail components act as acceptable substrates for receiving such antimicrobial quality via an antimicrobial coating. An "antimicrobial coating," and grammatical variants thereof, as described herein, refers to a film or layer of antimicrobial applied to a surface by any means including, but not limited to, through use of an adhesive, through surface functionalization (e.g., crosslinking, graft polymer linking, and the like of the surface and the antimicrobial), screen printing or other printing mechanisms, spray coating, and the like. Carriers may be used that, when applied to a surface, can themselves be degradable and allow a slow-release (e.g., upon water exposure, elevated temperatures, and the like over time) of an antimicrobial, the antimicrobial of which may itself be degradable or otherwise encapsulated or impregnated in another material, as previously discussed.

Suitable carriers that may be coated onto one or more of the surfaces of the sensor tail components described herein are not considered to be particularly limited and include any such substances that have or can carry an antimicrobial quality, adhere to a desired surface, and are themselves able to release the antimicrobial quality over time.

In any one or more embodiments, a suitable coating carrier for use in the present disclosure may include, but is not limited to, synthetic and natural biodegradable polymers. Suitable synthetic biodegradable polymer coating carriers may include, but are not limited to, poly(lactic-co-glycolic acid); polylactic acid; polyglycolic acid; polyethylene glycol; poly(D,L)lactide, poly(ε-caprolactone); polyhydroxyalkonate; poly(butylene succinate); polyvinyl alcohol; degradable polyurethanes; and the like; any derivatives thereof; any copolymers thereof; and any combination thereof. Suitable natural biodegradable polymer coating carriers for use in the present disclosure may include, but are not limited to, cellulose, chitosan, chitin, lignin, pullulan, polyhydroxyalkonate, collagen, alginate, whey protein, keratin, gelatin, dextran, starch, silk, any derivatives thereof, any salt thereof, any copolymers thereof, and any combination thereof. It is to be appreciated that any suitable other degradable synthetic or natural polymers or proteins may be used as an antimicrobial carrier coating in accordance with any or all of the embodiments described herein, without departing from the present disclosure. As used herein, the term "derivative," and grammatical variants thereof, refers to a compound that is derived from any one of the listed compounds herein, such as by replacement of one atom with another atom or group of atoms (e.g., a functional group). For instance, examples of cellulose derivatives may include, but are not limited to, hydroxyethylcellulose, carboxymethylhydroxyethylcellulose, carboxymethylcellulose, hydroxypropyl methylcellulose, and the like, and any combination thereof. The term "copolymer," and grammatical variants thereof, as used herein, refers to any polymer characterized by two or more different monomers, encompassing terpolymers and any higher polymers.

As alluded to above, in some instances, the carrier coating itself may provide the antimicrobial quality (e.g., the non-electrochemical functional layer, in some cases, for example). Such antimicrobial carriers may additionally carry a secondary (or tertiary, or any plurality) antimicrobial, without departing from the scope of the present disclosure. For example, an organosilane coating (e.g., nanocoating) may provide an abrasive surface to a sensor tail component, which inhibits microorganism attachment due to disruption of their outer membrane. The abrasive surface may be undetectable to humans, and thus suitable for use in the sensor components located in at least the lower portion of the sensor tail inserted into a tissue. In some instances, the organosilane may be coupled with a quaternary ammonium compound, which provides additional anchoring to a surface, such as by forming a chemical bond with one or more components of the sensor tail. Moreover, a quaternary ammonium compound may be used alone if desired to provide an antimicrobial quality to the sensor and/or skin.

A selected organosilane for use as the carrier coating and/or the antimicrobial compound itself is not considered to be particularly limiting and may include any suitable carrier coating that can carry an antimicrobial and/or provide antimicrobial qualities itself over time. In one or more embodiments, examples of suitable organosilane carrier coatings for use in the present disclosure may include, but are not limited to, methyl triethoxysilane, methyl trimethoxysilane, vinyl trimethoxysilane, phenyl trimethoxysilane, 3-aminopropyltrimethoxysilane, 3-glycidoxypropyltrimethoxysi lane, methacryloxypropyltrimethoxysilane, mercaptopropyltrimethoxysilane, and the like, any derivative thereof, and any combination thereof.

A selected quaternary ammonium compound for use as the carrier coating and/or the antimicrobial compound itself (e.g., alone or in combination with an organosilane) is not considered to be particularly limited. Examples of suitable quaternary ammonium compounds for use in the present disclosure may include, but are not limited to, dimethyloctadecyl (3-trimethoxysilyl propyl) ammonium chloride, alkyldimethylbenzylammonium chloride, didecyldimethylammonium chloride, benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride, quaternary ammonium polyethyleneimine, and the like, any derivatives thereof, and any combination thereof.

The attachment of the quaternary ammonium compound described above may be considered a surface functionalization of one or more components of the sensor described herein for imparting an antimicrobial quality to which it is covalently bound. Other carrier coatings comprising an antimicrobial quality may additionally be achieved by surface functionalization, without departing from the scope of the present disclosure. For example, a surface of one or more components the sensor tail (e.g., the lower portion of the sensor tail) as described herein may be functionalized by attaching a polymer or polypeptide to the surface, such as through a grafting process. Polymers may be grafted (e.g., through use of absorption or chemical bonding, crosslinking, or other immobilization means) or directly polymerized onto one or more surfaces of the sensor. Such polymers may form a matrix for acting as a carrier coating for one or more antimicrobial compounds in which the antimicrobial is free-floating (i.e., distributed without chemical bonding throughout the matrix). In other embodiments, the polymers may be functionalized to allow direct bonding with one or more antimicrobial compounds (e.g., to have quaternary amine functional groups).

In still other embodiments, the polymer coatings may additionally provide an antimicrobial quality themselves. Suitable such polymers for use in the embodiments of the present disclosure that may provide antimicrobial qualities may include, but are not limited to, those polymers specified above, an organosilane, a quaternary ammonium compounds, 4-vinyl-n-hexylpyridinium bromide, dimethyl(2-methacryloyloxyethyl) phosphonate, poly(ethylene glycol), poly(sulfobetaine methacrylate), poly[3-dimethyl (methacryloyloxyethyl) ammonium propane sulfonate-b-2-(diisopropylamino)ethyl methacrylate], poly(2-methyl-2-oxazoline), a polyphenol, polyhexadine, a chlorohexidine polymer, a nisin-immobilized organosilicon, poly(n,n-diethylethylenediamine-co-aerosol-based acrylic), a benzimidazole polymer, a halogen polymer, a N-halamine polymer, quaternary phosphonium modified epoxidized natural rubber, arginine-tryptophan-rich peptide, guanylated polymethacrylate, polyguanidine, olethyleneimine, chitosan, chitosan derivatives, ammonium ethyl methacrylate homopolymer, metallo-terpyridine carboxymethyl cellulose, poly(N-vinylimidazole) modified silicone rubber, poly-ε-lysine, cationic quaternary polyelectrolytes, 2-(dimethylamino)ethyl methacrylate, a benzaldehyde, 5-chloro-8-hydroxy-quinoline polymers, and the like, any derivatives thereof, any copolymers thereof, and any combination thereof.

One or more antimicrobial compounds may be encapsulated or impregnated in a slow-release compound where the antimicrobial is at least partially surrounded by the encapsulating material or permeating void space (e.g., pores) of an impregnatable material, respectively. Both of the encapsulating material and the impregnatable material may be degradable to allow slow release of the antimicrobial. In other instances, the impregnatable material is not degradable, but instead the antimicrobial is able to leach from the voids of the impregnatable material to provide the desired antimicrobial quality and amount of antimicrobial dosing, without degradation of the impregnatable material itself. Such compounds should be biocompatible and not negatively interfere with the functioning of the analyte sensor or the health of the surrounding tissue.

Moreover, the encapsulated and/or impregnated antimicrobial compounds may be incorporated into any of the compounds used to form the sensor tail components (e.g., the electrode ink (e.g., reference electrode material or ink), the sensing element(s), the membrane, the substrate, the dielectric, the non-electrochemical functional layer(s)) or coatings listed above by chemical means (e.g., chemical bonding) or by dispersion (e.g., without chemical bonding or by matrix stabilization), without departing from the scope of the present disclosure. In other embodiments, the encapsulated and/or impregnated antimicrobial compounds may themselves allow covalent or other, such as associative, bonding with one or more components of the sensor tail described herein, depending on the composition of the encapsulating material and/or impregnatable material, the composition of the sensor component, and the like.

An encapsulating material for use in the present disclosure is not considered to be particularly limited provided that as the material degrades and releases the encapsulated antimicrobial it does not interfere with the tissue health of a wearer or the functioning of the analyte sensor described herein, and may generally be any biocompatible, degradable material known to one of skill in the art. In some embodiments, the encapsulating material itself is able to provide an antimicrobial quality. Examples of suitable encapsulating materials for use in the embodiments of the present disclosure may include, but are not limited to, the degradable synthetic and natural polymers and proteins described herein, biocompatible or biodegradable ceramics, metallic biocompatible or biodegradable compounds, biocompatible or biodegradable micelle-forming materials (i.e., for micelle encapsulation of the antimicrobial, such as biocompatible or biodegradable polymeric micelle materials), and the like, and any combination thereof. Examples of biocompatible or biodegradable ceramics for use in the embodiments described herein may include, but are not limited to, calcium sulfate, calcium carbonate, calcium phosphates, dicalcium phosphates, tricalcium phosphates, hydroxyapatite, and the like, and any combination thereof. Examples of metallic biocompatible or biodegradable compounds for use in the embodiments described herein may include, but are not limited to, magnesium-based alloys such as magnesium alloyed with calcium, zinc, aluminum, manganese, indium, silver, zirconium, and the like, and any combination thereof.

An impregnatable material for use in the present disclosure is not considered to be particularly limited provided that the material is able to release an antimicrobial and does not interfere with the tissue health of a wearer (i.e., maintains skin health) or the functioning of the analyte sensor described herein, and may generally be any biocompatible material known to one of skill in the art for placement of an antimicrobial. In some embodiments, the impregnatable materials may be generally porous or have areas of void space for filling or penetration by an antimicrobial compound. In other embodiments, the impregnatable materials may be inclusion complexes, such as cyclodextrins (e.g., alpha, beta, or gamma), which may be particularly compatible with a hydrophobic antimicrobial compound (e.g., certain peptides, hydrophobically functionalized polymers, and the like) and which can be released from the cyclodextrin complex upon contact with water, for example, because the outer surface thereof is hydrophilic.

Suitable impregnatable materials may be any of the biocompatible materials, including those that are degradable and those that themselves impart antimicrobial qualities, described herein, and have an antimicrobial permeated therethrough. Some such materials may be made porous and have an antimicrobial permeated therethrough. For example, an antimicrobial may be impregnated into void space of a cellulose or other natural polymer, a metal, a synthetic polymer, a metal oxide, and the like, and any combination thereof.

In some embodiments, the impregnatable material is a nanoparticle composed of one or more of the materials described herein impregnated (or, in some embodiments, made wholly from) one or more antimicrobial compounds, which may be made from any of the biocompatible materials described herein and/or any biocompatible materials known to those of skill in the art. As used herein, the term "nanoparticle," and grammatical variants thereof, refers to a particle having a diameter in the range of about 1 nanometer (nm) to about 1000 nm, encompassing any value and size distribution therebetween. Preferably, a nanoparticle described herein has a diameter in the range of about 1 nm to about 100 nm, encompassing any value and size distribution therebetween. For example, an antimicrobial component may be permeated in void space within or on a nanoparticle (or other impregnatable material) by any means such as chemical deposition (e.g., chemical reduction), sonochemical deposition, solvent impregnation (e.g., supercritical solvent deposition), microwave deposition, simple diffusion (e.g., contained by surface interactions), absorption, adsorption, or any other mechanism known to one of skill in the art. In some embodiments, the nanoparticles may be incorporated with one or more coatings to impart antimicrobial quality. Alternatively, the nanoparticles may themselves have sufficient attraction to one or more surfaces of the sensor tail components (e.g., located at least in the lower portion) to achieve a thin film applied thereupon.

The mechanism by which the antimicrobial quality described herein prevents or reduces microorganism interference with the insertion site, tissue surrounding the sensor tail, and/or functioning of the analyte sensor may be any mechanism and may be dependent on the type or types of microorganisms being targeted. Examples of such mechanisms may include, but are not limited to, preventing microorganism attachment to one or more components of the sensor tail (e.g., preventing initial adhesion of the microorganism(s)), disruption of the microorganism(s) cell surface or membrane, disruption of the microorganism(s) internal organelles or functioning thereof, prevention of continued growth (e.g., by restricting nutrients and/or nutrient uptake or metabolism), and the like, and any combination thereof. In some instances, the mechanism may further be selected based on the placement of the antimicrobial quality, which may be applied or otherwise imparted to one or more components of the sensor tail described herein.

The antimicrobial compounds for use in the present disclosure include all biocompatible antimicrobial compounds, including those described hereinabove, regardless of their particular form (e.g., coating, particle, and the like), and including an organosilane, a quaternary ammonium, the antimicrobial polymers, and the like, and any combination thereof.

In some embodiments, metal-based antimicrobial compounds may be particularly useful for imparting the antimicrobial qualities to the sensor tail components (e.g., sensor substrate, electrode(s), sensing element(s), non-electrochemical functional layer). These metal-based antimicrobial compounds may be metal ion, a metal oxide, metal salts, metal coordination compounds including chelates, and the like. Specific examples of suitable metal-based antimicrobial compounds may include, but are not limited to, silver, sliver chloride, silver-silver chloride, silver iodide, silver carbonate, silver nitrate, copper, copper sulfate, cupric oxalate, silver oxalate, magnetite, gold, gallium, platinum, palladium, titanium dioxide, zinc oxide, magnesium oxide, silicon dioxide, iron oxide, carbon dioxide, copper oxide, nitric oxide, carbon nanotubes, and the like (e.g., other antimicrobial heavy metal ions and/or metal oxides), any alloys thereof, any salts thereof, any coordination complexes and/or chelates thereof, any combination thereof, and any combination thereof in addition to one or more of the antimicrobial compounds described herein.

In some embodiments, the metal-based antimicrobials may be metal-containing nanoparticles, such as impregnated or made whole from the antimicrobial compound, including as non-limiting examples, any nanoparticles comprised of the metal-based antimicrobial compounds described herein.

Examples of additional antimicrobial compounds, any of which may be used alone or in combination with the aforementioned compounds, may include, but are not limited to, iodine, povidone-iodine, chlorhexidine, amphotericin B, bacitracin, colistin, gramicidin, gramicidin S, ritipenem, acediasulfone, acetosulfone, bambermycin(s), brodimoprim, butirosin, capreomycin, carbomycin, dapsone, diathymosulfone, enviomycin, glucosulfone solasulfone, leucomycin(s), lucensomycin, micronomicin, mupirocin, p-sulfanilylbenzylamine, pipemidic acid, polymyxin, primycin, ristocetin, rosaramycin, salazosulfadimidine, succisulfone, sulfachrysoidine, sulfaloxic acid, sulfamidochrysoidine, sulfanilic acid, sulfoxone, teicoplanin, tetroxoprim, thiazolsulfone, thiostrepton, trimethoprim, trospectomycin, tuberactinomycin, vancomycin, azaserine, candicidin(s), chlorphenesin, dermostatin(s), filipin, fungichromin, nystatin, oligomycin(s), perimycin A, tubercidin, carbapenems (e.g., faropenem, imipenem, panipenem, biapenem, meropenem, doripenem, ertapenem, and the like), cephalosporins (e.g., cefoxitin, cefotaxime, cefepime, nitrocefin, cefpirome, ceftobiprole, ceftazidime, ceftriaxone, cefadroxil, cefamandole, cefatrizine, cefbuperazone, cefclidin, cefdinir, cefditoren, cefetamet, cefixime, cefinenoxime, cefminox, cefodizime, cefonicid, cefoperazone, ceforanide, cefotetan, cefotiam, cefozopran, cefpimizole, cefpiramide, cefprozil, cefroxadine, cefteram, ceftibuten, cefuzonam, cephalexin, cephaloglycin, cephalosporin C, cephradine, flomoxef, moxalactam, and the like), monocyclic beta-lactams (e.g., aztreonam, tigemonam, carumonam, BAL19764, nocardicin, BAL30072, and the like), oxazolidinones (e.g., linezolid, sutezolid, and the like), penicillins (e.g., aminopenicillanic acid, benzylpenicillin, ampicillin, amoxicillin, carbenicillin, ticarcillin, oxacillin, azlocillin, dicloxacillin, piperacillin, apalcillin, temocillin, aspoxicillin, cyclacillin, epicillin, hetacillin, quinacillin, and the like), quinolones (e.g., nalidixic acid, norfloxacin, enoxacin, ciprofloxacin, enrofloxacin, levofloxacin, fleroxacin, clinafloxacin, grepafloxacin, lomefloxacin, nadifloxacin, pazufloxacin, temafloxacin, tosufloxacin, trovafloxacin, ciproflaxacin, ofloxacin, pefloxacin, rosoxacin, amifloxacin, temafloaxcin, lomefloxacin, sparfloxacin, and the like), tetracyclins (e.g., tetracycline, minocycline, tigecycline, apicycline, chlortetracycline, clomocycline, demeclocycline, doxycycline, guamecycline, lymecycline, meclocycline, methacycline, oxytetracycline, pipacycline, rolitetracycline, sancycline, and the like), aminoglycosides (e.g., amikacin, and the like), beta-lactamase inhibitors (e.g., clavulanic acid, sulbactam, avibactam, tazobactam, BAL29880, and the like), aminonucleosides (e.g., puromycin, and the like), aminoglycosides (e.g., apramycin, a kanamycin, isepamicin, a fortimicin, a gentamicin, neomycin, netilmicin, streptomycin, spectinomycin, arbekacin, dibekacin, dihydrostreptomycin, paromomycin, ribostamycin, sisomicin, tobramycin, and the like), anthracyclines (e.g., doxorubicin, daunorubicin, and the like), pimaricins (e.g., natamycin, and the like), sulfanilamides (e.g., 4,4'-sulfinyldianiline, 2-p-sulfanilyanilinoethanol, 4-sulfanilamidosalicylic acid, and the like), macrolides (e.g., mepartricin, spiramycin, clarithromycin, dirithromycin, erythromycin, josamycin, a midecamycin, oleandomycin, rokitamycin, roxithromycin, and the like), peptidyl transferase amphenicols (e.g., azidamfenicol, azithromycin, chloramphenicol, thiamphenicol, and the like), lincosamides (e.g., clindamycin, lincomycin, and the like), ansamycins (e.g., rifamycin SV, rifampin, rifapentine, rifaximin, rifamide, and the like), and the like, and any combinations thereof.

The particular amount of antimicrobial provided to any one or more components of the sensor tail may depend on a number of factors including, but not limited to, the physiology and daily routine of a wearer, the component(s) of the sensor tail to which the antimicrobial quality is imparted, the particular antimicrobial mechanism and compound selected, and the like. In nonlimiting embodiments, the antimicrobial quality (or qualities) is imparted by incorporation of one or more antimicrobial compounds in an amount of about 0.1% to about 50% by weight of the antimicrobial carrier (e.g., membrane, sensing element, non-electrochemical functional layer, coating, encapsulant, and the like) or surface area to which it is applied (e.g., lower portion of the sensor tail), encompassing any value or subset therebetween, depending broadly on at least one or more of the factors provided above. In some embodiments, the antimicrobial compounds are present in an amount of about 0.1% to about 50% by weight of the membrane polymer before crosslinking, such as in the range of about 20% to about 40%, or about 30% to about 40%, encompassing any value and subset therebetween. It is to be understood that in some instances the antimicrobial compound forms the entirety of some of the sensor tail components (e.g., the non-electrochemical functional layer) in some cases, without departing from the scope of the present disclosure. Moreover, it is to be understood that the ideal antimicrobial quality amount will be based on ensuring adequate antimicrobial protection without compromising the functionality of the analyte sensor.

It is to be understood that the tissue interacting components of the sensor tail and the antimicrobial quality imparted thereto are to be biocompatible, such that the tissue of a typical wearer is not adversely effected, bearing in mind that various wearers will have different physiologies. Moreover, a component of the sensing element (e.g., enzyme such as glucose oxidase) for a particular desired analyte being measured may additionally provide an antimicrobial quality, without departing from the scope of the present disclosure.

Embodiment A: An analyte sensor comprising: a sensor tail substrate having a lower portion and configured for insertion into a tissue; at least one electrode disposed on the lower portion of the sensor tail substrate; a sensing element disposed upon a surface of the electrode; a membrane disposed over at least the sensing element; and an optional non-electrochemical functional layer located at least at the lower portion of the sensor tail substrate, wherein at least one or more of the lower portion of the sensor tail substrate, the at least one electrode, the sensing element, the membrane, and the optional non-electrochemical functional layer comprise an antimicrobial quality.

Embodiment B: A method comprising: diffusing an antimicrobial quality into a tissue from an analyte sensor, the analyte sensor comprising: a sensor tail substrate having a lower portion and configured for insertion into the tissue; at least one electrode disposed on the lower portion of the sensor tail substrate; a sensing element disposed upon a surface of the electrode; a membrane disposed over at least the sensing element; and an optional non-electrochemical functional layer located at least at the lower portion of the sensor tail substrate, wherein at least one or more of the lower portion of the sensor tail substrate, the at least one electrode, the sensing element, the membrane, and the optional non-electrochemical functional layer comprise an antimicrobial quality.

Embodiment C: A system comprising: a receiver; and an analyte sensor in electrical communication with the receiver, the analyte sensor comprising: a sensor tail substrate having a lower portion and configured for insertion into a tissue; at least one electrode disposed on the lower portion of the sensor tail substrate; a sensing element disposed upon a surface of the electrode; a membrane disposed over at least the sensing element; and an optional non-electrochemical functional layer located at least at the lower portion of the sensor tail substrate, wherein at least one or more of the lower portion of the sensor tail substrate, the at least one electrode, the sensing element, the membrane, and the optional non-electrochemical functional layer comprise an antimicrobial quality.

Each of Embodiments A, B, and C may have one or more of the following additional elements in any combination:

Element 1: Wherein the analyte sensor comprises the non-electrochemical functional layer.

Element 2: Wherein the lower portion of the sensor tail substrate comprises the lower 75% of the sensor tail substrate extending from a distal tip of the sensor tail substrate.

Element 3: Wherein the lower portion of the sensor tail substrate comprises at least the lower 50% of the sensor tail substrate extending from a distal tip of the sensor tail substrate.

Element 4: Wherein the antimicrobial quality is chemically bound to at least one of the lower portion of the sensor tail substrate, the at least one electrode, the sensing element, the optional non-electrochemical functional layer, and the membrane.

Element 5: Wherein the antimicrobial quality is coated onto at least one of the lower portion of the sensor tail substrate, the at least one electrode, the sensing element, the optional non-electrochemical functional layer, and the membrane.

Element 6: Wherein the antimicrobial quality is homogeneously or spatially intermixed with the membrane.

Element 7: Wherein the antimicrobial quality is configured to diffuse into the tissue.

Element 8: Wherein the antimicrobial quality is configured to diffuse into the tissue, and the diffusing reduces or prevents infection of the tissue.

Element 9: Wherein the diffusion is a bolus diffusion, a sustained delivery diffusion, or a dynamic diffusion.

Element 10: Wherein the antimicrobial quality is selected from the group consisting of silver, silver chloride, silver-silver chloride, silver iodide, silver carbonate, and any combination thereof.

Element 11: Wherein the sensing element detects an analyte.

Element 12: Wherein the sensing element detects an analyte and the analyte is glucose.

By way of non-limiting example, exemplary combinations applicable to Embodiments A, B, and C include: 1 and 2; 1 and 3; 1 and 4; 1 and 5; 1 and 6; 1 and 7; 1 and 8; 1 and 9; 1 and 10; 1 and 11; 1 and 12; 2 and 3; 2 and 4; 2 and 5; 2 and 6; 2 and 7; 2 and 8; 2 and 9; 2 and 10; 2 and 11; 2 and 12; 3 and 4; 3 and 5; 3 and 6; 3 and 7; 3 and 8; 3 and 9; 3 and 10; 3 and 11; 3 and 12; 4 and 5; 4 and 6; 4 and 7; 4 and 8; 4 and 9; 4 and 10; 2 and 11; 4 and 12; 5 and 6; 5 and 7; 5 and 8; 5 and 9; 5 and 10; 5 and 11; 5 and 12; 6 and 7; 6 and 8; 6 and 9; 6 and 10; 6 and 11; 6 and 12; 7 and 8; 7 and 9; 7 and 10; 7 and 11; 7 and 12; 8 and 9; 8 and 10; 8 and 11; 8 and 12; 9 and 10; 9 and 11; 9 and 12; 10 and 11; 10 and 12; 11 and 12; and any non-limiting combination of one, more, or all of 1, 2, 3, 4, 5, 6, 7, 8, 9, 10, 11, and/or 12.

Asymmetric, Double-Sided Adhesive Binders for On-Body Analyte Sensors

As discussed above, on-body analyte sensors may provide a number of advantages when assaying physiological levels of various analytes, such as glucose. Various types of adhesives may promote bonding of on-body analyte sensors to a skin surface. However, adhesive bonding of on-body analyte sensors to a skin surface can present various challenges, especially when the on-body analyte sensors are worn for extended periods of time. One significant issue associated with bonding of on-body analyte sensors to a skin surface is that many types of adhesives, as well as their common backing materials, are not innately permeable to moisture (breathable), which can lead to skin issues such as maceration, irritation, and/or infection. Moreover, it can be difficult for a single adhesive to promote sufficiently strong adhesive bonding to both a skin surface and an on-body analyte sensor, given the significant variance in surface morphology and other properties that usually exists between the two.

Accordingly, the present disclosure describes adhesive binders and associated constructs and methods that are capable of promoting ready adhesive bonding between a sensor housing and a skin surface, while still maintaining good breathability for moisture management to be realized. As used herein, the terms “skin” and “skin surface” synonymously refer to an outer epidermal layer upon which the housing of an on-body analyte sensor may be positioned. Thus, the features of the present disclosure may allow high moisture vapor transfer rate (MVTR) values to be realized when the sensor housing of an on-body analyte sensor is adhesively bound to a skin surface. Due to the high MVTR values afforded by the adhesive binders disclosed herein, efficient shedding of water from on-body analyte sensors may be realized. Shedding of water may be superior to alternative moisture management approaches in which water is sequestered during a period of sensor wear.

More particularly, the adhesive binders of the present disclosure are configured asymmetrically, with different pressure-sensitive adhesives being located on opposing faces of a suitable support material. The adhesive binders of the present disclosure may be fabricated in the form of a double-sided tape, sheet, or similar structure in which the different pressure-sensitive adhesives are located on opposite sides of the support material. Because different pressure-sensitive adhesives are positioned in each location, the pressure-sensitive adhesives may be chosen independently to promote good adhesion to both the housing of an on-body analyte sensor and to a skin surface, taking into account the particular surface properties and morphology of each. Thus, pressure-sensitive adhesives having complementarity for each type of surface may be independently chosen for incorporation within the adhesive binders disclosed herein.

The support material within the adhesive binders of the present disclosure allows the different pressure-sensitive adhesives to be spatially separated from one another and directed toward their intended bonding surfaces. Advantageously, the support material may be selected such that it has sufficient rigidity to allow the adhesive binders to be die cut in a desired shape, particularly after application of the adhesives, which may promote compatibility with high-throughput manufacturing processes. Non-woven scrims of various types may possess sufficient rigidity and low areal weights for suitability in this regard. As used herein, the term "scrim" refers to a non-woven material having an areal mass (basis weight) of less than about 20 g/m2, particularly an areal mass between about 3 g/m2 and about 20 g/m2. Desirably, an adhesive composition may penetrate into the interior of a scrim due to the high void area of common scrims (e.g., about 50% or greater, and particularly about 75% or greater), which is not typical of non-woven materials having a higher areal mass. Other non-woven materials of higher areal mass may similarly be suitable as a carrier material in some instances. Porous metallic fabrics, for example, having sufficiently high porosity may also be an acceptable alternative in certain instances. Further advantageously, the innate porosity and permeability of non-woven scrims and similar non-woven materials may promote breathability once incorporated upon a skin surface.

In addition to selection for their surface compatibility, at least one of the pressure-sensitive adhesives within the adhesive binders may be chosen from among those that are breathable and allow high MVTR values to be realized. Further physical modification of one or more of the pressure-sensitive adhesive layers may also be conducted in order to increase breathability still further, especially for pressure-sensitive adhesives lacking or deficient in innate breathability. In particular, multiple perforations may be introduced into a pressure-sensitive adhesive layer in manner consistent with high-throughput manufacturing processes, such as those in which various materials are provided from spooled sources and are assembled in-line into a finished product. As discussed above, the ability to die cut the presently described adhesive binders also may facilitate their production by high-throughput manufacturing processes.

While the double-sided adhesive binders of the present disclosure are capable, by themselves, of adhering a sensor housing directly to a skin surface they may be incorporated more desirably within a more extensive adhesive pad assembly to promote even better moisture management and improve wearer comfort. More specifically, the double-sided adhesive binders described herein may themselves be adhesively bonded to an interface material that is configured to become adhesively bonded to a skin surface by yet another pressure-sensitive adhesive. The combination of a double-sided adhesive binder coupled to an interface material is referred to herein as an "adhesive pad assembly." The interface material and its associated pressure-sensitive adhesive may likewise be selected to promote breathability for moisture management and to provide increased wearer comfort compared to when the double-sided adhesive binder is used alone. Accordingly, an adhesive pad assembly may facilitate longer-term wear following attachment to a skin surface. In particular configurations, the interface material may be a non-woven material suitable for being in contact with a skin surface. In more specific configurations, the interface material may be a non-woven material having a higher areal mass than the non-woven scrim comprising the carrier material of the double-sided adhesive binder.

The double-sided adhesive binders and adhesive pad assemblies disclosed herein may aid in promoting skin health at a site of attachment, contained or internal to the site attachment, and/or adjacent to the site of attachment of an analyte sensor. For example, an antimicrobial substance may be incorporated within any of the adhesive binders, adhesive pad assemblies, or components of the analyte sensor itself, or may be applied to the skin prior to contact with any components of the adhesive pad assemblies or components of the analyte sensor itself. In addition, an antimicrobial substance may be incorporated locally or homogeneously along, within, or upon any edge/perimeter/layer/surface of the analyte sensor. The antimicrobial substance may aid in preventing microorganism incursion into the wound at the site of sensor insertion, thereby lowering the likelihood of infection or skin irritation over extended sensor wear. In addition to promoting skin health, the antimicrobial substance may also inhibit formation of a biofilm residue and/or microbial colonization that may or may not form a biofilm residue upon the inserted sensor tail, which may promote better sensor performance over extended wear times.

Before discussing the features of the present disclosure in further detail, a brief overview of on-body analyte sensors will be provided so that the embodiments of the present disclosure can be better understood. On-body analyte sensors suitable for use in conjunction with the features of the present disclosure may be dermal sensors, according to some embodiments. Illustrative on-body analyte sensors, particularly dermal sensors, that may be utilized in conjunction with the features of the present disclosure include those described in more detail in commonly owned U.S. Pat. No. 9,668,686 and commonly owned U.S. Patent Application Publications 2012/0190941, 2016/0331283 and 2017/0196487, each of which is incorporated herein by reference in its entirety.

FIG. 1 shows a diagram of an illustrative in vivo analyte monitoring system that may be compatible with the double-sided adhesive binders and adhesive pad assemblies of the present disclosure. As shown, analyte monitoring system 100 includes sensor device 102 and reader device 120 that are configured to communicate with one another over a local communication path or link, which may be wired or wireless, uni- or bi-directional, and encrypted or non-encrypted. Reader device 120 may also be in communication with remote terminal 170 and/or trusted computer system 180 via communication path(s)/link(s) 141 and/or 142, respectively, which also may be wired or wireless, uni- or bi-directional, and encrypted or non-encrypted. Any suitable electronic communication protocol may be used for each of the local communication paths or links. Reader device 120 may comprise display 122 and optional input component 121.

Sensor control device 102 includes sensor housing 103, which may contain a sensor module, circuitry and a power source (not shown in FIG. 1). As shown in more detail hereinafter, sensor housing 103 may also contain a receptacle sized to contain the sensor module (see FIG. 8). Sensor 104 protrudes from sensor housing 103 through bottom face 105, which is configured to adhere to a wearer's skin, as discussed in more detail herein.

Sensor 104 may be adapted to penetrate a skin surface in order to affect sensor seating at a desired depth. Sensor 104 may comprise a sensor tail of sufficient length for insertion to a desired depth. At least a portion of the sensor tail may comprise the active sensing region of sensor 104. One or more analyte levels may be determined using sensor 104 and undergo communication to reader device 120, according to one or more embodiments. Once sensor 104 has been seated to a desired depth, the analyte may be monitored in any biological fluid of interest such as dermal fluid, plasma, blood, lymph, or the like. Analytes that may be monitored are not considered to be particularly limited, provided that a suitable sensing chemistry can be identified. In certain illustrative embodiments, the analyte may be glucose. Other analytes commonly subject to physiological dysregulation that may similarly be desirable to monitor include, but are not limited to, lactate, oxygen, pH, A1c, ketones, drug levels, and the like.

A needle may reside transiently in proximity to sensor 104 to promote insertion in a tissue. Other introducers, such as blades and sheaths, may be present instead of a needle and provide similar functionality. While present, the needle or similar introducer may facilitate insertion of sensor 104 into the skin by opening an access pathway for sensor 104 to follow. For example, the needle may facilitate penetration of the epidermis to allow dermal implantation of sensor 104 to take place, according to one or more embodiments. In some or other illustrative embodiments, sensor 104 may reside within a lumen or groove of the needle, with the needle similarly opening an access pathway for sensor 104. In some or other illustrative embodiments, the needle may be solid or hollow, beveled or non-beveled, and/or circular or non-circular. In more particular embodiments, the needle may be an acupuncture needle having a diameter of about 250 microns, although both larger and smaller diameters similarly reside within the scope of the present disclosure. In alternative embodiments, the needle or a similar introducer may be absent, provided that sensor 104 is able to penetrate a skin surface satisfactorily to establish communication with a bodily fluid of interest. When used, the needle or other similar introducer is wholly retracted or otherwise removed from contact with the skin surface and beneath the skin surface after making the skin penetration.

Figure 8:
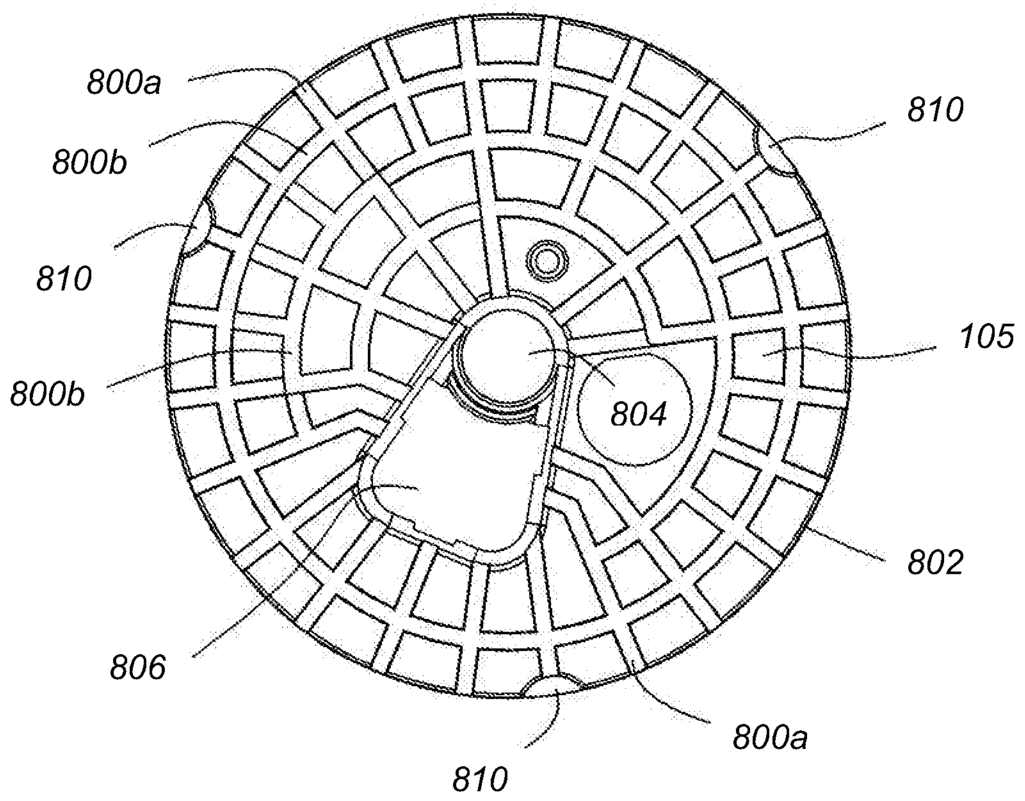
FIG. 8 shows a diagram of the bottom face of a sensor housing in an illustrative configuration.

FIG. 8 shows a diagram of bottom face 105 of sensor housing 103 in an illustrative configuration. As shown, aperture 804 extends through bottom face 105, through which a needle (not shown) may extend and then retract when deploying sensor housing 103 on a tissue surface. Also in proximity to aperture 804 is receptacle 806, within which a sensor module (not shown) may be seated and from which sensor 104 extends once sensor housing 103 is deployed on a skin surface. Bottom face 105 may be grooved and contain a plurality of grooves. At least a portion of the grooves may be radial grooves **800*a* that extend from aperture 804 and/or receptacle 806 to outer perimeter face 802. Radial grooves 800*a* may establish fluid communication between aperture 804 and/or receptacle 806 and outer perimeter face 802 and thus may promote lateral fluid drainage away from sensor housing 103. In some embodiments, at least a portion of radial grooves 800*a* may not extend all the way to aperture 804 and/or receptacle 806. Moreover, in some embodiments, at least a portion of the grooves may be circumferential grooves 800*b* that intersect with radial grooves 800*a*. Also shown in FIG. 8 are recessed carrier grips 810, which may aid in releasing sensor housing 103 from a deployment tool used for attachment to a skin surface. The deployment tool may seat a sensor module in receptacle 806** in the course of skin attachment.

The double-sided adhesive binders and adhesive pad assemblies of the present disclosure will now be described in further detail with reference being made to the drawings. Where feasible, and in the interest of brevity, common reference characters are used to denote elements previously described. Moreover, previously described elements are only addressed in brief in the description that follows. The drawings are not necessarily to scale.

Figure 9:
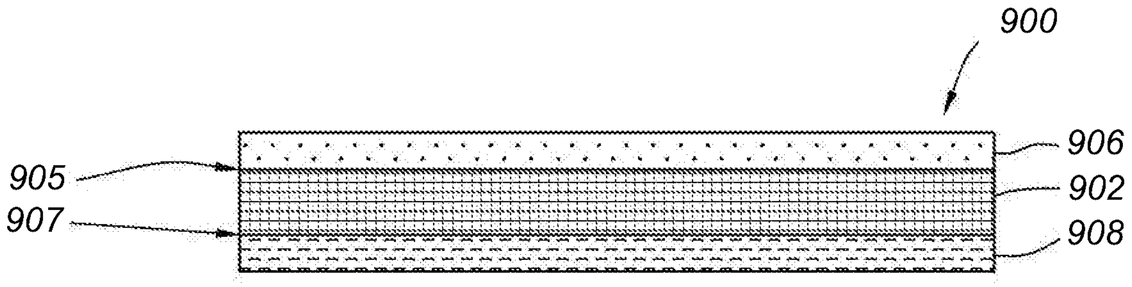
FIGS. 9 and 10 show side and top view diagrams, respectively, of an illustrative double-sided adhesive binder of the present disclosure.
Figure 10:
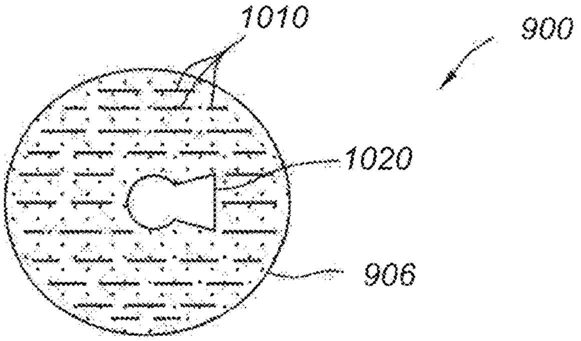

FIG. 9 shows a side view of an illustrative double-sided adhesive binder of the present disclosure. FIG. 10 shows a corresponding top view of the illustrative double-sided adhesive binder. As shown in FIG. 9, double-sided adhesive binder 900 includes non-woven scrim 902 or a similar non-woven material as a support for pressure-sensitive adhesive layers 906 and 908. Pressure-sensitive adhesive layers 906 and 908 contain first and second pressure-sensitive adhesives, respectively, that differ from one another in some manner. In particular, the first and second pressure-sensitive adhesives may differ compositionally from one another such that they exhibit one or more different functional properties, especially with respect to their adhesive bonding characteristics. For example, the first pressure-sensitive adhesive may be adapted to bond to a sensor housing (see FIG. 12), and the second pressure-sensitive adhesive may be adapted to bond to a skin surface or to a non-woven material in an adhesive pad assembly (see FIG. 11). Although FIG. 9 has depicted non-woven scrim 902 and pressure-sensitive adhesive layers 906 and 908 as having substantially the same dimensions, it is to be recognized that these elements may differ in size, according to some embodiments. For example, in some embodiments, pressure-sensitive adhesive layer 906 may not span the entire width of non-woven scrim 902, such as a middle portion of double-sided adhesive binder 900 in contact with an analyte sensor.

Suitable scrim materials comprising non-woven scrim 902 are not considered to be particularly limited, provided that they can acceptably carry the first and second pressure-sensitive adhesives. Adhesive bonding of the first and second pressure-sensitive adhesives to non-woven scrim 902 may also be a consideration. In more particular embodiments, non-woven scrim 902 may comprise a polyester scrim. Other suitable materials for non-woven scrim 902 may include, for example, polyethylene, polypropylene and other rigid thermoplastics. Sufficient rigidity may promote die-cutting. Suitable scrim materials may have an areal mass ranging between about 3 g/m2 and about 20 g/m2, or between about 3 g/m2 and about 10 g/m2, or between 5 g/m2 and about 10 g/m2, or between about 6 g/m2 and about 10 g/m2, according to some embodiments. In some or other embodiments, suitable scrim materials for non-woven scrim 902 may have an areal mass of about 8 g/m2 or below.

Referring still to FIG. 9, pressure-sensitive adhesive layer 906 is located upon face 905 of non-woven scrim 902, and pressure-sensitive adhesive layer 908 is located upon face 907 of non-woven scrim 902. Faces 905 and 907 are oriented in opposite directions so that pressure-sensitive adhesive layers 906 and 908, which contain different pressure-sensitive adhesives, may contact different surfaces. In more particular embodiments, pressure-sensitive adhesive layer 906 may be adapted to face away from a skin surface during use, and pressure-sensitive adhesive layer 908 may be adapted to face a skin surface during use. The first and second pressure-sensitive adhesives, located within pressure-sensitive adhesive layers 906 and 908, respectively, may be selected for compatibility with the surface to which they are to become adhesively bonded.

In addition, one or more of the first and second pressure-sensitive adhesives may be selected such that they afford breathability and high MVTR values. In some embodiments, however, one or more of the first and second pressure-sensitive adhesives may be non-breathable or less breathable than desired. In the event of poor breathability, one or more of pressure-sensitive adhesive layers 906 and 908 may be perforated to improve breathability, as discussed in more detail herein. MVTR values, according to some embodiments, may be in a range of about 200 g/m2/day to about 2,000 g/m2/day.

In some embodiments, the first pressure-sensitive adhesive within pressure-sensitive adhesive layer 906 may be suitable for bonding to a polymer such as polycarbonate. Sensor housings comprising a polycarbonate may be particularly desirable for bonding to a skin surface using double-sided adhesive binder 900. In more particular embodiments, the first pressure-sensitive adhesive may comprise a rubber-based adhesive. Suitable rubber-based adhesives are not considered to be particularly limited, provided that they are capable of forming a sufficiently strong adhesive bond to a sensor housing. In more specific embodiments, a polybutadiene copolymer may comprise a suitable rubber-based adhesive for incorporation within pressure-sensitive adhesive layer 906. In still more specific embodiments, a polybutadiene-acrylate copolymer may suitably be present in pressure-sensitive adhesive layer 906. Acrylic adhesives and acrylated polyurethane adhesives may also be suitable for incorporation within pressure-sensitive adhesive layer 906, in some embodiments.

In some embodiments, the first pressure-sensitive adhesive within pressure-sensitive adhesive layer 906 may lack sufficient breathability in its own right to allow high MVTR values to be realized. Accordingly, in various embodiments, a plurality of perforations may be defined in pressure-sensitive adhesive layer 906 in order to promote breathability, as best shown in FIG. 10. More specifically, as shown in FIG. 10, perforations 1010 are located upon the surface of pressure-sensitive adhesive layer 906 and may extend therethrough to, into or through non-woven scrim 902. Extension of perforations 1010 into non-woven scrim 902 may further promote breathability upon bonding to a skin surface.

As depicted in FIG. 10, perforations 1010 may comprise a plurality of slots, which may all be substantially the same in length and width, according to some embodiments. Slots differing in length and/or width also reside within the scope of the present disclosure. According to some embodiments, and as depicted in FIG. 10, the plurality of slots may all be oriented in substantially the same direction. More particularly, in some embodiments and as depicted in FIG. 10, the plurality of slots may substantially parallel to one another. Although parallel or substantially parallel slots may be present in pressure-sensitive adhesive layer 906, non-parallel slots also reside within the scope of the present disclosure. Parallel slot alignment may be advantageous for facilitating high-throughput manufacturing processes for double-sided adhesive binder 900. Perforations 1010 other than slots may be present instead of, or present in combination with slots, in alternative embodiments of the present disclosure. Suitable alternative perforations 1010 may include, for example, circular, ovular, chevron-shaped, cross-shaped, or polyhedral perforations, in various embodiments of the present disclosure.

In some or other various embodiments of the present disclosure, pressure-sensitive adhesive layer 908 may comprise an acrylic adhesive. Suitable acrylic adhesives for use in this location are not considered to be particularly limited. Acrylic adhesives can be particularly advantageous for incorporation in pressure-sensitive adhesive layer 908 based upon their good bonding properties to a skin surface or to a non-woven material in an adhesive pad assembly, as discussed below. Acrylic adhesives, moreover, are readily breathable and are well adapted for contacting a skin surface as a result. It is to be recognized, however, that in alternative embodiments of the present disclosure, pressure-sensitive adhesive layer 908 may be perforated, if needed to facilitate breathability.

In more specific embodiments of the present disclosure, pressure-sensitive adhesive layer 906 may comprise a rubber-based adhesive, such as a polybutadiene copolymer, and pressure-sensitive adhesive layer 908 may comprise an acrylic adhesive. In further embodiments, non-woven scrim 902 may comprise a polyester scrim, upon which the rubber-based adhesive and the acrylic adhesive are disposed.

Double-sided adhesive binder 900 may be further adapted such that a sensor can extend longitudinally therethrough and contact a tissue surface, without interacting with any of non-woven scrim 902 and pressure-sensitive adhesive layers 906 and 908. Accordingly, referring still to FIG. 10, macroaperture 1020 may extend longitudinally through pressure-sensitive adhesive layer 906, non-woven material 902, and pressure-sensitive adhesive layer 908. Macroaperture 1020 may extend through the interior of double-sided adhesive binder 900 and not contact an outer perimeter edge thereof. Moreover, macroaperture 1020 may be sized and shaped to circumferentially surround a sensor module of an on-body analyte sensor. In particular embodiments, macroaperture 1020 may be sized and shaped similarly (e.g., keyhole-shaped) to the sensor module designed to fit within receptacle 806 (see FIG. 8). As such, the depicted size and shape of macroaperture 1020 in FIG. 10 should not be considered limiting.

Accordingly, in various embodiments, the present disclosure describes die-cut asymmetric double-sided adhesive binders comprising: a non-woven scrim having a first face and a second face in opposition to one another; a first pressure-sensitive adhesive layer comprising a first pressure-sensitive adhesive disposed upon the first face of the non-woven scrim; and a second pressure-sensitive adhesive layer comprising a second pressure-sensitive adhesive disposed upon the second face of the non-woven scrim. The first and second pressure-sensitive adhesives differ from one another, and a plurality of perforations are defined in at least the first pressure-sensitive adhesive layer, and the second pressure-sensitive adhesive layer is adapted to face a skin surface.

Figure 11:
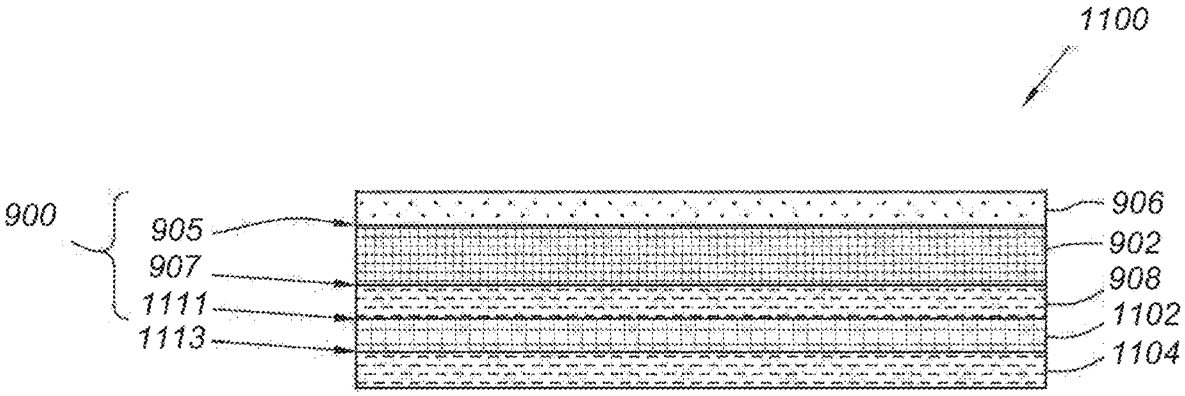
FIG. 11 shows a side view diagram of an illustrative adhesive pad assembly.

As indicated above, double-sided adhesive binder 900 may be incorporated in more extensive adhesive pad assemblies, an illustrative example of which is shown in FIG. 11. The adhesive pad assemblies may promote more robust adhesive bonding of an on-body analyte sensor to a skin surface and improve comfort for a wearer compared to double-sided adhesive binder 900 alone.

FIG. 11 shows a side view of adhesive pad assembly 1100, in which double-sided adhesive binder 900 is further adhesively bonded to non-woven material 1102 via pressure-sensitive adhesive layer 908. Non-woven material 1102 may be the same as or different than non-woven scrim 902, according to various embodiments. More desirably, non-woven scrim 902 and non-woven material 1102 may differ in at least one of areal mass and/or composition. For example, in some embodiments, non-woven material 1102 may have a higher areal mass than does non-woven scrim 902. In more specific embodiments, non-woven material 1102 may have an areal mass that is at least about five times higher than that of non-woven scrim 902, or at least about ten times higher than that of non-woven scrim 902. In some embodiments, non-woven material 1102 may have an areal mass ranging between about 50 g/m2 and about 200 g/m2, or between about 100 g/m2 and about 150 g/m2, or between about 60 g/m2 and about 100 g/m2, or between about 75 g/m2 and about 90 g/m2.

The material comprising non-woven material 1102 is not considered to be particularly limited. In particular embodiments, non-woven material 1102 may comprise a polyester, a polyurethane, a polyethylene, a polypropylene, or any combination thereof. In still more particular embodiments, non-woven material 1102 may be a polyurethane.

Adhesive pad assembly 1100 also comprises pressure-sensitive adhesive layer 1104 disposed upon face 1113 of non-woven material 1102. Pressure-sensitive adhesive layer 1104 may comprise a third pressure-sensitive adhesive. Face 1113 of non-woven material 1102 is opposite face 1111, which is contacted by and adhered to pressure-sensitive adhesive layer 908 via the second pressure-sensitive adhesive. That is, non-woven material 1102 is sandwiched between pressure-sensitive adhesive layers 908 and 1104, according to the various embodiments of the present disclosure.

The third pressure-sensitive adhesive within pressure-sensitive adhesive layer 1104 may be the same as or different than the first and second pressure-sensitive adhesives. In some embodiments, the third pressure-sensitive adhesive may comprise an acrylic adhesive. In more specific embodiments, both the second pressure-sensitive adhesive and the third pressure-sensitive adhesive may comprise an acrylic adhesive, which may comprise the same acrylic adhesive or different acrylic adhesives. In still more specific embodiments, the first pressure-sensitive adhesive may comprise a rubber-based adhesive, the second pressure-sensitive adhesive may comprise an acrylic adhesive, and the third pressure-sensitive adhesive may comprise an acrylic adhesive.

As with double-sided adhesive binder 900, pressure-sensitive adhesive layer 906 in adhesive pad assembly 1100 may likewise have a plurality of perforations 1010 defined therein. Perforations 1010 may extend into at least non-woven scrim 902, according to various embodiments. Suitable perforations may comprise slots, which may be substantially parallel to one another, in some embodiments.

Also like double-sided adhesive binder 900, macroaperture 1020 may likewise be present in adhesive pad assembly 1100 and be sized to circumferentially surround a sensor module of an on-body analyte sensor. In adhesive pad assembly 1100, macroaperture 1020 extends not only through non-woven material 902, pressure-sensitive adhesive layer 906 and pressure-sensitive adhesive layer 908, but also through non-woven material 1102 and pressure-sensitive adhesive layer 1104. Again, macroaperture 1020 may allow a sensor to contact a skin surface or similar tissue surface without interacting with a component of adhesive pad assembly 1100.

Accordingly, adhesive pad assembly 1100 may comprise: a non-woven scrim having a first face and a second face in opposition to one another; a first pressure-sensitive adhesive layer comprising a first pressure-sensitive adhesive disposed upon the first face of the non-woven scrim; a second pressure-sensitive adhesive layer comprising a second pressure-sensitive adhesive disposed upon the second face of the non-woven scrim; a non-woven material adhesively bonded to the second pressure-sensitive adhesive layer, the non-woven material having a higher areal mass than the non-woven scrim; and a third pressure-sensitive adhesive layer comprising a third pressure-sensitive adhesive disposed upon the non-woven material opposite the second pressure-sensitive adhesive layer. The first and second pressure-sensitive adhesives differ from one another, and a plurality of perforations are defined in at least the first pressure-sensitive adhesive layer.

Adhesively bound sensor constructs are also described in the present disclosure. As used herein, the term "adhesively bound sensor construct" refers to a sensor housing adhesively coupled to a skin surface or other tissue surface via adhesive pad assembly 1100 or via double-sided adhesive binder 900 alone. The adhesively bound sensor constructs of the present disclosure may aid in managing moisture retention in proximity to the skin surface, as described hereinafter.

Figure 12:
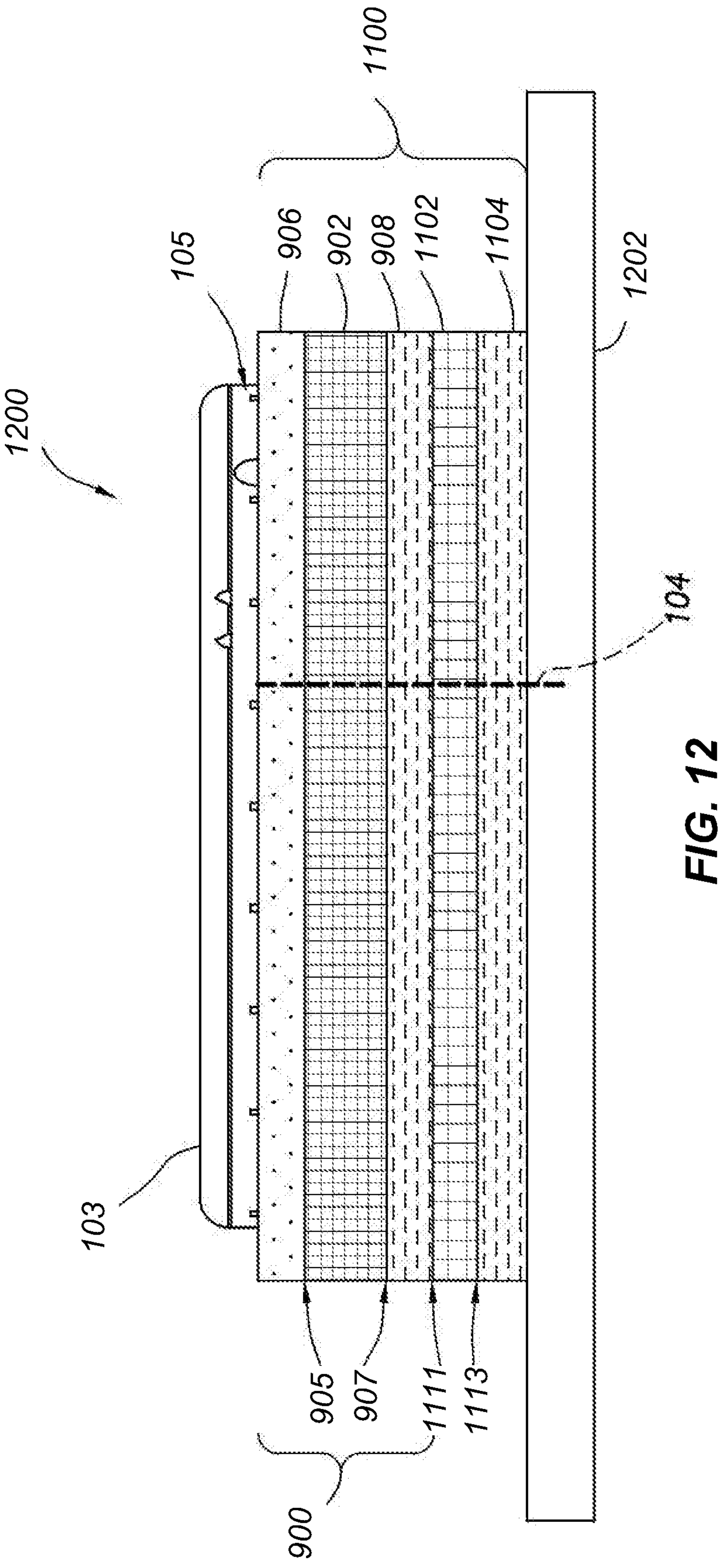
FIG. 12 shows a side view diagram of an illustrative adhesively bound sensor construct upon a skin surface.

FIG. 12 shows a side view diagram of illustrative adhesively bound sensor construct 1200. As shown, adhesively bound sensor construct 1200 includes sensor housing 103 in contact with adhesive pad assembly 1100 via bottom surface 105, which may be grooved, according to various embodiments. As such, sensor housing 103 may be adhesively bonded to skin surface 1202 via adhesive pad assembly 1100. As described previously, macroaperture 1120 (not visible in FIG. 12) extends through adhesive pad assembly 1100 to provide clearance for a needle or a similar introducer. Sensor 104 (shown in phantom in FIG. 12) may likewise extend through adhesive pad assembly 1100 in proximity to a transiently present needle and become seated at a desired depth in skin surface 1202, such as within a dermal layer.

Accordingly, in various embodiments, adhesively bound sensor construct 1200 may comprise: a non-woven scrim having a first face and a second face in opposition to one another; a first pressure-sensitive adhesive layer comprising a first pressure-sensitive adhesive disposed upon the first face of the non-woven scrim; a second pressure-sensitive adhesive layer comprising a second pressure-sensitive adhesive disposed upon the second face of the non-woven scrim; a non-woven material adhesively bonded to the second pressure-sensitive adhesive layer, the non-woven material having a higher areal mass than the non-woven scrim; a third pressure-sensitive adhesive layer comprising a third pressure-sensitive adhesive disposed upon the non-woven material opposite the second pressure-sensitive adhesive layer; and a sensor housing adhesively bonded to the first pressure-sensitive adhesive layer, the sensor housing having a sensor protruding therefrom, and the sensor extending longitudinally through the first pressure-sensitive adhesive layer, the non-woven scrim, the second pressure-sensitive adhesive layer, the non-woven material, and the third pressure-sensitive adhesive layer. The first and second pressure-sensitive adhesives differ from one another, and a plurality of perforations are defined in at least the first pressure-sensitive adhesive layer. It is to be appreciated that related adhesively bound sensor constructs lacking the non-woven material and the third pressure-sensitive adhesive also reside within the scope of the present disclosure, in which case the second pressure sensitive adhesive may facilitate adhesive bonding to a skin surface.

Adhesively bound sensor construct 1200 may facilitate lateral movement of moisture therein, such that the moisture does not remain in proximity to skin surface 1202. In particular, adhesive layers 906, 908 and non-woven scrim 902 and non-woven material 1102 are configured to provide high MVTR values to construct 1200 as a whole to promote moisture transfer to the interface between adhesive layer 906 and bottom surface 105. The presence of grooves upon bottom surface 105, particularly radial grooves 800*a*, may facilitate lateral movement of moisture out of adhesively bound sensor construct 1200, according to various embodiments. Radial grooves 800*a* may particularly facilitate removal of moisture entering adhesively bound sensor construct 1200 via aperture 804 in sensor housing 103.

Non-woven scrim 902 and non-woven material 1102 may become adhesively bonded to one another at various points during the course of applying sensor construct 1200 to a skin surface. In some embodiments, non-woven material 1102 may be applied to a skin surface first, and non-woven scrim 902 may thereafter be applied on top of non-woven material 1102. In other embodiments, non-woven scrim 902 and non-woven material 1102 may be adhesively bonded together first and then be applied concurrently to a skin surface. In some or other embodiments, non-woven scrim 902 and non-woven material 1102 may be disposed together in an applicator that is configured for applying sensor construct 1200 directly to a skin surface. Non-woven scrim 902 and non-woven material 1102 may be adhesively bonded together in the applicator or disposed separately, according to various embodiments.

In some embodiments, an antimicrobial quality may be included as part of one or more of the sensor components, such as the sensor housing, an upper portion of the sensor tail, and/or the adhesive pad assembly. As used herein, the terms "antimicrobial" or "antimicrobial compound," and grammatical variants thereof, refer to a substance or material that is detrimental (microbicidal) or microstatic (i.e., preventing or reducing colonization, expansion, and/or proliferation without necessarily being detrimental) to a microorganism, including bacteria, fungi, viruses, protozoans, and the like. The term "antimicrobial quality," and grammatical variants thereof, refers to any mechanism, structure, system, or other technique for imparting any antimicrobial characteristic to a tangible material, including one or more components of the analyte sensors described herein and/or human skin to which the one or more sensor components come into contact.

As described above, when positioning an analyte sensor onto the skin of a wearer, a needle or other introducer is used to puncture the skin and allow transcutaneous implantation through the dermal region. Implantation may extend only to the dermis, or through to the subcutis. Accordingly, a transdermal skin wound is created in order for the sensor to undergo positioning for analyte monitoring, wherein the sensor tail is positioned trans- or subcutaneously into the skin through the wound (also referred to as the "insertion site"). Generally, an analyte sensor may be worn for a prolonged period of time, such as 7 days, 10 days, 14 days, 21 days, 30 days, or more. That is, the analyte sensor may be worn for a time period of less than 30 days or a period of 30 days or more. As such, the sensor and its various components may be exposed to various activities or atmospheres, including contact with the external environment, clothing, bath or shower water, rain or swimming water, social contact with other persons, and the like. While the adhesive pad assemblies of the present disclosure may provide complete protection from such exposure to the skin wound itself (insertion site), the possibility of existing microorganisms near the insertion site and/or migration of microorganisms from adjacent skin or areas, including the external environment, may still present a risk of incursion to the skin wound. Such exposure may create a rich environment for microorganism growth, which may be harmful to the wearer and/or may lead to altered functioning of the analyte sensor itself, such as causing a shortened life of the sensor and/or providing erroneous or altered data or perceived sensitivity and/or response times.

Various microorganisms (e.g., bacteria, fungi, viruses, and the like) are present naturally on the skin (i.e., skin flora) and in the surrounding environment (e.g., air, clothing, bedding, water, social engagement, and the like), which may contact the wound area or adjacent skin while the analyte sensor is in use. Moisture contact (e.g., during daily showering, bathing, or submersion (e.g., such as when swimming, for example in a public pool or natural body of water), inability to access and wash skin having the sensor applied thereto, failure to adequately clean the skin prior to insertion of the sensor tail and application of the sensor, nosocomial (i.e., hospital) exposure to microorganisms (e.g., a nurse or other medical professional may apply an analyte sensor in a hospital setting), and the like, may further exacerbate the possibility of microorganism growth. As used herein, the term "skin flora," and grammatical variants thereof, refers to microorganisms that innately reside on human skin and/or within a human body that may contact human skin. While various embodiments of the present disclosure may be discussed with reference to protecting against such skin flora, it is to be understood that other microorganisms (e.g., bacteria, fungi, viruses, and the like) may also be controlled or otherwise treated to protect the insertion site and adjacent areas of the wearer and to promote better sensor functionality.

The various microorganisms that may be desirably controlled or otherwise treated as part of the use of an analyte sensor described herein are not believed to be particularly limited and include any such microorganisms generally encountered by a person during various life activities, including symbiotic microorganisms and parasitic microorganisms.

Microorganisms in skin flora may include, but are not limited to, actinobacteria (e.g., *Corynebacterium, Propionibacterium*, and the like), firmicutes (e.g., *Staphylococcus, Clostridia, Lactobacillus*, and the like), proteobacteria (e.g., alphaproteobacteria, betaproteobacteria, gammaproteobacteria, and the like), bacteriodetes (e.g., flavobacteriales, and the like), cyanobacteria, and the like, and any combination thereof. Examples of specific such skin flora may include, but are not limited to, *Staphylococcus epidermidis, Staphylococcus aureus, Staphylococcus warneri, Streptococcus pyogenes, Streptococcus mitis, Staphylococcus hominis, Propionibacterium acnes, Corynebacterium* spp., *Acinetobacter johnsonii, Pseudomonas aeruginosa, Demodex folliculorum, Bacillus oleronius, Bacteroides fragilis, Bacteroides melaninogenicus, Bacteroides oralis, Enterococcus faecalis, Escherichia coli, Enterobacter* spp., *Klebsiella* spp., *Bifidobacterium bifidum, Lactobacillus* spp., *Clostridium perfringens, Clostridium tetani, Clostridium septicum, Proteus mirabilis, Pseudomonas aeruginosa, Salmonella enterica, Faecalibacterium prausnitzii, Peptostreptococcus* spp., *Peptococcus* spp., and the like, and any combination thereof.

Environmental microorganisms may be any microorganisms that overlap with the skin flora described above, and further include microorganisms that are present in the environment, including internal and external environments and encountered during various life activities. For example, such microorganisms may include those that are encountered during sleeping, bathing and/or showering, working, exercising, eating, attending recreational excursions or events, handling pets, and the like. Such microorganisms may include, but are not limited to, those listed above, as well as *Escherichia* (e.g., *E. coli*, and the like), firmicutes, *Mycobacterium* (e.g., *Mycobacterium avium* subspecies paratuberculosis, and the like), enterobacteriaceae (e.g., *Salmonella*, and the like), yeast, bacteriophages, and the like, and any combination thereof.

The mechanism by which the antimicrobial quality described herein prevents or reduces microorganism interference with the insertion site and/or functioning of the analyte sensor may be any mechanism and may be dependent on the type or types of microorganisms being targeted. Suitable mechanisms may include, but are not limited to, preventing microorganism attachment to one or more components of the sensor (e.g., preventing initial adhesion of the microorganism(s)), disruption of the microorganism(s) cell surface or membrane, disruption of the microorganism(s) internal organelles or functioning thereof, prevention of continued growth (e.g., by restricting nutrients and/or nutrient uptake or metabolism), and the like, and any combination thereof. In some instances, the mechanism may further be selected based on the placement of the antimicrobial quality, which may be applied or otherwise coated onto one or more components of the sensor. Optionally, the antimicrobial quality may be imparted to one or more components of the analyte sensor and/or particular area of the skin to which the sensor is adhered in the form of a wipe or cleaning pad, which may be used alone or in combination with other cleaning aspects, such as for imparting disinfecting qualities prior to sensor implantation.

In some embodiments, the antimicrobial quality for use in the present disclosure is a slow-release antimicrobial quality. The mechanism by which the antimicrobial may be slowly released is not considered to be particularly limited. In some embodiments, the antimicrobial is released slowly by contact with water (e.g., during bathing or sweating), exposure to elevated temperature, encapsulation, impregnation, degradation, and the like, and any combination thereof. As used herein, the term "encapsulation," and grammatical variants thereof, refers to envelopment in whole or in part (i.e., less than 100%) of an antimicrobial substance, such as by a wax, degradable polymer or biopolymer, or other suitably degradable material. The term "impregnation," and grammatical variants thereof, as used herein, refers to filling, permeating, doping, chemically binding (e.g., covalently binding), or saturating an antimicrobial substance into a carrier, such as an adhesive, an alcohol, a nanoparticle, and the like. Encapsulated antimicrobial substances may generally be released as the encapsulation material degrades or at least are released in greater amounts as such degradation occurs (e.g., if the encapsulation is not in whole). Impregnated antimicrobial substances may generally be released as the antimicrobial leaches out of voids in various carrier materials or as the carrier materials degrade. For example, another substance or material, such as any of the multiple layers of the adhesive pad assemblies of the present disclosure, may be used as a carrier for the antimicrobial, which is distributed therethrough such that its release is prolonged over a period of time. Accordingly, the antimicrobial quality may be directly applied to the surface of a portion of the adhesive pad assemblies and/or analyte sensor component (e.g., upper portion of the sensor tail), or may be otherwise provided in a carrier. Other alternatives are further discussed hereinbelow and are within the scope of the present disclosure.

Prolonged exposure to an antimicrobial may be particularly advantageous for the embodiments of the present disclosure because the analyte sensor may be worn over an extended period of time, and thus may experience potential contact with microorganisms, such as skin or environmental flora, over the period of time. Accordingly, the action of the antimicrobial can occur throughout the duration in which the sensor is in use, not merely at a beginning portion, thereby ensuring protection to the wearer (e.g., maintaining skin health of the wearer) and proper functioning of the analyte sensor.

Figure 13:
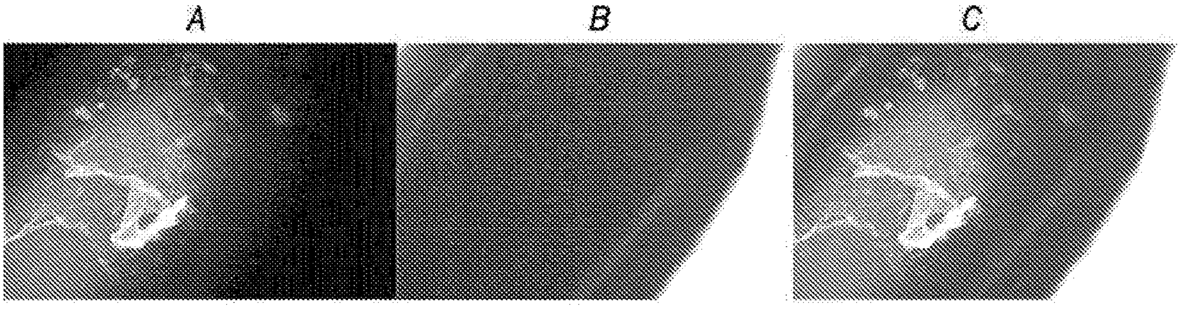
FIG. 13 is a composite fluorescence and visible light image showing a biofilm comprised of microorganisms formed on the sensor tail of an analyte sensor having no antimicrobial quality.

Referring now to FIG. 13, illustrated is a composite visible light and fluorescence image of a biofilm comprised of microorganisms formed on a sensor component of an analyte sensor having no antimicrobial quality. The biofilm on the sensor component is visualized at 10× OM magnification using fluorescence microscopy (labeled as "A"), light microscopy (labeled as "B"), and an overlay of the fluorescence and light microscopy images (labeled as "C") after the analyte sensor was worn for 21 days. As shown, the biofilm is characterized by small, coccus-shaped (i.e., spherical or roughly spherical in shape) microorganisms. This biofilm may potentially migrate down the sensor tail of the analyte sensor toward the sensing region, which is located at a bottom portion of the sensor tail. As used herein, the term "sensing region," and grammatical variants thereof, refers a portion of an analyte sensor comprising one or more components to facilitate measurement of one or more analytes (e.g., via electrochemical oxidation or reduction, or other sensing chemistry). The sensing region may include, for example, an analyte-specific reactant (e.g., enzyme or other chemical) that reacts with the analyte to produce a response at or near a working electrode. Accordingly, the sensing region includes at least the analyte-specific chemical and a working electrode. Other elements in the sensing region may include, but are not limited to, a membrane (e.g., a limited permeability membrane), other electrodes (e.g., reference and/or counter electrodes), an electron transfer agent to transfer electrons between the analyte and the working electrode (or other component), such as a suitable redox species, or both.

The antimicrobial quality described herein may be placed on any portion or component of the adhesive pad assemblies and/or the analyte sensor described herein, excluding the sensing region of the sensor tail. That is, as provided above, the antimicrobial quality may be provided only to an upper portion of a sensor tail of an analyte sensor in accordance with the embodiments of the present disclosure. Accordingly, as used herein, the term "upper portion of the sensor tail," and grammatical variants thereof, refers to a portion of the sensor tail that does not extend beyond the dermis and, generally, includes the top 25% of the sensor tail beginning from the proximal-most of the sensor tail extending from the base of an analyte sensor, encompassing any value and subset therebetween. The "upper portion" of the sensor tail is more proximal to the skin surface than the sensing region of the sensor tail comprising electrode(s) and analyte sensing element(s).

Contact of a biofilm, such as that depicted in FIG. 13, with or adjacent to the sensing region may affect various characteristics of the sensor, such as the accuracy of the sensor. If the biofilm reaches the sensing region, sensor sensitivity may be altered over the wear duration of the analyte sensor. Accordingly, protection of the sensing region from microorganisms may increase the life and functionality of the analyte sensor. Thus, protection of the insertion site from exposure to such microorganisms that can migrate to the implantation site may confer advantageous and unexpected operational benefits.

The present disclosure therefore preferably provides an antimicrobial quality to one or more components of an analyte sensor described herein (e.g., a glucose analyte sensor) that prevents or reduces contact of the sensing region with microorganisms, such as those that may result in erroneous measures from those that would be expected due to formation of a biofilm. In order to protect the sensing region, then, the location of the antimicrobial quality may include, but is not limited to, one or more portions of the adhesive pad assemblies described in the present disclosure or one or more portions of the analyte sensor (excluding the bottom portion or sensing region of the sensor tail).

For example, in any one or all of the embodiments of the present disclosure, one more of the one or more pressure-sensitive adhesive layers, the non-woven scrim, and/or the support material may have an antimicrobial quality coated thereon, including functionalized thereto, impregnated therein, or otherwise adhered thereto to impart the antimicrobial quality to the adhesive pad assembly, each of which is described in greater detail below. The scrim and the pressure-sensitive adhesive layers may provide for gaps or voids that permit their functioning as a carrier material not only for the adhesive, but also for application of the antimicrobial quality and release dynamics. The gaps or voids in these materials may allow slow-release of the antimicrobial, such that it is continuously leaching the antimicrobial through the layers of the adhesive pad assembly and to the insertion site. In some embodiments, the leaching may occur sequentially, such that during a time earlier in the wear duration of the analyte sensor, the antimicrobial is delivered to the insertion site and skin contact area via the layer most proximal to the skin contact area. Over time, the antimicrobial may be exhausted in the proximal layer(s) and replenished from a layer more distal to the skin contact area.

Alternatively, localized placement of one or more antimicrobials may be provided such that delivery of a particular antimicrobial occurs prior to delivery of a second (or third, etc.) antimicrobial. For example, it may be known that a particular microorganism is likely to be most problematic during the initial implantation of an analyte sensor, followed by a different microorganism over time; the controlled release of two or more antimicrobials in accordance with the embodiments described herein may be provided to address such a situation. In yet other alternatives, the combination of multiple antimicrobials may be used simultaneously to combat against a larger spectrum of microorganisms as compared to any one alone (e.g., the use of rifampin and minocycline together). In still other alternatives, the localized placement of various antimicrobial(s) maybe used to create a wave-like effect where higher doses of antimicrobial are followed by lower or no antimicrobial dosage. In these ways, the amount and type of antimicrobial delivered to or adjacent to a wearer's skin may be controlled to achieve desired tolerance levels (e.g., lower drug load to the wearer). Accordingly, the present disclosure provides for multiple release profiles of the antimicrobial quality described herein.

In other embodiments, alone or in combination with an antimicrobial quality in one or more (or all) layers of the adhesive pad assemblies described herein, the upper portion of the sensor tail is provided with an antimicrobial quality. The sensor tail extends into the skin of the wearer via a skin wound and is thus the primary route through which microorganisms may traverse to contact the sensing region of the analyte sensor. As discussed above, microorganism contact with the sensing region may cause alteration in the perceived sensitivity of the sensor, interfere with other functionality of the sensor, and/or harm the wearer (e.g., result in infection). As such, whether the sole antimicrobial quality provided to the analyte sensor or in combination with one or more antimicrobial qualities provided thereto, treating the upper portion of the sensor tail with an antimicrobial quality may be particularly beneficial.

Figure 14:
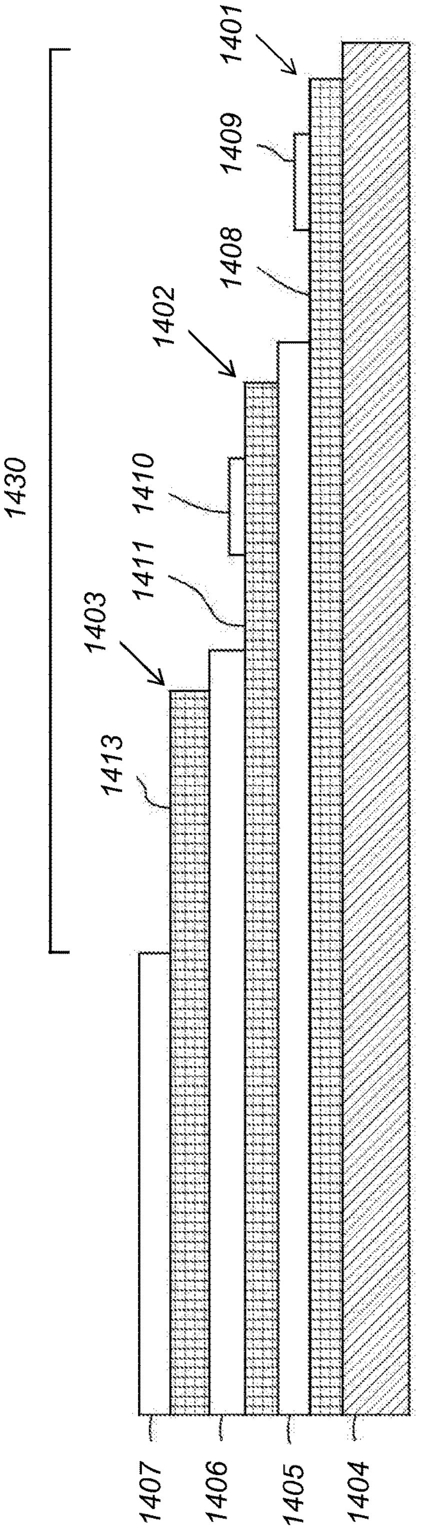
FIG. 14 is a cross-sectional view depicting a portion of an analyte sensor that is compatible with one or more embodiments of the present disclosure.
Figure 15:
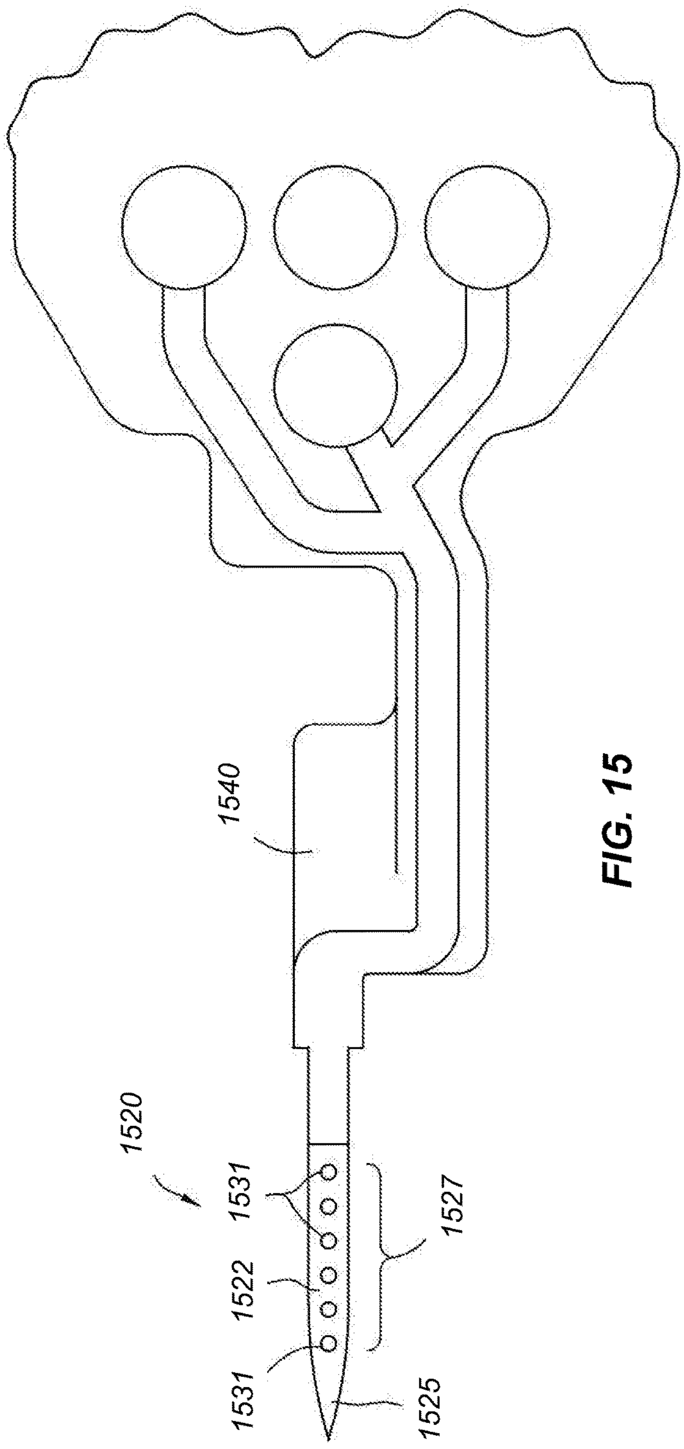
FIG. 15 shows a plan view of an implantable analyte sensor that is compatible with one or more embodiments of the present disclosure.
Figure 16:
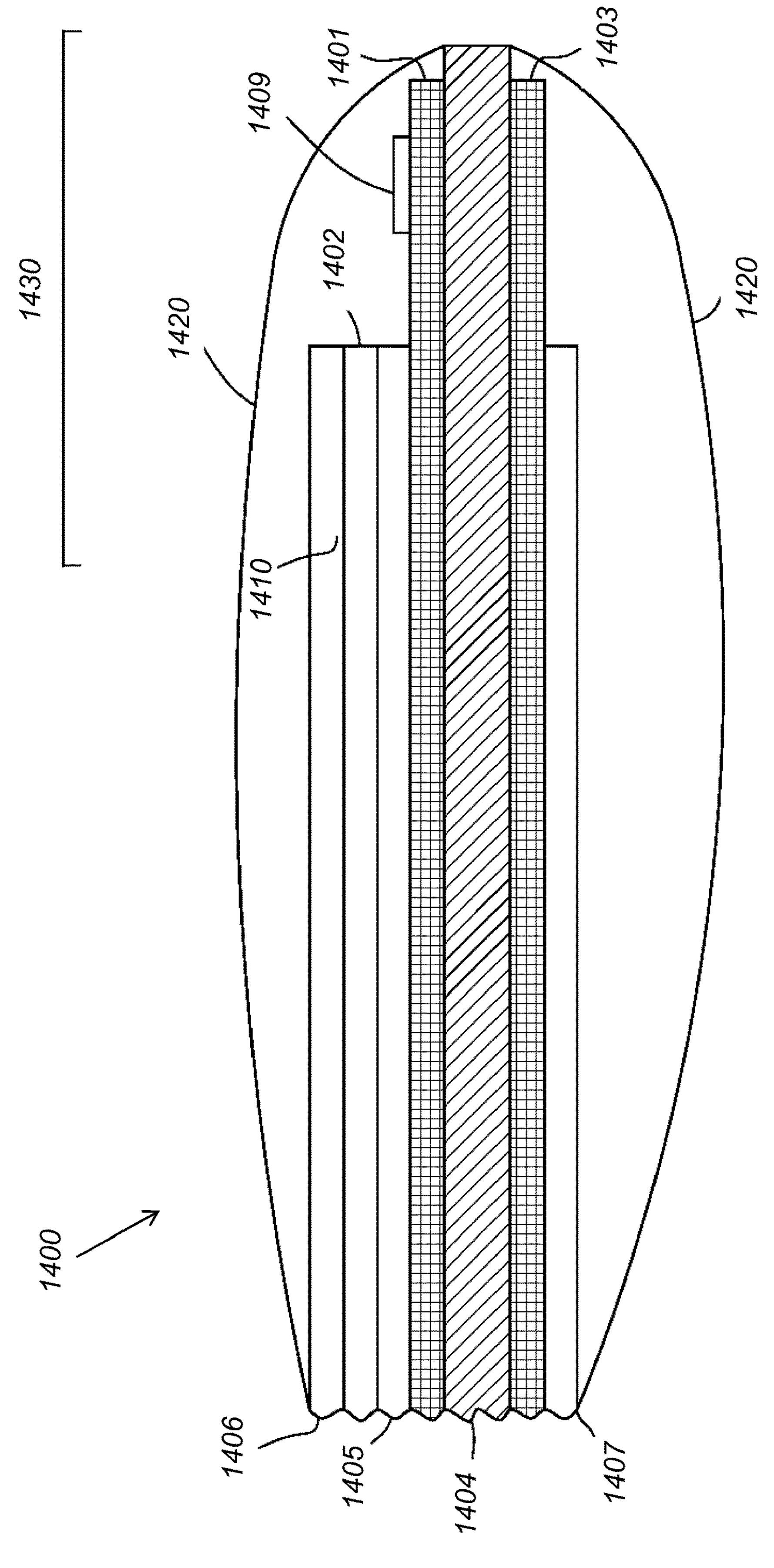
FIG. 16 is a cross-sectional view depicting a portion of an analyte sensor having a membrane that is compatible with one or more embodiments of the present disclosure.

To facilitate a better understanding of the sensor tail architecture and sensing region, one or more embodiments thereof are shown in FIGS. 14-16. Placement of the antimicrobial quality onto (e.g., coating, functionalization, and the like) may be illustrated herein with reference to the sensor tail and sensing regions depicted in FIGS. 14-16. However, it is to be understood that the antimicrobial quality may be provided on or about the upper portion of the sensor tail of the analyte sensors of the present disclosure to provide antimicrobial protection in the surrounding area and, in particular, to the sensing region where analyte measurements are determined, regardless of the configuration of said sensor tail or sensing region. The antimicrobial quality of the present disclosure is not provided to the sensing region (i.e., bottom portion of the sensor tail) according to the present disclosure.

For example, the sensor tail may have a plurality of electrodes located at a distal (bottom) end of the sensor tail (e.g., deeper into the subcutaneous space of a wearer's skin). One or more sensing regions may be associated with (e.g., coated upon or adjacent to) one or more of such electrodes, such as a working electrode. Such electrodes may be coplanar relative to each other, stacked relative to each other, helically wound about one another, incorporated with one or more insulating materials, and the like. The antimicrobial quality may then be provided in any location that imparts antimicrobial protection to the sensor, provided that it is not located at the bottom portion of the sensor tail and does not interfere with the operation of the sensing region or functionality of the sensor as a whole. That is, in some embodiments, the antimicrobial quality is exterior to the body or only in contact dermally (i.e., passing through intact skin but not contacting the fatty subcutis layer under the skin) via the upper portion of the sensor tail.

FIG. 14 shows a cross-sectional view of an embodiment of an analyte sensor 1400 having a first portion (which in this embodiment may be characterized as a major portion) positionable above a surface of the skin, and a second portion (which in this embodiment may be characterized as a minor portion) that includes a sensor tail 1430 (which may also be referred to herein as an insertion tip) positionable below the surface of the skin (e.g., penetrating through the skin (dermis) and into the subcutaneous space) and in contact with the wearer's biofluid, such as interstitial fluid. Electrode contacts (not shown) are positioned on the first portion of the sensor 1400 situated above the skin surface and extend to a location in sensor tail 1430. A working electrode 1401, a reference electrode 1402, and a counter electrode 1403 are shown at the second portion of the sensor 1400 and particularly at the bottom portion of sensor tail 1430. It is to be understood that greater or fewer electrodes may be provided on a sensor, without departing from the scope of the present disclosure. For example, a sensor may include more than one working electrode and/or the counter and reference electrodes may be a single counter/reference electrode, and the like.

Referring still to FIG. 14, the sensor 1400 (such as the sensor device 102 of FIG. 1), includes a substrate layer 1404 and a first conducting layer 1408 such as carbon, gold, etc., that is in electrical communication with sensing area 1409, thereby collectively defining working electrode 1401. Sensing area 1409 may be protected from microorganisms by providing on one or more components of the sensor 1400 an antimicrobial quality, designed to protect the skin health of the wearer and/or to protect the sensing area 1409 from potential interference with such microorganisms (e.g., formation of a biofilm due to potential migration of the microorganisms). The various electrodes and sensing areas defined on the bottom portion of the sensor tail 1430 in FIG. 14 may be collectively a sensing region, and any such antimicrobial quality provided to the sensor tail 1430 described herein, is provided in the upper portion (upper 25%) of the sensor tail 1430 above said region (e.g., above sensing area 1409, or above electrode 1403).

A first insulation layer 1405, such as a first dielectric layer in some embodiments, may be disposed or layered on at least a portion of the first conducting layer 1408, and further, a second conducting layer 1411 may be disposed or stacked on top of at least a portion of the first insulation layer (or dielectric layer) 1405. As shown in FIG. 14, the second conducting layer 1411 in conjunction with a second conducting material 1410, such as a layer of silver/silver chloride (Ag/AgCl), may collectively provide the reference electrode 1402. Another possible disposition of second conducting material 1410 is shown in FIG. 16, along with an outer membrane 620 overcoating the various layers.

A second insulation layer 1406, such as a second dielectric layer in some embodiments, may be disposed or layered on at least a portion of the second conducting layer 1411. Further, a third conducting layer 1413 may be disposed on at least a portion of the second insulation layer 1406 and may provide the counter electrode 1403. Finally, a third insulation layer 1407 may be disposed or layered on at least a portion of the third conducting layer 1413. In this manner, the sensor 1400 may be layered such that at least a portion of each of the conducting layers is separated by a respective insulation layer (e.g., a dielectric layer). Another possible layer configuration is shown in FIG. 16. The embodiments of FIGS. 14 and 16 show the layers having different lengths; however, some or all of the layers may have the same or different lengths and/or widths, without departing from the scope of the present disclosure.

In any one or all embodiments, some or all of the electrodes 1401, 1402, and 1403 may be provided on the same side of the substrate 1404 in the layered construction described above, or alternatively, may be provided in a co-planar manner such that two or more electrodes may be positioned on the same plane (e.g., side-by side, parallel, or angled relative to each other) on the substrate 1404. For example, co-planar electrodes may include a suitable spacing therebetween and/or include a dielectric material or insulation material disposed between the conducting layers/electrodes. Furthermore, in some embodiments, one or more of the electrodes 1401, 1402, and 1403 may be disposed on opposing sides of the substrate 1404. In such embodiments, contact pads may be on the same or different sides of the substrate. For example, an electrode may be on a first side and its respective contact may be on a second side, for example, a trace connecting the electrode and the contact may traverse through the substrate.

With reference now to FIG. 15, shown is another embodiment of an analyte sensor in accordance with one or more embodiments of the present disclosure, and representing a variation of the sensor 1400 of FIGS. 14 and 16. Referring to FIG. 15, shown is an implantable (e.g., subcutaneous or transcutaneous) sensing region 1520 according to one or more embodiments of the present disclosure including a working electrode 1522. Proximal end 1540 is configured to be connected to various electrical connections for transmitting the output signals of the sensing region 1520. Collectively, the spans between the distal end 1525 and the proximal end 1540 form the sensor tail. Sensing region 1520 encompasses a bottom portion of the sensor tail. As depicted, sensing region 1520 comprises a rounded tip, but other tip shapes may alternately be present to facilitate insertion into a wearer's skin.

Additionally, in one or more embodiments, sensing region 1520 may include a reference electrode, a counter electrode, or counter-reference electrodes, such as those shown in FIGS. 14 and 16. Alternative electrode configurations may be employed without departing from the scope of the present disclosure. Sensing region 1520 may include one or more discrete sensing spots 1531, for example, in an area, such as area 1527.

With reference to FIGS. 14-16, it is notable that the sensor 1400, 1520 includes sensing functionality at a distal portion of their respective sensor tails. As described above, this location may allow for enhanced contact with deeper locations beneath a wearer's skin (e.g., the subcutaneous space), where greater access to the wearer's interstitial fluid may permit greater access the analyte of interest being measured (e.g., concentration thereof). That is, the sensing region is placed sufficiently deep within a wearer's skin to allow accurate measurement of the particular analyte, whereas placing the sensing region at a more proximate location to the skin surface may be inadequate to correctly determine the concentration or other characteristic of a desired analyte. In some embodiments, the length of the sensor tail extending from the bottom face 105 (FIGS. 1 and 14) may be in the range of less than about 20 millimeters (mm), such as in the range of about 1 mm to about 15 mm, or about 1 mm to about 6 mm, encompassing any value and subset therebetween. Longer sensor tails may be inserted at an angle in some embodiments.

In some embodiments, the sensing region of an analyte sensor according to one or more embodiments of the present disclosure is within the distal-most portion of the sensor tail, including less than about 50% of the length of the sensor tail beginning at the distal-most portion, encompassing any value and subset therebetween. That is, if the sensor tail extending from the bottom face 105 (FIG. 1) of a sensor is determined, the sensing region may be located at a position that is within about 50% of the length of the sensor tail beginning from the deepest point within the skin of a wearer. In other embodiments, the sensing region is included in less than about 45%, 40%, 35%, 30%, 35%, 20%, 15%, or 10% of the length of the sensor tail beginning at the distal-most portion, encompassing any value and subset therebetween. The location of the sensing region may depend on the length of the sensor tail, the length or area of the sensing region, and the like, and any combination thereof.

The antimicrobial quality of the sensor that may be applied according to one or more embodiments described herein to the upper portion of the sensor tail, located at a distant sufficiently far from the sensing region of the sensor tail such that the antimicrobial does not interfere with the functioning of the sensing region or sensor as a whole, and does not adversely react with the skin of the wearer (e.g., it is not so deep within the skin to cause a reaction). In some embodiments, if the sensor tail extending from the bottom face 105 (FIG. 1) of a sensor is determined, the antimicrobial quality is applied by any means or mechanism to an upper (proximal) portion of the sensor tail, including less than about 25% of the length of the sensor tail beginning at the proximal-most portion, encompassing any value and subset therebetween. Some such portions may be located at the insertion site and/or slightly above or below the insertion site, depending on the length of the sensor tail. Accordingly, if the sensor tail extending from the bottom face 105 (FIG. 1) of a sensor is determined, the antimicrobial quality may be located at a position that is within about 25% of the length of the sensor tail extending from the bottom face 105. In other embodiments, the antimicrobial quality is included in less than about 25%, 20%, 15%, or 10% of the length of the sensor tail beginning at the proximal-most portion, encompassing any value and subset therebetween. The location of the antimicrobial quality may depend on the length of the sensor tail, the length or area of the sensing region, and the like, and any combination thereof.

Accordingly, in some embodiments, the antimicrobial quality may be at a distance of at least 25% of the length of the sensor tail measured from the bottom face 105 of the sensor away from the sensing region (the "upper portion" of the sensor tail), encompassing any value and subset therebetween increasing in greater distance. That is, the antimicrobial quality and the sensing region may be sufficiently separated such that the two do not interact directly, but instead any pathway to the sensing region along the sensor tail by a microorganism first encounters the antimicrobial quality, which may prevent or reduce contact by the microorganism to the sensing region.

In any one or more other embodiments and with reference again to FIG. 1, any of the sensor housing 103, the bottom face 105, the needle, and/or the sensor 104 that protrudes from sensor housing 103 and through bottom face 105 into the skin of a wearer (i.e., upper portion of the sensor tail and excluding the sensing region at the insertion tip) may be provided with an antimicrobial quality, including any sub-components thereof (e.g., see FIG. 14). The antimicrobial quality may be coated thereon, functionalized thereto, impregnated therein (depending on the material or component to which the antimicrobial quality is imparted), or otherwise adhered thereto to impart the antimicrobial quality to the sensor device 102 and, in particular, for protection of the sensing region of the sensor tail and a wearer's skin. With reference to FIGS. 1 and 8, for example, the perimeter of the sensor housing 103 and/or the outer perimeter 802 of the bottom face 105 may be provided with an antimicrobial quality. During use, microorganisms may come into contact with the antimicrobial quality along perimeter edges prior to any potential wicking (e.g., microorganisms carried in water) along the bottom face 105 toward the receptacle 806 and/or aperture 804 (FIG. 14). The receptacle 806 may provide a seating for a sensor module (e.g., electronics of the sensor 1400) and the aperture 804 may provide a space for the sensor tail to extend from the sensor housing 103 into a wearer's skin through an insertion site. That is, the aperture 804 may provide an avenue to a sensing region. Further, contact with a microorganism at the receptacle 806 may allow for formation of a biofilm or other microbial colonization that may interfere with the working electronics of the sensor 1400.

In any one or more embodiments, an antimicrobial quality may further be provided along any or all of the radial grooves 800*a* and/or circumferential grooves of 800*b* of the bottom face 105. As provided above, the radial grooves 800*a*, alone or in combination with the circumferential grooves 800*b* may establish fluid communication between the aperture 804 and/or the receptacle 806 and the outer perimeter 802 of the bottom face 105. Accordingly, incorporation of an antimicrobial quality coated, functionalized, impregnated, or otherwise adhered to one or more portions of the grooves of the bottom face 105 may protect the receptacle 806 and/or aperture 804 from microorganisms, including related components (e.g., a sensor module, a sensor tail upper or lower portion, a sensing region, and the like, and any combination thereof).

Any sub-components of the sensor 1400 may further be provided with an antimicrobial quality (e.g., carrier grip(s) 810), without departing from the scope of the present disclosure, provided that inclusion of such antimicrobial quality does not interfere with the functioning and/or seating on the skin of the sensor 1400 and is not located beyond (deeper into the dermis/subcutis space than) the upper portion of the sensor tail.

The antimicrobial quality of the present disclosure for application to the skin prior to implantation of an analyte sensor (e.g., as an antimicrobial wipe) and/or to any one or more components of the analyte sensor itself may be by any mechanism, such as a coating, surface functionalization, encapsulation, impregnation, and the like, or any combination thereof.

In some embodiments, the antimicrobial quality is imparted to the sensor components described herein as acceptable substrates for receiving such antimicrobial quality of the present disclosure via an antimicrobial coating. An "antimicrobial coating," and grammatical variants thereof, as described herein, refers to a film or layer of antimicrobial applied to a surface by any means including, but not limited to, through use of an adhesive, through surface functionalization (e.g., crosslinking, graft polymer linking, and the like of the surface and the antimicrobial). Carriers may be used that, when applied to a surface, can themselves be degradable and allow a slow-release (e.g., upon water exposure, elevated temperatures, and/or exposure to light over time) of an antimicrobial, the antimicrobial of which may itself be degradable or otherwise encapsulated or impregnated in another material.

Suitable carriers that may be coated onto one or more of the surfaces described herein, including any one or more components of the sensor and a skin surface of a sensor wearer, are not considered to be particularly limited and include any such substances that have or can carry an antimicrobial quality, adhere to a desired surface, and are themselves able to release the antimicrobial quality over time.

In any one or more embodiments, a suitable coating carrier for use in the present disclosure may include, but is not limited to, synthetic and natural biodegradable polymers. Suitable synthetic biodegradable polymer coating carriers may include, but are not limited to, polymethylmethacrylate; poly(lactic-co-glycolic acid); polylactic acid; polyglycolic acid; polyethylene glycol; poly(D,L)lactide, poly(ε-caprolactone); polyhydroxyalkonate; poly(butylene succinate); polyvinyl alcohol; degradable polyurethanes; and the like; any derivatives thereof; any copolymers thereof; and any combination thereof. Suitable natural biodegradable polymer coating carriers for use in the present disclosure may include, but are not limited to, cellulose, chitosan, lignin, pullulan, polyhydroxyalkonate, collagen, alginate, whey protein, keratin, gelatin, dextran, any derivatives thereof, any copolymers thereof, and any combination thereof. It is to be appreciated that any suitable other degradable synthetic or natural polymers or proteins may be used as an antimicrobial carrier coating in accordance with any or all of the embodiments described herein, without departing from the present disclosure. As used herein, the term "derivative," and grammatical variants thereof, refers to a compound that is derived from any one of the listed compounds herein, such as by replacement of one atom with another atom or group of atoms (e.g., a functional group). For instance, examples of cellulose derivatives may include, but are not limited to, hydroxyethylcellulose, carboxymethylhydroxyethylcellulose, carboxymethylcellulose, hydroxypropyl methylcellulose, and the like, and any combination thereof. The term "copolymer," and grammatical variants thereof, as used herein, refers to any polymer characterized by two or more different monomers, encompassing terpolymers and any higher polymers.

As alluded to above, in some instances, the carrier coating itself may provide the antimicrobial quality. Such antimicrobial carriers may additionally carry a secondary (or tertiary, or any plurality) antimicrobial, without departing from the scope of the present disclosure. For example, an organosilane coating (e.g., nanocoating) may provide an abrasive surface to a sensor component or skin, which inhibits microorganism attachment due to disruption of their outer membrane. The abrasive surface may be undetectable to humans, and thus suitable for contact with a sensor wearer's skin and/or at or near the insertion site (e.g., at an upper portion of the sensor tail or otherwise above the dermis). In some instances, the organosilane may be coupled with a quaternary ammonium compound, which provides additional anchoring to a surface, such as by forming a chemical bond with one or more components of a sensor or the formation of a film on skin. Moreover, a quaternary ammonium compound may be used alone if desired to provide an antimicrobial quality to the sensor and/or skin.

A selected organosilane for use as the carrier coating and/or the antimicrobial compound itself is not considered to be particularly limiting and may include any suitable carrier coating that can carry an antimicrobial and/or provide antimicrobial qualities itself over time. In one or more embodiments, examples of suitable organosilane carrier coatings for use in the present disclosure may include, but are not limited to, methyl triethoxysilane, methyl trimethoxysilane, vinyl trimethoxysilane, phenyl trimethoxysilane, 3-aminopropyltrimethoxysilane, 3-glycidoxypropyltrimethoxysi lane, methacryloxypropyltrimethoxysilane, mercaptopropyltrimethoxysilane, and the like, any derivative thereof, and any combination thereof.

A selected quaternary ammonium compound for use as the carrier coating and/or the antimicrobial compound itself (e.g., alone or in combination with an organosilane) is not considered to be particularly limited. Examples of suitable quaternary ammonium compounds for use in the present disclosure may include, but are not limited to, dimethyloctadecyl (3-trimethoxysilyl propyl) ammonium chloride, alkyldimethylbenzylammonium chloride, didecyldimethylammonium chloride, benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride, quaternary ammonium polyethyleneimine, and the like, any derivatives thereof, and any combination thereof.

The attachment of the quaternary ammonium compound described above may be considered a surface functionalization of one or more components of the sensor described herein for imparting an antimicrobial quality to which it is covalently bound. Other carrier coatings comprising an antimicrobial quality may additionally be achieved by surface functionalization, without departing from the scope of the present disclosure. For example, a surface of one or more components of a sensor as described herein may be functionalized by attaching a polymer or polypeptide to the surface, such as through a grafting process. Polymers may be grafted (e.g., through use of absorption or chemical bonding, crosslinking, or other immobilization means) or directly polymerized onto one or more surfaces of the sensor. Such polymers may form a matrix for acting as a carrier coating for one or more antimicrobial compounds in which the antimicrobial is free-floating (i.e., distributed without chemical bonding throughout the matrix). In other embodiments, the polymers may be functionalized to allow direct bonding with one or more antimicrobial compounds (e.g., to have quaternary amine functional groups).

In still other embodiments, the polymer coatings may additionally provide an antimicrobial quality themselves. Suitable such polymers for use in the embodiments of the present disclosure that may provide antimicrobial qualities may include, but are not limited to, those polymers specified above, an organosilane, a quaternary ammonium compounds, 4-vinyl-n-hexylpyridinium bromide, dimethyl(2-methacryloyloxyethyl) phosphonate, poly(ethylene glycol), poly(sulfobetaine methacrylate), poly[3-dimethyl (methacryloyloxyethyl) ammonium propane sulfonate-b-2-(diisopropylamino)ethyl methacrylate], poly(2-methyl-2-oxazoline), a polyphenol, polyhexadine, a chlorohexidine polymer, a nisin-immobilized organosilicon, poly(n,n-diethylethylenediamine-co-aerosol-based acrylic), a benzimidazole polymer, a halogen polymer, a N-halamine polymer, quaternary phosphonium modified epoxidized natural rubber, arginine-tryptophan-rich peptide, guanylated polymethacrylate, polyguanidine, olethyleneimine, chitosan, chitosan derivatives, ammonium ethyl methacrylate homopolymer, metallo-terpyridine carboxymethyl cellulose, poly(N-vinylimidazole) modified silicone rubber, poly-ε-lysine, cationic quaternary polyelectrolytes, 2-(dimethylamino)ethyl methacrylate, a benzaldehyde, 5-chloro-8-hydroxy-quinoline polymers, and the like, any derivatives thereof, any copolymers thereof, and any combination thereof.

One or more antimicrobial compounds may be encapsulated or impregnated in a slow-release compound where the antimicrobial is at least partially surrounded by the encapsulating material or permeating void space (e.g., pores) of an impregnatable material, respectively. Both of the encapsulating material and the impregnatable material may be degradable to allow slow release of the antimicrobial. In other instances, the impregnatable material is not degradable, but instead the antimicrobial is able to leach from the voids of the impregnatable material to provide the desired antimicrobial quality, without degradation of the impregnatable material itself. Such compounds may be located as part of the adhesive pad assemblies and/or the sensor components located at or above the dermis (e.g., the upper portion of the sensor tail or above toward the skin surface and including the skin surface).

Moreover, the encapsulated and/or impregnated antimicrobial compounds may be incorporated into any of the coatings listed above by chemical means (e.g., chemical bonding) or by dispersion (e.g., without chemical bonding or by matrix stabilization), without departing from the scope of the present disclosure. In other embodiments, the encapsulated and/or impregnated antimicrobial compounds may themselves allow covalent or other, such as associative, bonding with one or more components of a sensor described herein, depending on the composition of the encapsulating material and/or impregnatable material, the composition of the sensor component, the location of the sensor component relative to the insertion site, and the like.

An encapsulating material for use in the present disclosure is not considered to be particularly limited provided that as the material degrades and releases the encapsulated antimicrobial it does not interfere with the skin health of a wearer or the functioning of the analyte sensor described herein, and may generally be any biocompatible, degradable material known to one of skill in the art. In some embodiments, the encapsulating material itself is able to provide an antimicrobial quality. Examples of suitable encapsulating materials for use in the embodiments of the present disclosure may include, but are not limited to, the degradable synthetic and natural polymers and proteins described herein, biocompatible or biodegradable ceramics, metallic biocompatible or biodegradable compounds, and the like, and any combination thereof. Examples of biocompatible or biodegradable ceramics for use in the embodiments described herein may include, but are not limited to, calcium sulfate, calcium carbonate, calcium phosphate, dicalcium phosphate, tricalcium phosphate, hydroxyapatite, and the like, and any combination thereof. Examples of metallic biocompatible or biodegradable compounds for use in the embodiments described herein may include, but are not limited to, magnesium-based alloys such as magnesium alloyed with calcium, zinc, aluminum, manganese, indium, silver, zirconium, and the like, and any combination thereof.

An impregnatable material for use in the present disclosure is not considered to be particularly limited provided that the material is able to release an antimicrobial and does not interfere with the skin health of a wearer (i.e., maintains skin health) or the functioning of the analyte sensor described herein, and may generally be any biocompatible material known to one of skill in the art for placement of an antimicrobial. In some embodiments, the impregnatable materials may be generally porous or have areas of void space for filling or penetration by an antimicrobial compound. In other embodiments, the impregnatable materials may be inclusion complexes, such as cyclodextrins (e.g., alpha, beta, or gamma), which may be particularly compatible with a hydrophobic antimicrobial compound (e.g., certain peptides, hydrophobically functionalized polymers, and the like) and which can be released from the cyclodextrin complex upon contact with water, for example, because the outer surface thereof is hydrophilic.

Suitable impregnatable materials may be any of the biocompatible materials, including those that are degradable and those that themselves impart antimicrobial qualities, described herein, and have an antimicrobial permeated therethrough. Some such materials may be made porous and have an antimicrobial permeated therethrough. For example, an antimicrobial may be impregnated into void space of a cellulose or other natural polymer, a metal, a synthetic polymer, a metal oxide, and the like, and any combination thereof.

In some embodiments, the impregnatable material is a nanoparticle composed of one or more of the materials described herein impregnated (or, in some embodiments, made wholly from) one or more antimicrobial compounds, which may be made from any of the biocompatible materials described herein and/or any biocompatible materials known to those of skill in the art. As used herein, the term "nanoparticle," and grammatical variants thereof, refers to a particle having a diameter in the range of about 1 nanometer (nm) to about 1000 nm, encompassing any value and size distribution therebetween. Preferably, a nanoparticle described herein has a diameter in the range of about 1 nm to about 100 nm, encompassing any value and size distribution therebetween. For example, an antimicrobial component may be permeated in void space within or on a nanoparticle (or other impregnatable material) by any means such as chemical deposition (e.g., chemical reduction), sonochemical deposition, solvent impregnation (e.g., supercritical solvent deposition), microwave deposition, simple diffusion (e.g., contained by surface interactions), absorption, adsorption, or any other mechanism known to one of skill in the art. In some embodiments, the nanoparticles may be incorporated with one or more coatings to impart antimicrobial quality. Alternatively, the nanoparticles may themselves have sufficient attraction to one or more surfaces of an analyte sensor to achieve a thin film applied thereupon.

The antimicrobial compounds for use in the present disclosure include all skin-compatible antimicrobial compounds, including those described hereinabove, regardless of their particular form (e.g., coating, particle, and the like), and including an organosilane, a quaternary ammonium, the antimicrobial polymers, and the like, and any combination thereof. Examples of additional antimicrobial compounds, any of which may be used alone or in combination with the aforementioned compounds, may include, but are not limited to, metal-based compounds (e.g., a metal ion, a metal oxide, metal salts, metal coordination compounds including chelates, and the like), iodine, povidone-iodine, chlorhexidine, amphotericin B, bacitracin, colistin, gramicidin, gramicidin S, ritipenem, acediasulfone, acetosulfone, bambermycin(s), brodimoprim, butirosin, capreomycin, carbomycin, dapsone, diathymosulfone, enviomycin, glucosulfone solasulfone, leucomycin(s), lucensomycin, micronomicin, mupirocin, p-sulfanilylbenzylamine, pipemidic acid, polymyxin, primycin, ristocetin, rosaramycin, salazosulfadimidine, succisulfone, sulfachrysoidine, sulfaloxic acid, sulfamidochrysoidine, sulfanilic acid, sulfoxone, teicoplanin, tetroxoprim, thiazolsulfone, thiostrepton, trimethoprim, trospectomycin, tuberactinomycin, vancomycin, azaserine, candicidin(s), chlorphenesin, dermostatin(s), filipin, fungichromin, nystatin, oligomycin(s), perimycin A, tubercidin, carbapenems (e.g., faropenem, imipenem, panipenem, biapenem, meropenem, doripenem, ertapenem, and the like), cephalosporins (e.g., cefoxitin, cefotaxime, cefepime, nitrocefin, cefpirome, ceftobiprole, ceftazidime, ceftriaxone, cefadroxil, cefamandole, cefatrizine, cefbuperazone, cefclidin, cefdinir, cefditoren, cefetamet, cefixime, cefinenoxime, cefminox, cefodizime, cefonicid, cefoperazone, ceforanide, cefotetan, cefotiam, cefozopran, cefpimizole, cefpiramide, cefprozil, cefroxadine, cefteram, ceftibuten, cefuzonam, cephalexin, cephaloglycin, cephalosporin C, cephradine, flomoxef, moxalactam, and the like), monocyclic beta-lactams (e.g., aztreonam, tigemonam, carumonam, BAL19764, nocardicin, BAL30072, and the like), oxazolidinones (e.g., linezolid, sutezolid, and the like), penicillins (e.g., aminopenicillanic acid, benzylpenicillin, ampicillin, amoxicillin, carbenicillin, ticarcillin, oxacillin, azlocillin, dicloxacillin, piperacillin, apalcillin, temocillin, aspoxicillin, cyclacillin, epicillin, hetacillin, quinacillin, and the like), quinolones (e.g., nalidixic acid, norfloxacin, enoxacin, ciprofloxacin, enrofloxacin, levofloxacin, fleroxacin, clinafloxacin, grepafloxacin, lomefloxacin, nadifloxacin, pazufloxacin, temafloxacin, tosufloxacin, trovafloxacin, ciproflaxacin, ofloxacin, pefloxacin, rosoxacin, amifloxacin, temafloaxcin, lomefloxacin, sparfloxacin, and the like), tetracyclins (e.g., tetracycline, minocycline, tigecycline, apicycline, chlortetracycline, clomocycline, demeclocycline, doxycycline, guamecycline, lymecycline, meclocycline, methacycline, oxytetracycline, pipacycline, rolitetracycline, sancycline, and the like), aminoglycosides (e.g., amikacin, and the like), beta-lactamase inhibitors (e.g., clavulanic acid, sulbactam, avibactam, tazobactam, BAL29880, and the like), aminonucleosides (e.g., puromycin, and the like), aminoglycosides (e.g., apramycin, a kanamycin, isepamicin, a fortimicin, a gentamicin, neomycin, netilmicin, streptomycin, spectinomycin, arbekacin, dibekacin, dihydrostreptomycin, paromomycin, ribostamycin, sisomicin, tobramycin, and the like), anthracyclines (e.g., doxorubicin, daunorubicin, and the like), pimaricins (e.g., natamycin, and the like), sulfanilamides (e.g., 4,4'-sulfinyldianiline, 2-p-sulfanilyanilinoethanol, 4-sulfanilamidosalicylic acid, and the like), macrolides (e.g., mepartricin, spiramycin, clarithromycin, dirithromycin, erythromycin, josamycin, a midecamycin, oleandomycin, rokitamycin, roxithromycin, and the like), peptidyl transferase amphenicols (e.g., azidamfenicol, azithromycin, chloramphenicol, thiamphenicol, and the like), lincosamides (e.g., clindamycin, lincomycin, and the like), ansamycins (e.g., rifamycin SV, rifampin, rifapentine, rifaximin, rifamide, and the like), and the like, and any combinations thereof.

Examples of metal-based antimicrobial compounds may include, but are not limited to, silver, copper, magnetite, gold, gallium, platinum, palladium, titanium dioxide, zinc oxide, magnesium oxide, silicon dioxide, iron oxide, carbon dioxide, copper oxide, nitric oxide, carbon nanotubes, and the like (e.g., other antimicrobial heavy metal ions and/or metal oxides), any alloys thereof, any salts thereof, any coordination complexes and/or chelates thereof, any combination thereof, and any combination thereof in addition to one or more of the aforementioned antimicrobial compounds described herein.

In some embodiments, these metal-based antimicrobials may be metal-containing nanoparticles, such as impregnated or made whole from the antimicrobial compound, including as non-limiting examples, silver nanoparticles, zinc oxide nanoparticles, iron oxide nanoparticles, copper nanoparticles, and the like.

The particular amount of antimicrobial provided to any one or more components of the sensor and/or to the skin of a sensor wearer may depend on a number of factors including, but not limited to, the physiology and daily routine of a wearer, the area of the sensor to which the antimicrobial quality is imparted, the particular antimicrobial mechanism and compound selected, and the like. In nonlimiting embodiments, the antimicrobial quality (or qualities) is incorporated in an amount of about 0.01% to about 20% by weight of the antimicrobial carrier (e.g., coating, encapsulant, and the like) or surface area to which it is applied (e.g., upper portion of the sensor tail), encompassing any value or subset therebetween, depending broadly on at least one or more of the factors provided above. It is to be understood that the ideal antimicrobial quality amount will be based on ensuring adequate antimicrobial protection without compromising the functionality of the sensor.

It is to be understood that the skin interacting components of the sensor itself may impart an antimicrobial quality in addition to the one or more adhered or applied antimicrobial qualities described herein. Moreover, a component of the sensing element (e.g., enzyme such as glucose oxidase) for a particular desired analyte being measured may additionally provide an antimicrobial quality, without departing from the scope of the present disclosure.

Embodiments disclosed herein include:

Embodiment D: Die-cut, asymmetric double-sided adhesive binders. The binders comprise: a non-woven scrim having a first face and a second face in opposition to one another; a first pressure-sensitive adhesive layer comprising a first pressure-sensitive adhesive disposed upon the first face of the non-woven scrim; and a second pressure-sensitive adhesive layer comprising a second pressure-sensitive adhesive disposed upon the second face of the non-woven scrim; wherein the first and second pressure-sensitive adhesives differ from one another; and wherein a plurality of perforations are defined in at least the first pressure-sensitive adhesive layer, and the second pressure-sensitive adhesive layer is adapted to face a skin surface.

Embodiment E: Adhesive pad assemblies. The assemblies comprise: a non-woven scrim having a first face and a second face in opposition to one another; a first pressure-sensitive adhesive layer comprising a first pressure-sensitive adhesive disposed upon the first face of the non-woven scrim; a second pressure-sensitive adhesive layer comprising a second pressure-sensitive adhesive disposed upon the second face of the non-woven scrim; wherein the first and second pressure-sensitive adhesives differ from one another; and wherein a plurality of perforations are defined in at least the first pressure-sensitive adhesive layer; a non-woven material adhesively bonded to the second pressure-sensitive adhesive layer, the non-woven material having a higher areal mass than the non-woven scrim; and a third pressure-sensitive adhesive layer comprising a third pressure-sensitive adhesive disposed upon the non-woven material opposite the second pressure-sensitive adhesive layer.

Embodiment F: Adhesively bound sensor constructs. The constructs comprise: a non-woven scrim having a first face and a second face in opposition to one another; a first pressure-sensitive adhesive layer comprising a first pressure-sensitive adhesive disposed upon the first face of the non-woven scrim; a second pressure-sensitive adhesive layer comprising a second pressure-sensitive adhesive disposed upon the second face of the non-woven scrim; wherein the first and second pressure-sensitive adhesives differ from one another; and wherein a plurality of perforations are defined in at least the first pressure-sensitive adhesive layer; a non-woven material adhesively bonded to the second pressure-sensitive adhesive layer, the non-woven material having a higher areal mass than the non-woven scrim; a third pressure-sensitive adhesive layer comprising a third pressure-sensitive adhesive disposed upon the non-woven material opposite the second pressure-sensitive adhesive layer; and a sensor housing adhesively bonded to the first pressure-sensitive adhesive layer, the sensor housing having a sensor protruding therefrom, and the sensor extending longitudinally through the first pressure-sensitive adhesive, the non-woven scrim, the second pressure-sensitive adhesive, the non-woven material, and the third pressure-sensitive adhesive layer.

Each of embodiments D, E, and F may have one or more of the following additional elements in any combination Element 1: wherein the non-woven scrim comprises a polyester or a polyethylene.

Element 2: wherein the non-woven scrim has an areal mass ranging between about 3 g/m2 and about 20 g/m2.

Element 3: wherein the first pressure-sensitive adhesive comprises a rubber-based adhesive.

Element 4: wherein the second pressure-sensitive adhesive comprises an acrylic adhesive.

Element 5: wherein the non-woven scrim comprises a polyester or a polyethylene, the first pressure-sensitive adhesive comprises a rubber-based adhesive, and the second pressure-sensitive adhesive comprises an acrylic adhesive.

Element 6: wherein the plurality of perforations comprise a plurality of slots defined in at least the first pressure-sensitive adhesive layer.

Element 7: wherein the plurality of slots are each substantially parallel to one another.

Element 8: wherein the binder further comprises: a macroaperture extending longitudinally through the non-woven scrim, the first pressure-sensitive adhesive layer and the second pressure-sensitive adhesive layer; wherein the macroaperture is sized to circumferentially surround a sensor module of an on-body analyte sensor.

Element 9: wherein the areal mass of the non-woven material is at least about five times higher than that of the non-woven scrim.

Element 10: wherein the non-woven material comprises a polyester or a polyethylene.

Element 11: wherein the first pressure-sensitive adhesive comprises a rubber-based adhesive, and the second pressure-sensitive adhesive comprises an acrylic adhesive.

Element 12: wherein the third pressure-sensitive adhesive comprises an acrylic adhesive.

Element 13: wherein the non-woven scrim comprises a polyester or a polyethylene, and the non-woven material comprises a polyester or a polyethylene.

Element 14: wherein the adhesive pad assembly further comprises: a macroaperture extending longitudinally through the first pressure-sensitive adhesive layer, the non-woven scrim, the second pressure-sensitive adhesive layer, the non-woven material, and the third pressure-sensitive adhesive layer; wherein the macroaperture is sized to circumferentially surround a sensor module of an on-body analyte sensor.

Element 15: wherein the sensor housing comprises a grooved surface that is adhesively bonded to the first pressure-sensitive adhesive layer.

Element 16: wherein at least one of the non-woven scrim, the first pressure-sensitive adhesive layer, the second pressure-sensitive adhesive layer, the non-woven material, and the third pressure-sensitive adhesive layer comprises an antimicrobial quality.

By way of non-limiting example, exemplary combinations applicable to D, E, and F include:

The binder of D in combination with elements 1 and 2; 1 and 3; 2 and 3; 3 and 4; 2 and 5; 1 and 6; 1, 6 and 7; 2 and 6; 2, 6 and 7; 3 and 6; 3, 6 and 7; 4 and 6; 4, 6 and 7; 1 and 8; 2 and 8; 3 and 8; 4 and 8; 5 and 8; 6 and 8; 6-8, 1 and 16; 2 and 16; 3 and 16; 4 and 16; 5 and 16; 6 and 16; 7 and 16; and 8 and 16. The assembly of E in combination with elements 1 and 2; 1 and 3; 2 and 3; 3 and 4; 2 and 5; 1 and 6; 1, 6 and 7; 2 and 6; 2, 6 and 7; 3 and 6; 3, 6 and 7; 4 and 6; 4, 6 and 7; 1 and 8; 2 and 8; 3 and 8; 4 and 8; 5 and 8; 6 and 8; 6-8; 1 and 9; 2 and 9; 3 and 9; 4 and 9; 5 and 9; 6 and 9; 6, 7 and 9; 1 and 10; 2 and 10; 3 and 10; 4 and 10; 6 and 10; 6, 7 and 10; 11 and 12; 12 and 13; 1 and 14; 2 and 14; 3 and 14; 4 and 14; 5 and 14; 6 and 14; 6, 7 and 14; 10 and 14; 11 and 14; 12 and 14; 13 and 14; 1 and 16; 2 and 16; 3 and 16; 4 and 16; 5 and 16; 6 and 16; 7 and 16; 8 and 16; 9 and 16; 10 and 16; 11 and 16; 12 and 16; 13 and 16; and 14 and 16. The construct of F in combination with elements 1 and 2; 1 and 3; 2 and 3; 3 and 4; 2 and 5; 1 and 6; 1, 6 and 7; 2 and 6; 2, 6 and 7; 3 and 6; 3, 6 and 7; 4 and 6; 4, 6 and 7; 1 and 8; 2 and 8; 3 and 8; 4 and 8; 5 and 8; 6 and 8; 6-8; 1 and 9; 2 and 9; 3 and 9; 4 and 9; 5 and 9; 6 and 9; 6, 7 and 9; 1 and 10; 2 and 10; 3 and 10; 4 and 10; 6 and 10; 6, 7 and 10; 11 and 12; 12 and 13; 1 and 14; 2 and 14; 3 and 14; 4 and 14; 5 and 14; 6 and 14; 6, 7 and 14; 10 and 14; 11 and 14; 12 and 14; 13 and 14; 1 and 16; 2 and 16; 3 and 16; 4 and 16; 5 and 16; 6 and 16; 7 and 16; 8 and 16; 9 and 16; 10 and 16; 11 and 16; 12 and 16; 13 and 16; and 14 and 16, and any of which in further combination with element 15.

Adhesive Overbandages for On-Body Analyte Sensors

As discussed above, on-body analyte sensors may provide a number of advantages when assaying physiological levels of one or more analytes. Overbandages may be used in combination with on-body analyte sensors to promote more secure sensor adherence to a wearer's skin. However, it can sometimes be difficult to seat an overbandage properly against a sensor housing, particularly when the on-body analyte sensor resides in a location that is difficult for a wearer to access or see, such as upon the underside of the triceps. In some instances, improper overbandage seating can lead to sensor displacement or movement in its own right, which may lead to inaccurate measurement of in vivo analyte levels.

The present disclosure is directed to overbandages configured for ready attachment to a skin surface in proximity to a sensor housing of an on-body analyte sensor. As used herein, the term "skin surface" refers to the actual skin surface of an on-body sensor wearer or an adhesive layer applied to a wearer's skin. The term "skin surface" may be used interchangeably with the term "skin" when referencing the attachment location of an overbandage. Thus, the present disclosure encompasses both direct and indirect skin surface contact with an overbandage, either of which can aid in securing an on-body analyte sensor in place. Advantageously, the overbandages of the present disclosure are capable of providing tactile feedback to a wearer when performing an attachment thereof to the skin, such that the wearer can determine when the overbandage has been correctly seated against a sensor housing. By being capable of self-promoting their proper seating, the overbandages disclosed herein may lessen the likelihood of inadvertent sensor displacement resulting from overbandage misalignment.

More specifically, the overbandages of the present disclosure are configured such that they may receive the sensor housing within a recess during overbandage seating and then circumferentially surround and engage the sensor housing upon a skin surface after unfolding the overbandage to reveal an enclosed aperture. The overbandages of the present disclosure are further advantageously configured to receive the sensor housing laterally, rather than through the more common longitudinal loading direction, which allows the features herein to be realized.

The overbandages of the present disclosure are also designed such that various adhesive portions thereof can be exposed sequentially in the course of being seated in engagement with a sensor housing. In particular, the overbandages may comprise multiple peelable release liners that are independently releasable (removable) to expose a given adhesive surface at a desired time. By exposing an adhesive surface only just before skin adherence is desired, the overbandages of the present disclosure may be less susceptible to twisting and/or adhesive fouling that may be common with other types of overbandages. At least some of the peelable release liners may also comprise a rigid material for lessening the likelihood of overbandage twisting, thereby conveying rigidity to the overbandage prior to exposing the adhesive surface.

In addition, the overbandages of the present disclosure may comprise an anchoring adhesive strip that is exposed early in the course of overbandage attachment to a skin surface. The anchoring adhesive strip may aid in holding the overbandage in its proper location on a skin surface while revealing other adhesive surfaces, such as through the removal of additional peelable release liners, and promoting correct seating of the overbandage on the skin surface in proximity to an on-body analyte sensor.

Finally, the overbandages disclosed herein may be advantageously fabricated from breathable materials that provide a high moisture vapor transfer rate (MVTR), such as within a range of about 200 g/m2/day or greater (e.g., about 200 g/m2/day to about 2500 g/m2/day), when applied to a skin surface in proximity to an on-body analyte sensor. By choosing materials that promote high MVTR values, issues associated with moisture retention at the skin surface, such as maceration, irritation, infection and the like, can be significantly lessened. Various materials capable of promoting high MVTR values are readily compatible with the overbandages of the present disclosure, as discussed hereinbelow.

The overbandages disclosed herein may aid in promoting skin health at a site of attachment, contained or internal site of attachment, and/or adjacent to the site of attachment of an analyte sensor. For example, an antimicrobial substance may be incorporated within any of the adhesive binders, contact adhesive layer, or components of the analyte sensor itself, or may be applied to the skin prior to contact with any components of the overbandage or components of the analyte sensor itself. In addition, an antimicrobial substance may be incorporated locally or homogeneously along, within, or upon any edge/perimeter/layer/surface of the analyte sensor. The antimicrobial substance may aid in preventing microorganism incursion into the wound at the site of sensor insertion, thereby lowering the likelihood of infection or skin irritation over extended sensor wear. In addition to promoting skin health, the antimicrobial substance may also inhibit formation of a biofilm residue and/or microbial colonization that may or may not form a biofilm residue upon the inserted sensor tail, which may promote better sensor performance over extended wear times.

Before discussing the overbandages of the present disclosure in further detail, a brief overview of on-body analyte sensors will be provided so that the embodiments of the present disclosure can be better understood. On-body analyte sensors suitable for use in conjunction with the overbandages of the present disclosure may be dermal sensors, according to some embodiments. Illustrative on-body analyte sensors, particularly dermal sensors that may be utilized in conjunction with the overbandages of the present disclosure include those described in more detail in commonly owned U.S. Pat. No. 9,668,686 and commonly owned U.S. Patent Application Publications 2012/0190941, 2016/0331283 and 2017/0196487, each of which is incorporated herein by reference in its entirety.

FIG. 8 shows a diagram of bottom face 105 of sensor housing 103 in an illustrative configuration. As shown, aperture 804 extends through bottom face 105, through which a needle (not shown) may extend and then retract when deploying sensor housing 103 on a tissue surface. Also in proximity to aperture 804 is receptacle 806, within which a sensor module (not shown) may be seated and from which sensor 104 extends once sensor housing 103 is deployed on a skin surface. Bottom face 105 may be grooved and contain a plurality of grooves. At least a portion of the grooves may be radial grooves 800*a* that extend from aperture 804 and/or receptacle 806 to outer perimeter face 802. Radial grooves 800*a* may establish fluid communication between aperture 804 and/or receptacle 806 and outer perimeter face 802 and thus may promote fluid drainage away from sensor housing 103. In some embodiments, at least a portion of radial grooves 800*a* may not extend all the way to aperture 804 and/or receptacle 806. Moreover, in some embodiments, at least a portion of the grooves may be circumferential grooves 800*b* that intersect with radial grooves 800*a*. Also shown in FIG. 2 are recessed carrier grips 810, which may aid in releasing sensor housing 103 from a deployment tool used for attachment to a skin surface. The deployment tool may seat a sensor module in receptacle 806 in the course of skin attachment.

The overbandages of the present disclosure may be configured to circumferentially surround sensor housing 103, according to one or more embodiments, particularly by engaging at least a portion of sensor housing 103 upon outer perimeter face 802 in the course of seating the overbandage. Although the term "circumferential" and variants thereof may be associated with a generally circular shape in some instances, it is to be understood that this term herein refers to any closed geometric shape having an interior space therein, particularly a symmetrical closed geometric shape. As such, the overbandages of the present disclosure may be adapted to circumferentially surround both circular and substantially circular sensor housings 103, as well as those having non-circular geometric shapes, such as ovular, square, rectangular, triangular, pentagonal, hexagonal, and the like, as well as asymmetrical sensor housings. Overbandages of the present disclosure may, in some embodiments, engage sensor housing 103 around the entirety of outer perimeter face 802, or at one or more discontinuous points around outer perimeter face 802, in other embodiments.

Accordingly, in some embodiments, overbandages of the present disclosure may comprise: a vapor-permeable backing, an aperture defined in the vapor-permeable backing and sized to circumferentially surround a sensor housing that is adapted for adhering to a skin surface, and a contact adhesive layer disposed on one side of the vapor-permeable backing. According to various embodiments, a second side of the vapor-permeable backing may be substantially adhesive-free. The contact adhesive layer comprises an anchoring adhesive strip contacting the aperture, a first adhesive portion laterally arranged to a first side of the anchoring adhesive strip, and a second adhesive portion laterally arranged to a second side of the anchoring adhesive strip. Additionally, the overbandages comprise first and second peelable release liners disposed upon first and second adhesive portions, and a third peelable release liner disposed upon the anchoring adhesive strip.

The overbandages of the present disclosure will now be described in greater detail with reference to the drawings. Where feasible, and in the interest of brevity, common reference characters are used to denote elements previously described. Moreover, previously described elements are only addressed in brief in the description that follows.

Figure 17A:
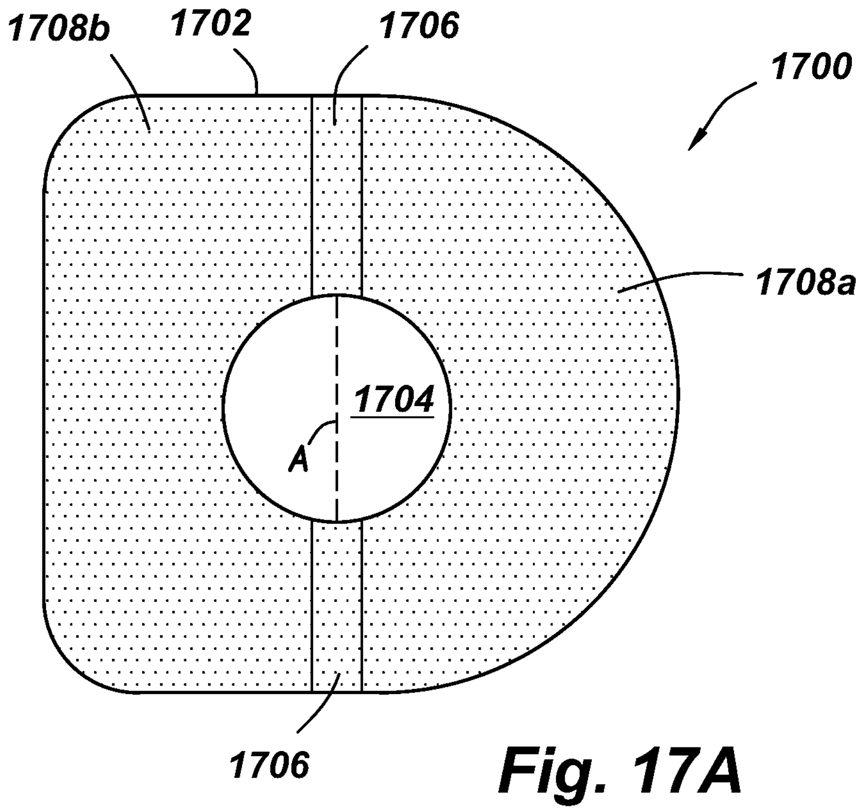
FIGS. 17A-17G show top or bottom perspective view diagrams of various overbandage configurations of the present disclosure.
Figure 17B:
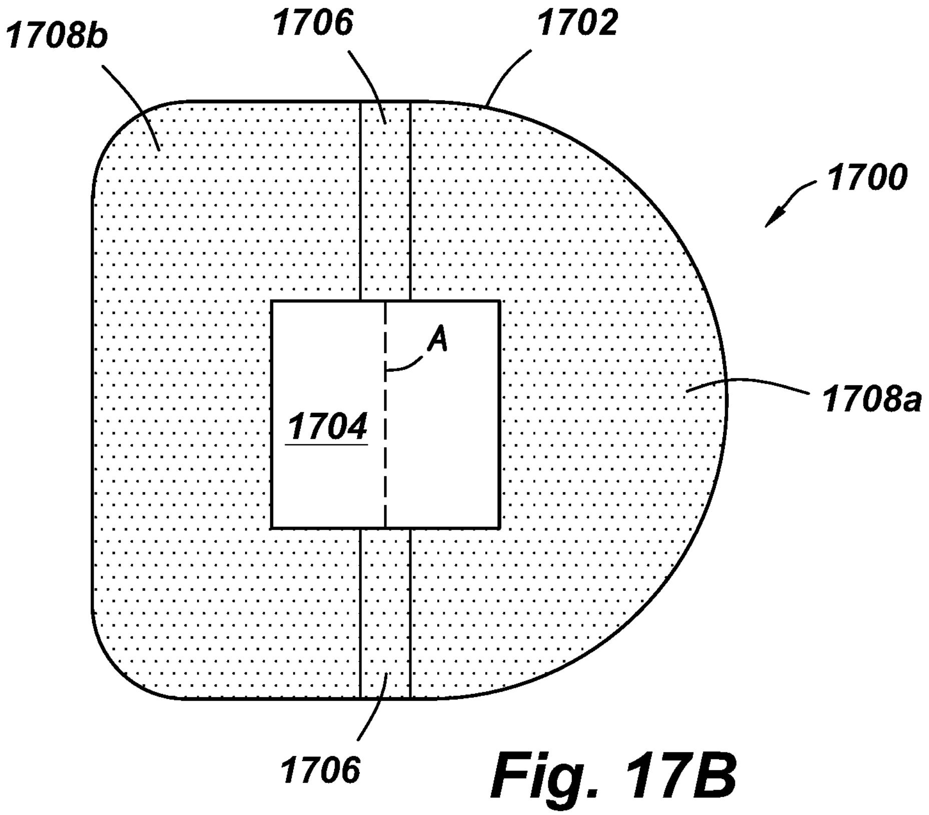

FIGS. 17A-17H show top or bottom perspective views of various overbandage configurations of the present disclosure. FIG. 17A shows top face 1702 of overbandage 1700. No contact adhesive (pressure-sensitive adhesive) layer is present upon the vapor-permeable backing at top face 1702. Aperture 1704 is defined within the interior of the vapor-permeable backing, such that aperture 1704 can circumferentially surround sensor housing 103 once overbandage 1700 has been applied to a skin surface (e.g., see FIGS. 18A and 18B). Although depicted as being circular in FIG. 17A, aperture 1704 may comprise any symmetrical geometric shape, such as ovular, square, rectangular, or the like (e.g., see FIG. 17B for an alternative configuration, in which aperture 1704 is square), according to some embodiments.

Asymmetrical geometric shapes for aperture 1704 can also be suitable in some instances. Choice of a suitable shape for aperture 1704 may be dictated by the shape of a sensor housing to be located therein. As used herein, the term "symmetrical" refers to a geometric shape that can be bisected by at least one symmetry line. As such, the depiction of aperture 1704 as being circular in various drawings herein should not be considered limiting, unless clearly specified as representing one or more particular embodiments. Top face 1702 further includes crease 1706 and non-folding faces 1708*a,b* arranged on opposing lateral sides of crease 1706, wherein at least crease 1706 contacts aperture 1704. Non-folding faces 1708*a,b* may also contact aperture 1704, in some embodiments.

Figure 17C:
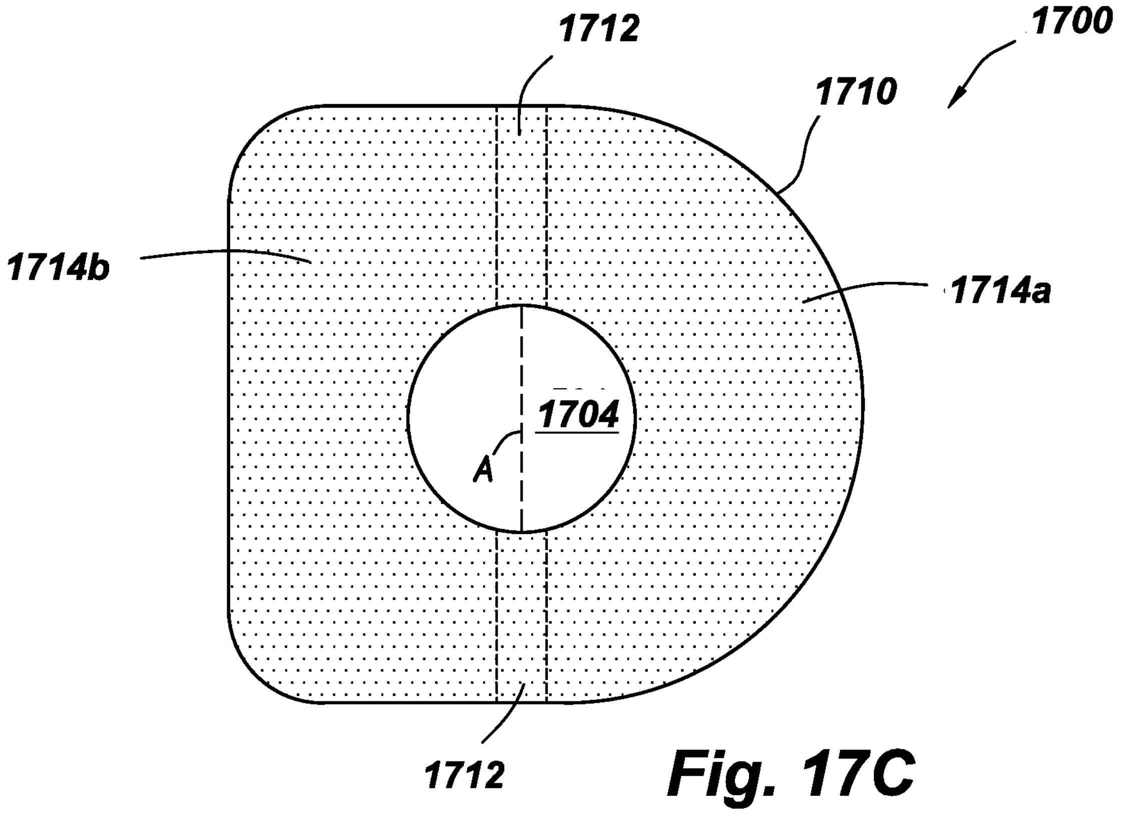
Figure 17D:
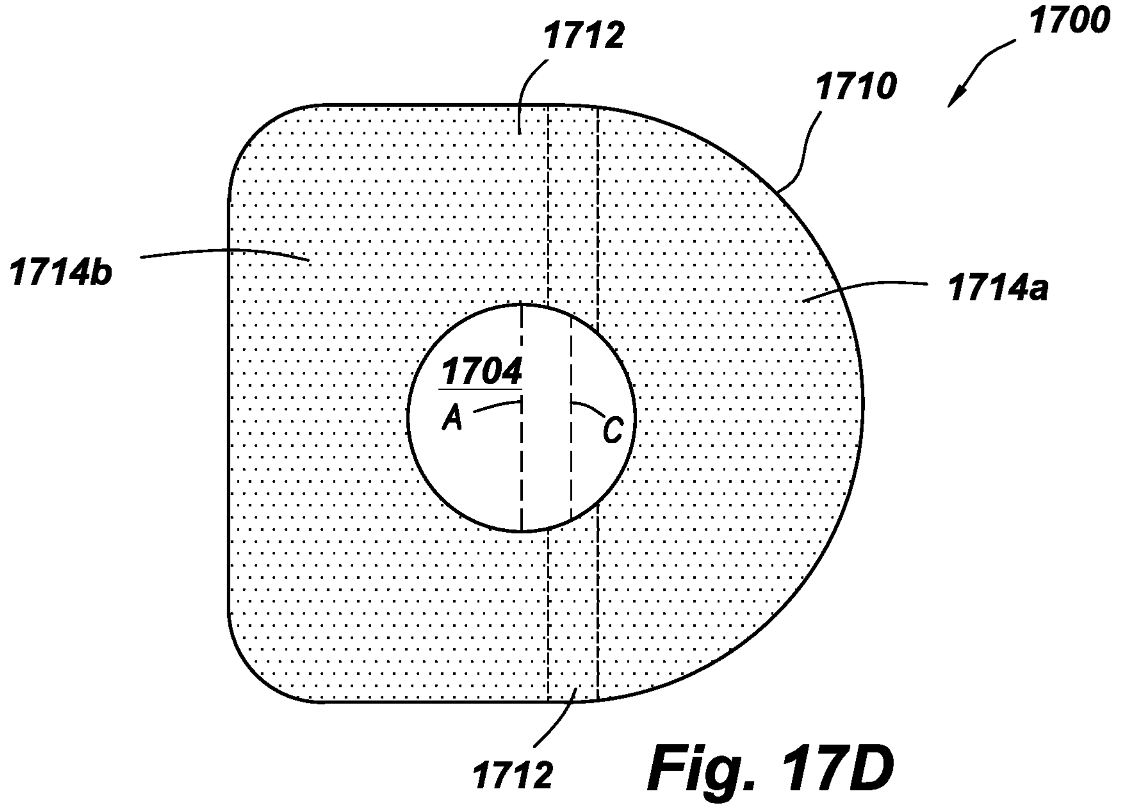
Figure 17E:
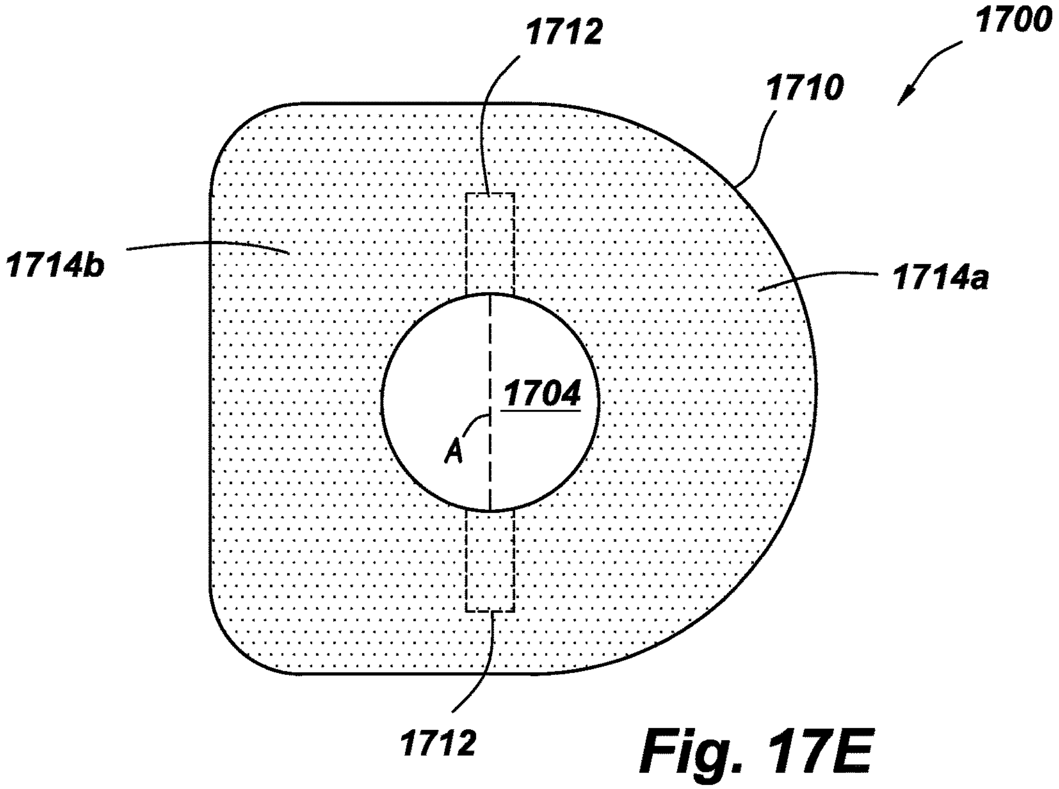

FIGS. 17C-17G show bottom face 1710 of overbandage 1700, in which aperture 1704 is circular. A contact adhesive layer, regionally disposed as described hereinafter, is present upon the vapor-permeable backing at this location. Various peelable release liners may be located upon the contact adhesive layer (see FIGS. 17F and 17G) in a manner such that they can be removed sequentially from bottom face 1710 in the course of seating overbandage 1700 proximate to sensor housing 103, as desired herein. FIGS. 17C-17E have omitted the various peelable release liners in order to depict the regional adhesive disposition more clearly within the contact adhesive layer. More specifically, as shown in FIG. 17C, bottom face 1710 of overbandage 1700 comprises anchoring adhesive strip 1712. The width of anchoring adhesive strip 1712 may be defined by the size of the peelable release liner initially covering it or by the width of crease 1706. In general, crease 1706 on top face 1702 is disposed opposite anchoring adhesive strip 1712 on bottom face 1710. Anchoring adhesive strip 1712 contacts aperture 1704 in a manner such that first and second strip portions are disposed on opposing sides of aperture 1704. As such, according to various embodiments, anchoring adhesive strip 1712 is discontinuous at aperture 1704. Bottom face 1710 of overbandage 1700 also comprises adhesive portions 1714*a,b* that are laterally arranged on first and second sides of anchoring adhesive strip 1712. Non-folding faces 1708*a,b* on top face 1702 are disposed opposite adhesive portions 1714*a,b* on bottom face 1710.

As depicted, adhesive portions 1714*a,b* are contiguous with anchoring adhesive strip 1712, such that substantially all of bottom face 1710 is covered with a continuous contact adhesive layer. It is to be recognized, however, that the contact adhesive layer may, in some embodiments, comprise one or more discontinuities while still fulfilling its intended purpose. For example, anchoring adhesive strip 1712 and/or adhesive portions 1714*a,b* may comprise a patterned contact adhesive (e.g., discrete strips, dots, lines, or a combination thereof), such that less than the entirety of bottom face 1710 is covered with a contact adhesive layer. In either configuration, anchoring adhesive strip 1712 may comprise the same contact adhesive as adhesive portions 1714*a,b* or the contact adhesive may be different in one or more locations. In particular embodiments, anchoring adhesive strip 1712 and adhesive portions 1714*a,b* may comprise the same contact adhesive and have the same adhesive thickness at each location.

In some embodiments and as depicted in FIGS. 17C and 17E, anchoring adhesive strip 1712 may reside coincident (centered) with symmetry line A, which divides aperture 1704 into equal-sized portions of identical shape. As used herein, the term "coincident" refers to a placement of anchoring adhesive strip 1712 upon symmetry line A, such that symmetry line A also symmetrically divides anchoring adhesive strip 1712. Symmetry line A may represent a diameter when aperture 1704 is circular. In alternative embodiments, anchoring adhesive strip 1712 may reside off-center while still remaining consistent with the features of the present disclosure. Off-center positioning of anchoring adhesive strip 1712 may include embodiments in which anchoring adhesive strip 1712 overlaps symmetry line A but is not centered thereon or embodiments in which anchoring adhesive strip 1712 does not overlap symmetry line A. In both of these alternative embodiments, anchoring adhesive strip 1712 remains parallel to symmetry line A. Accordingly, FIG. 17D shows an alternative configuration of overbandage 1700, in which anchoring adhesive strip 1712 is centered upon chord C while still remaining parallel to symmetry line A. Anchoring adhesive strip 1712 does not overlap symmetry line A in the depicted configuration, although it may do so in some instances, as described above. Adhesive portions 1714*a,b* continue to remain laterally arranged on opposing sides of anchoring adhesive strip 1712 in these alternative configurations.

Moreover, although anchoring adhesive strip 1712 is depicted as spanning entirely across bottom face 1710 in FIGS. 17C and 17D (i.e., edge-to-edge across bottom face 1710), anchoring adhesive strip 1712 may span less than the entirety of bottom face 1710 in some alternative configurations. For example, FIG. 17E shows an alternative configuration of overbandage 1700, in which anchoring adhesive strip 1712 still contacts aperture 1704 but does not span across the entirety of bottom face 1710.

Various peelable release liners may be removably affixed to the contact adhesive layer prior to application of overbandage 1700 to a skin surface. The various peelable release liners may be configured for sequential removal to expose a particular portion of the contact adhesive layer at a desired time for adherence to a skin surface, as described hereinbelow. Before further describing the manner in which overbandage 1700 may be applied to a skin surface in proximity to sensor housing 103, a more detailed description of the disposition of the various peelable release liners will first be provided.

Figure 17F:
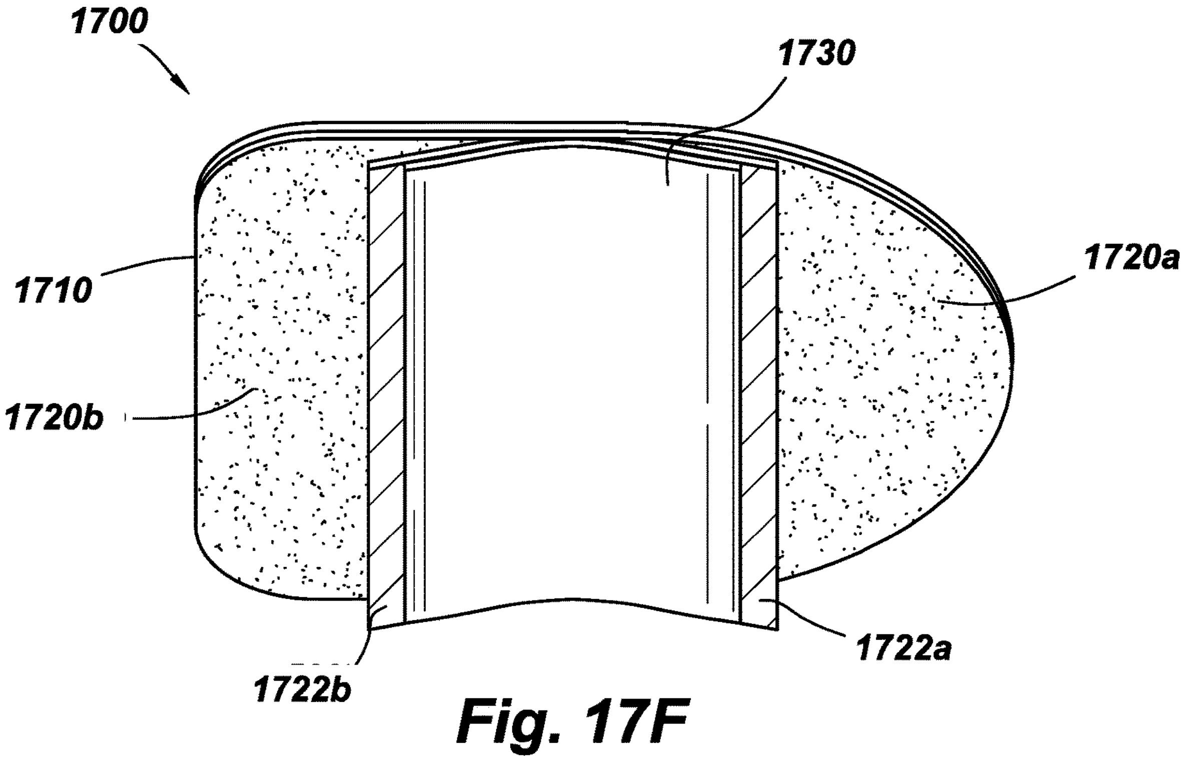
Figure 17G:
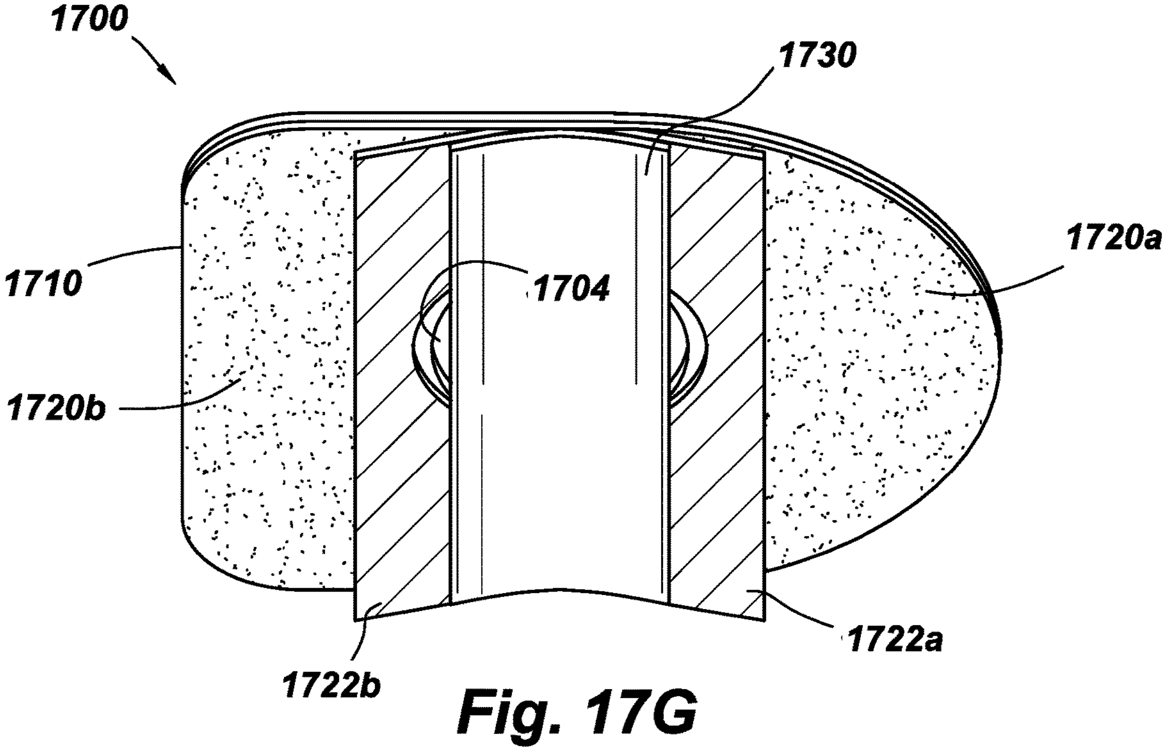

FIGS. 17F and 17G show perspective views of bottom face 1710 of overbandage 1700 with various peelable release liners in place upon the contact adhesive layer. As shown in FIGS. 17F and 17G, peelable release liners 1720*a,b* are positioned to overlay corresponding adhesive portions 1714*a,b*. Peelable release liners 1720*a,b* contain corresponding flaps 1722*a,b*, which are each folded upwardly with respect to the plane of the contact adhesive layer. Flaps 1722*a,b* enable a user to affect removal of peelable release liners 1720*a,b* by pulling on flaps 1722*a,b* at a desired time in the course of seating overbandage 1700 around sensor housing 103, as described hereinbelow. Peelable release liner 1730 is positioned to overlay at least anchoring adhesive strip 1712. As depicted in FIG. 17F, peelable release liner 1730 is sized such that it occludes aperture 1704 (obscured in FIG. 17F) and overlays at least a portion of peelable release liners 1720*a,b*, specifically a portion of flaps 1722*a,b*. Accordingly, in the configuration depicted in FIG. 17F, peelable release liner 1730 needs to be removed first before removing either of peelable release liners 1720*a,b* in order to affect sequential removal. Peelable release liner 1730 may be smaller in alternative configurations, however. For example, as depicted in FIG. 17G, peelable release liner 1730 may still overlay a portion of flaps 1722*a,b* without occluding the entirety of aperture 1704. In still other embodiments, peelable release liner 1730 may include a punchout, such that at least a portion of aperture 1704 is not occluded. In still other alternative configurations, peelable release liner 1730 may abut peelable release liners 1720*a,b* but without overlapping flaps 1722*a,b*.

Figure 17H:
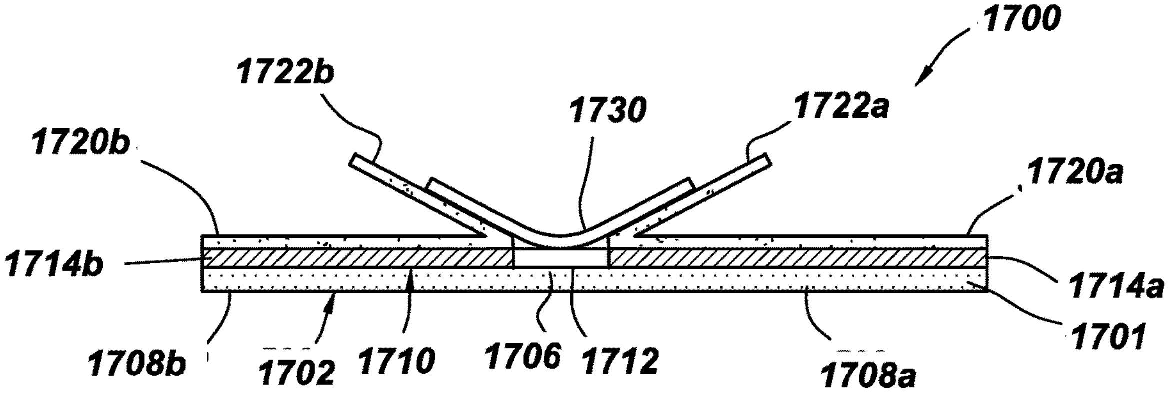
FIG. 17H shows a side view diagram of the overbandage configuration of FIG. 17F, with all peelable release liners in place.

FIG. 17H shows a side view diagram of the overbandage configuration of FIG. 17F, with peelable release liners 1720*a,b* and 1730 all in place upon bottom face 1710 of vapor-permeable backing 1701. As depicted, peelable release liners 1720*a,b* are positioned upon corresponding adhesive portions 1714*a,b* and peelable release liner 1730 is positioned upon anchoring adhesive strip 1712. Peelable release liner 1730 further overlays at least a portion of flaps 1722*a,b* in the depicted configuration. Although FIG. 17H has shown peelable release liner 1730 as having a substantially curvilinear shape, the depicted shape should not be considered limiting. Moreover, in some embodiments, peelable release liner 1730 may be planar or substantially planar, which may force flaps 1722*a,b* downward in order for peelable release liner 1730 to engage anchoring adhesive strip 1712 to a sufficient degree. More rigid materials within peelable release liner 1730 may favor the folding of flaps 1722*a,b* downward. When peelable release liner 1730 comprises sufficiently flexible materials, the configuration depicted in FIG. 17H may be more prevalent. Ridigity within peelable release liner 1730 may also aid in precluding overbandage 1700 from becoming twisted or bent prior to becoming adhered to a skin surface.

Overbandages of the present disclosure, such as overbandage 1700, may be configured to afford high MVTR values when used in combination with a sensor housing in an adhesive bonding configuration upon a skin surface. Factors that may determine attainable MVTR values include, for example, the identity and thickness of vapor-permeable backing 1701, the identity and thickness of the contact adhesive within the contact adhesive layer, the manner in which the sensor housing is adhered to the skin surface, and the like.

Particular materials that may comprise vapor-permeable backing 1701 in overbandage 1700 are not considered to be especially limited. In various embodiments, vapor-permeable backing 1701 may comprise a woven or non-woven fabric material comprising natural fibers, synthetic fibers, or any combination thereof. Illustrative synthetic fibers that may be present in vapor-permeable backing 1701 include, but are not limited to, polyurethane fibers, polyester fibers, polyamide fibers, polyolefin fibers, polyvinyl acetate fibers, polyethylene oxide fibers, ethylene vinyl acetate fibers, copolymers thereof, combinations thereof, and the like. Especially suitable materials for vapor-permeable backing 1701 may include, for example, polyurethanes, polyethylene, polypropylene, polyesters, and the like. In more particular embodiments of the present disclosure, vapor-permeable backing 1701 may comprise polyethyleneterephthalate (PET) fibers or similar polyester fibers, such as a non-woven PET fabric vapor-permeable backing.

Vapor-permeable backing 1701, upon which the contact adhesive layer is disposed, may be single-layered or multilayered, in various embodiments. The thickness of vapor-permeable backing 1701 is not considered to be especially limited. In various embodiments, vapor-permeable backing 1701 may have a thickness that is less than sensor housing 103. In still more particular embodiments, vapor-permeable backing 1701 may have a thickness that is less than about 90% that of sensor housing 103, or less than about 50% that of sensor housing 103, or less than about 25% that of sensor housing 103, or less than about 10% that of sensor housing 103. In more specific embodiments, the thickness of vapor permeable backing 1701 plus the contact adhesive layer thereon may range between about 0.005 mm to about 5 mm. Maintaining vapor-permeable backing 1701 at a thickness that is as thin as feasibly possible can both promote vapor permeability and facilitate folding of overbandage 1700 during seating, as described in more detail below.

In some embodiments, the thickness of vapor-permeable backing 1701 at crease 1706/anchoring adhesive strip 1712 may be greater than the rest of vapor-permeable backing 1701. Having an increased thickness in this location may aid in rigidifying overbandage 1700 sufficiently to limit twisting during application to a skin surface.

The shape of vapor-permeable backing 1701, as well as the shape of resulting overbandage 1700, is likewise not considered to be particularly limited. Illustrative shapes that may be suitable for overbandage 1700 include, but are not limited to, square, rectangular, circular, ovular, polygonal (regular or irregular), and non-polygonal. In some embodiments, overbandage 1700 may be symmetrical. In other embodiments, overbandage 1700 may comprise at least one plane of dissymmetry. When overbandage 1700 is asymmetrical, a user may be able to choose a particular orientation more easily for adhering overbandage 1700 to a skin surface. FIGS. 17A-17G show an asymmetrical D-shaped configuration for overbandage 1700, from which a user can select an orientation for adherence to a skin surface. In light of the above, however, the depicted configuration should not be considered as limiting.

Moreover, in some embodiments, top face 1702 of overbandage 1700 may be ornamented in various ways. For example, top face 1702 may be colored and/or include one or more ornamental designs, which a wearer may choose based on personal stylistic preferences.

The contact adhesive layer may comprise one or more contact adhesives (pressure-sensitive adhesives). The contact adhesive layer may be filmic, woven, non-woven, foamed or any combination thereof. Particular contact adhesives are not considered to be particularly limited and, in some embodiments, may be selected to aid in maintaining high MVTR values. Standard medical grade contact adhesive materials may be suitable for use in the contact adhesive layer of overbandage 1700. Illustrative contact adhesive materials that may be present in the contact adhesive layer include, but are not limited to, acrylic adhesives, silicone adhesives, polyisobutylene and other hydrocarbon adhesives, polyurethane adhesives, natural rubber adhesives, synthetic rubber adhesives, and the like. Acrylate, polyurethane and silicone adhesives may be particularly desirable for their ability to promote high MVTR values in systems employing overbandage 1700 and may be selected in embodiments in which high MVTR values are desired, for example. Various water-absorbing materials, such as carboxymethylcellulose, may be present in combination with the contact adhesive material, in some embodiments.

In some embodiments, overbandage 1700 may further comprise a wicking layer disposed upon vapor-permeable backing 1701, which may promote conveyance of water away from a wearer's skin. Suitable materials that may be present in a wicking layer include, for example, hydrocolloids, hydrogels, and/or super-adsorbent polymers.

Particular materials for peelable release liners 1720*a,b* and 1730 are likewise not considered to be particularly limited. In some embodiments, peelable release liners 1720*a,b* and 1730 may comprise the same materials, and in other embodiments, two or more of peelable release liners 1720*a,b* and 1730 may comprise different materials. In some embodiments, peelable release liner 1730 may comprise different materials than peelable release liners 1720*a,b*. In some or other embodiments, peelable release liners 1720*a,b* and 1730 may all have the same rigidity, and in other embodiments, the rigidity values may be different. In more particular embodiments, peelable release liner 1730 may exhibit higher rigidity than do peelable release liners 1720*a, b*. Peelable release liner 1730 may be made more rigid by employing one or more different materials than do peelable release liners 1720*a,b* and/or by being made thicker than peelable release liners 1720*a,b*. Suitable materials may include, for example, 80 pound or greater kraft paper, polyesters, polyethylene, and the like. Release liners used in conventional adhesive bandages may also be suitable, in some embodiments.

Figure 18A:
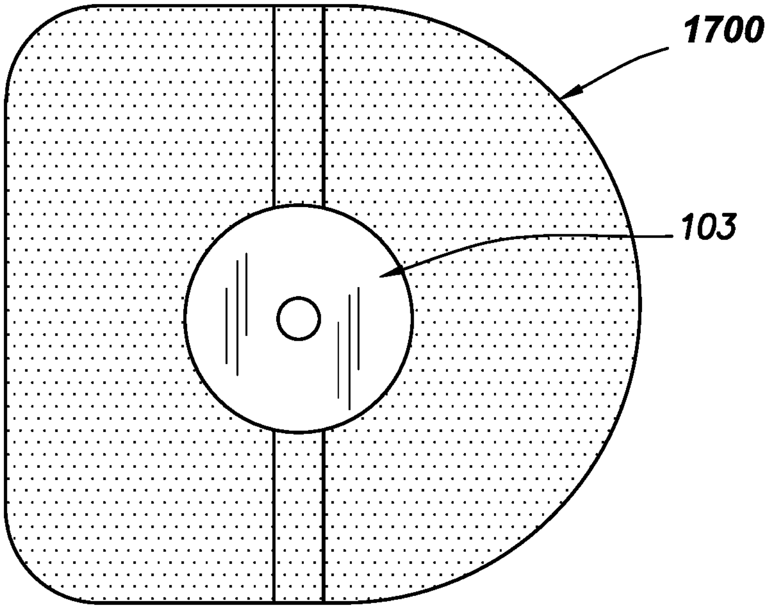
FIGS. 18A and 18B show perspective view diagrams of various configurations of an overbandage circumferentially surrounding a sensor housing.
Figure 18B:
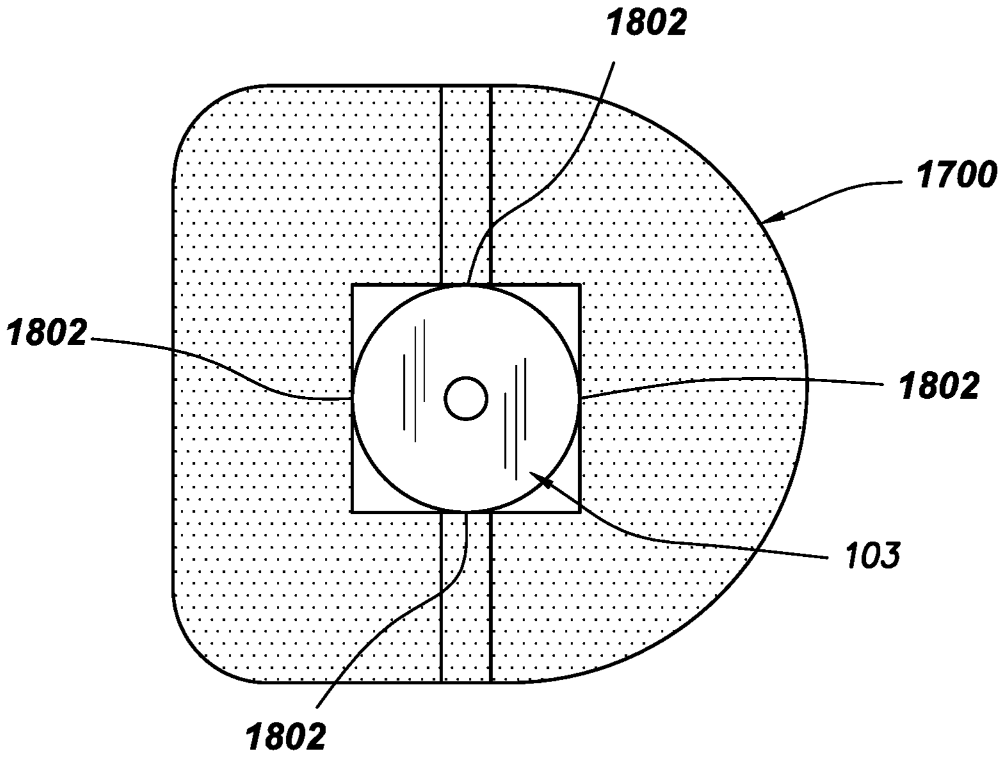

Overbandage 1700 may be placed in proximity to sensor housing 103 upon a skin surface during use. In particular embodiments, overbandage 1700 may circumferentially surround sensor housing 103, as shown in FIGS. 18A and 18B. Overbandage 1700 may be adhered directly or indirectly to the skin surface. As shown in FIG. 18A, overbandage 1700 includes aperture 1704 that is circular, which circumferentially surrounds sensor housing 103 around its outer perimeter. In the depicted configuration, overbandage 1700 engages sensor housing 103 about the entirety of its perimeter but does not substantially occlude grooves 200*a* (FIG. 2), thereby maintaining fluid drainage capabilities beneath sensor housing 103. Moreover, overbandage 1700 does not overlay any portion of the top surface of sensor housing 103 in the depicted configuration. Less than complete perimeter engagement between overbandage 1700 and sensor housing 103 may also be sufficient to maintain sensor housing 103 in place upon a skin surface. For example, as shown in FIG. 18B, overbandage 1700 includes aperture 1704 that is square, which may engage sensor housing 103 tangentially at touch points 1802 in the depicted configuration. Other geometric shapes for aperture 1704 may tangentially engage a circular sensor housing 103 as well, such as a hexagonal aperture 1704.

Twisting or distortion within anchoring adhesive strip 1712 may also be discouraged by making the width of anchoring adhesive strip 1712 as small as possible while still maintaining its intended function. Namely, according to various embodiments of the present disclosure, the width of anchoring adhesive strip 1712 (as defined by the width exposed upon removing peelable release liner 1730) may be just wide enough to hold overbandage 1700 in place after seating against sensor housing 103 and prior to contacting adhesive portions 1714*a,b* with a skin surface (i.e., before peelable release liners 1720*a,b* have been removed). That is, anchoring adhesive strip 1712 may hold overbandage 1700 in place until a larger surface area of contact adhesive has been exposed. According to more specific embodiments, anchoring adhesive strip 1712 may have a width ranging between about 1 mm and about 10 mm, or between about 1 mm and about 5 mm, or between about 1 mm and about 3 mm, or between about 2 mm and about 4 mm, or between about 3 mm and about 5 mm. Moreover, whether anchoring adhesive strip 1712 spans completely or partially across bottom face 1710 may determine an appropriate width of anchoring adhesive strip 1712 to be exposed upon removing peelable release liner 1730.

Accordingly, in more specific embodiments of the present disclosure, overbandages described herein may comprise: a vapor-permeable backing, a symmetrical aperture defined in the vapor-permeable backing that is sized to circumferentially surround a sensor housing adapted for adhering to a skin surface, and a contact adhesive layer disposed on one side of the vapor-permeable backing. The contact adhesive layer comprises an anchoring adhesive strip that contacts the symmetrical aperture and is coincident with or parallel to a symmetry line of the symmetrical aperture such that portions of the anchoring adhesive strip reside on opposing sides of the symmetrical aperture. The contact adhesive layer also comprises a first adhesive portion laterally arranged to a first side of the anchoring adhesive strip, and a second adhesive portion laterally arranged to a second side of the anchoring adhesive strip. The overbandages also comprise first and second peelable release liners disposed upon the first and second adhesive portions, and a third peelable release liner disposed upon the anchoring adhesive strip. The overbandage is foldable along the anchoring adhesive strip when the third peelable release liner has been removed. Further configurations of such overbandages may include any of the variations described hereinabove, either alone or in combination with one or more additional variations.

The overbandages of the present disclosure will now be further described structurally in relation to their contemplated methods of use, particularly the manner in which the overbandages may be positioned proximate to a sensor housing upon a skin surface in the course of becoming adhered thereto. As mentioned above, the overbandages disclosed herein are configured to provide tactile feedback during their application to a skin surface, such that a wearer or other individual may position an overbandage with little to no visual access to a skin mounting site of a sensor housing. In particular, the overbandages of the present disclosure are designed so that they may be accurately seated in engagement with a sensor housing, such that they do not significantly overlay the sensor housing when adhered to a skin surface. Avoiding overbandage overlay upon a sensor housing can be desirable to lessen the likelihood of sensor displacement or pullout due to the overbandage tugging upon the sensor housing during wear.

The manner in which the overbandages of the present disclosure become attached to a skin surface may lessen the likelihood of their becoming overlaid upon a sensor housing, thereby leading to the issues referenced above. The overbandages of the present disclosure could, in principle, be seated around a sensor housing by removing all of the peelable release liners and lowering the overbandage axially over the sensor housing. However, this approach can be problematic and lead to poor seating and/or overlay of the overbandage upon the sensor housing, particularly for sensor housings positioned in locations that are difficult for a wearer or other individual to access. Accordingly, the overbandages of the present disclosure are configured such that they can be seated against a sensor housing through a lateral engagement process, rather than through an axial engagement process. Moreover, the lateral engagement process may be conducted with sequential engagement of the contact adhesive layer around the sensor housing, rather than engaging substantially all of the contact adhesive layer at a single time, as in axial engagement processes. Lateral engagement of the overbandages against a sensor housing, as described hereinafter in reference to the drawings, may considerably lessen the likelihood of improper overbandage seating, thereby lessening the likelihood of displacement and/or dislodgment of an implanted sensor from below a skin surface.

FIGS. 19A-19F and 20A-20F show diagrams of an illustrative sequence of operations through which an overbandage of the present disclosure may be become laterally engaged with and circumferentially surround a sensor housing adhered to a skin surface. FIGS. 19A-19F show the illustrative sequence of operations in side view with respect to the overbandage, and FIGS. 20A-20F show corresponding top views with respect to the overbandage.

Figure 19B:
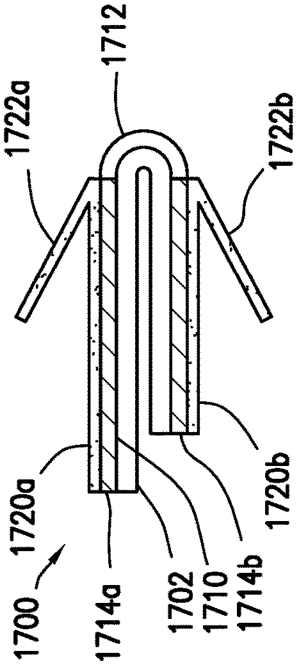
FIGS. 19A-19F and 20A-20F show diagrams of an illustrative sequence of operations through which an overbandage of the present disclosure may be become laterally engaged with and circumferentially surround a sensor housing adhered to a skin surface.
Figure 20B:
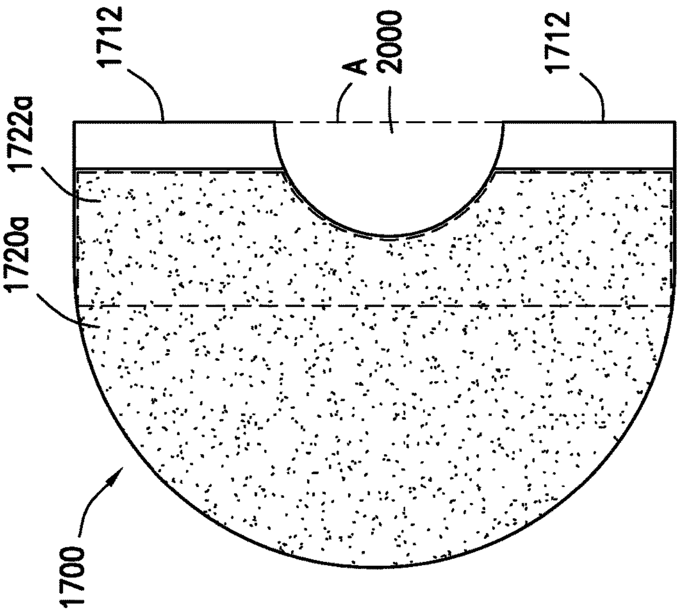
Figure 19A:
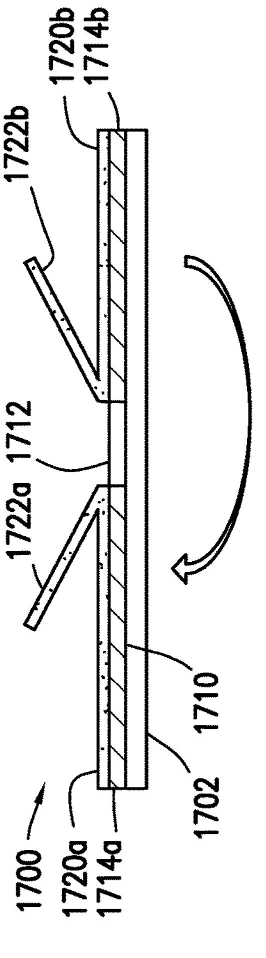
Figure 20A:
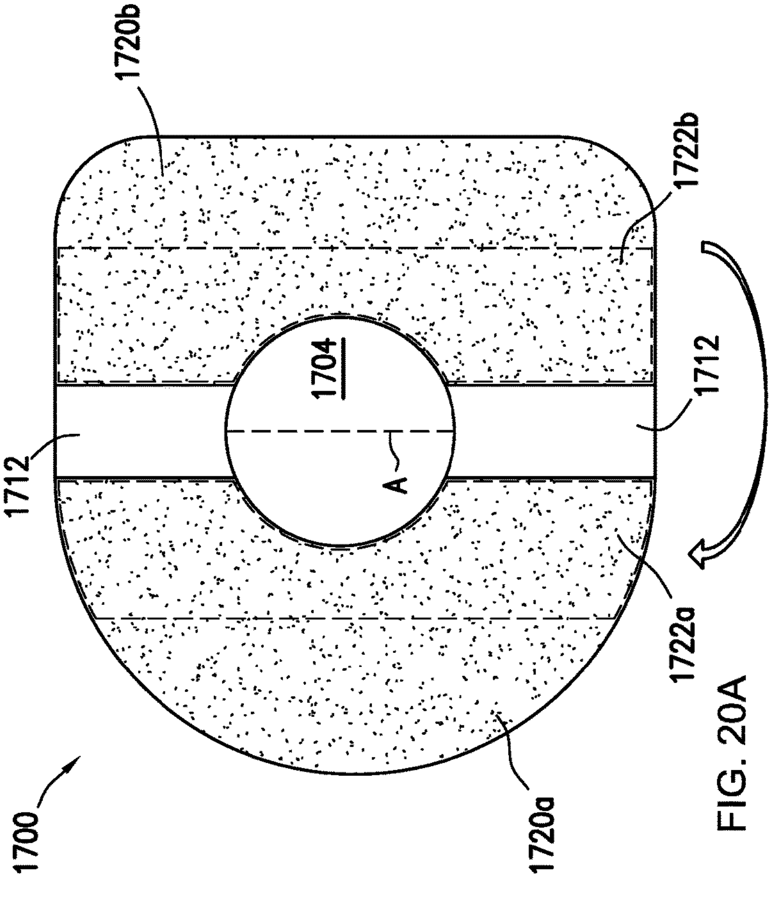

In FIGS. 19A and 20A, peelable release liner 1730 has already been removed from overbandage 1700 to expose anchoring adhesive strip 1712 and aperture 1704. Next, overbandage 1700 is folded along anchoring adhesive strip 1712 (e.g., along symmetry line A), such that opposing surfaces of top face 1702 meet or nearly meet each other interiorly within the fold, thereby dividing aperture 1704 into hemispherical recess 2000, as shown in FIGS. 19B and 20B. As depicted, adhesive portion 1714*b* is facing downward so that it can be attached to a skin surface after adhesive portion 1714*a*. The order of skin adherence may be reversed from that depicted without departing from the principles of the present disclosure. That is, overbandage 1700 may be folded along anchoring adhesive strip 1712 in a direction opposite that depicted. Accordingly, the depicted folding orientation is exemplary for purposes of illustration and should not be considered limiting.

Figure 19D:
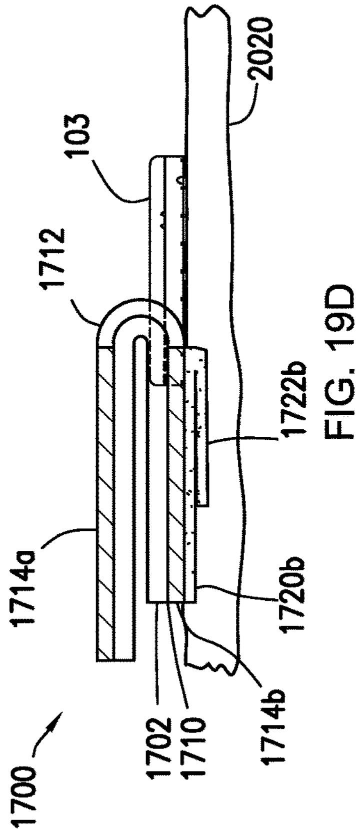
Figure 20D:
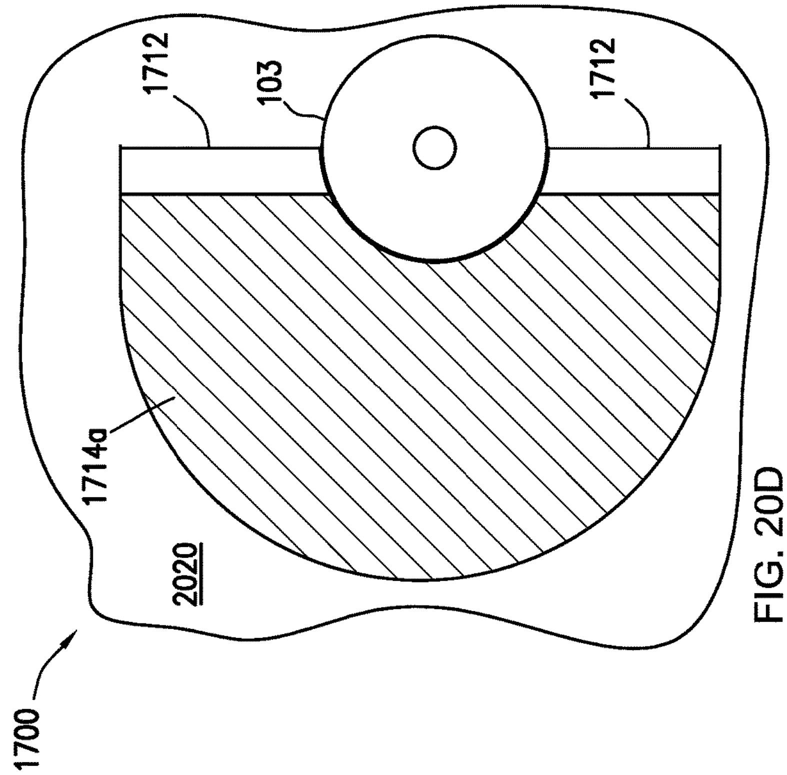
Figure 19C:
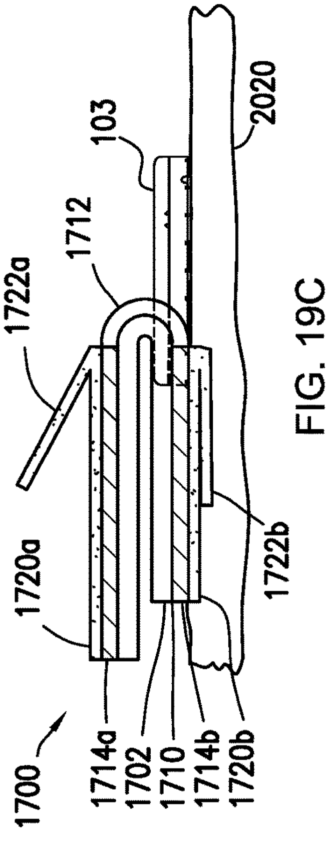
Figure 20C:
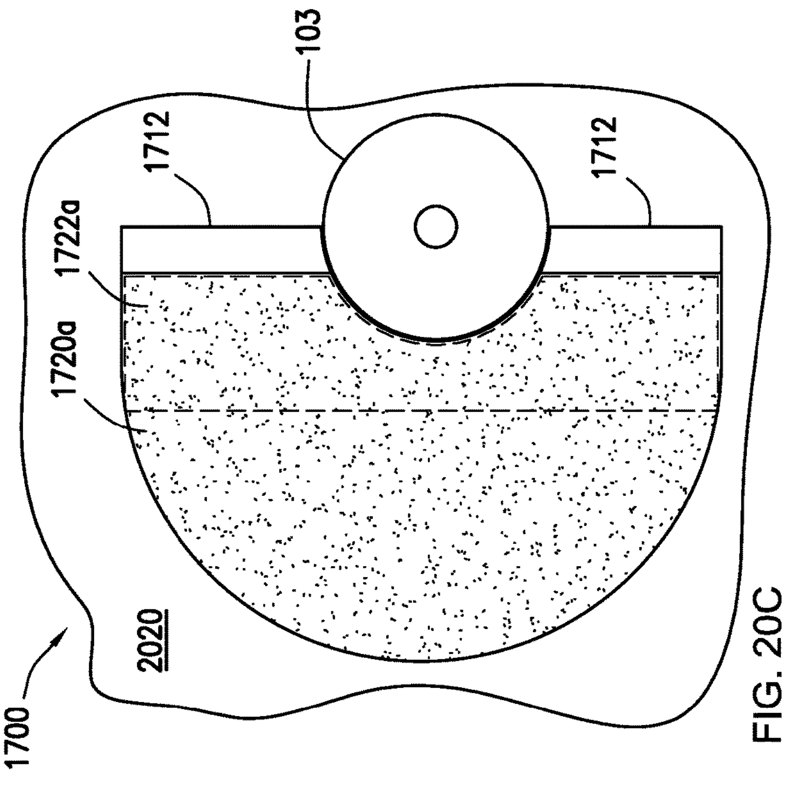

After overbandage 1700 has been folded, hemispherical recess 2000 may be abutted against sensor housing 103 disposed on skin surface 2020, as shown in FIGS. 19C and 20C. Hemispherical recess 2000 is sized, based upon the size of aperture 1704, for a complementary fit with sensor housing 103. As such, a wearer or other individual may receive tactile feedback once overbandage 1700 has been seated properly against sensor housing 103. For example, overbandage 1700 may slide side-to-side along skin surface 2020 until sensor housing 103 is received within hemispherical recess 2000 and becomes engaged therewith. Once received within hemispherical recess 2000, overbandage 1700 may no longer move side-to-side relative to the direction of lateral loading.

Once overbandage 1700 has been initially seated in place against sensor housing 103, a portion of anchoring adhesive strip 1712 (i.e., the portion of anchoring adhesive strip 1712 in contact with skin surface 2020) may become adhered to skin surface 2020. Adherence between anchoring adhesive strip 1712 and skin surface 2020 may hold overbandage 1700 in place while conducting further operations to connect overbandage 1700 to skin surface 2020 more securely. Moreover, by initially securing anchoring adhesive strip 1712 to skin surface 2020, twisting and distortion of overbandage 1700 may be minimized while conducting further manipulations, thereby lessening the likelihood of overbandage 1700 itself promoting sensor displacement or pullout through improper positioning proximate to sensor housing 103.

Figure 19E:
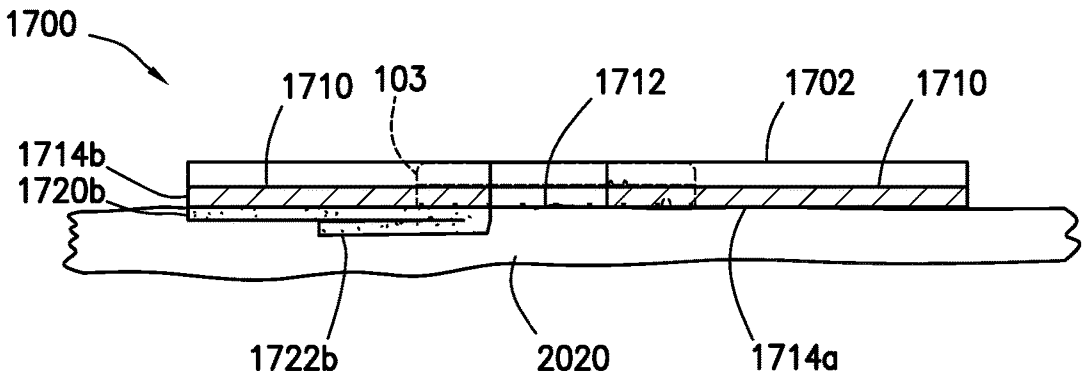
Figure 20E:
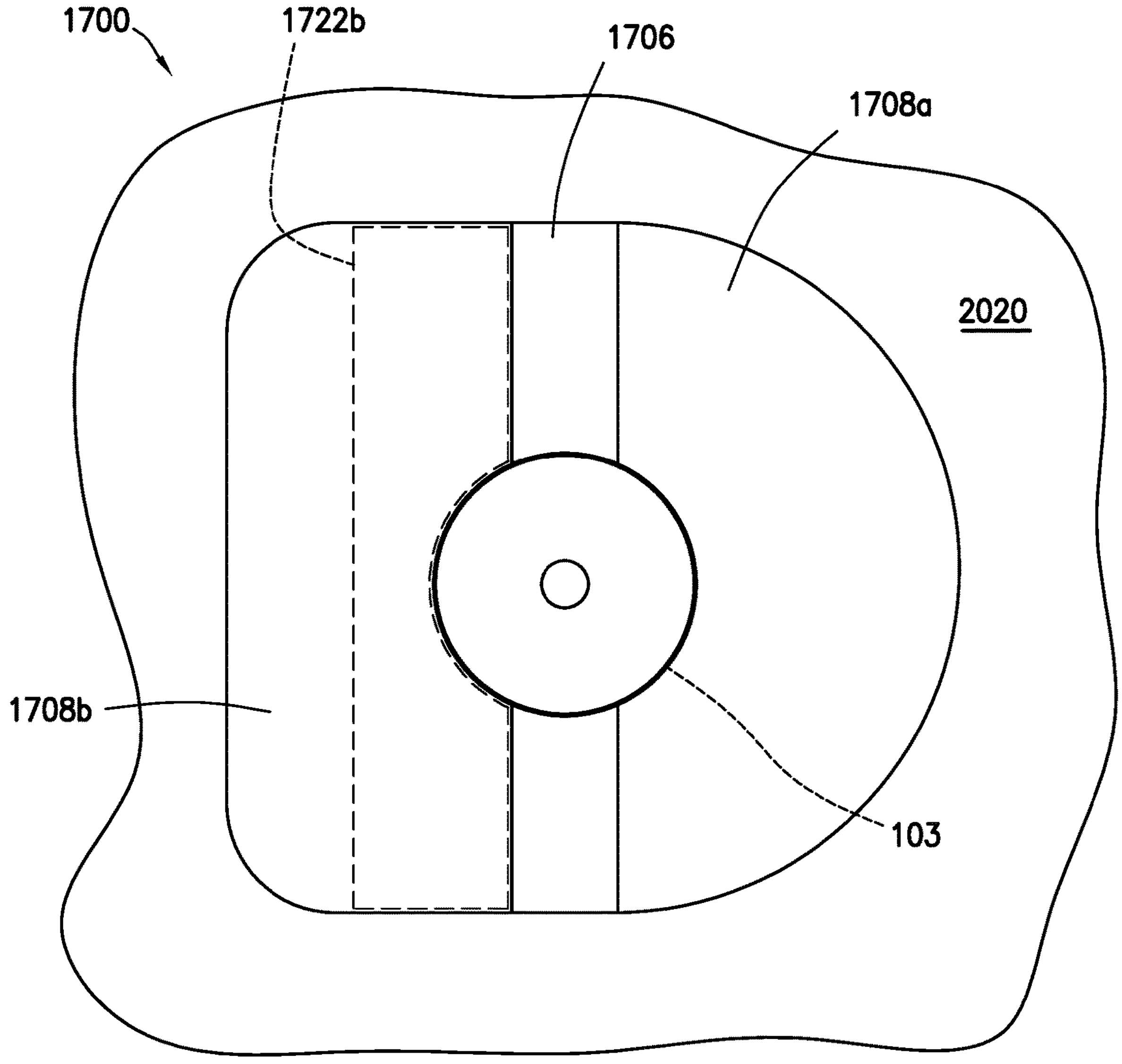

After overbandage 1700 has been seated against sensor housing 103 and partially adhered to skin surface 2020, peelable release liner 1720*a* may be removed (e.g., by pulling upon flap 1722*a*) to expose corresponding adhesive portion 1714*a*, as shown in FIGS. 19D and 20D. Once adhesive portion 1714*a* has been exposed, overbandage 1700 may be unfolded to bring adhesive portion 1714*a* into contact with skin surface 2020. Anchoring adhesive strip 1712 may remain attached to skin surface 2020 during this process. Following unfolding and adherence of adhesive portion 1714*a* to skin surface 2020, overbandage 1700 circumferentially surrounds sensor housing 103, with adhesive portion 1714*b* remaining non-adhered. FIGS. 19E and 20E show overbandage 1700 after unfolding and adherence of adhesive portion 1714*a* to skin surface 2020.

Figure 19F:
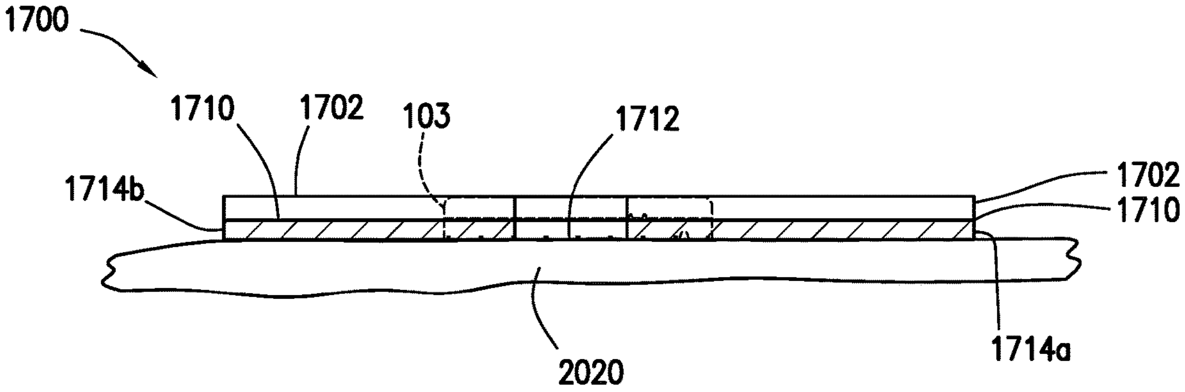
Figure 20F:
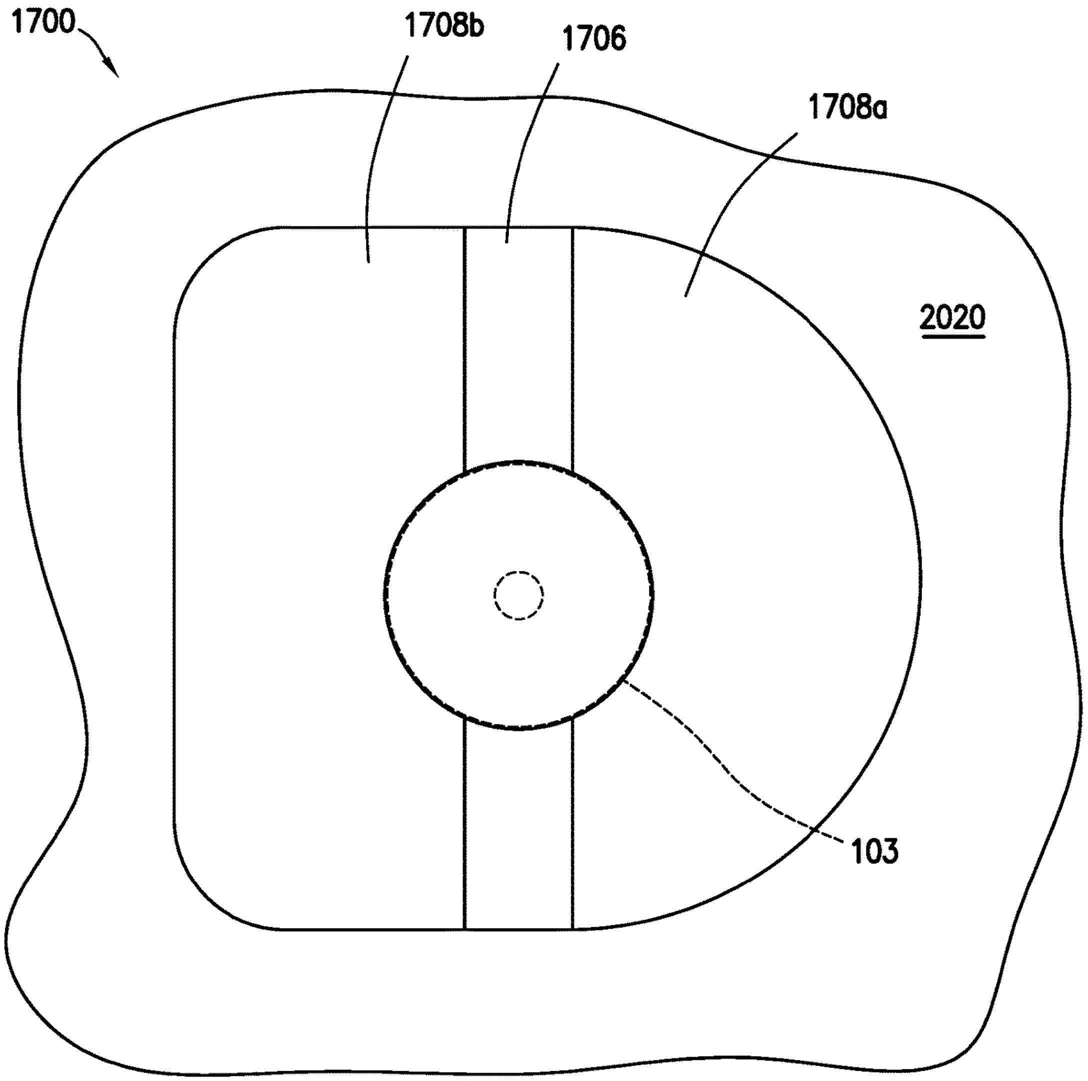
Figure 21:
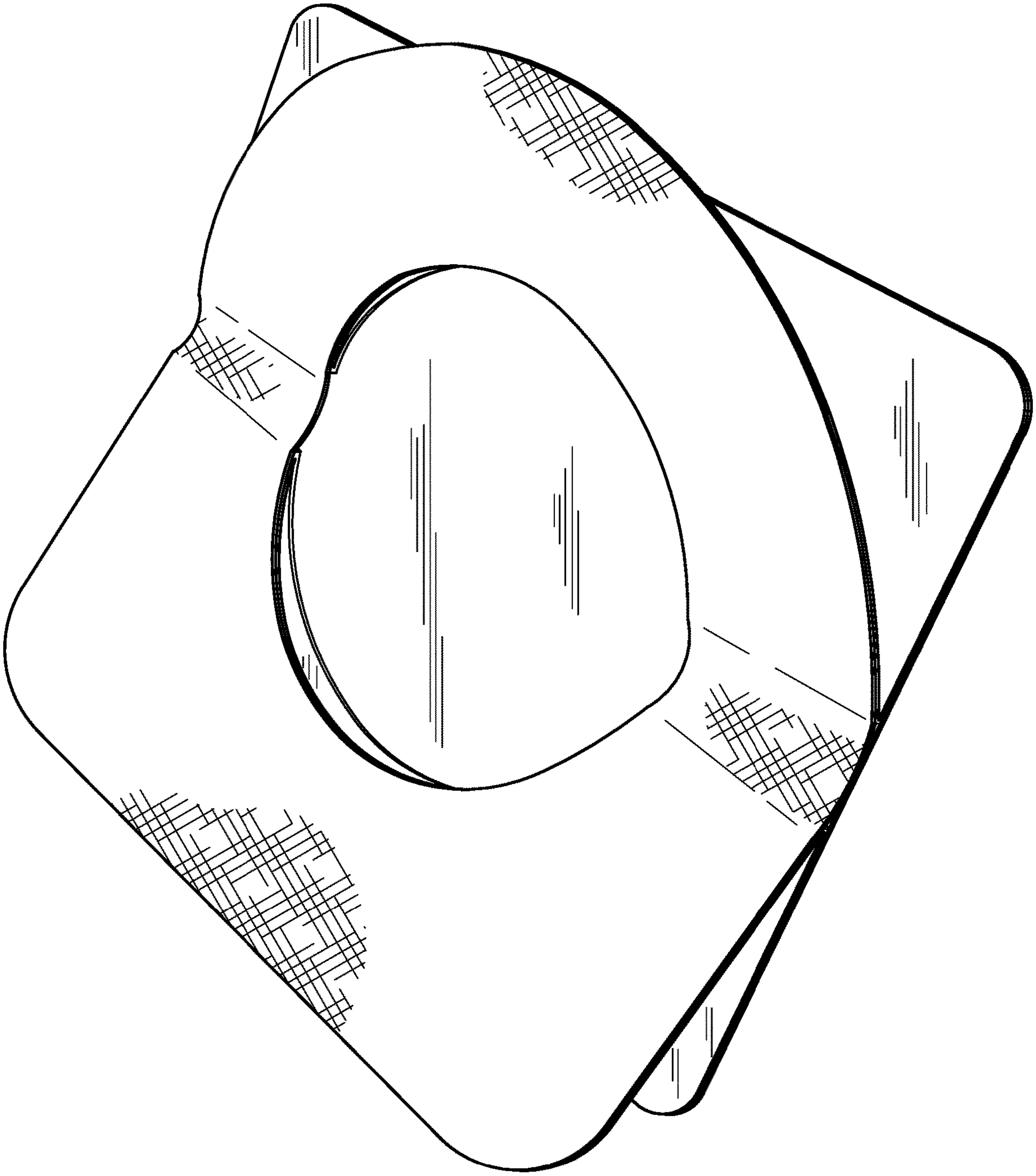
FIGS. 21-27 show various views of an illustrative overbandage of the present disclosure.
Figure 22:
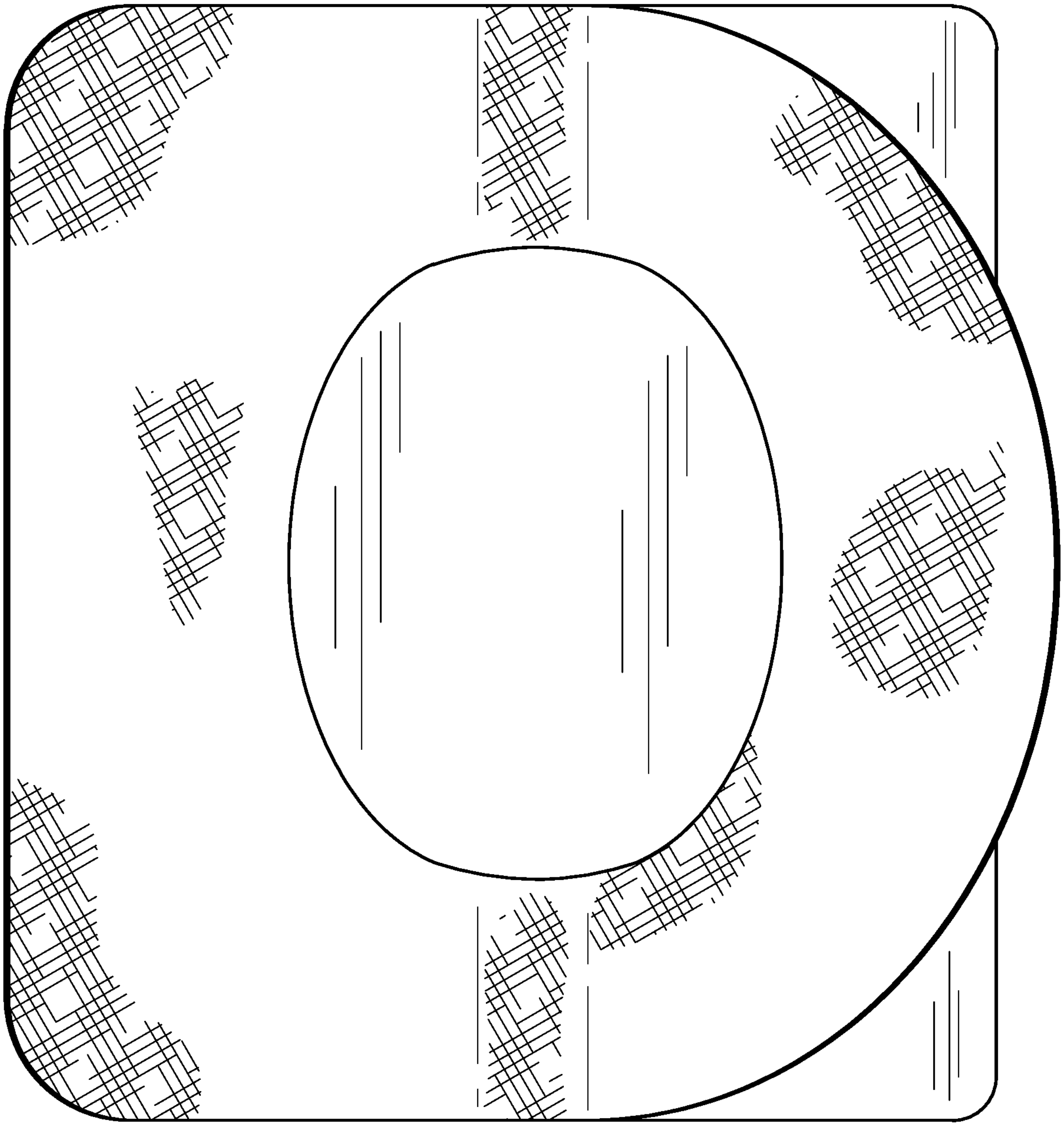
Figure 23:
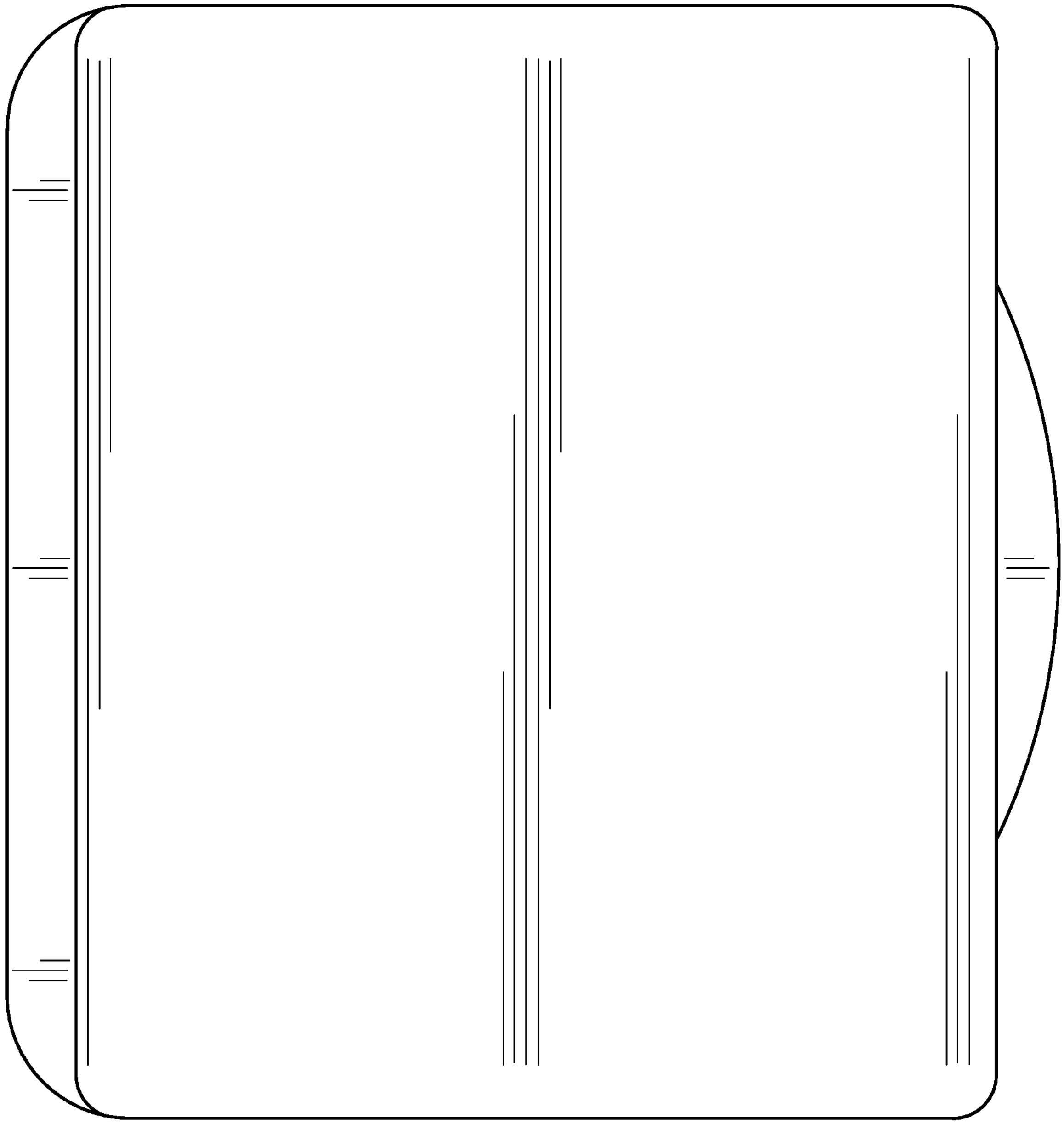
Figure 24:
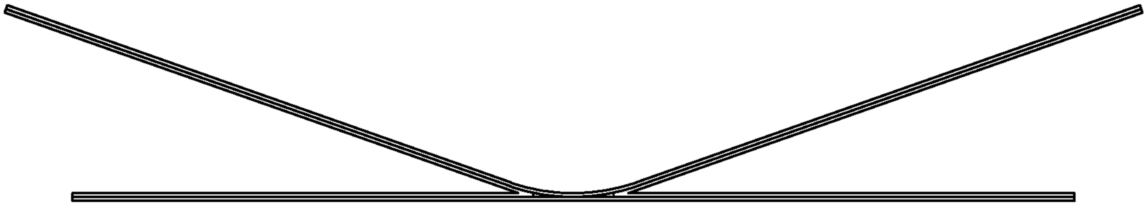
Figure 25:
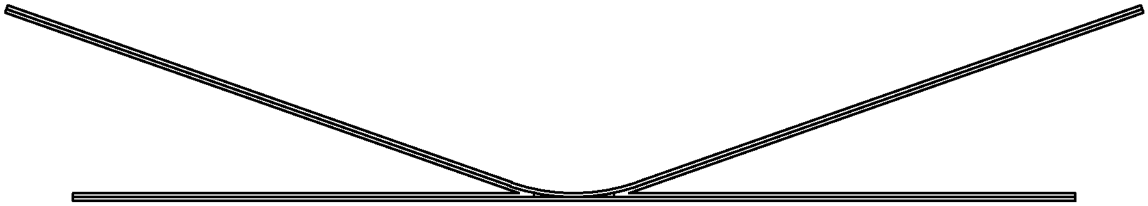
Figure 26:
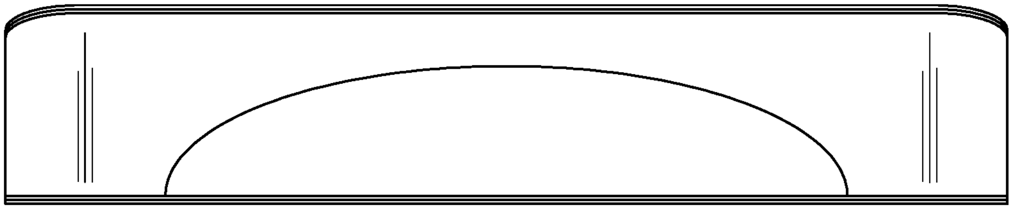
Figure 27:
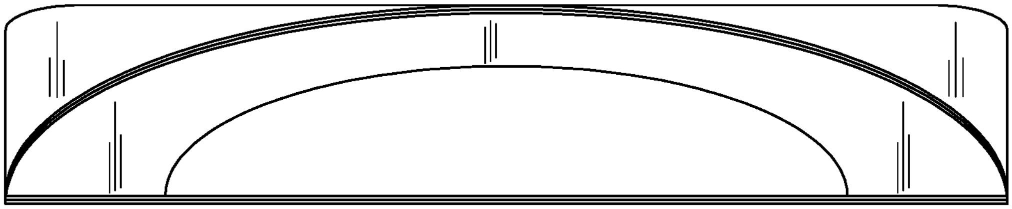

Once adhesive portion 1714*a* has been adhered to skin surface 2020, adhesive portion 1714*b* may be exposed for adherence to skin surface 2020. Namely, the non-adhered side of overbandage 1700 may be lifted or tilted up slightly to access peelable release liner 1720*b*. Removal of peelable release liner 1720*b* may then expose adhesive portion 1714*b*. Contact between skin surface 2020 and adhesive portion 1714*b* may the complete adherence of overbandage 1700 to skin surface 2020. At this point, overbandage 1700 circumferentially surrounds sensor housing 103 and is adhesively bonded to skin surface 2020 at all locations around the perimeter of sensor housing 103. FIGS. 19F and 20F show overbandage 1700 fully adhered to skin surface 2020 around sensor housing 103, according to various embodiments of the present disclosure. It is to be understood that, while there may be a preferred order of exposure for adhesive portions 1714*a,b* for some overbandage configurations, exposure may occur in either order, without departing from the scope of the present disclosure.

Figure 28:
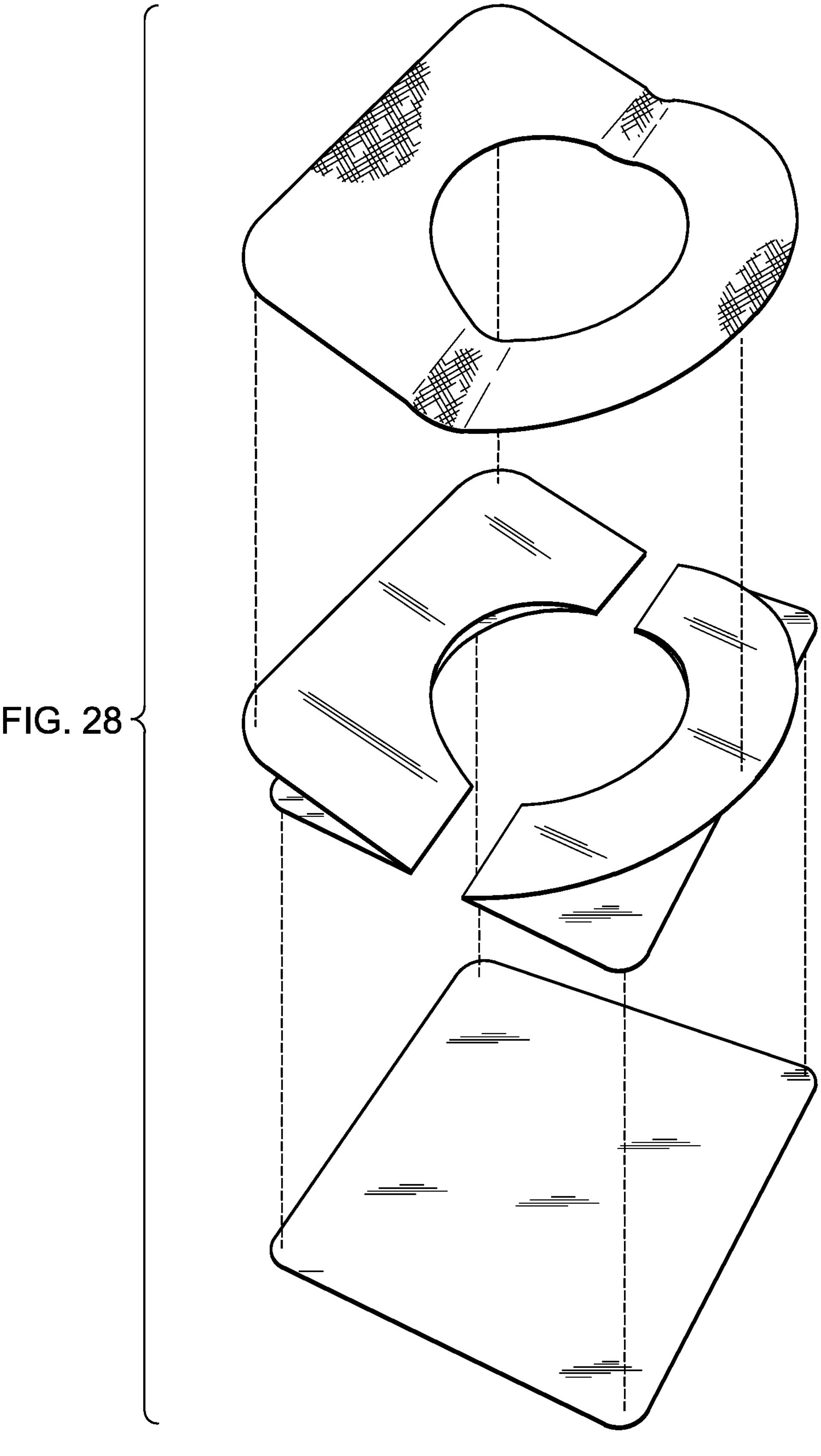
FIG. 28 shows an exploded perspective view of an illustrative overbandage of the present disclosure.

Additional views of an illustrative overbandage of the present disclosure are shown in FIGS. 21-28. FIGS. 21-27 respectively show top perspective, top, bottom, front, rear, left and right views. FIG. 28 shows an exploded perspective view corresponding to the overbandage depicted in FIG. 21.

In some embodiments, an antimicrobial quality may be included as part of one or more of the sensor components, such as the sensor housing, an upper portion of the sensor tail, and/or the overbandage. As used herein, the terms “antimicrobial” or “antimicrobial compound,” and grammatical variants thereof, refers to a substance or material that is detrimental (microbicidal) or microstatic (i.e., preventing or reducing colonization, expansion, and/or proliferation without necessarily being detrimental) to a microorganism, including bacteria, fungi, viruses, protozoans, and the like. The term “antimicrobial quality,” and grammatical variants thereof, refers to any mechanism, structure, system, or other technique for imparting any antimicrobial characteristic to a tangible material, including one or more components of the analyte sensors described herein and/or human skin to which the one or more sensor components come into contact.

As described above, when positioning an analyte sensor onto the skin of a wearer, a needle or other introducer is used to puncture the skin and allow transcutaneous implantation through the dermal region. Implantation may extend only to the dermis, or through to the subcutis. Accordingly, a transdermal skin wound is created in order for the sensor to undergo positioning for analyte monitoring, wherein the sensor tail is positioned trans- or subcutaneously into the skin through the wound (also referred to as the “insertion site”). Generally, an analyte sensor may be worn for a prolonged period of time, such as 7 days, 10 days, 14 days, 21 days, 30 days, or more. That is, the analyte sensor may be worn for a time period of less than 30 days or a period of 30 days or more. As such, the sensor and its various components may be exposed to various activities or atmospheres, including contact with the external environment, clothing, bath or shower water, rain or swimming water, social contact with other persons, and the like. While the overbandage alone or in combination with other sensor adhesives of the present disclosure may provide complete protection from such exposure to the skin wound itself (insertion site), the possibility of existing microorganisms near the insertion site and/or migration of microorganisms from adjacent skin or areas, including the external environment, may still present a risk of incursion to the skin would. Such exposure may create a rich environment for microorganism growth, which may be harmful to the wearer and/or may lead to altered functioning of the analyte sensor itself, such as causing a shortened life of the sensor and/or providing erroneous or altered data or perceived sensitivity and/or response times.

Various microorganisms (e.g., bacteria, fungi, viruses, and the like) are present naturally on the skin (i.e., skin flora) and in the surrounding environment (e.g., air, clothing, bedding, water, social engagement, and the like), which may contact the wound area or adjacent skin while the analyte sensor is in use. Moisture contact (e.g., during daily showering, bathing, or submersion (e.g., such as swimming, for instance, in a public pool or natural body of water), inability to access and wash skin having the sensor applied thereto, failure to adequately clean the skin prior to insertion of the sensor tail and application of the sensor, nosocomial (i.e., hospital) exposure to microorganisms (e.g., a nurse or other medical professional may apply an analyte sensor in a hospital setting), and the like, may further exacerbate the possibility of microorganism growth. As used herein, the term "skin flora," and grammatical variants thereof, refers to microorganisms that innately reside on human skin and/or within a human body that may contact human skin. While various embodiments of the present disclosure may be discussed with reference to protecting against such skin flora, it is to be understood that other microorganisms (e.g., bacteria, fungi, viruses, and the like) may also be controlled or otherwise treated to protect the insertion site and adjacent areas of the wearer and to promote sensor functionality.

The various microorganisms that may be desirably controlled or otherwise treated as part of the use of an analyte sensor described herein are not believed to be particularly limited and include any such microorganisms generally encountered by a person during various life activities, including symbiotic microorganisms and parasitic microorganisms.

Microorganisms in skin flora may include, but are not limited to, actinobacteria (e.g., *Corynebacterium, propionibacterium*, and the like), firmicutes (e.g., *Staphylococcus, Clostridia, Lactobacillus*, and the like), proteobacteria (e.g., alphaproteobacteria, betaproteobacteria, gammaproteobacteria, and the like), bacteriodetes (e.g., flavobacteriales, and the like), cyanobacteria, and the like, and any combination thereof. Examples of specific such skin flora may include, but are not limited to, *Staphylococcus epidermidis, Staphylococcus aureus, Staphylococcus warneri, Streptococcus pyogenes, Streptococcus mitis, Staphylococcus hominis, Propionibacterium acnes, Corynebacterium* spp., *Acinetobacter johnsonii, Pseudomonas aeruginosa, Demodex folliculorum, Bacillus oleronius, Bacteroides fragilis, Bacteroides melaninogenicus, Bacteroides oralis, Enterococcus faecalis, Escherichia coli, Enterobacter* spp., *Klebsiella* spp., *Bifidobacterium bifidum, Lactobacillus* spp., *Clostridium perfringens, Clostridium tetani, Clostridium septicum, Proteus mirabilis, Pseudomonas aeruginosa, Salmonella enterica, Faecalibacterium prausnitzii, Peptostreptococcus* spp., *Peptococcus* spp., and the like, and any combination thereof.

Environmental microorganisms may be any microorganisms that overlap with the skin flora described above, and further include microorganisms that are present in the environment, including internal and external environments and encountered during various life activities. For example, such microorganisms may include those that are encountered during sleeping, bathing and/or showering, working, exercising, eating, attending recreational excursions or events, handling pets, and the like. Such microorganisms may include, but are not limited to, those listed above, as well as *Escherichia* (e.g., *E. coli*, and the like), firmicutes, *Mycobacterium* (e.g., *Mycobacterium avium* subspecies paratuberculosis, and the like), enterobacteriaceae (e.g., *Salmonella*, and the like), yeast, bacteriophages, and the like, and any combination thereof.

The mechanism by which the antimicrobial quality described herein prevents or reduces microorganism interference with the insertion site and/or functioning of the analyte sensor may be any mechanism, and may be dependent on the type or types of microorganisms being targeted. Suitable mechanisms may include, but are not limited to, preventing microorganism attachment to one or more components of the sensor (e.g., preventing initial adhesion of the microorganism(s)), disruption of the microorganism(s) cell surface or membrane, disruption of the microorganism(s) internal organelles or functioning thereof, prevention of continued growth (e.g., by restricting nutrients and/or nutrient uptake or metabolism), and the like, and any combination thereof. In some instances, the mechanism may further be selected based on the placement of the antimicrobial quality, which may be applied or otherwise coated onto one or more components of the sensor. Optionally, the antimicrobial quality may be imparted to one or more components of the analyte sensor and/or particular area of the skin to which the sensor is adhered in the form of a wipe or cleaning pad, which may be used alone or in combination with other cleaning aspects, such as for imparting disinfecting qualities prior to sensor implantation.

In some embodiments, the antimicrobial quality for use in the present disclosure is a slow-release antimicrobial quality. The mechanism by which the antimicrobial may be slowly released is not considered to be particularly limited. In some embodiments, the antimicrobial is released slowly by contact with water (e.g., during bathing or sweating), exposure to elevated temperature, encapsulation, impregnation, degradation, and the like, and any combination thereof. As used herein, the term "encapsulation," and grammatical variants thereof, refers to envelopment in whole or in part (i.e., less than 100%) of an antimicrobial substance, such as by a wax, a degradable polymer or biopolymer, or other suitably degradable material. The term "impregnation," and grammatical variants thereof, as used herein, refers to filling, permeating, doping, chemically binding (e.g., covalently binding), or saturating an antimicrobial substance into a carrier, such as an adhesive, an alcohol, a nanoparticle, and the like. Encapsulated antimicrobial substances may generally be released as the encapsulation material degrades or at least are released in greater amounts as such degradation occurs (e.g., if the encapsulation is not in whole). Impregnated antimicrobial substances may generally be released as the antimicrobial leaches out of voids in various carrier materials or as the carrier materials degrade. For example, another substance or material, such as any of the one or more contact layer portions of the overbandages of the present disclosure, may be used as a carrier for the antimicrobial, which is distributed therethrough such that its release is prolonged over a period of time. Accordingly, the antimicrobial quality may be directly applied to the surface of a portion of the overbandages and/or analyte sensor component (e.g., upper portion of the sensor tail), or may be otherwise provided in a carrier. Other alternatives are further discussed hereinbelow and are within the scope of the present disclosure.

Prolonged exposure to an antimicrobial is particularly advantageous for the embodiments of the present disclosure because the analyte sensor may be worn over an extended period of time, and thus may experience potential contact with microorganisms, such as skin or environmental flora, over the period of time. Accordingly, the action of the antimicrobial can occur throughout the duration in which the sensor is in use, not merely at a beginning portion, thereby ensuring protection to the wearer (e.g., maintaining skin health of the wearer) and proper functioning of the analyte sensor.

Referring now to FIG. 13, illustrated is a composite visible light and fluorescence image of a biofilm comprised of microorganisms formed on a sensor component of an analyte sensor having no antimicrobial quality. The biofilm on the sensor component is visualized at 10× OM magnification using fluorescence microscopy (labeled as "A"), light microscopy (labeled as "B"), and an overlay of the fluorescence and light microscopy images (labeled as "C") after the analyte sensor was worn for 21 days. As shown, the biofilm is characterized by small, coccus-shaped (i.e., spherical or roughly spherical in shape) microorganisms. This biofilm may potentially migrate down the sensor tail of an analyte sensor toward the sensing region, which is located at a bottom portion of the sensor tail. As used herein, the term "sensing region," and grammatical variants thereof, refers a portion of an analyte sensor comprising one or more components to facilitate measurement of one or more analytes (e.g., via electrochemical oxidation or reduction, or other sensing chemistry). The sensing region may include, for example, an analyte-specific reactant (e.g., enzyme or other chemical) that reacts with the analyte to produce a response at or near a working electrode. Accordingly, the sensing region includes at least the analyte-specific chemical and a working electrode. Other elements in the sensing region may include, but are not limited to, a membrane (e.g., a limited permeability membrane), other electrodes (e.g., reference and/or counter electrodes), an electron transfer agent to transfer electrons between the analyte and the working electrode (or other component), such as a suitable redox species, or both.

The antimicrobial quality described herein may be placed on any portion or component of the adhesive pad assemblies and/or the analyte sensor described herein, excluding the sensing region of the sensor tail. That is, as provided above, the antimicrobial quality may be provided only to an upper portion of a sensor tail of an analyte sensor in accordance with the embodiments of the present disclosure. Accordingly, as used herein, the term "upper portion of the sensor tail," and grammatical variants thereof, refers to a portion of the sensor tail that does not extend beyond the dermis and, generally, includes the top 25% of the sensor tail beginning from the proximal-most of the sensor tail extending from the base of an analyte sensor, encompassing any value and subset therebetween. The "upper portion" of the sensor tail is more proximal to the skin surface than the sensing region of the sensor tail comprising electrode(s) and analyte sensing element(s).

Contact of a biofilm, such as that depicted in FIG. 13, with or adjacent to the sensing region may affect various characteristics of the sensor, such as the accuracy of the sensor. If the biofilm reaches the sensing region, sensor sensitivity may be altered over the wear duration of the analyte sensor. Accordingly, protection of the sensing region from microorganisms may increase the life and functionality of the analyte sensor. Thus, protection of the insertion site from exposure to such microorganisms that can migrate to the implantation site may confer advantageous and unexpected operational benefits.

The present disclosure therefore preferably provides an antimicrobial quality to one or more components of an analyte sensor described herein (e.g., a glucose analyte sensor) that prevents or reduces contact of the sensing region with microorganisms, such as those that may result in erroneous measures from those that would be expected due to formation of a biofilm. In order to protect the sensing region, then, the location of the antimicrobial quality is of importance and may include, but is not limited to, one or more portions of the overbandages described in the present disclosure or one or more portions of the analyte sensor (excluding the bottom portion or sensing region of the sensor tail).

For example, in any one or all of the embodiments of the present disclosure, one more of the one or more portions of the contact adhesive layer of the overbandages of the present disclosure may have an antimicrobial quality coated thereon, including functionalized thereto, impregnated therein, or otherwise adhered thereto to impart the antimicrobial quality, each of which is described in greater detail below. Such portions of the contact adhesive layer include any one, more, or all of the anchoring adhesive strip, the first adhesion portion, and/or the second adhesion portion. The contact adhesion layer may provide for gaps or voids that permit their functioning as a carrier material not only for the adhesive, but also for application of the antimicrobial quality and release dynamics. The gaps or voids in these materials may allow slow-release of the antimicrobial, such that it is continuously leaching the antimicrobial through the contact adhesion layer and to the insertion site. In some embodiments, the leaching may occur radially, such that during a time earlier in the wear duration of the analyte sensor, the antimicrobial is delivered to the insertion site and skin contact area via the contact adhesive layer area most proximal to the sensor housing 103, such as aperture 1704 area. Over time, the antimicrobial may be exhausted in the proximal layer area and replenished from a layer area more distal to the aperture 1704 area.

Alternatively, localized placement of one or more antimicrobials may be provided such that delivery of a particular antimicrobial occurs prior to delivery of a second (or third, etc.) antimicrobial. For example, it may be known that a particular microorganism is likely to be most problematic during the initial implantation of an analyte sensor, followed by a different microorganism over time; the controlled release of two or more antimicrobials in accordance with the embodiments described herein may be provided to address such a situation. In yet other alternatives, the combination of multiple antimicrobials may be used simultaneously to combat against a larger spectrum of microorganisms as compared to any one alone (e.g., the use of rifampin and minocycline together). In still other alternatives, the localized placement of various antimicrobial(s) may be used to create a wave-like effect where higher doses of antimicrobial are followed by lower or no antimicrobial dosage. In these ways, the amount and type of antimicrobial delivered to or adjacent to a wearer's skin may be controlled to achieve desired tolerance levels (e.g., lower drug load to the wearer). Accordingly, the present disclosure provides for multiple release profiles of the antimicrobial quality described herein.

In other embodiments, alone or in combination with an antimicrobial quality in one or more (or all) portions of the overbandages described herein, the upper portion of the sensor tail is provided with an antimicrobial quality. The sensor tail extends into the skin of the wearer via a skin wound and is thus the primary route through which microorganisms may traverse to contact the sensing region of the analyte sensor. As discussed above, microorganism contact with the sensing region may cause alteration in the perceived sensitivity of the sensor, interfere with other functionality of the sensor, and/or harm the wearer (e.g., result in infection). As such, whether the sole antimicrobial quality provided to the analyte sensor or in combination with one or more antimicrobial qualities provided thereto, treating the upper portion of the sensor tail with an antimicrobial quality may be particularly beneficial.

To facilitate a better understanding of the sensor tail architecture and sensing region, one or more embodiments thereof are shown in FIGS. 8-10. Placement of the antimicrobial quality onto (e.g., coating, functionalization, and the like) may be illustrated herein with reference to the sensor tail and sensing regions depicted in FIGS. 8-10. However, it is to be understood that the antimicrobial quality may be provided on or about the upper portion of the sensor tail of the analyte sensors of the present disclosure to provide antimicrobial protection in the surrounding area and, in particular, to the sensing region where analyte measurements are determined, regardless of the configuration of said sensor tail or sensing region. The antimicrobial quality of the present disclosure is not provided to the sensing region (i.e., bottom portion of the sensor tail) according to the present disclosure.

For example, the sensor tail may have a plurality of electrodes located at a distal (bottom) end of the sensor tail (e.g., deeper into the subcutaneous space of a wearer's skin). One or more sensing regions may be associated with (e.g., coated upon or adjacent to) one or more of such electrodes, such as a working electrode. Such electrodes may be co-planar relative to each other, stacked relative to each other, helically wound about one another, incorporated with one or more insulating materials, and the like. The antimicrobial quality may then be provided in any location that imparts antimicrobial protection to the sensor, provided that it is not located at the bottom portion of the sensor tail and it does not interfere with the operation of the sensing region or functionality of the sensor as a whole. That is, in some embodiments, the antimicrobial quality is exterior to the body or only in contact dermally (i.e., passing through intact skin but not contacting the fatty subcutis layer under the skin) via the upper portion of the sensor tail.

FIG. 14 shows a cross-sectional view of an embodiment of an analyte sensor 1400 having a first portion (which in this embodiment may be characterized as a major portion) positionable above a surface of the skin, and a second portion (which in this embodiment may be characterized as a minor portion) that includes a sensor tail 1430 (which may also be referred to herein as an insertion tip) positionable below the surface of the skin (e.g., penetrating through the skin (dermis) and into the subcutaneous space 1420) and in contact with the wearer's biofluid, such as interstitial fluid. Electrode contacts (not shown) are positioned on the first portion of the sensor 1400 situated above the skin surface and extend to a location in sensor tail 1430. A working electrode 1401, a reference electrode 1402, and a counter electrode 1403 are shown at the second portion of the sensor 1400 and particularly at the bottom portion of sensor tail 1430. It is to be understood that greater or fewer electrodes may be provided on a sensor, without departing from the scope of the present disclosure. For example, a sensor may include more than one working electrode and/or the counter and reference electrodes may be a single counter/reference electrode, and the like.

Referring still to FIG. 14, the sensor 1400 (such as the sensor device 102 of FIG. 1), includes a substrate layer 1404 and a first conducting layer 1408, such as carbon, gold, etc., that is in electrical communication with sensing area 1409, thereby collectively defining working electrode 1401. Sensing area 1409 may be protected from microorganisms by providing on one or more components of the sensor 1400 an antimicrobial quality, designed to protect the skin health of the wearer and/or to protect the sensing area 1409 from potential interference with such microorganisms (e.g., formation of a biofilm due to potential migration of the microorganisms). The various electrodes and sensing areas defined on the bottom portion of the sensor tail 1430 in FIG. 14 may be collectively a sensing region, and any such antimicrobial quality provided to the sensor tail described herein, is provided in the upper portion (upper 25%) of the sensor tail 1430 above said region (e.g., above sensing area 1409, or above electrode 1403).

A first insulation layer 1405, such as a first dielectric layer in some embodiments, may be disposed or layered on at least a portion of the first conducting layer 1408, and further, a second conducting layer 1411 may be disposed or stacked on top of at least a portion of the first insulation layer (or dielectric layer) 1405. As shown in FIG. 14, the second conducting layer 1411 in conjunction with a second conducting material 1410, such as a layer of silver/silver chloride (Ag/AgCl), may provide the reference electrode 1402. Another possible disposition of second conducting material 1410 is shown in FIG. 16, along with an outer membrane 1420 overcoating the various layers.

A second insulation layer 1406, such as a second dielectric layer in some embodiments, may be disposed or layered on at least a portion of the second conducting layer 1411. Further, a third conducting layer 1413 may be disposed on at least a portion of the second insulation layer 1406 and may provide the counter electrode 1403. Finally, a third insulation layer 1407 may be disposed or layered on at least a portion of the third conducting layer 1413. In this manner, the sensor 1400 may be layered such that at least a portion of each of the conducting layers is separated by a respective insulation layer (e.g., a dielectric layer). Another possible layer configuration is shown in FIG. 16. The embodiments of FIGS. 14 and 16 show the layers having different lengths; however, some or all of the layers may have the same or different lengths and/or widths, without departing from the scope of the present disclosure.

In any one or all embodiments, some or all of the electrodes 1401, 1402, and 1403 may be provided on the same side of the substrate 1404 in the layered construction described above, or alternatively, may be provided in a co-planar manner such that two or more electrodes may be positioned on the same plane (e.g., side-by side, parallel, or angled relative to each other) on the substrate 1404. For example, co-planar electrodes may include a suitable spacing therebetween and/or include a dielectric material or insulation material disposed between the conducting layers/electrodes. Furthermore, in some embodiments, one or more of the electrodes 1401, 1402, and 1403 may be disposed on opposing sides of the substrate 1404. In such embodiments, contact pads may be on the same or different sides of the substrate. For example, an electrode may be on a first side and its respective contact may be on a second side, for example, a trace connecting the electrode and the contact may traverse through the substrate.

With reference now to FIG. 15, shown is another embodiment of an analyte sensor in accordance with one or more embodiments of the present disclosure, and representing a variation of the sensor 1400 of FIGS. 8 and 10. Referring to FIG. 15, shown is an implantable (e.g., subcutaneous or transcutaneous) sensing region 1520 according to one or more embodiments of the present disclosure including a working electrode 1522. Proximal end 1540 is configured to be connected to various electrical connections for transmitting the output signals of the sensing region 1520. Collectively, the spans between the distal end 1525 and the proximal end 1540 form the sensor tail. Sensing region 1520 encompasses a bottom portion of the sensor tail. As depicted, sensing region 1520 comprises a rounded tip, but other tip shapes may alternately be present to facilitate insertion into a wearer's skin.

Additionally, in one or more embodiments, sensing region 1520 may include a reference electrode, a counter electrode, or counter-reference electrodes, such as those shown in FIGS. 8 and 10. Alternative electrode configurations may be employed without departing from the scope of the present disclosure.

With reference to FIGS. 8-10, it is notable that the sensor 1400, 1520 includes sensing functionality at a distal portion of their respective sensor tails. As described above, this location may allow for enhanced contact with deeper locations beneath a wearer's skin (e.g., the subcutaneous space), where greater access to the wearer's interstitial fluid may permit greater access the analyte of interest being measured (e.g., concentration thereof). That is, the sensing region is placed sufficiently deep within a wearer's skin to allow accurate measurement of the particular analyte, whereas placing the sensing region at a more proximate location to the skin surface may be inadequate to correctly determine the concentration or other characteristic of a desired analyte. In some embodiments, the length of the sensor tail extending from the bottom face 105 (FIGS. 1 and 2) may be in the range of less than about 20 millimeters (mm), such as in the range of about 1 millimeters to about 15 mm, or 1 mm to about 6 mm, encompassing any value and subset therebetween. Longer sensor tails may be inserted at an angle in some embodiments.

In some embodiments, the sensing region of an analyte sensor according to one or more embodiments of the present disclosure is within the distal-most portion of the sensor tail, including less than about 50% of the length of the sensor tail beginning at the distal-most portion, encompassing any value and subset therebetween. That is, if the sensor tail extending from the bottom face 105 (FIG. 1) of a sensor is determined, the sensing region may be located at a position that is within about 50% of the length of the sensor tail beginning from the deepest point within the skin of a wearer. In other embodiments, the sensing region is included in less than about 45%, 40%, 35%, 30%, 35%, 20%, 15%, or 10% of the length of the sensor tail beginning at the distal-most portion, encompassing any value and subset therebetween. The location of the sensing region may depend on the length of the sensor tail, the length or area of the sensing region, and the like, and any combination thereof.

The antimicrobial quality of the sensor that may be applied according to one or more embodiments described herein to the upper portion of the sensor tail, located at a distant sufficiently far from the sensing region of the sensor tail such that the antimicrobial does not interfere with the functioning of the sensing region or sensor as a whole, and does not adversely react with the skin of the wearer (e.g., it is not so deep within the skin to cause a reaction). In some embodiments, if the sensor tail extending from the bottom face 105 (FIG. 1) of a sensor is determined, the antimicrobial quality is applied by any means or mechanism to the upper (proximal) portion of the sensor tail, including less than about 25% of the length of the sensor tail beginning at the proximal-most portion, encompassing any value and subset therebetween. Some such portion may be located at the insertion site and/or slightly above or below the insertion site, depending on the length of the sensor tail. Accordingly, if the sensor tail extending from the bottom face 105 (FIG. 1) of a sensor is determined, the antimicrobial quality may be located at a position that is within about 25% of the length of the sensor tail extending from the bottom face 105. In other embodiments, the antimicrobial quality is included in less than about 25%, 20%, 15%, or 10% of the length of the sensor tail beginning at the proximal-most portion, encompassing any value and subset therebetween. The location of the antimicrobial quality may depend on the length of the sensor tail, the length or area of the sensing region, and the like, and any combination thereof.

Accordingly, in some embodiments, the antimicrobial quality may be at a distance of at least 25% of the length of the sensor tail measured from the bottom face 105 of the sensor away from the sensing region (the "upper portion" of the sensor tail), encompassing any value and subset therebetween increasing in greater distance. That is, the antimicrobial quality and the sensing region may be sufficiently separated such that the two do not interact directly, but instead any pathway to the sensing region along the sensor tail by a microorganism first encounters the antimicrobial quality, which prevents or reduces contact by the microorganism to the sensing region.

In any one or more other embodiments and with reference again to FIG. 1, any of the sensor housing 103, the bottom face 105, the needle, and/or the sensor 104 that protrudes from sensor housing 103 and through bottom face 105 into the skin of a wearer (i.e., the upper portion of the sensor tail and excluding the sensing region at the insertion tip) may be provided with an antimicrobial quality, including any subcomponents thereof (e.g., see FIG. 2). The antimicrobial quality may be coated thereon, functionalized thereto, impregnated therein (depending on the material or component to which the antimicrobial quality is imparted), or otherwise adhered thereto to impart the antimicrobial quality to the sensor device 102 and, in particular, for protection of the sensing region of the sensor tail and a wearer's skin. With reference to FIGS. 1 and 2, for example, the perimeter of the sensor housing 103 and/or the outer perimeter 202 of the bottom face 105 may be provided with an antimicrobial quality. During use, microorganisms may come into contact with the antimicrobial quality along perimeter edges prior to any potential wicking (e.g., microorganisms carried in water) along the bottom face 105 toward the receptacle 206 and/or aperture 204 (FIG. 2). The receptacle 206 may provide a seating for a sensor module (e.g., electronics of the sensor 1400) and the aperture 204 may provide a space for the sensor tail to extend from the sensor housing 103 into a wearer's skin through an insertion site. That is, the aperture 204 may provide an avenue to a sensing region. Further, contact with a microorganism at the receptacle 206 may allow for formation of a biofilm or other microbial colonization that may interfere with the working electronics of the sensor 1400.

In any one or more embodiments, an antimicrobial quality may further be provided along any or all of the radial grooves 200*a* and/or circumferential grooves of 200*b* of the bottom face 105. As provided above, the radial grooves 200*a*, alone or in combination with the circumferential grooves 200*b* may establish fluid communication between the aperture 204 and/or the receptacle 206 and the outer perimeter 202 of the bottom face 105. Accordingly, incorporation of an antimicrobial quality coated, functionalized, impregnated, or otherwise adhered to one or more portions of the grooves of the bottom face 105 may protect the receptacle 206 and/or aperture 204 from microorganisms, including related components (e.g., a sensor module, a sensor tail upper or lower portion, a sensing region, and the like, and any combination thereof).

Any sub-components of the sensor 1400 may further be provided with an antimicrobial quality (e.g., carrier grip(s) 210), without departing from the scope of the present disclosure, provided that inclusion of such antimicrobial quality does not interfere with the functioning and/or seating on the skin of the sensor 1400 and is not located beyond (deeper into the dermis/subcutis space than) the upper portion of the sensor tail.

The antimicrobial quality of the present disclosure for application to the skin prior to implantation of an analyte sensor (e.g., as an antimicrobial wipe) and/or to any one or more components of the analyte sensor itself may be by any mechanism, such as a coating, surface functionalization, encapsulation, impregnation, and the like, or any combination thereof.

In some embodiments, the antimicrobial quality is imparted to the sensor components described herein as acceptable substrates for receiving such antimicrobial quality of the present disclosure via an antimicrobial coating. An "antimicrobial coating," and grammatical variants thereof, as described herein, refers to a film or layer of antimicrobial applied to a surface by any means including, but not limited to, through use of an adhesive, through surface functionalization (e.g., crosslinking, graft polymer linking, and the like of the surface and the antimicrobial). Carriers may be used that, when applied to a surface, can themselves be degradable and allow a slow-release (e.g., upon water exposure, elevated temperatures, and/or exposure to light over time) of an antimicrobial, the antimicrobial of which may itself be degradable or otherwise encapsulated or impregnated in another material.

Suitable carriers that may be coated onto one or more of the surfaces described herein, including any one or more components of the sensor and a skin surface of a sensor wearer, are not considered to be particularly limited and include any such substances that have or can carry an antimicrobial quality, adhere to a desired surface, and/or are themselves able to provide or release the antimicrobial quality over time.

In any one or more embodiments, a suitable coating carrier for use in the present disclosure may include, but is not limited to, synthetic and natural biodegradable polymers. Suitable synthetic biodegradable polymer coating carriers may include, but are not limited to, polymethylmethacrylate; poly(lactic-co-glycolic acid); polylactic acid; polyglycolic acid; polyethylene glycol; poly(D,L)lactide, poly(ε-caprolactone); polyhydroxyalkonate; poly(butylene succinate); polyvinyl alcohol; degradable polyurethanes; and the like; any derivatives thereof; any copolymers thereof; and any combination thereof. Suitable natural biodegradable polymer coating carriers for use in the present disclosure may include, but are not limited to, cellulose, chitosan, lignin, pullulan, polyhydroxyalkonate, collagen, alginate, whey protein, keratin, gelatin, dextran, any derivatives thereof, any copolymers thereof, and any combination thereof. It is to be appreciated that any suitable other degradable synthetic or natural polymers or proteins may be used as an antimicrobial carrier coating in accordance with any or all of the embodiments described herein, without departing from the present disclosure. As used herein, the term "derivative," and grammatical variants thereof, refers to a compound that is derived from any one of the listed compounds herein, such as by replacement of one atom with another atom or group of atoms (e.g., a functional group). For instance, examples of cellulose derivatives may include, but are not limited to, hydroxyethylcellulose, carboxymethylhydroxyethylcellulose, carboxymethylcellulose, hydroxypropyl methylcellulose, and the like, and any combination thereof. The term "copolymer," and grammatical variants thereof, as used herein, refers to any polymer characterized by two or more different monomers, encompassing terpolymers and any higher polymers.

As alluded to above, in some instances, the carrier coating itself may provide the antimicrobial quality. Such antimicrobial carriers may additionally carry a secondary (or tertiary, or any plurality) antimicrobial, without departing from the scope of the present disclosure. For example, an organosilane coating (e.g., nanocoating) may provide an abrasive surface to a sensor component or skin, which inhibits microorganism attachment due to disruption of their outer membrane. The abrasive surface may be undetectable to humans, and thus suitable for contact with a sensor wearer's skin and/or at or near the insertion site (e.g., at an upper portion of the sensor tail or otherwise above the dermis). In some instances, the organosilane may be coupled with a quaternary ammonium compound, which provides additional anchoring to a surface, such as by forming a chemical bond with one or more components of a sensor or the formation of a film on skin. Moreover, a quaternary ammonium compound may be used alone if desired to provide an antimicrobial quality to the sensor and/or skin.

A selected organosilane for use as the carrier coating and/or the antimicrobial compound itself is not considered to be particularly limiting and may include any suitable carrier coating that can carry an antimicrobial and/or provide antimicrobial qualities itself over time. In one or more embodiments, examples of suitable organosilane carrier coatings for use in the present disclosure may include, but are not limited to, methyl triethoxysilane, methyl trimethoxysilane, vinyl trimethoxysilane, phenyl trimethoxysilane, 3-aminopropyltrimethoxysilane, 3-glycidoxypropyltrimethoxysi lane, methacryloxypropyltrimethoxysilane, mercaptopropyltrimethoxysilane, and the like, any derivative thereof, and any combination thereof.

A selected quaternary ammonium compound for use as the carrier coating and/or the antimicrobial compound itself (e.g., alone or in combination with an organosilane) is not considered to be particularly limited. Examples of suitable quaternary ammonium compounds for use in the present disclosure may include, but are not limited to, dimethyloctadecyl (3-trimethoxysilyl propyl) ammonium chloride, alkyldimethylbenzylammonium chloride, didecyldimethylammonium chloride, benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride, quaternary ammonium polyethyleneimine, and the like, any derivatives thereof, and any combination thereof.

The attachment of the quaternary ammonium compound described above may be considered a surface functionalization of one or more components of the sensor described herein for imparting an antimicrobial quality to which it is covalently bound. Other carrier coatings comprising an antimicrobial quality may additionally be achieved by surface functionalization, without departing from the scope of the present disclosure. For example, a surface of one or more components of a sensor as described herein may be functionalized by attaching a polymer or polypeptide to the surface, such as through a grafting process. Polymers may be grafted (e.g., through use of absorption or chemical bonding, crosslinking, or other immobilization means) or directly polymerized onto one or more surfaces of the sensor. Such polymers may form a matrix for acting as a carrier coating for one or more antimicrobial compounds in which the antimicrobial is free-floating (i.e., distributed without chemical bonding throughout the matrix). In other embodiments, the polymers may be functionalized to allow direct bonding with one or more antimicrobial compounds (e.g., to have quaternary amine functional groups).

In still other embodiments, the polymer coatings may additionally provide an antimicrobial quality themselves. Suitable such polymers for use in the embodiments of the present disclosure that may provide antimicrobial qualities may include, but are not limited to, those polymers specified above, an organosilane, a quaternary ammonium compounds, 4-vinyl-n-hexylpyridinium bromide, dimethyl(2-methacryloyloxyethyl) phosphonate, poly(ethylene glycol), poly(sulfobetaine methacrylate), poly[3-dimethyl (methacryloyloxyethyl) ammonium propane sulfonate-b-2-(diisopropylamino)ethyl methacrylate], poly(2-methyl-2-oxazoline), a polyphenol, polyhexadine, a chlorohexidine polymer, a nisin-immobilized organosilicon, poly(n,n-diethylethylenediamine-co-aerosol-based acrylic), a benzimidazole polymer, a halogen polymer, a N-halamine polymer, quaternary phosphonium modified epoxidized natural rubber, arginine-tryptophan-rich peptide, guanylated polymethacrylate, polyguanidine, olethyleneimine, chitosan, chitosan derivatives, ammonium ethyl methacrylate homopolymer, metallo-terpyridine carboxymethyl cellulose, poly(N-vinylimidazole) modified silicone rubber, poly-ε-lysine, cationic quaternary polyelectrolytes, 2-(dimethylamino)ethyl methacrylate, a benzaldehyde, 5-chloro-8-hydroxy-quinoline polymers, and the like, any derivatives thereof, any copolymers thereof, and any combination thereof.

One or more antimicrobial compounds may be encapsulated or impregnated in a slow-release compound where the antimicrobial is at least partially surrounded by the encapsulating material or permeating void space (e.g., pores) of an impregnatable material, respectively. Both of the encapsulating material and the impregnatable material may be degradable to allow slow release of the antimicrobial. In other instances, the impregnatable material is not degradable, but instead the antimicrobial is able to leach from the voids of the impregnatable material to provide the desired antimicrobial quality, without degradation of the impregnatable material itself. Such compounds may be located as part of the overbandages and/or the sensor components located at or above the dermis (e.g., the upper portion of the sensor tail or above toward the skin surface and including the skin surface).

Moreover, the encapsulated and/or impregnated antimicrobial compounds may be incorporated into any of the coatings listed above by chemical means (e.g., chemical bonding) or by dispersion (e.g., without chemical bonding or by matrix stabilization), without departing from the scope of the present disclosure. In other embodiments, the encapsulated and/or impregnated antimicrobial compounds may themselves allow covalent or other, such as associative, bonding with one or more components of a sensor described herein, depending on the composition of the encapsulating material and/or impregnatable material, the composition of the sensor component, the location of the sensor component relative to the insertion site, and the like.

An encapsulating material for use in the present disclosure is not considered to be particularly limited provided that as the material degrades and releases the encapsulated antimicrobial it does not interfere with the skin health of a wearer or the functioning of the analyte sensor described herein, and may generally be any biocompatible, degradable material known to one of skill in the art. In some embodiments, the encapsulating material itself is able to provide an antimicrobial quality. Examples of suitable encapsulating materials for use in the embodiments of the present disclosure may include, but are not limited to, the degradable synthetic and natural polymers and proteins described herein, biocompatible or biodegradable ceramics, metallic biocompatible or biodegradable compounds, and the like, and any combination thereof. Examples of biocompatible or biodegradable ceramics for use in the embodiments described herein may include, but are not limited to, calcium sulfate, calcium carbonate, calcium phosphate, dicalcium phosphate, tricalcium phosphate, hydroxyapatite, and the like, and any combination thereof. Examples of metallic biocompatible or biodegradable compounds for use in the embodiments described herein may include, but are not limited to, magnesium-based alloys such as magnesium alloyed with calcium, zinc, aluminum, manganese, indium, silver, zirconium, and the like, and any combination thereof.

An impregnatable material for use in the present disclosure is not considered to be particularly limited provided that the material is able to release an antimicrobial and does not interfere with the skin health of a wearer (i.e., maintains skin health) or the functioning of the analyte sensor described herein, and may generally be any biocompatible material known to one of skill in the art for placement of an antimicrobial. In some embodiments, the impregnatable materials may be generally porous or have areas of void space for filling or penetration by an antimicrobial compound. In other embodiments, the impregnatable materials may be inclusion complexes, such as cyclodextrins (e.g., alpha, beta, or gamma), which may be particularly compatible with a hydrophobic antimicrobial compound (e.g., certain peptides, hydrophobically functionalized polymers, and the like) and which can be released from the cyclodextrin complex upon contact with water, for example, because the outer surface thereof is hydrophilic.

Suitable impregnatable materials may be any of the biocompatible materials, including those that are degradable and those that themselves impart antimicrobial qualities, described herein, and have an antimicrobial permeated therethrough. Some such materials may be made porous and have an antimicrobial permeated therethrough. For example, an antimicrobial may be impregnated into void space of a cellulose or other natural polymer, a metal, a synthetic polymer, a metal oxide, and the like, and any combination thereof.

In some embodiments, the impregnatable material is a nanoparticle composed of one or more of the materials described herein impregnated (or, in some embodiments, made wholly from) one or more antimicrobial compounds, which may be made from any of the biocompatible materials described herein and/or any biocompatible materials known to those of skill in the art. As used herein, the term "nanoparticle," and grammatical variants thereof, refers to a particle having a diameter in the range of about 1 nanometer (nm) to about 1000 nm, encompassing any value and size distribution therebetween. Preferably, a nanoparticle described herein has a diameter in the range of about 1 nm to about 100 nm, encompassing any value and size distribution therebetween. For example, an antimicrobial component may be permeated in void space within or on a nanoparticle (or other impregnatable material) by any means such as chemical deposition (e.g., chemical reduction), sonochemical deposition, solvent impregnation (e.g., supercritical solvent deposition), microwave deposition, simple diffusion (e.g., contained by surface interactions), absorption, adsorption, or any other mechanism known to one of skill in the art. In some embodiments, the nanoparticles may be incorporated with one or more coatings to impart antimicrobial quality. Alternatively, the nanoparticles may themselves have sufficient attraction to one or more surfaces of an analyte sensor to achieve a thin film applied thereupon.

The antimicrobial compounds for use in the present disclosure include all skin-compatible antimicrobial compounds, including those described hereinabove, regardless of their particular form (e.g., coating, particle, and the like), and including an organosilane, a quaternary ammonium, the antimicrobial polymers, and the like, and any combination thereof. Examples of additional antimicrobial compounds, any of which may be used alone or in combination with the aforementioned compounds, may include, but are not limited to, metal-based compounds (e.g., a metal ion, a metal oxide, metal salts, metal coordination compounds including chelates, and the like), iodine, povidone-iodine, chlorhexidine, amphotericin B, bacitracin, colistin, gramicidin, gramicidin S, ritipenem, acediasulfone, acetosulfone, bambermycin(s), brodimoprim, butirosin, capreomycin, carbomycin, dapsone, diathymosulfone, enviomycin, glucosulfone solasulfone, leucomycin(s), lucensomycin, micronomicin, mupirocin, p-sulfanilylbenzylamine, pipemidic acid, polymyxin, primycin, ristocetin, rosaramycin, salazosulfadimidine, succisulfone, sulfachrysoidine, sulfaloxic acid, sulfamidochrysoidine, sulfanilic acid, sulfoxone, teicoplanin, tetroxoprim, thiazolsulfone, thiostrepton, trimethoprim, trospectomycin, tuberactinomycin, vancomycin, azaserine, candicidin(s), chlorphenesin, dermostatin(s), filipin, fungichromin, nystatin, oligomycin(s), perimycin A, tubercidin, carbapenems (e.g., faropenem, imipenem, panipenem, biapenem, meropenem, doripenem, ertapenem, and the like), cephalosporins (e.g., cefoxitin, cefotaxime, cefepime, nitrocefin, cefpirome, ceftobiprole, ceftazidime, ceftriaxone, cefadroxil, cefamandole, cefatrizine, cefbuperazone, cefclidin, cefdinir, cefditoren, cefetamet, cefixime, cefinenoxime, cefminox, cefodizime, cefonicid, cefoperazone, ceforanide, cefotetan, cefotiam, cefozopran, cefpimizole, cefpiramide, cefprozil, cefroxadine, cefteram, ceftibuten, cefuzonam, cephalexin, cephaloglycin, cephalosporin C, cephradine, flomoxef, moxalactam, and the like), monocyclic beta-lactams (e.g., aztreonam, tigemonam, carumonam, BAL19764, nocardicin, BAL30072, and the like), oxazolidinones (e.g., linezolid, sutezolid, and the like), penicillins (e.g., aminopenicillanic acid, benzylpenicillin, ampicillin, amoxicillin, carbenicillin, ticarcillin, oxacillin, azlocillin, dicloxacillin, piperacillin, apalcillin, temocillin, aspoxicillin, cyclacillin, epicillin, hetacillin, quinacillin, and the like), quinolones (e.g., nalidixic acid, norfloxacin, enoxacin, ciprofloxacin, enrofloxacin, levofloxacin, fleroxacin, clinafloxacin, grepafloxacin, lomefloxacin, nadifloxacin, pazufloxacin, temafloxacin, tosufloxacin, trovafloxacin, ciproflaxacin, ofloxacin, pefloxacin, rosoxacin, amifloxacin, temafloaxcin, lomefloxacin, sparfloxacin, and the like), tetracyclins (e.g., tetracycline, minocycline, tigecycline, apicycline, chlortetracycline, clomocycline, demeclocycline, doxycycline, guamecycline, lymecycline, meclocycline, methacycline, oxytetracycline, pipacycline, rolitetracycline, sancycline, and the like), aminoglycosides (e.g., amikacin, and the like), beta-lactamase inhibitors (e.g., clavulanic acid, sulbactam, avibactam, tazobactam, BAL29880, and the like), aminonucleosides (e.g., puromycin, and the like), aminoglycosides (e.g., apramycin, a kanamycin, isepamicin, a fortimicin, a gentamicin, neomycin, netilmicin, streptomycin, spectinomycin, arbekacin, dibekacin, dihydrostreptomycin, paromomycin, ribostamycin, sisomicin, tobramycin, and the like), anthracyclines (e.g., doxorubicin, daunorubicin, and the like), pimaricins (e.g., natamycin, and the like), sulfanilamides (e.g., 4,4'-sulfinyldianiline, 2-p-sulfanilyanilinoethanol, 4-sulfanilamidosalicylic acid, and the like), macrolides (e.g., mepartricin, spiramycin, clarithromycin, dirithromycin, erythromycin, josamycin, a midecamycin, oleandomycin, rokitamycin, roxithromycin, and the like), peptidyl transferase amphenicols (e.g., azidamfenicol, azithromycin, chloramphenicol, thiamphenicol, and the like), lincosamides (e.g., clindamycin, lincomycin, and the like), ansamycins (e.g., rifamycin SV, rifampin, rifapentine, rifaximin, rifamide, and the like), and the like, and any combinations thereof.

Examples of metal-based antimicrobial compounds may include, but are not limited to, silver, copper, magnetite, gold, gallium, platinum, palladium, titanium dioxide, zinc oxide, magnesium oxide, silicon dioxide, iron oxide, carbon dioxide, copper oxide, nitric oxide, carbon nanotubes, and the like (e.g., other antimicrobial heavy metal ions and/or metal oxides), any alloys thereof, any salts thereof, any coordination complexes and/or chelates thereof, any combination thereof, and any combination thereof in addition to one or more of the aforementioned antimicrobial compounds described herein.

In some embodiments, these metal-based antimicrobials may be metal-containing nanoparticles, such as impregnated or made whole from the antimicrobial compound, including as non-limiting examples, silver nanoparticles, zinc oxide nanoparticles, iron oxide nanoparticles, copper nanoparticles, and the like.

The particular amount of antimicrobial provided to any one or more components of the sensor and/or to the skin of a sensor wearer may depend on a number of factors including, but not limited to, the physiology and daily routine of a wearer, the area of the sensor to which the antimicrobial quality is imparted, the particular antimicrobial mechanism and compound selected, and the like. In nonlimiting embodiments, the antimicrobial quality (or qualities) is incorporated in an amount of about 0.01% to about 20% by weight of the antimicrobial carrier (e.g., coating, encapsulant, and the like) or surface area to which it is applied (e.g., upper portion of the sensor tail), encompassing any value or subset therebetween, depending broadly on at least one or more of the factors provided above. It is to be understood that the ideal antimicrobial quality amount will be based on ensuring adequate antimicrobial protection without compromising the functionality of the sensor.

It is to be understood that the skin interacting components of the sensor itself may impart an antimicrobial quality in addition to the one or more adhered or applied antimicrobial qualities described herein. Moreover, a component of the sensing element (e.g., enzyme such as glucose oxidase) for a particular desired analyte being measured may additionally provide an antimicrobial quality, without departing from the scope of the present disclosure.

Embodiments disclosed herein include:

Embodiment G: Overbandages. The overbandages comprise: a vapor-permeable backing; an aperture defined in the vapor-permeable backing, the aperture being sized to circumferentially surround a sensor housing that is adapted for adhering to a skin surface; a contact adhesive layer disposed on one side of the vapor-permeable backing; wherein the contact adhesive layer comprises an anchoring adhesive strip contacting the aperture, a first adhesive portion laterally arranged to a first side of the anchoring adhesive strip, and a second adhesive portion laterally arranged to a second side of the anchoring adhesive strip; first and second peelable release liners disposed upon the first and second adhesive portions; and a third peelable release liner disposed upon the anchoring adhesive strip.

Embodiment H: Overbandages having a symmetrical aperture.

The overbandages comprise: a vapor-permeable backing; a symmetrical aperture defined in the vapor-permeable backing, the symmetrical aperture being sized to circumferentially surround a sensor housing that is adapted for adhering to a skin surface; a contact adhesive layer disposed on one side of the vapor-permeable backing; wherein the contact adhesive layer comprises an anchoring adhesive strip that contacts the symmetrical aperture and is coincident with or parallel to a symmetry line of the symmetrical aperture such that portions of the anchoring adhesive strip reside on opposing sides of the symmetrical aperture, a first adhesive portion laterally arranged to a first side of the anchoring adhesive strip, and a second adhesive portion laterally arranged to a second side of the anchoring adhesive strip; first and second peelable release liners disposed upon the first and second adhesive portions; and a third peelable release liner disposed upon the anchoring adhesive strip; wherein the overbandage is foldable along the anchoring adhesive strip when the third peelable release liner has been removed.

Embodiment I: Methods for applying an overbandage to a skin surface. The methods comprise: providing the overbandage of "A" and a sensor housing that is adhered to a skin surface; removing the third peelable release liner from the anchoring adhesive strip; folding the overbandage along the anchoring adhesive strip, thereby converting the aperture into a recess; abutting an edge of the recess against the sensor housing and adhering the anchoring adhesive strip to the skin surface, the first peelable release liner facing outward from the skin surface and the second peelable release liner facing inward toward the skin surface; removing the first peelable release liner from the first adhesive portion, unfolding the overbandage and adhering the first adhesive portion to the skin surface, and after adhering the first adhesive portion to the skin surface, removing the second peelable release liner from the second adhesive portion and adhering the second adhesive portion to the skin surface; wherein the aperture circumferentially surrounds the sensor housing after adhering the first and second adhesive portions to the skin surface.

Each of embodiments G, H, and I may have one or more of the following additional elements in any combination Element 1: wherein the anchoring adhesive strip exhibits a higher rigidity than do the first and second adhesive portions, the third peelable release liner exhibits a higher rigidity than do the first and second peelable release liners, or both.

Element 2: wherein the anchoring adhesive strip has a width ranging between about 1 mm and about 5 mm.

Element 3: wherein the anchoring adhesive strip has a width that is smaller than a width of the aperture.

Element 4: wherein the anchoring adhesive strip is arranged coincident with or parallel to a symmetry line of the aperture.

Element 5: wherein the aperture is circular and the anchoring adhesive strip is arranged coincident with or parallel to a diameter of the aperture.

Element 6: wherein the anchoring adhesive strip spans edge-to-edge across the vapor-permeable backing.

Element 7: wherein the third peelable release liner is configured for removal from the contact adhesive layer before the first and second peelable release liners.

Element 8: wherein the third peelable release liner overlays at least a portion of the first and second peelable release liners.

Element 9: wherein the third peelable release liner occludes the aperture.

Element 10: wherein the overbandage further comprises an antimicrobial quality.

By way of non-limiting example, exemplary combinations applicable to G, H, and I include: The overbandage of G or the method of I in combination with elements 1 and 2; 1 and 3; 1 and 4; 1 and 5; 1 and 6; 1 and 7; 1 and 8; 1 and 9; 2 and 4; 3 and 4; 2 and 5; 3 and 5; 2 and 6; 3 and 6; 2 and 7; 3 and 7; 2 and 8; 3 and 8; 2 and 9; 3 and 9; 5 and 6; 5 and 7; 5 and 8; 5 and 9; 6 and 7; 6 and 8; 8 and 9; 1 and 10; 2 and 10; 3 and 10; 4 and 10; 5 and 10; 6 and 10; 7 and 10; 8 and 10; and 9 and 10. The overbandage of H in combination with elements 1 and 2; 1 and 3; 1 and 5; 1 and 6; 1 and 7; 1 and 8; 1 and 9; 2 and 5; 3 and 5; 2 and 6; 3 and 6; 2 and 7; 3 and 7; 2 and 8; 3 and 8; 2 and 9; 3 and 9; 5 and 6; 5 and 7; 5 and 8; 5 and 9; 6 and 7; 6 and 8; 8 and 9; 1 and 10; 2 and 10; 3 and 10; 4 and 10; 5 and 10; 6 and 10; 7 and 10; 8 and 10; and 9 and 10.

To facilitate a better understanding of the embodiments described herein, the following examples of various representative embodiments are given. In no way should the following examples be read to limit, or to define, the scope of the invention.

EXAMPLES

Figure 3:
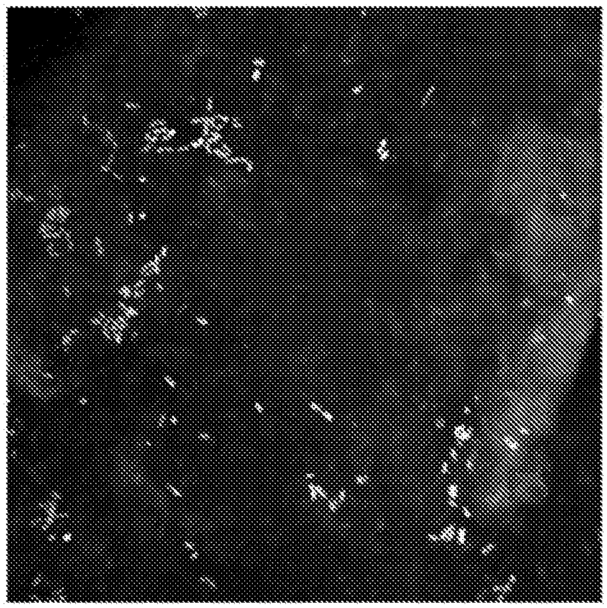
FIG. 3 is a fluorescent micrograph image showing a biofilm comprised of microorganisms formed on the sensor tail of an analyte sensor having no antimicrobial quality.

Example 1: Biofilm Observation and Signal Attenuation. In this example, analyte sensors for measuring glucose were observed for potential late signal attenuation after formation of a biofilm on the surface of the lower portion of a sensor tail comprising the sensing element. As shown in FIG. 3, illustrated is a fluorescent micrograph image showing 4',6-diamidino-2-phenylindole (DAPI) staining of a biofilm comprised of microorganisms formed on a sensor tail of an analyte sensor having no antimicrobial quality. As shown, the biofilm is characterized by small rod-shaped (bacilli) and spherical-shaped (rod) microorganisms.

Figure 4:
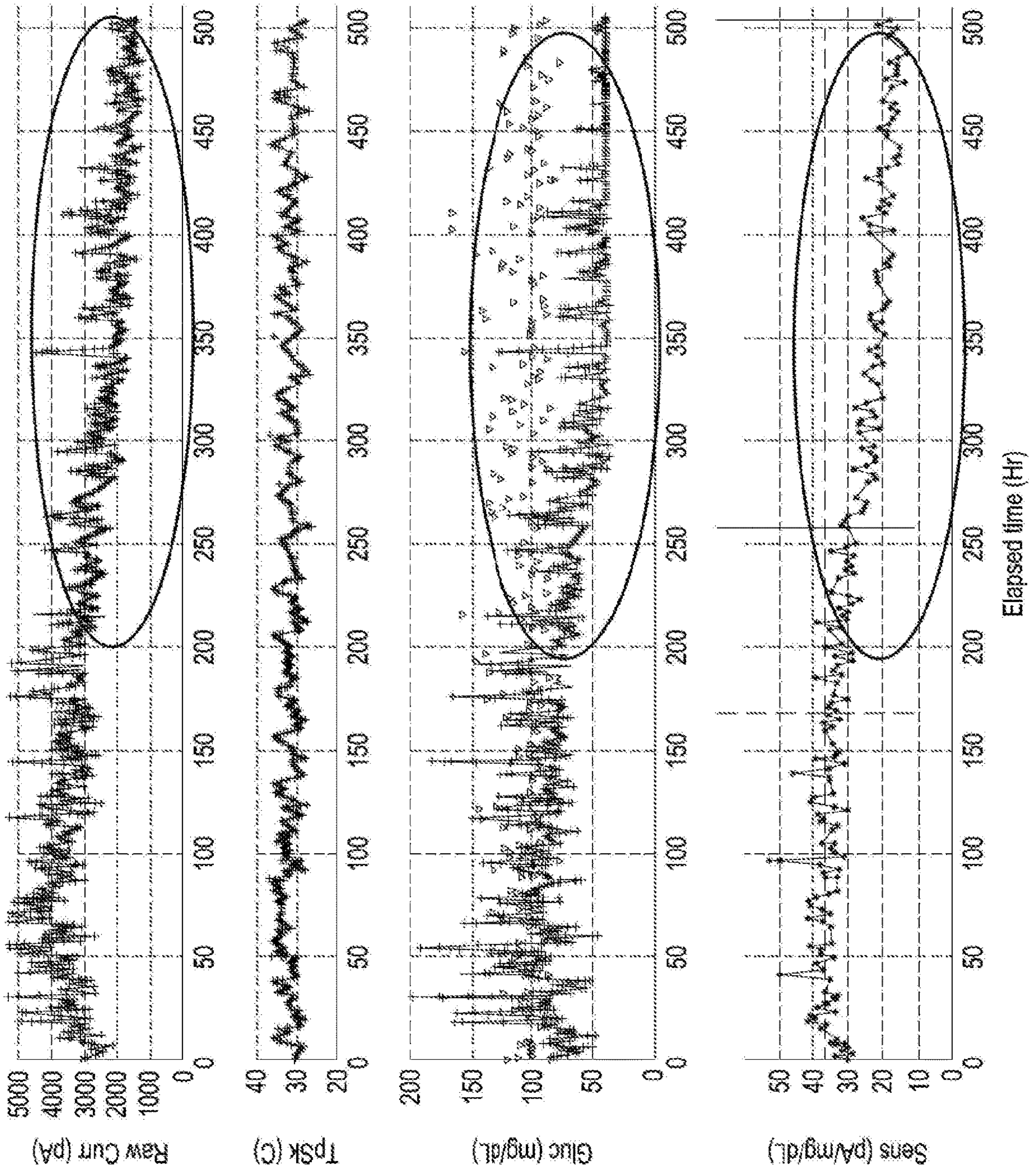
FIG. 4 shows glucose analyte sensor measurements having no antimicrobial quality and reduced sensitivity in the later half to two thirds of the sensor life due to biofilm comprised of microorganisms formed on the sensor tail thereof.

An analyte sensor comprising a representative biofilm, such as that shown in FIG. 3, was tested for glucose signal measurements over time. As shown in FIG. 4, the sensor signal showed late signal attenuation. As used herein, the term "late signal attenuation," and grammatical variants thereof, refers to dynamic signal reduction or sudden signal reduction in sensitivity, indicating potential loss in analyte sensor functionality of accuracy. The term "late" with reference to late signal attenuation refers to any time or time period after which an analyte sensor has been positioned and functioning properly (e.g., obtaining accurate analyte measurements). As shown in FIG. 4, the x-axis represents elapsed time in hours (Hr), and the y-axis shows various data associated with a single analyte sensor. The "Raw Curr" represents the raw data (also termed "counts") received from the operational amplifier of the analyte sensor, having units in picoamperes (pA). The "TpSk" represents the temperature readout of the analyte sensor, having units in Celsius (C); because the temperature is stable, the late signal attenuation discussed herein is not applicable. The "Gluc" represents glucose measurements derived from the raw data counts, having units in milligrams per deciliter (mg/dL). The "Sens" represents the sensitivity of the analyte sensor determined using reference blood glucose measurements, having units in picoamperes per milligram per deciliter (pA/mg/dL).

As shown in FIG. 4, the raw current, glucose measurement, and sensitivity measurement each demonstrated late signal attenuation when the glucose sensor tail is coated with a biofilm and lacks any antimicrobial quality, such as roughly at about 200 hours in this particular example. Notably, the glucose sensor results shown in FIG. 4 may not be identical to those of other analyte sensors, where such trends of accuracy reduction may be characterized by reduced or increased dynamics, cyclic, or inconsistent in nature, for example.

Example 2: Incorporation of Silver-Based Antimicrobial Quality into an Analyte Sensor Membrane. In this example, various silver-based antimicrobial compounds were evaluated for their effect on sensor performance when incorporated into a membrane composition. The antimicrobial compounds selected included silver carbonate ($Ag_2CO_3$), silver chloride (AgCl), silver iodide (AgI), and silver nanoparticles (Ag) and each were e-beam sterilized. The silver-based antimicrobial compound was intermixed with a membrane composition, as described in one or more embodiments of the present disclosure, and compared to controls. The antimicrobial compounds were intermixed at 50% by weight of Formula 1 polymer (see above), which was crosslinked with Gly3 and additionally included PDMS-DGE leveling agent.

Sensor evaluation was determined by testing the current performance of each of the silver-containing sensor membranes as compared to a control over time (in duplicate). Amperometry was run on custom built equipment with independent p-stats for each channel and data acquisition was performed. The sensors were evaluated in PBS at 37° C. An initial multistep calibration was performed from zero (0) to 30 millimoles (mmol) of glucose and, thereafter, the concentration was held at 30 mmol for the remainder of the evaluation.

Figure 5A:
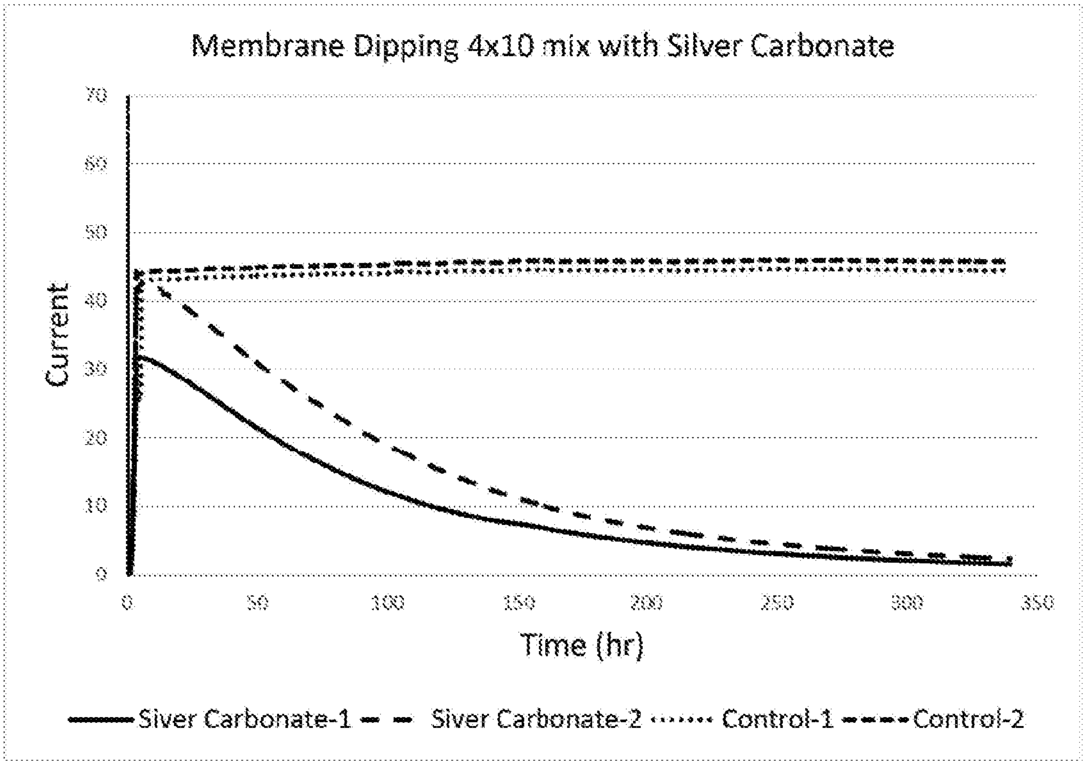
FIGS. 5A-5D show plots of the current response for a sensor coated with a silver-containing membrane polymer against a control.
Figure 5B:
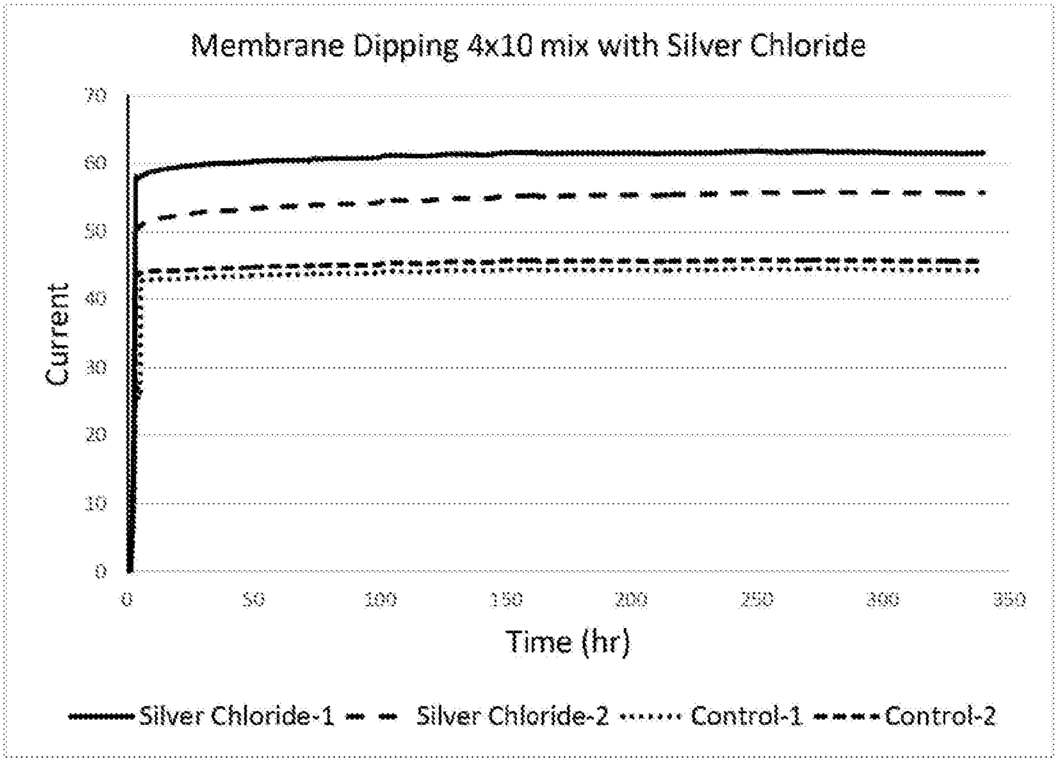
Figure 5C:
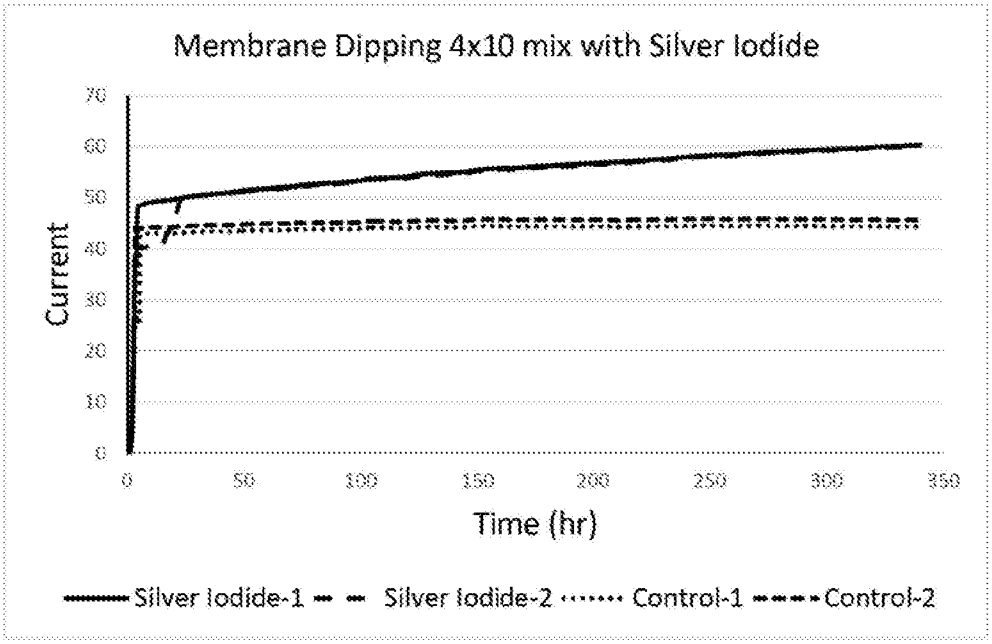
Figure 5D:
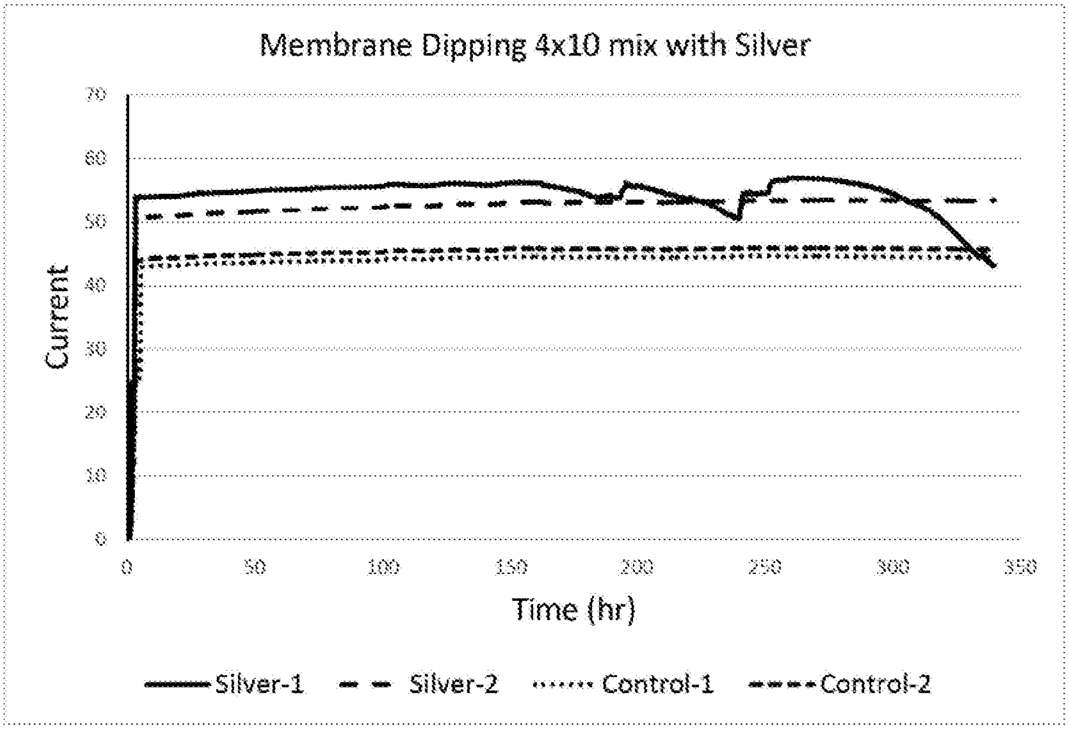

FIG. 5A shows a plot of the current response for a sensor coated with a $Ag_2CO_3$-containing membrane polymer against a control (duplicate measurements); FIG. 5B shows a plot of the current response for a sensor coated with a AgCl-containing membrane polymer against a control (duplicate measurements); FIG. 5C shows a plot of the current response for a sensor coated with a AgI-containing membrane polymer against a control (duplicate measurements); and FIG. 5D shows a plot of the current response for a sensor coated with a Ag-containing (nanoparticles) membrane polymer against a control (duplicate measurements). Each current response was measured in nanoamperes (nA).

As shown in FIG. 5A, the antimicrobial compound silver carbonate intermixed in the sensor membranes of the composition described in this Example resulted in relatively poor stability performance, dropping in current substantially within less than 50 hours.

FIG. 5B shows that silver chloride antimicrobial compounds incorporated into the glucose analyte sensor and membrane composition of this Examples (and extrapolated to others described herein) provided steady signal performance and thus no or very minimal interference with the operation of the sensor and/or membrane. Similarly, only minimal signal drift was observed in FIG. 5C with silver iodide incorporation, and such signal drift may be corrected by incorporating other compounds or adjusting specific concentrations, for example. FIG. 5D also demonstrates that the inclusion of silver nanoparticles into the membrane composition of this Example (and extrapolated to others described herein) resulted in relatively steady signal performance. It is noted that Silver-1 (Duplicate 1 in FIG. 5D) is thought to have encountered an electrical or other flaw during testing, resulting in the sporadic signal performance not observed in Silver-2. Accordingly, for the membrane formulation of Example 2 (and extrapolated to others described herein), silver chloride, silver iodide, and silver nanoparticles show particular suitability.

Example 3: In Vivo Testing of Silver-Based Antimicrobial Quality. In this example, sensors membranes comprising the silver-based antimicrobial compounds of Example 2 (tested in quadruplicate for each of the sensors in Example 2) and the Control of Example 2 were evaluated in vivo against a variety of gram-positive bacteria strains associated with common skin flora and wound infection, and which were nosocomial-derived using a modified Kirby-Bauer disk diffusion assay for antibiotic susceptibility testing. The bacteria used for evaluation were *Staphylococcus aureus* (MRSA) (ATCC #33591), *Staphylococcus epidermidis* (ATCC #12228), *Enterococcus faecalis* (ATCC #4082), and *Streptococcus pyogenes* (ATCC #19615). Each were cultured on Tryptic Soy Agar, except for *S. pyogenes*, which were cultured on Blood Agar. The zone of inhibition measurements are shown in Table 1 below.

TABLE 1

| | | Diameter of the Zone Including Test Article (mm) | |
|---|---|---|---|
| Organism | Sample ID | Maximum Distance | Minimum Distance |
| *S. aureus* (MRSA) | $Ag_2CO_3$-1 | 4.72 | 2.10 |
| | $Ag_2CO_3$-2 | 4.33 | 1.94 |
| | $Ag_2CO_3$-3 | 3.97 | 1.08 |
| | $Ag_2CO_3$-4 | 3.58 | 0.99 |
| | Control | No Zone | No Zone |
| *S. epidermidis* | AgCl-1 | 6.50 | 4.73 |
| | AgCl-2 | 5.78 | 4.15 |
| | AgCl-3 | 5.26 | 2.45 |
| | AgCl-4 | 4.87 | 2.19 |
| | Control | No Zone | No Zone |
| *E. faecalis* | AgI-1 | 4.45 | 2.48 |
| | AgI-2 | 3.98 | 1.57 |
| | AgI-3 | 3.28 | 0.93 |
| | AgI-4 | 3.93 | 1.71 |
| | Control | No Zone | No Zone |
| *S. pyogenes* | Ag-1 | 5.54 | 3.43 |
| | Ag-2 | 4.40 | 2.19 |
| | Ag-3 | 3.28 | 0.95 |
| | Ag-4 | 3.99 | 1.88 |
| | C1 | No Zone | No Zone |

Accordingly, each of the silver-based antimicrobial compounds from Example 1 (i.e., silver carbonate ($Ag_2CO_3$), silver chloride (AgCl), silver iodide (AgI), and silver nanoparticles (Ag)) demonstrate antimicrobial properties, as defined herein.

Example 4: Incorporation of Silver-Iodide Antimicrobial Quality into an Analyte Sensor Membrane. In this example, silver-iodide antimicrobial compound concentrations were further evaluated for their effect on sensor performance when incorporated into a membrane composition. The silver-based antimicrobial compound was intermixed with a membrane composition, as described in one or more embodiments of the present disclosure. The antimicrobial compounds were intermixed at 40%, 30%, 20%, 10%, and 5%% by weight of Formula 1 polymer (see above), which was crosslinked with Gly3 and additionally included PDMS-DGE leveling agent.

Sensor evaluation was determined by testing the current performance of each of the silver-iodide sensor membranes as compared to a control over time (in various replicates), as described in Example 2 above.

Figure 6A:
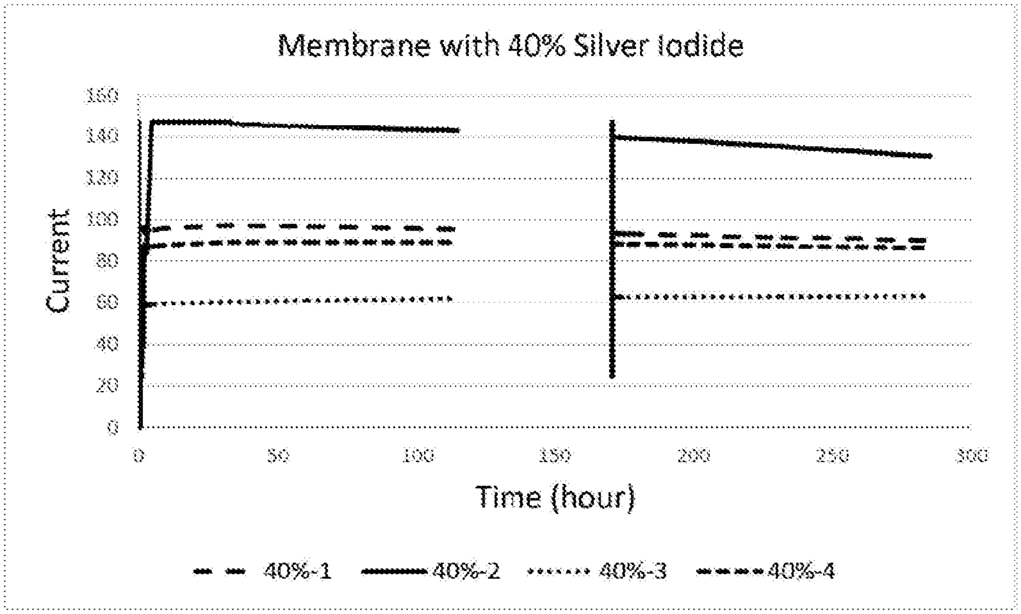
FIGS. 6A-6E show plots of the current response for a sensor coated with a silver-iodide containing membrane polymer against a control.
Figure 6B:
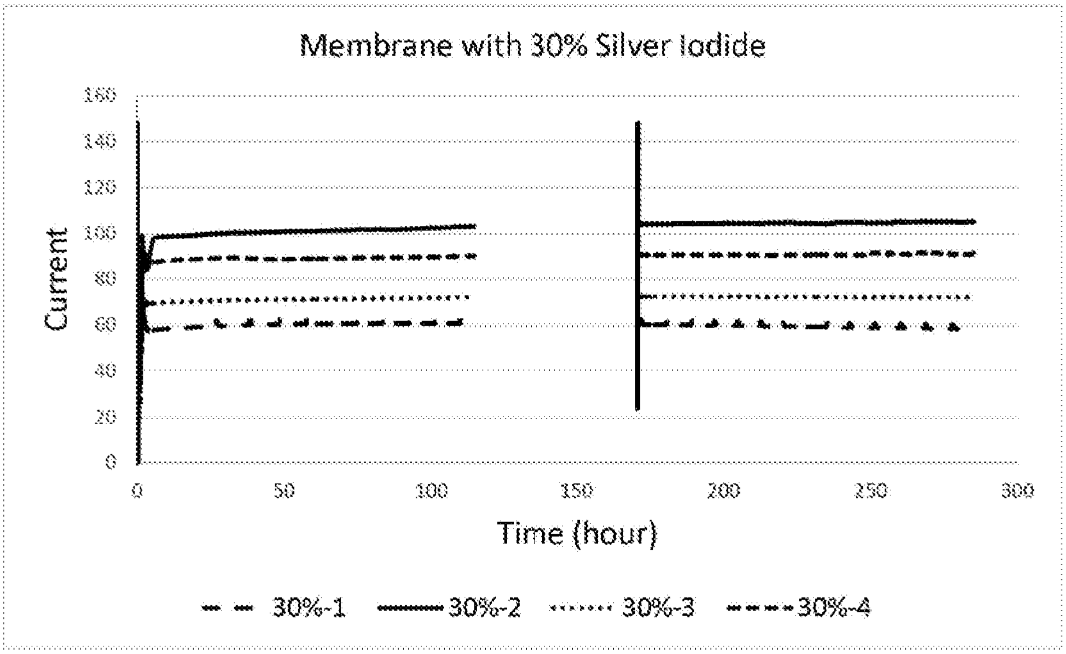
Figure 6C:
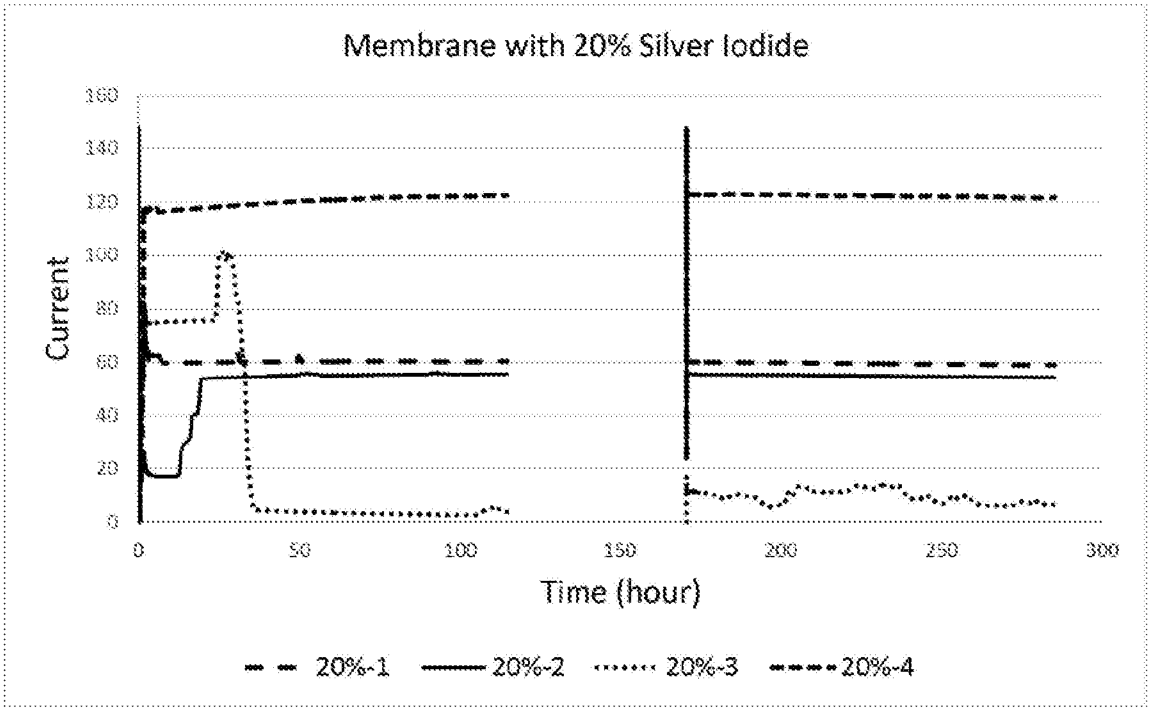
Figure 6D:
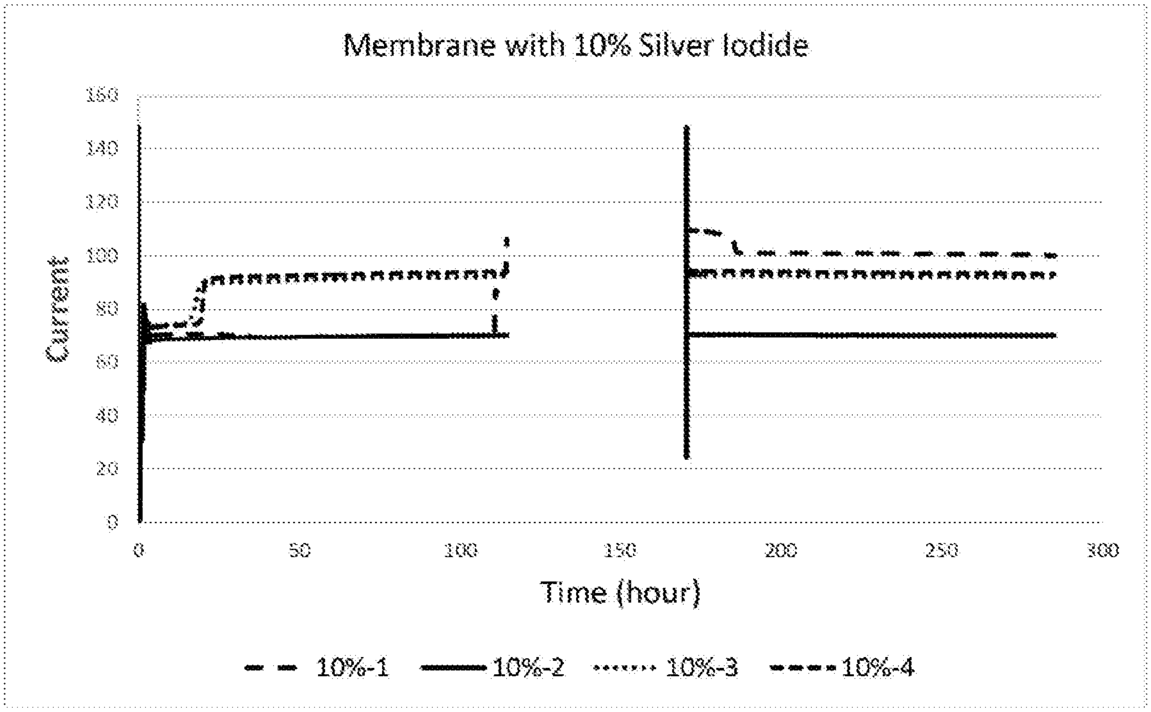
Figure 6E:
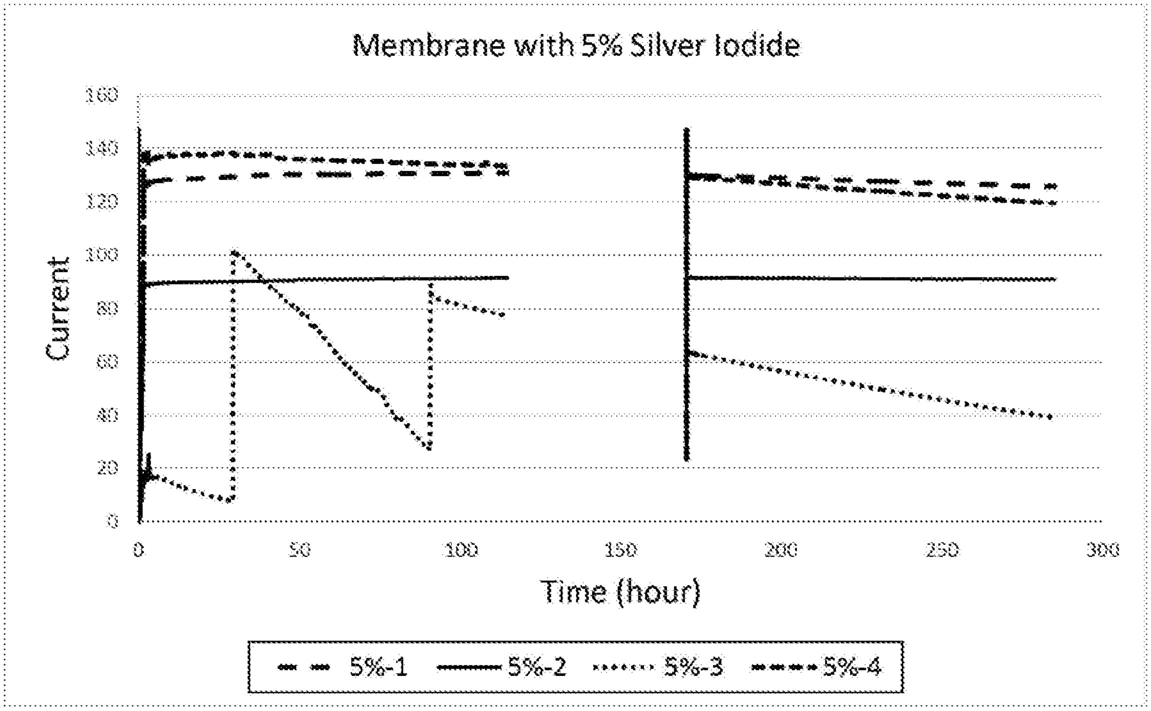

FIG. 6A shows a plot of the current response for a sensor coated with a 40% AgI-containing membrane polymer (quadruplicate measurements); FIG. 6B shows a plot of the current response for a sensor coated with a 30% AgI-containing membrane polymer (quadruplicate measurements); FIG. 6C shows a plot of the current response for a sensor coated with a 20% AgI-containing membrane polymer (quadruplicate measurements); FIG. 6D shows a plot of the current response for a sensor coated with a 10% AgI-containing membrane polymer (quadruplicate measurements); and FIG. 6E shows a plot of the current response for a sensor coated with a 5% AgI-containing membrane polymer (quadruplicate measurements). Each current response was measured in nanoamperes (nA). The break in data of FIGS. 6A-6E merely represents a time duration in which data was not received from the testing equipment.

As shown in FIGS. 6A and 6B, the 40% and 30% AgI-containing membrane polymers demonstrate a comparatively stabile current signal and less signal drift.

Example 5: Incorporation of Copper-Based Antimicrobial Quality into Membrane of Analyte Sensor. In this example, various copper-based antimicrobial compounds were evaluated for their effect on sensor performance when incorporated into a membrane composition. The antimicrobial compounds selected included Copper (II) Oxalate ($CuC_2O_4$), copper oxide (CuO), and copper iodide (CuI), copper metal (Cu), copper (II) chloride ($CuCl_2$) and copper metal blended with silver metal (Cu/Ag) (ratio of 1:1 by weight of Cu and Ag). The antimicrobial compound was intermixed with a membrane composition, as described in one or more embodiments of the present disclosure, and compared to a Control. The antimicrobial compounds were intermixed with various loadings of the Formula 1 polymer (see above) (i.e., 10%, 5%, or 2%) by weight of Formula 1 polymer, which was crosslinked with Gly3 and additionally included PDMS-DGE leveling agent, in a syringe.

Sensor evaluation was determined by testing the current performance of each of the copper-containing sensor membranes as compared to a control over time (in various replicates), as described in Example 2 above.

Figure 7A:
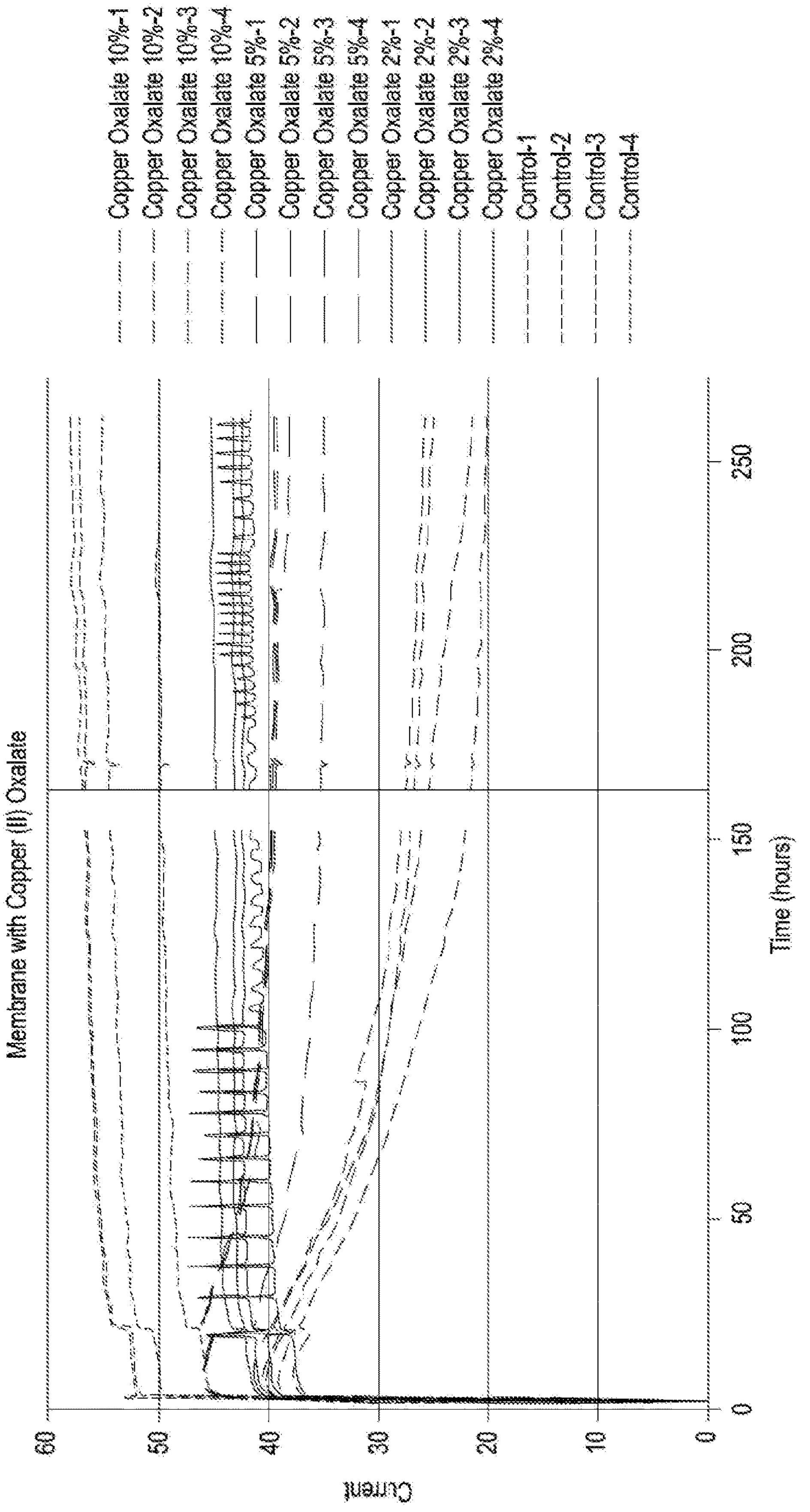
FIGS. 7A-7D show plots of the current response for sensors coated with different concentrations of copper-containing membrane polymer against a control.
Figure 7B:
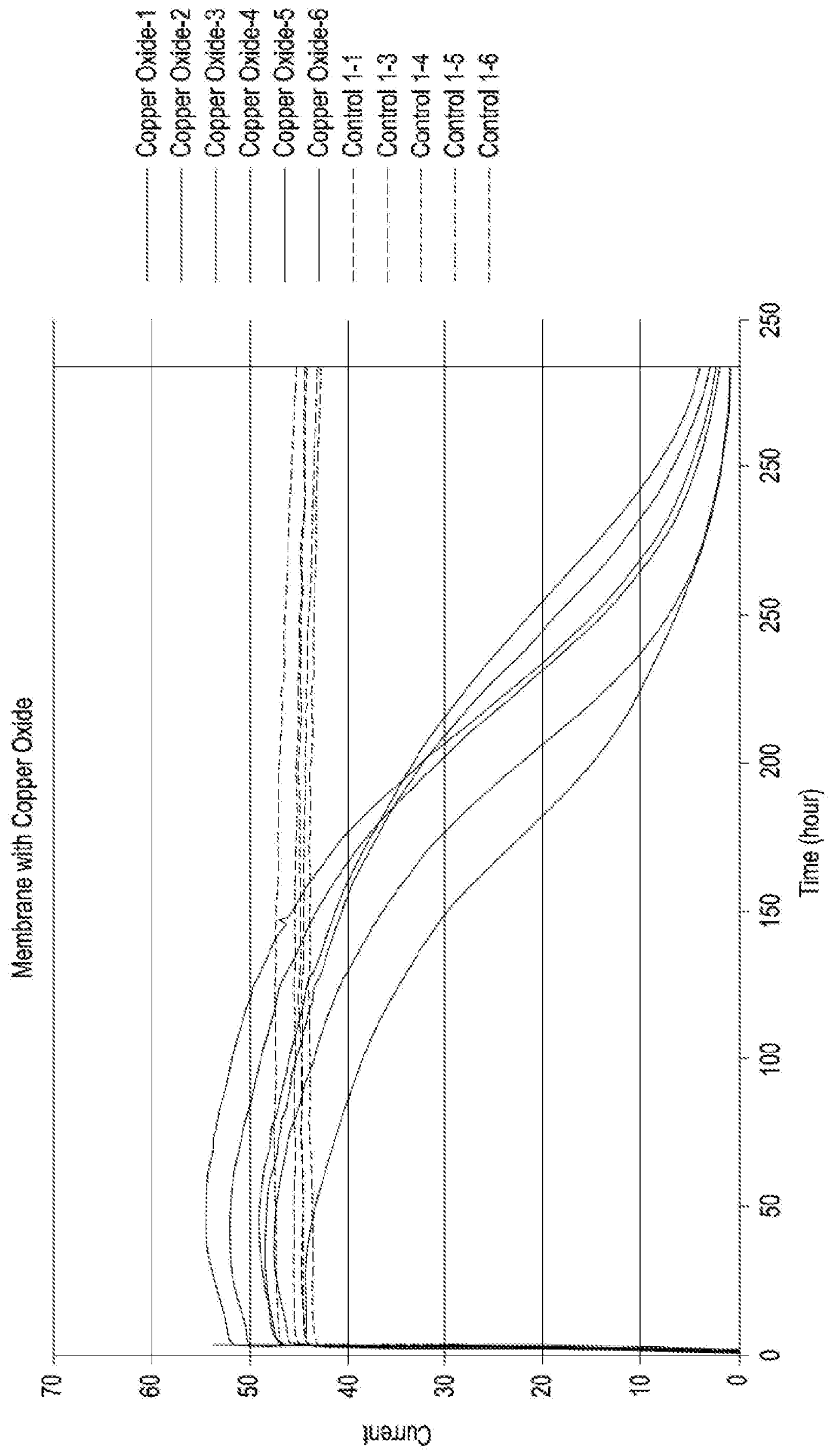
Figure 7C:
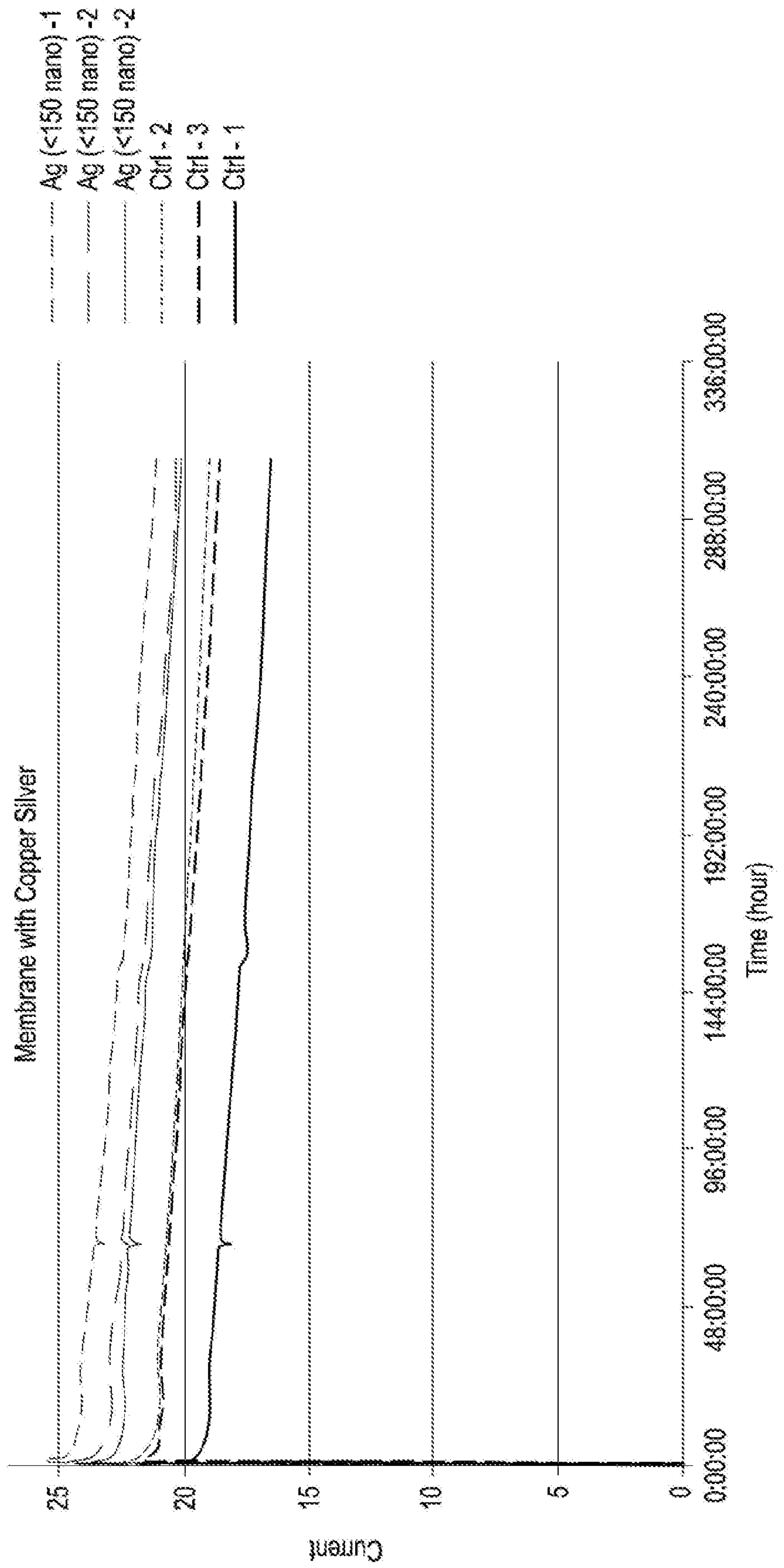
Figure 7D:
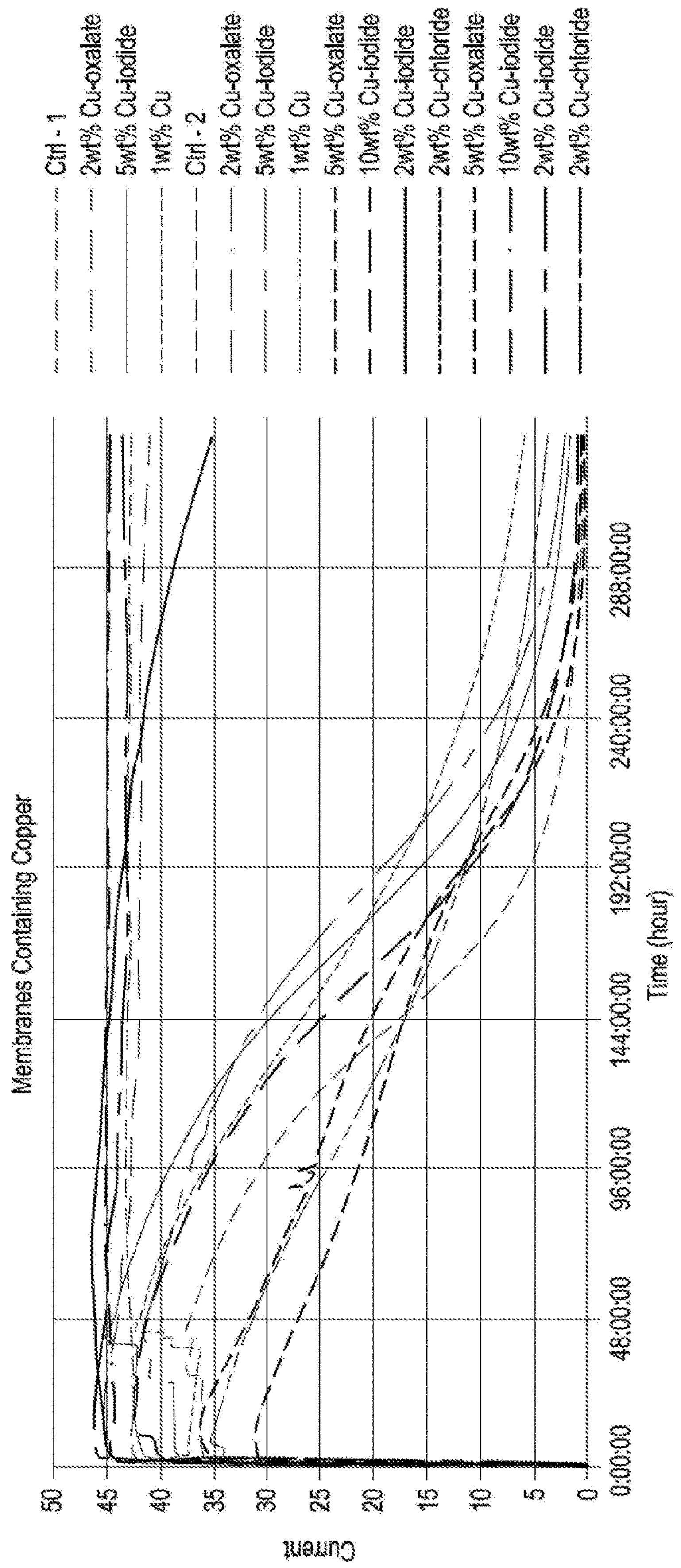

FIG. 7A shows a plot of the current response for a sensor coated with 10%, 5%, and 2% $CuC_2O_4$-containing membrane polymers against a control (quadruplicate measurements); FIG. 7B shows a plot of the current response for a sensor coated with 2% CuO-containing membrane polymer against a control (sextuplicate measurements); FIG. 7C shows a plot of the current response for a sensor coated with 2% Cu-containing membrane polymer (triplicate measurements), having Cu particles of less than 150 μm, against a control (triplicate measurements); and FIG. 7D shows a plot of the current response for a sensor coated with 1% Cu-containing membrane polymer (duplicate measurements), 5% or 2% $CuC_2O_4$-containing membrane polymers (duplicate measurements), 10%, 5%, or 2% CuI-containing membrane polymers (duplicate measurements), and 2% $CuCl_2$-containing membrane polymers (duplicate measurements) against a control (duplicate measurements). Each current response was measured in nanoamperes (nA).

As shown in FIGS. 7A-7D, the various copper-based antimicrobial compounds intermixed in the sensor membranes of the composition described in this Example (and extrapolated to others described herein) may be effective at providing antimicrobial qualities and good sensor performance at relatively low loading levels. At high Cu loading levels, sensor performance decreased with time. Moreover, only certain copper-based compounds appear compatible with the membrane composition of this Example (and extrapolated to others described herein) as compared to others. For example, copper (II) oxalate and copper (I) iodide appears particularly compatible.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of"

the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is:

1. A continuous glucose monitoring system, comprising:

an on-body analyte sensor comprising:

a subcutaneous glucose sensor configured to be located under a skin surface of a user, the subcutaneous glucose sensor comprising a proximal portion and a distal portion, wherein the proximal portion is configured to be connected to an electrical connection and wherein the distal portion is in contact with an interstitial fluid for sensing signals representative of glucose levels;

a sensor housing comprising the subcutaneous glucose sensor, wherein the sensor housing comprises a plurality of grooves on a bottom face of the sensor housing, and wherein the sensor housing is configured with an adhesive binder comprising a non-woven support material; and the electrical connection configured to be located above the skin surface and further configured to wirelessly transmit the signals representative of glucose levels via a Bluetooth protocol;

an overbandage configured to circumferentially surround the sensor housing and adhere to the skin surface of the user, wherein the overbandage comprises a vapor-permeable backing, wherein the vapor-permeable backing comprises an aperture and a contact adhesive layer comprising an anchoring adhesive strip comprising a first strip portion and a second strip portion, a first adhesive layer laterally arranged to a first side of the anchoring adhesive strip, and a second adhesive layer laterally arranged to a second side of the anchoring adhesive strip, wherein the vapor-permeable backing comprises a first portion along the anchoring adhesive strip and a second portion for a remainder of the vapor-permeable backing, and wherein a thickness of the first portion is greater than a thickness of the second portion, wherein the non-woven support material has a first areal mass of less than 20 $g/m^2$, wherein the overbandage has a moisture vapor transfer rate (MVTR) between 200 $g/m^2$/day to 2,000 $g/m^2$/day, and wherein the anchoring adhesive strip is in contact with the aperture such that the first strip portion and the second strip portion are disposed on opposing sides of the aperture, and wherein the overbandage further comprises first and second peelable release liners disposed upon first and second adhesive layers, respectively, and a third peelable release liner disposed upon the anchoring adhesive strip, wherein the overbandage is configured to be foldable along the anchoring adhesive strip when the third peelable release liner is removed, and wherein the overbandage, when folded along the anchoring adhesive strip, is configured to be seated against the sensor housing through a lateral engagement process with the anchoring adhesive strip, the first adhesive layer, and the second adhesive layer.

2. The continuous glucose monitoring system of claim 1, wherein the overbandage comprises the adhesive binder that forms an adhesive pad assembly with an interface material, wherein the interface material comprises a second non-woven support material that is different from the non-woven support material, and wherein the second adhesive layer is in contact with the interface material.

3. The continuous glucose monitoring system of claim 2, wherein the first adhesive layer does not span an entire width of the non-woven support material.

4. The continuous glucose monitoring system of claim 2, wherein the adhesive binder is asymmetric.

5. The continuous glucose monitoring system of claim 2, wherein the interface material comprises a third adhesive layer, wherein the interface material is configured to adhere to the second adhesive layer and the third adhesive layer comprises a third adhesive configured to adhere to the skin surface of the user, and wherein a second areal mass of the interface material is higher than the first areal mass of the non-woven support material.

6. The continuous glucose monitoring system of claim 5, wherein the second areal mass is between 50 $g/m^2$ and 200 $g/m^2$.

7. The continuous glucose monitoring system of claim 5, wherein the second areal mass is between 100 $g/m^2$ and 150 $g/m^2$.

8. The continuous glucose monitoring system of claim 5, wherein the second areal mass is between 60 $g/m^2$ and 100 $g/m^2$.

9. The continuous glucose monitoring system of claim 5, wherein the second areal mass is between 75 $g/m^2$ and 90 $g/m^2$.

10. The continuous glucose monitoring system of claim 1, wherein at least one of the first adhesive layer and the second adhesive layer have a MVTR between 200 $g/m^2$/day to 2,000 $g/m^2$/day.

11. The continuous glucose monitoring system of claim 1, wherein the first areal mass is between 3 $g/m^2$ and 20 $g/m^2$.

12. The continuous glucose monitoring system of claim 1, wherein the first areal mass is between 3 $g/m^2$ and 10 $g/m^2$.

13. The continuous glucose monitoring system of claim 1, wherein the first areal mass is between 5 $g/m^2$ and 10 $g/m^2$.

14. The continuous glucose monitoring system of claim 1, wherein the sensor housing further comprises an aperture and an outer perimeter face and wherein a portion of the plurality of grooves comprises radial grooves extending from the aperture of the sensor housing to the outer perimeter face.

15. The continuous glucose monitoring system of claim 1, wherein at least one of the non-woven support material, the first adhesive layer, and the second adhesive layer are breathable.

16. The continuous glucose monitoring system of claim 1, wherein the plurality of grooves are configured to promote fluid drainage away from the sensor housing.

17. A continuous glucose monitoring system, comprising:

an on-body analyte sensor comprising:

a subcutaneous glucose sensor configured to be located under a skin surface of a user, the subcutaneous glucose sensor comprising a proximal portion and a distal portion, wherein the proximal portion is configured to be connected to an electrical connection, and wherein the distal portion is in contact with an interstitial fluid for sensing signals representative of glucose levels;

a sensor housing, wherein the sensor housing comprises a first aperture and a plurality of grooves on a bottom face of the sensor housing, and wherein the sensor housing is configured with an adhesive binder comprising a non-woven support material; and the electrical connection configured to be located above the skin surface and further configured to wirelessly transmit the signals representative of glucose levels via a Bluetooth protocol; and an overbandage configured to circumferentially surround the sensor housing and adhere to the skin surface of the user, wherein the overbandage comprises a vapor-permeable backing, wherein the vapor-permeable backing comprises a second aperture and a contact adhesive layer comprising an anchoring adhesive strip comprising a first strip portion and a second strip portion, a first adhesive layer laterally arranged to a first side of the anchoring adhesive strip, and a second adhesive layer laterally arranged to a second side of the anchoring adhesive strip, wherein the vapor-permeable backing comprises a first portion along the anchoring adhesive strip and a second portion for a remainder of the vapor-permeable backing, and wherein a thickness of the first portion is greater than a thickness of the second portion, wherein the non-woven support material has a first areal mass of less than 20 $g/m^2$, and wherein the anchoring adhesive strip is in contact with the second aperture such that first strip portion and a second strip portion are disposed on opposing sides of the second aperture, and wherein the overbandage further comprises first and second peelable release liners disposed upon first and second adhesive layers, respectively, and a third peelable release liner disposed upon the anchoring adhesive strip, wherein the overbandage is configured to be foldable along the anchoring adhesive strip when the third peelable release liner is removed, and wherein the overbandage is configured to circumferentially surround the sensor housing and, when folded, adhere to the skin surface through a lateral engagement process with the anchoring adhesive strip, the first adhesive layer, and the second adhesive layer.

18. The continuous glucose monitoring system of claim 17, wherein the first areal mass is between 3 $g/m^2$ and 20 $g/m^2$.

19. The continuous glucose monitoring system of claim 17, wherein the first areal mass is between 3 $g/m^2$ and 10 $g/m^2$.

20. The continuous glucose monitoring system of claim 17, wherein the first areal mass is between 5 $g/m^2$ and 10 $g/m^2$.

21. The continuous glucose monitoring system of claim 17, wherein the first areal mass is between 6 $g/m^2$ and 10 $g/m^2$.

22. The continuous glucose monitoring system of claim 17, wherein the sensor housing further comprises an outer perimeter face and a portion of the plurality of grooves comprises radial grooves extending from the first aperture to the outer perimeter face.

23. The continuous glucose monitoring system of claim 17, wherein the first adhesive layer does not span an entire width of the non-woven support material.

24. The continuous glucose monitoring system of claim 17, wherein the overbandage comprises the adhesive binder that is asymmetric.

25. The continuous glucose monitoring system of claim 17, wherein the overbandage comprises the adhesive binder that forms an adhesive pad assembly with an interface material, wherein the interface material comprises a second non-woven support material that is different from the non-woven support material, and wherein the second adhesive layer is in contact with the interface material, and wherein the interface material comprises a third adhesive layer, wherein the interface material is configured to adhere to the second adhesive layer and the third adhesive layer comprises a third adhesive configured to adhere to the skin surface of the user, and wherein a second areal mass of the interface material is higher than first areal mass of the non-woven material.

26. The continuous glucose monitoring system of claim 25, wherein the interface material has an areal mass between 50 $g/m^2$ and 200 $g/m^2$.

27. The continuous glucose monitoring system of claim 25, wherein the interface material has an areal mass between 100 $g/m^2$ and 150 $g/m^2$.

28. The continuous glucose monitoring system of claim 25, wherein the interface material has an areal mass between 60 $g/m^2$ and 100 $g/m^2$.

29. The continuous glucose monitoring system of claim 25, wherein the interface material has an areal mass between 75 $g/m^2$ and 90 $g/m^2$.

30. The continuous glucose monitoring system of claim 17, wherein the plurality of grooves are configured to promote fluid drainage away from the sensor housing.

* * * * *